United States Patent
Brownell et al.

(10) Patent No.: US 9,844,576 B2
(45) Date of Patent: Dec. 19, 2017

(54) COMPOSITIONS AND METHODS FOR MANAGING WEIGHT

(71) Applicants: Unigen, Inc., Seattle, WA (US); Unigen, Inc., Cheonan-si (KR)

(72) Inventors: Lidia Alfaro Brownell, Tacoma, WA (US); Byong-Il Choi, Cheongwon-gun (KR); Brandon Corneliusen, Tenino, WA (US); Mei-Feng Hong, Lacey, WA (US); Eu-Jin Hyun, Cheonan-si (KR); Qi Jia, Olympia, WA (US); Ping Jiao, Lacey, WA (US); Hyun-Jin Kim, Asan-si (KR); Mi-Ran Kim, Cheonan-si (KR); Tae-Woo Kim, Ulsan (KR); Bo-Su Lee, Pohang-si (KR); Young-Chul Lee, Daejeon (KR); Jeong-Bum Nam, Cheongwon-gun (KR); Mesfin Yimam, Kent, WA (US); Ji-Hye Hwang, Jecheon-si (KR); Mi-Sun Oh, Cheonan-si (KR)

(73) Assignees: Unigen, Inc., Seattle, WA (US); Unigen, Inc., Songjungli, Byeongchun-Myeon, Dongnam Gu, Cheonan-Si, Chungcheongnam-Do (KR)

( * ) Notice: Subject to any disclaimer, the term of this patent is extended or adjusted under 35 U.S.C. 154(b) by 619 days.

(21) Appl. No.: 13/904,851

(22) Filed: May 29, 2013

(65) Prior Publication Data
US 2014/0004215 A1    Jan. 2, 2014

Related U.S. Application Data

(60) Provisional application No. 61/652,807, filed on May 29, 2012, provisional application No. 61/783,729, filed on Mar. 14, 2013.

(51) Int. Cl.
| | |
|---|---|
| *A61K 36/575* | (2006.01) |
| *A61K 36/37* | (2006.01) |
| *A61K 36/53* | (2006.01) |
| *A61K 36/185* | (2006.01) |
| *A61K 36/752* | (2006.01) |
| *A61K 36/889* | (2006.01) |
| *A61K 36/10* | (2006.01) |
| *A61K 36/258* | (2006.01) |
| *A61K 36/346* | (2006.01) |
| *A61K 36/38* | (2006.01) |
| *A61K 36/56* | (2006.01) |
| *A61K 36/605* | (2006.01) |
| *A61K 36/67* | (2006.01) |
| *A61K 31/352* | (2006.01) |
| *A61K 45/06* | (2006.01) |
| *A61K 31/12* | (2006.01) |
| *A61K 31/343* | (2006.01) |

(52) U.S. Cl.
CPC ............ *A61K 36/575* (2013.01); *A61K 31/12* (2013.01); *A61K 31/343* (2013.01); *A61K 31/352* (2013.01); *A61K 36/10* (2013.01); *A61K 36/185* (2013.01); *A61K 36/258* (2013.01); *A61K 36/346* (2013.01); *A61K 36/37* (2013.01); *A61K 36/38* (2013.01); *A61K 36/53* (2013.01); *A61K 36/56* (2013.01); *A61K 36/605* (2013.01); *A61K 36/67* (2013.01); *A61K 36/752* (2013.01); *A61K 36/889* (2013.01); *A61K 45/06* (2013.01)

(58) Field of Classification Search
None
See application file for complete search history.

(56) References Cited

U.S. PATENT DOCUMENTS

2006/0018975 A1* 1/2006 Talbott ................. A61K 31/375
424/646
2011/0300175 A1* 12/2011 Lavalle Gonzalez ..... A23F 3/34
424/195.18

FOREIGN PATENT DOCUMENTS

JP    2010202558 A  *  9/2010

OTHER PUBLICATIONS

Yerba Mate website (http://www.herbwisdom.com/herb-yerba-mate.html—accessed Sep. 2016).*

* cited by examiner

*Primary Examiner* — Susan Hoffman
(74) *Attorney, Agent, or Firm* — Sandra Thompson; Slater Hersey & Lieberman LLP

(57) ABSTRACT

The present disclosure provides Diels-Alder adducts of chalcone and prenylphenyl moieties capable of modulating the activity of cannabinoid receptors, and to oligomers of flavan-3-ol capable of modulating fat absorption and storage. Such Diels-Alder adducts of chalcone and prenylphenyl moieties or oligomers of flavan-3-ol can optionally be used in combination with other weight management agents, such as anorectic agents, a lipase inhibitors, other cannabinoid receptor modulators, psychotropic agents, insulin sensitizers, stimulants, or satiety agents, as well as to methods of use thereof such as treating or preventing weight gain or obesity, promoting weight loss, appetite suppression, modifying satiety, or the like.

1 Claim, 3 Drawing Sheets

COMPOSITIONS AND METHODS FOR MANAGING WEIGHT

CROSS-REFERENCE TO RELATED APPLICATIONS

This application claims the benefit under 35 U.S.C. §119 (e) of U.S. Provisional Patent Application No. 61/652,807, filed May 29, 2012, and U.S. Provisional Patent Application No. 61/783,729, filed Mar. 14, 2013, where these two provisional applications are incorporated herein by reference in their entireties.

BACKGROUND

Technical Field

The present disclosure relates to compositions and methods for weight management and, more particularly, to Diels-Alder adducts of chalcone and prenylphenyl moieties, to oligomers of flavan-3-ol, or both, optionally in combination with other weight management agents, such as anorectic agents, a lipase inhibitors, cannabinoid receptor modulators, psychotropic agents, insulin sensitizers, stimulants, or satiety agents, as well as to methods of use thereof such as treating or preventing weight gain or obesity, promoting weight loss, appetite suppression, modifying satiety, or the like.

Description of the Related Art

Obesity is a food problem. In industrialized countries, affluence provides abundant and variable food items to the general public. Food, with the associated taste and olfactory pleasures, is an indulgence, not just for basic survival. As a result, obesity and obesity-related health issues are increasing rapidly and there is a strong need for dietary supplements that help with weight control. The market size for food supplements that decrease body weight is large and there are few effective products.

For many years, *Cannabis sativa* (marijuana) has been known to stimulate food consumption through the action of its active component, delta-9-tetrahydrocannabinol (THC), an exogenous cannabinoid. This effect prompted research into its mechanism of action. The binding sites for THC were eventually cloned and named CB1 and CB2. These receptors belong to the G-protein coupled family characterized by seven trans-membrane loop domains. Both receptors belong to $G_{i/o}$ subclass and signal by negatively regulating cyclic AMP levels. CB1 was also shown to activate potassium channels. CB2 receptor is present in immune cells and is not involved in regulation of food consumption. CB1, the cannabinoid receptor involved in feeding behavior, is widely expressed both in brain and peripheral tissues, including adipose tissue, skeletal muscles, liver, and gastrointestinal (GI) tract.

Most of the published CB1 receptor antagonists might be better termed "inverse agonists" as they are capable of inhibiting constitutive activity of non-occupied CB1 receptors. The major clinical indications for this group of compounds are obesity and substance abuse. In the past, five CB1 compounds have been tested in clinical studies. They include Rimonabant (Sanofi-Aventis, launched in 2006), MK-0364 (Merck, Phase III), Surinabant and AVE-1625 (Sanofi-Aventis, Phase II), and SLV-319 (Solvay, Phase II). Rimonabant (marketed as Acomplia®, Rimoslim™ or Zimulti®) was the first selective CB1 antagonist discovered in 1994. It was approved in 37 countries, but it has since been withdrawn from obesity treatment due to neurological side effects.

Another product on the market is tetrahydrolipstatin (orlistat, sold as Alli® or Xenical®). Orlistat was identified from a chemical library based on its inhibition of fatty acid synthase, but was developed as a pancreatic triglyceride lipase inhibitor. But, orlistat has been placed on a list of drugs having a potential signal of serious risk due to cases of liver toxicity, which has led to a change in the product labeling and the FDA is continuing to evaluate this issue to determine the need for any further regulatory action (see www.fda.gov/Drugs/GuidanceComplianceRegulatoryInformation/Surveillance/AdverseDrugEffe cts/ucm161063.htm).

From the foregoing, a need is apparent for improved compositions and methods for weight management.

BRIEF SUMMARY

In brief, the present disclosure is directed to compounds and compositions useful for weight management and related methods, including stereoisomers, pharmaceutically or nutraceutically acceptable salts, tautomers, glycosides and prodrugs of the disclosed compounds.

In certain embodiments, this disclosure provides a composition comprising a mixture of a *Morus* extract enriched for one or more Diels-Alder adducts of a chalcone and a prenylphenyl moiety, a *Magnolia* extract, and a Yerba Mate extract. In further embodiments, this disclosure provides a composition comprising a mixture of a *Morus* extract enriched for Diels-Alder adducts of a chalcone and a prenylphenyl moiety, a *Magnolia* extract, and a Mutamba extract. In further embodiments, this disclosure provides a composition comprising a mixture of a *Morus* extract enriched for Diels-Alder adducts of a chalcone and a prenylphenyl moiety, a Rosemary extract, and a Yerba Mate extract.

Exemplary Diels-Alder adducts of a chalcone and a prenylphenyl moiety include compounds having a structure of Formula I or II:

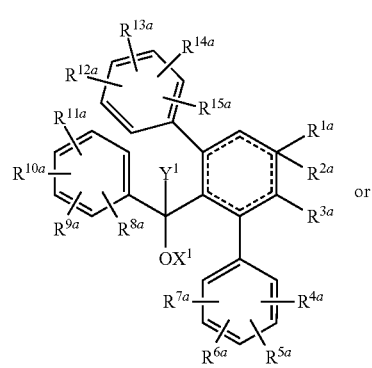

I or

-continued

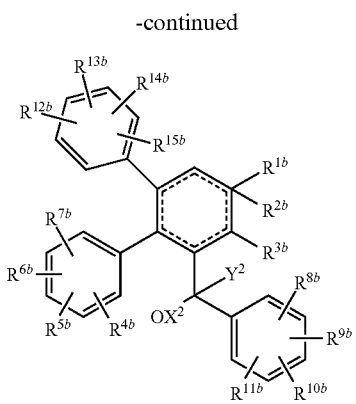

II or a pharmaceutically or nutraceutically acceptable salt, tautomer, glycoside or stereoisomer thereof, wherein the substituents are as defined herein.

In another aspect, the present disclosure provides methods for managing weight. In certain embodiments, the compositions of this disclosure can be used in methods for treating, preventing, or managing weight gain or obesity or excess weight, promoting or managing weight loss, appetite suppression, reducing food craving, reducing eating between meals and in the evening hours, modifying satiety, modifying fat uptake or fat absorption, increasing metabolism to promote weight loss or prevent weight gain, maintaining body weight, promoting fat burn, increasing lipolysis, reducing body fat or fatty tissues, increasing muscle or lean body mass, reducing hepato-steatosis, improving fatty liver, improving one or more liver NASH scores, enhancing fat metabolism, reducing the release of pro-inflammatory adipokines, increasing adiponectin from fat tissues, promoting a healthy lipid profile (by, e.g., lowering LDL cholesterol, lowering total cholesterol, lowering triglyceride, or increasing HDL), promoting glucose metabolism, reducing fasting glucose levels, block absorption of carbohydrates, maintaining healthy glucose levels, reducing caloric intake, improving caloric efficiency, reducing food intake, reducing visceral fat, reducing waist circumference, reducing body-to-mass index (BMI), or any combination thereof.

These and other aspects of the invention will be apparent upon reference to the following detailed description.

DETAILED DESCRIPTION

Figure 1:
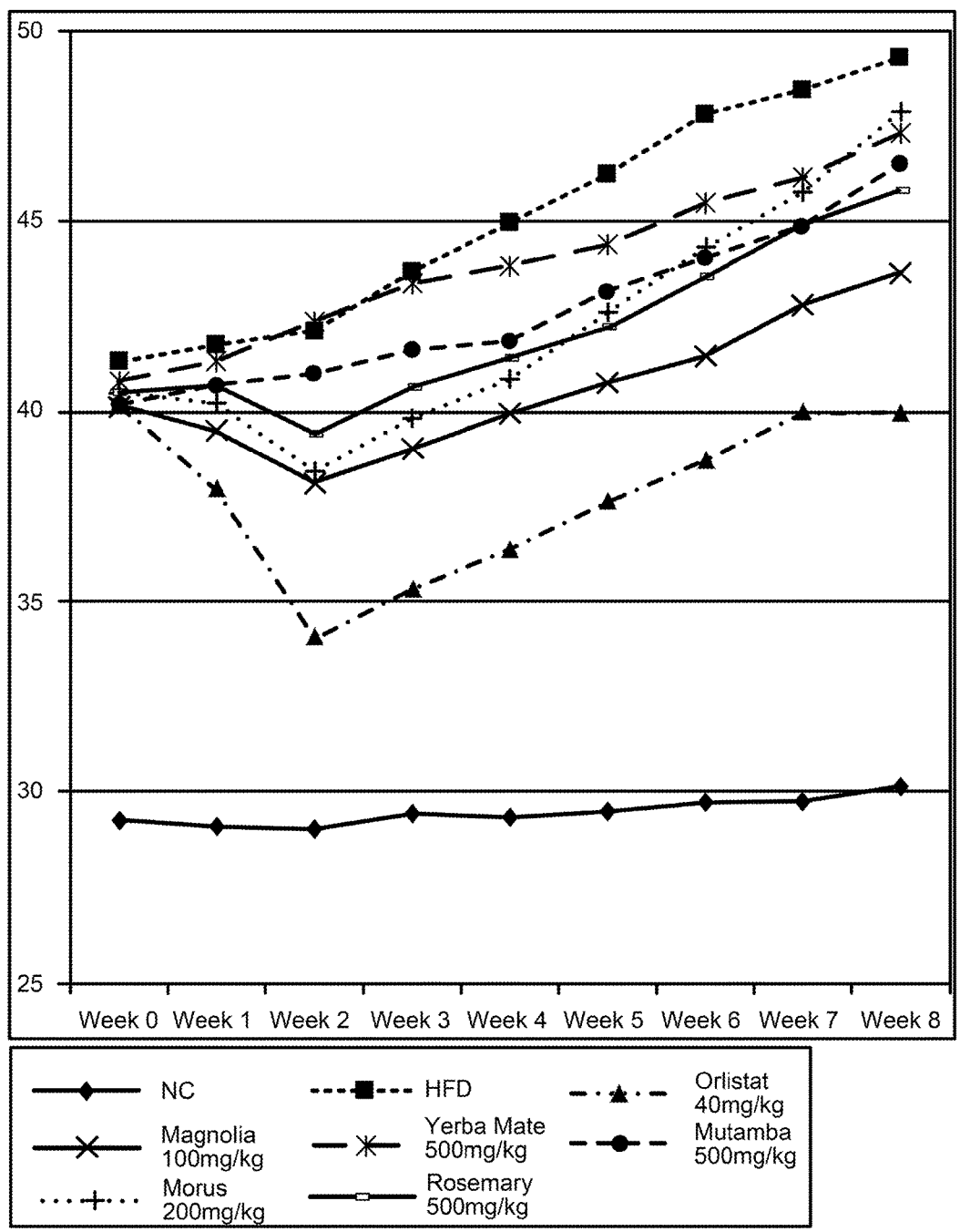
FIG. 1 shows a graph of mean body weights for mice on a high fat diet that had been treated for 8 weeks with one of the following: *Magnolia* extract, *Morus alba* extract, Mutamba extract, Rosemary extract, or Yerba Mate extract. The negative controls included mice on the high fat diet that received no treatment (HFD) and mice kept on a normal diet control (NC), while the positive control was mice on a high fat diet treated with orlistat.

The present disclosure provides compositions of Diels-Alder adducts of a chalcone and a prenylphenyl moiety and at least one other weight management agent. The Diels-Alder adducts of a chalcone and a prenylphenyl moiety can be obtained or enriched from certain plants or certain plant parts, such as *Morus alba* root bark, and can be used as a cannabinoid receptor (e.g., CB1, CB2) modulator. Modulation of cannabinoid receptor activity can be helpful in managing weight or diabetes. Exemplary weight management agents for use with the Diels-Alder adducts of a chalcone and a prenylphenyl moiety include anorectic agents, lipase inhibitors, other cannabinoid receptor modulators, psychotropic agents, insulin sensitizers, stimulants, satiety agents, or any combination thereof. Furthermore, the Diels-Alder adducts of a chalcone and a prenylphenyl moiety of the present disclosure, as well as compositions thereof, can be used in methods to treat or prevent weight associated disorders.

In the following description, certain specific details are set forth in order to provide a thorough understanding of various embodiments of this disclosure. However, one skilled in the art will understand that the invention may be practiced without these details.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. Unless the context requires otherwise, throughout the present specification and claims, the word "comprise" and variations thereof, such as, "comprises" and "comprising," as well as synonymous terms like "include" and "have" and variants thereof, are to be construed in an open, inclusive sense; that is, as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ radical.

"Cyano" refers to the —CN radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double or triple bonds), having from one to twelve carbon atoms ($C_1$-$C_{12}$ alkyl), or one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may include fused or bridged ring systems. Aryl radicals include aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, or having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of this disclosure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl), wherein at least one hydrogen atom is replaced by a bond to a non-hydrogen atoms such as a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl group. In addition, each of the foregoing substituents may also be optionally substituted with one or more of the above substituents.

"Glycoside" refers to a molecule in which a sugar group is bonded through its anomeric carbon to another group via a glycosidic bond. Exemplary sugars include glucose, rhamnose, manose, galactose, arabinose, glucuronide and others. Glycosides can be linked by an O- (an O-glycoside), N- (a glycosylamine), S- (a thioglycoside), or C- (a C-glycoside) glycosidic bond. Compounds of this disclosure can form glycosides at any suitable attachment point.

"Prenyl" refers to the

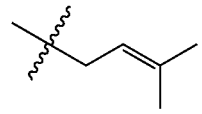 [SMILES: *CC=C(C)C]

radical. Prenyl includes isoprenyl, which refers to the

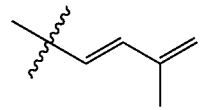 [SMILES: */C=C/C(=C)C]

radical (cis or trans). Prenyl groups may be substituted or unsubstituted.

"Prenylphenyl" refers to a phenyl moiety connected to a prenyl moiety as defined above. Prenylphenyls include substituted phenyls such as flavonoids and other substituted phenyls and heteroaryls, provided there is at least one prenyl group in the molecule. In the case of substituted phenyls and heteroaryl, the prenyl moiety need not be directly attached to the phenyl ring, but can be attached at any point in the molecule.

"Chalcone" refers to a compound comprising the following core structure:

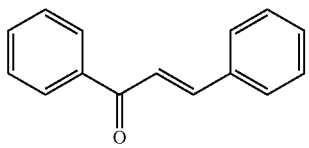 [SMILES: O=C(/C=C/c1ccccc1)c1ccccc1]

Chalcones can be variously substituted at any of the above carbon atoms.

"Prodrug" is meant to indicate a compound that may be converted under physiological conditions or by solvolysis to a biologically active compound of this disclosure. Thus, the term "prodrug" refers to a metabolic precursor of a compound of this disclosure that is pharmaceutically and nutraceutically acceptable. A prodrug may be inactive when administered to a subject in need thereof, but is converted in vivo to an active compound of this disclosure. Prodrugs are typically rapidly transformed in vivo to yield the parent compound of this disclosure, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical and Nutraceutical Association and Pergamon Press, 1987.

The term "prodrug" is also meant to include any covalently bonded carriers, which release the active compound of this disclosure in vivo when such prodrug is administered to a mammalian subject. Prodrugs of a compound of this disclosure may be prepared by modifying functional groups present in the compound of this disclosure in such a way that the modifications are cleaved, either in routine manipulation or in vivo, to the parent compound of this disclosure. Prodrugs include compounds of this disclosure wherein a hydroxy, amino or mercapto group is bonded to any group that, when the prodrug of the compound of this disclosure is administered to a mammalian subject, cleaves to form a free hydroxy, free amino or free mercapto group, respectively. Examples of prodrugs include acetate, formate and benzoate derivatives of alcohol or amide derivatives of amine functional groups in the compounds of this disclosure and the like.

The instant disclosure is also meant to encompass all pharmaceutically or nutraceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The instant disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, this disclosure includes compounds produced by a process comprising administering a compound of this invention to a mammal for a period of time sufficient to yield a metabolic product thereof. Such products are typically identified by administering a radiolabelled compound of this disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals, such as laboratory animals or household pets (e.g., cats, dogs, swine, cattle, sheep, goats, horses, rabbits), and non-domestic animals, such as wildlife or the like.

"Optional" or "optionally" means that the subsequently described element, component, event or circumstances may or may not occur, and that the description includes instances where the element, component, event or circumstance occur and instances in which they do not. For example, "optionally substituted aryl" means that the aryl radical may or may not be substituted and that the description includes both substituted aryl radicals and aryl radicals having no substitution.

"Pharmaceutically or nutraceutically acceptable carrier, diluent or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically or nutraceutically acceptable salt" includes both acid and base addition salts.

"Pharmaceutically or nutraceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2- disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically or nutraceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include the sodium, potassium, lithium, ammonium, calcium, magnesium, iron, zinc, copper, manganese, aluminum salts and the like. In certain embodiments, the inorganic salts are ammonium, sodium, potassium, calcium, or magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases are isopropylamine, diethylamine, ethanolamine, trimethylamine, dicyclohexylamine, choline and caffeine.

Often crystallizations produce a solvate of the compound of this disclosure. As used herein, the term "solvate" refers to an aggregate that comprises one or more molecules of a compound of this disclosure with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of this disclosure may be true solvates, while in other cases, the compound of this disclosure may merely retain adventitious water or be a mixture of water plus some adventitious solvent.

A "pharmaceutical composition" or "nutraceutical composition" refers to a formulation of a compound of this disclosure and a medium generally accepted in the art for the delivery of the biologically active compound to mammals, e.g., humans. For example, a pharmaceutical composition of the present disclosure may be formulated or used as a stand alone composition, or as a component in a prescription drug, an over the counter (OTC) medicine, a botanical drug, an herbal medicine, a homeopathic agent, or any other form of health care product reviewed and approved by a government agency. Exemplary nutraceutical compositions of the present disclosure may be formulated or used as a stand alone composition, or as a nutritional or bioactive component in food, a functional food, a beverage, a bar, a food flavor, a medical food, a dietary supplement, or an herbal product. A medium generally accepted in the art includes all pharmaceutically or nutraceutically acceptable carriers, diluents or excipients therefor.

As used herein, "enriched for" refers to a plant extract or other preparation having at least a two-fold up to about a 1000-fold increase of one or more active compounds as compared to the amount of one or more active compounds found in the weight of the plant material or other source before extraction or other preparation. In certain embodiments, the weight of the plant material or other source before extraction or other preparation may be dry weight, wet weight, or a combination thereof.

As used herein, "major active ingredient" or "major active component" refers to one or more active compounds found in a plant extract or other preparation, or enriched for in a plant extract or other preparation, which is capable of at least one biological activity. In certain embodiments, a major active ingredient of an enriched extract will be the one or more active compounds that were enriched in that extract. Generally, one or more major active components will impart, directly or indirectly, most (i.e., greater than 50%) of one or more measurable biological activities or effects as compared to other extract components. In certain embodiments, a major active ingredient may be a minor component by weight percentage of an extract (e.g., less than 50%, 25%, or 10% of the components contained in an extract) but still provide most of the desired biological activity. Any composition of this disclosure containing a major active ingredient may also contain minor active ingredients that may or may not contribute to the pharmaceutical or nutraceutical activity of the enriched composition, but not to the level of major active components, and minor active components alone may not be effective in the absence of a major active ingredient.

"Effective amount" or "therapeutically effective amount" refers to that amount of a compound or composition of this disclosure which, when administered to a mammal, such as a human, is sufficient to effect treatment, including any one or more of: (1) treating or preventing weight gain in a mammal; (2) promoting weight loss; (3) suppressing appetite in a mammal; (4) modifying satiety in a mammal; (5) treating or preventing obesity in a mammal; (6) modifying fat uptake in a mammal; and (7) increasing metabolism to promote weight loss or prevent weight gain in a mammal. The amount of a compound or composition of this disclosure that constitutes a "therapeutically effective amount" will vary depending on the compound, the condition being treated and its severity, the manner of administration, the duration of treatment, or the age of the subject to be treated, but can be determined routinely by one of ordinary skill in the art having regard to his own knowledge and to this disclosure.

"Dietary supplements" as used herein are a product that improves, promotes, increases, manages, controls, maintains, optimizes, modifies, reduces, inhibits, or prevents a particular condition associated with a natural state or biological process (i.e., are not used to diagnose, treat, mitigate, cure, or prevent disease). For example, with regard to weight-related conditions, dietary supplements may be used to promote weight loss, manage weight gain, maintain weight, modify satiety, reduce caloric intake, increase muscle mass, or the like. Exemplary dietary supplements include one or more of a dietary ingredient such as a vitamin, a mineral, an herb or other botanical, an amino acid, or any other substance used to supplement the diet by increasing total dietary intake, or a concentrate, metabolite, constituent, extract, or any combination thereof. In certain embodiments, dietary supplements are a special category of food and are not a drug.

"Treating" or "treatment" as used herein refers to the treatment of the disease or condition of interest in a mammal, such as a human, having the disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition, (e.g., relieving pain, reducing inflammation, causing weight loss) without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, "statistical significance" refers to a p value of 0.050 or less when calculated using the Students t-test and indicates that it is unlikely that a particular event or result being measured has arisen by chance.

The compounds of this disclosure, or their pharmaceutically or nutraceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L). For example, the compounds of structure I or II may have chiral centers at least at the positions noted with * in the structures below.

Accordingly, in certain embodiments the positions marked with an * above (and various other positions within compounds I and II) can each independently exist as either R or S isomers, and the present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program or ChemDraw Ultra Version 11.0 software naming program (CambridgeSoft), wherein the compounds of this disclosure are named herein as derivatives of the central core structure, e.g., the imidazopyridine structure. For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

As noted herein, in certain embodiments, the present disclosure provides a composition comprising a Diels-Alder adduct of a chalcone and a prenylphenyl moiety, and at least one other weight management agent, wherein the weight management agent is an anorectic agent, a lipase inhibitor, a cannabinoid receptor modulator, a psychotropic agent, an insulin sensitizer, a stimulant, or a satiety agent, wherein the Diels-Alder adduct of a chalcone and a prenylphenyl moiety is a compound having a structure of Formula I or II:

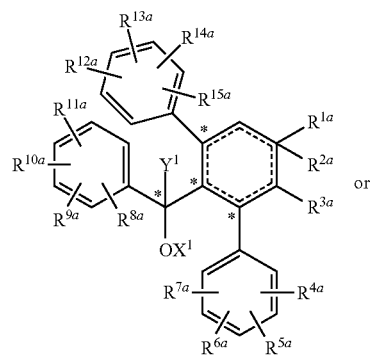

I or

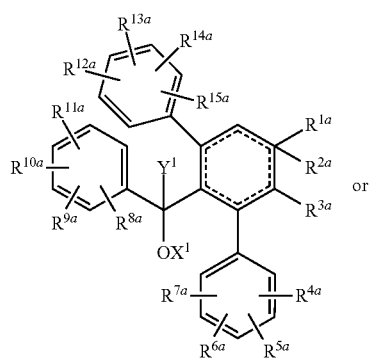

I

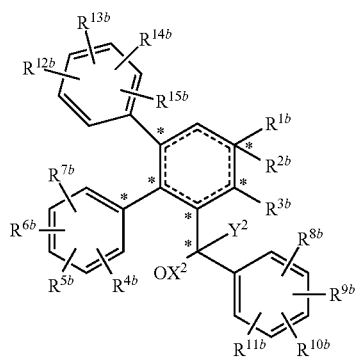

II

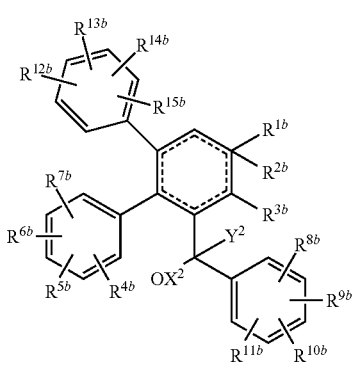

or a pharmaceutically or nutraceutically acceptable salt, tautomer, glycoside, prodrug or stereoisomer thereof, wherein:

$R^{1a}$ and $R^{1b}$ are each independently $C_{1-12}$ alkyl;

$R^{2a}$ and $R^{2b}$ are each independently H or $R^{2a}$ or $R^{2b}$ joins with one of $R^{4a}$, $R^{5a}$, $R^{6a}$, $R^{7a}$, $R^{12a}$, $R^{13a}$, $R^{14a}$ or $R^{15a}$ or $R^{4b}$, $R^{5b}$, $R^{6b}$, $R^{7b}$, $R^{12b}$, $R^{13b}$, $R^{14b}$ or $R^{15b}$, respectively, to form an ether bond;

$R^{3a}$ and $R^{3b}$ are each independently H, hydroxyl or oxo;

$R^{4a}$, $R^{5a}$, $R^{6a}$ and $R^{7a}$ are each independently H, hydroxyl, halogen, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl, aralkylcarbonyl or one of $R^{4a}$, $R^{5a}$, $R^{6a}$ or $R^{7a}$ joins with another of $R^{4a}$, $R^{5a}$, $R^{6a}$ or $R^{7a}$ to form a heterocyclic or heteroaromatic ring or one of $R^{4a}$, $R^{5a}$, $R^{6a}$ or $R^{7a}$ joins with $X^1$ to form a direct bond;

$R^{4b}$, $R^{5b}$, $R^{6b}$ and $R^{7b}$ are each independently H, hydroxyl, halogen, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl, aralkylcarbonyl or one of $R^{4b}$, $R^{5b}$, $R^{6b}$, $R^{7b}$ joins with another of $R^{4b}$, $R^{5b}$, $R^{6b}$, $R^{7b}$ to form a heterocyclic or heteroaromatic ring or one of $R^{4b}$, $R^{5b}$, $R^{6b}$ or $R^{7b}$ joins with $X^2$ to form a direct bond;

$R^{8a}$, $R^{8b}$, $R^{9a}$, $R^{9b}$, $R^{10a}$, $R^{10b}$, $R^{11a}$ and $R^{11b}$ are each independently H, hydroxyl, halogen, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl, aralkylcarbonyl or one of $R^{8a}$, $R^{9a}$, $R^{10a}$ or $R^{11a}$ or one of $R^{8b}$, $R^{9b}$, $R^{10b}$ or $R^{11b}$ joins with another of $R^{8a}$, $R^{9a}$, $R^{10a}$ or $R^{11a}$ or another one of $R^{8b}$, $R^{9b}$, $R^{10b}$ or $R^{11b}$, respectively, to form a heterocyclic or heteroaromatic ring;

$R^{12b}$, $R^{13a}$, $R^{14a}$ or $R^{15a}$ are each independently H, hydroxyl, halogen, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl, aralkylcarbonyl or one of $R^{12a}$, $R^{13a}$, $R^{14a}$, $R^{15a}$ joins with another of $R^{12a}$, $R^{13a}$, $R^{14a}$ or $R^{15a}$ to form a heterocyclic or heteroaromatic ring or one of $R^{12a}$, $R^{13a}$, $R^{14a}$ or $R^{15a}$ joins with $Y^1$ to form an ether bond;

$R^{12b}$, $R^{13b}$, $R^{14b}$ and $R^{15b}$ are each independently H, hydroxyl, halogen, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl, aralkylcarbonyl or one of $R^{12b}$, $R^{13b}$, $R^{14b}$, $R^{15b}$ joins with another of $R^{12b}$, $R^{13b}$, $R^{14b}$ or $R^{15b}$ to form a heterocyclic or heteroaromatic ring;

$X^1$ joins with one of $R^{4a}$, $R^{5a}$, $R^{6a}$ or $R^{7a}$ to form a direct bond or $X^1$ joins with $Y^1$ to form an oxo moiety;

$X^2$ joins with one of $R^{4b}$, $R^{5b}$, $R^{6b}$ or $R^{6b}$ to form a direct bond or $X^2$ joins with $Y^2$ to form an oxo moiety;

$Y^1$ is H or $Y^1$ joins with one of $R^{12a}$, $R^{13a}$, $R^{14a}$ or $R^{15a}$ to form an ether bond or $Y^1$ joins with an adjacent aliphatic carbon to form an oxirane ring;

$Y^2$ is H or $Y^2$ joins with an adjacent aliphatic carbon to form an oxirane ring; and a dashed bond represents an optional double bond such that all valences are satisfied.

In further embodiments of the foregoing, $R^{1a}$ and $R^{1b}$ are each independently methyl,

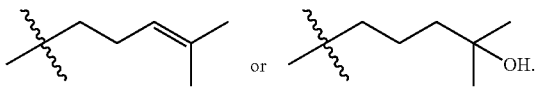

In some embodiments, $R^{2a}$ and $R^{2b}$ are H. In other embodiments, $R^{3a}$ and $R^{3b}$ are H.

In yet other embodiments, the compound has the following structure (Ia) or (IIa):

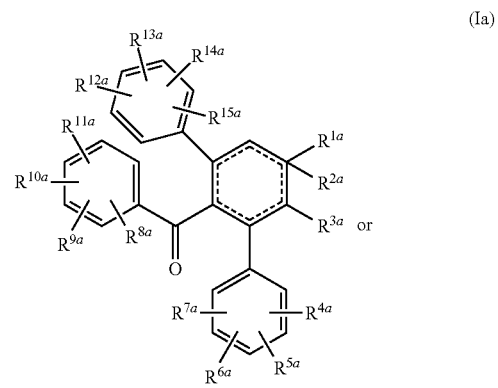

In still other embodiments, the compound has the following structure (Ib) or (IIb):

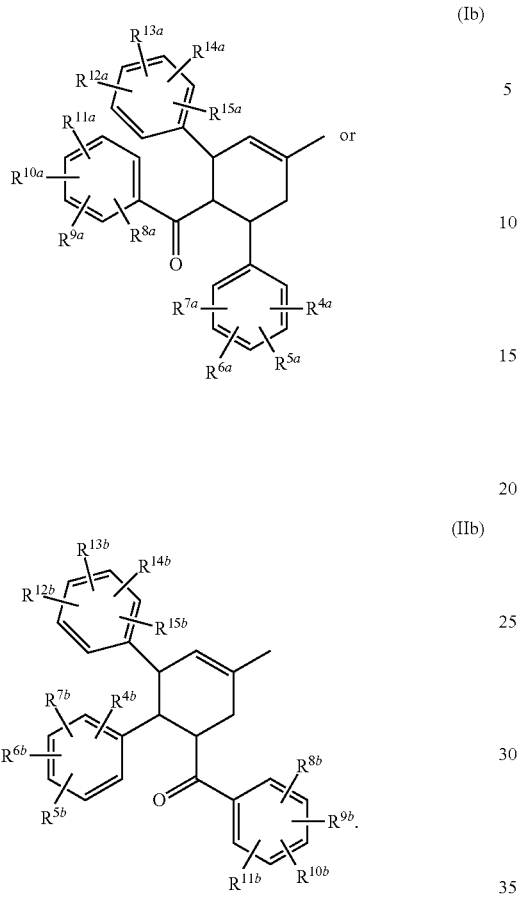
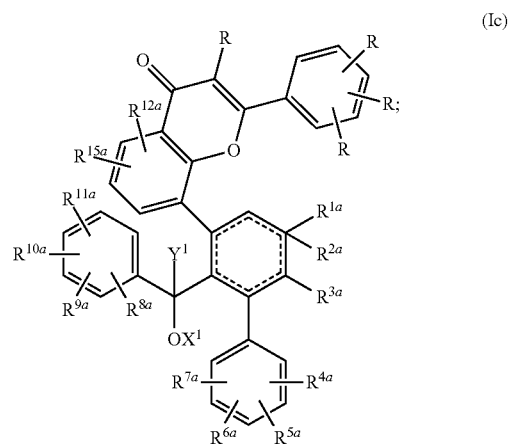
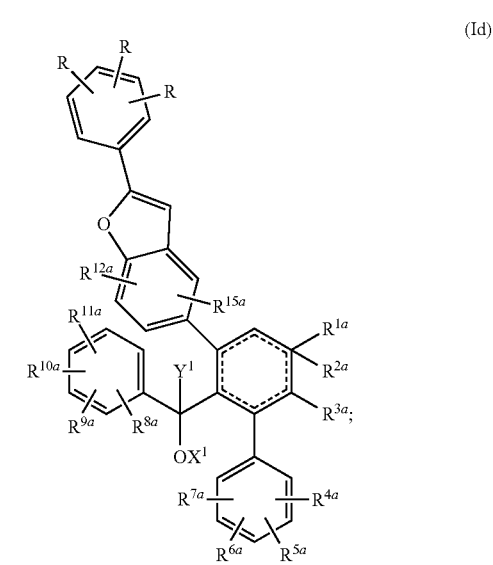
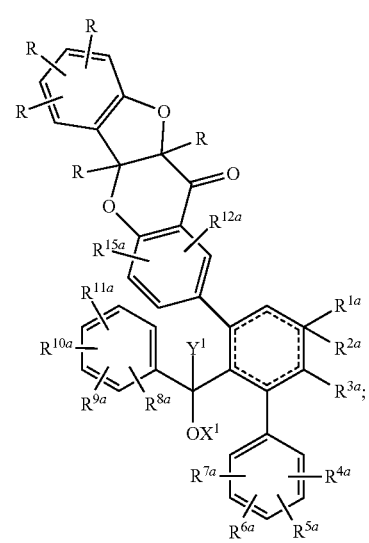

In other aspects of the foregoing composition, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, $R^{12b}$, $R^{13a}$, $R^{13b}$, $R^{14a}$, $R^{14b}$, $R^{15a}$ and $R^{15b}$ are each independently H, hydroxyl, halogen, $C_{1-12}$ alkoxy, $C_{1-12}$ alkyl or heteroaryl, or one of $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, $R^{12b}$, $R^{13a}$, $R^{13b}$, $R^{14a}$, $R^{14b}$, $R^{15a}$ or $R^{15b}$ joins with another of $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, $R^{12b}$, $R^{13a}$, $R^{13b}$, $R^{14a}$, $R^{14b}$, $R^{15a}$ and $R^{15b}$ on the same ring to form a heteroaromatic ring.

In some embodiments, one of $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, $R^{12b}$, $R^{13a}$, $R^{13b}$, $R^{14a}$, $R^{14b}$, $R^{15a}$ or $R^{15b}$ joins with another of $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, $R^{12b}$, $R^{13a}$, $R^{13b}$, $R^{14a}$, $R^{14b}$, $R^{15a}$ and $R^{15b}$ on the same ring to form a heteroaromatic ring. For example, in some embodiments the foregoing R groups may join to form a dioxymethylene group and the heteroaromatic ring thus formed is an optionally substituted benzodiaoxazole.

In still other embodiments, the compound has one of the following structures (Ic), (Id), (Ie), (If), (Ig), (IIc), (IId), (IIe), (IIf) or (IIg):

-continued
(If)
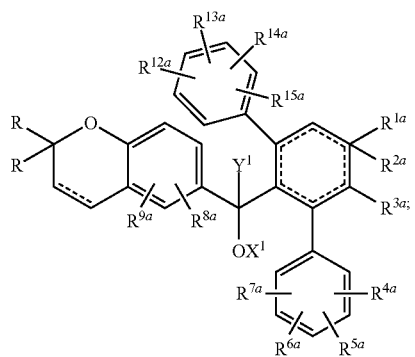
(Ie)
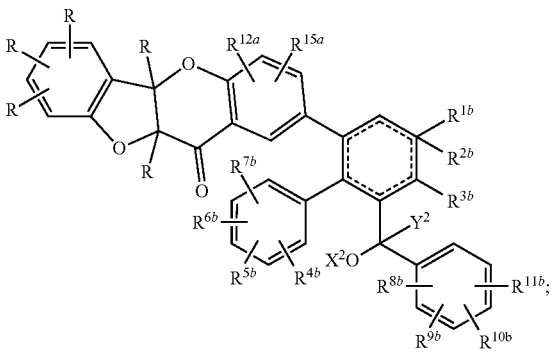
(Ig)
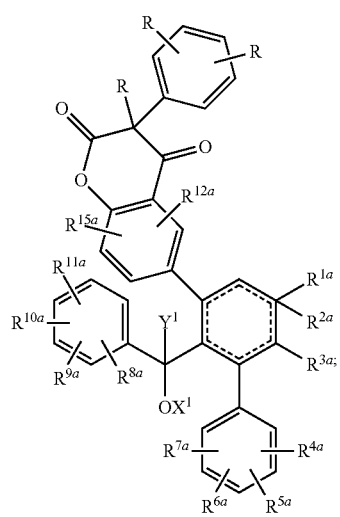
(IIf)
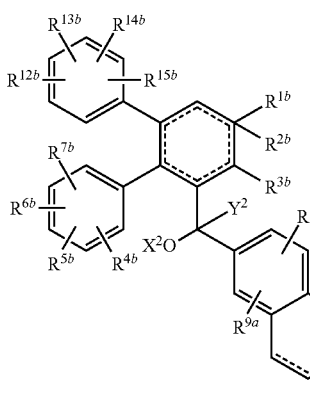
(IIc)
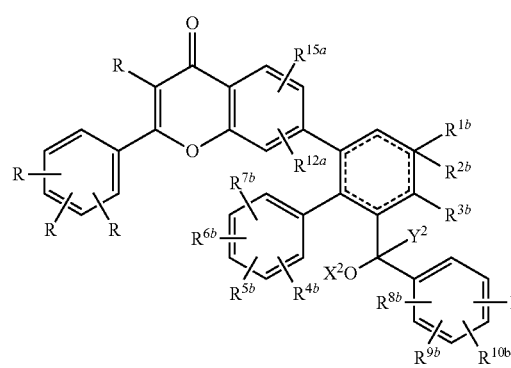
(IIg)
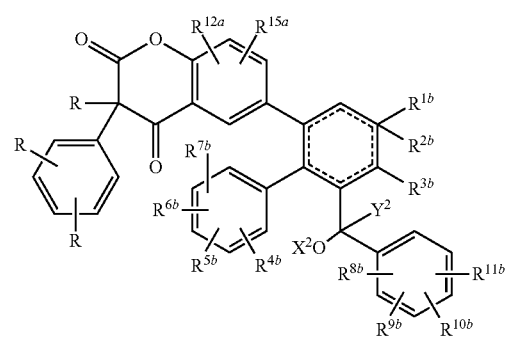
(IId)
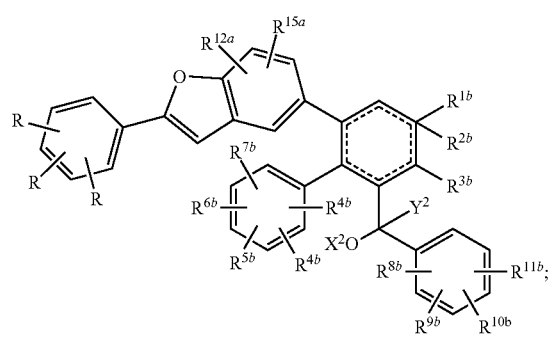
wherein R is, at each occurrence, independently H, hydroxyl or $C_{1-12}$ alkyl.
In further embodiments of the foregoing, the compound has one of the following structures (Ih), (Ii), (Ij), (Ik), (Il), (IIh), (IIi), (IIj), (IIk) or (III):

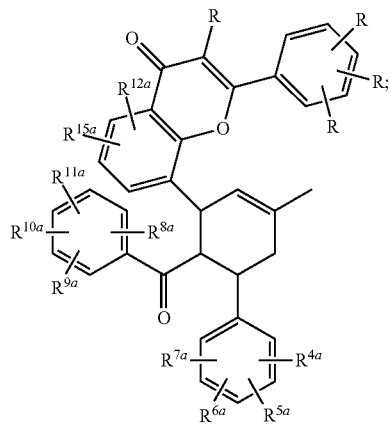
(Ih)
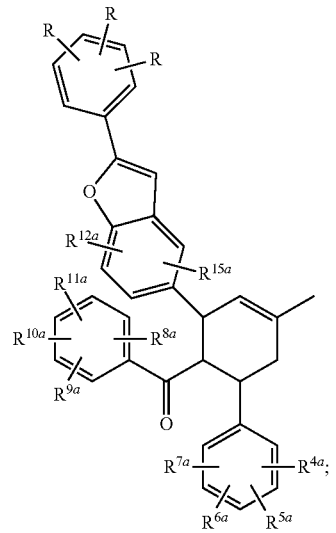
(Ii)
(Ij)
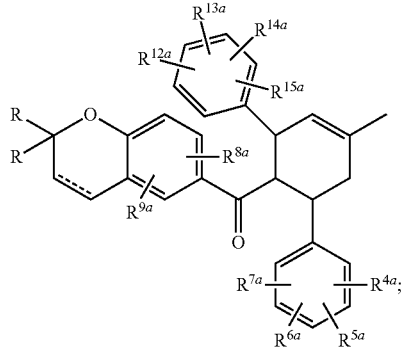
(Ik)
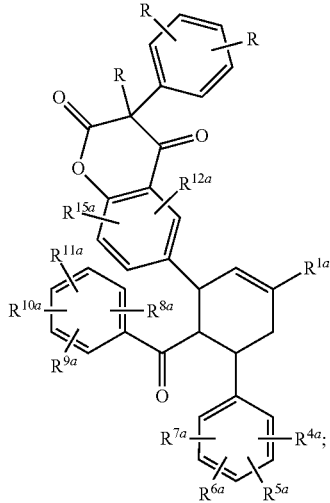
(Il)
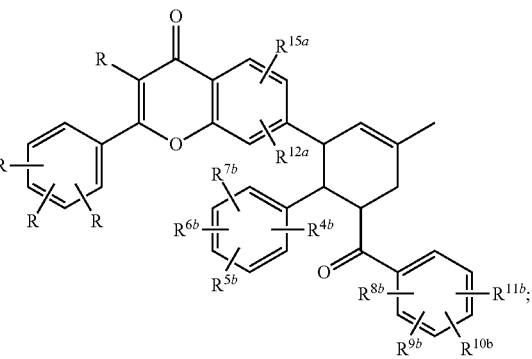
(IIh)
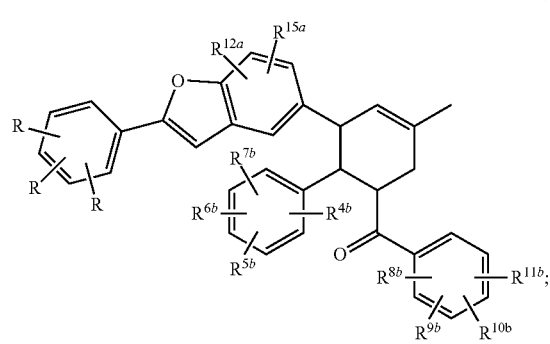
(IIi)

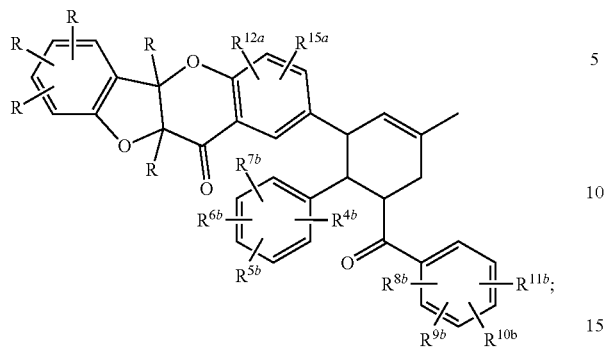
(IIj)

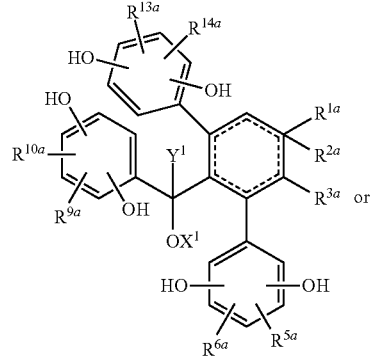
(Im)

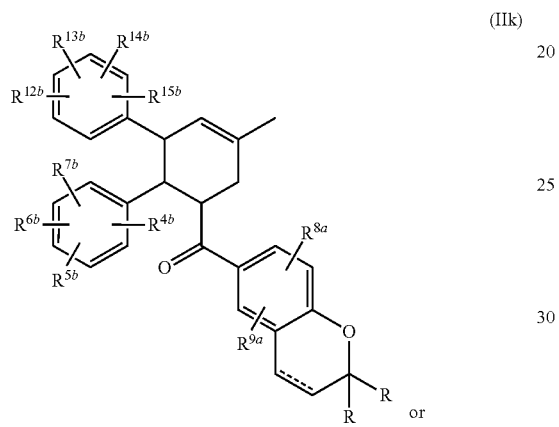
(IIk)

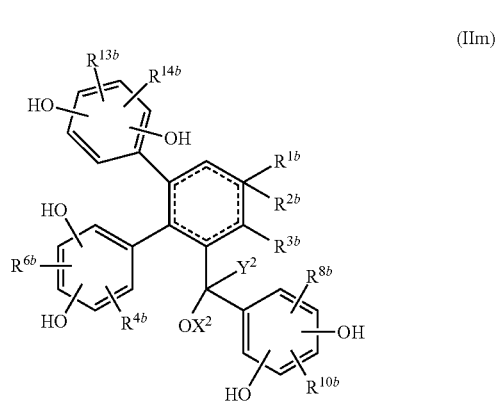
(IIm)

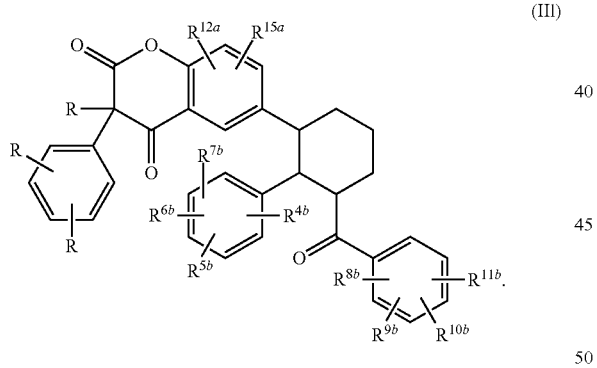
(III)

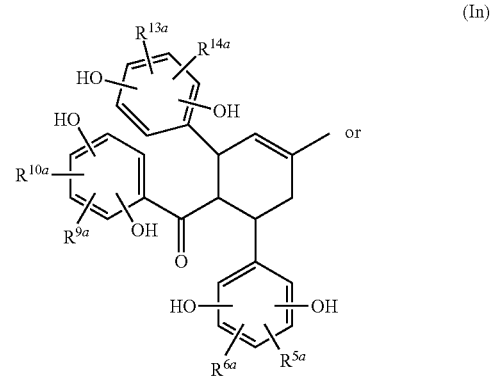
(In)

In still other embodiments, at least one R is hydroxyl, and in other embodiments at least one R is

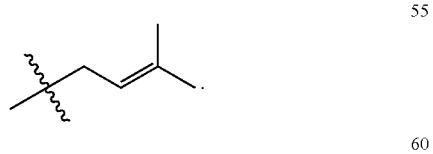

In other related embodiments, at least two of $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, $R^{12b}$, $R^{13a}$, $R^{13b}$, $R^{14a}$, $R^{14b}$, $R^{15a}$ and $R^{15b}$ are hydroxyl.

In some exemplary compositions, the compound has one of the following structures (Im), (In), (IIm) or (IIn):

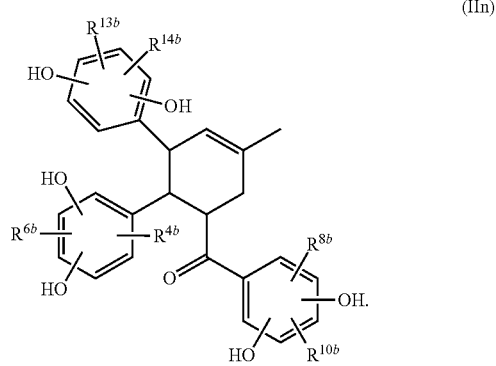
(IIn)

In some embodiments, at least one of $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, $R^{12b}$, $R^{13a}$, $R^{13b}$, $R^{14a}$, $R^{14b}$, $R^{15a}$ or $R^{15b}$ is

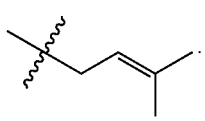 [SMILES: *CC=C(C)C ; "."]

In other embodiments, at least one of $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, $R^{12b}$, $R^{13a}$, $R^{13b}$, $R^{14a}$, $R^{14b}$, $R^{15a}$ or $R^{15b}$ is heteroaryl. For example, in some embodiments, the heteroaryl is selected from:

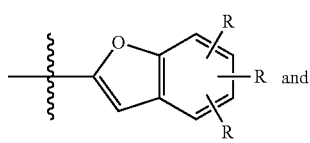

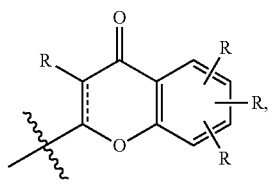

wherein R is, at each occurrence, independently H, hydroxyl or $C_{1-12}$ alkyl. For example, in some embodiments at least one R is hydroxyl, and in other embodiments at least one R is

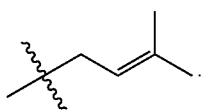 [SMILES: *CC=C(C)C ; "."]

In still other embodiments, $X^1$ joins with one of $R^{4a}$, $R^{5a}$, $R^{6a}$ or $R^{7a}$ to form a direct bond or $X^2$ joins with one of $R^{12b}$, $R^{13b}$, $R^{14b}$ or $R^{15b}$ to form a direct bond and the compound has one of the following structures (Io) or (IIo):

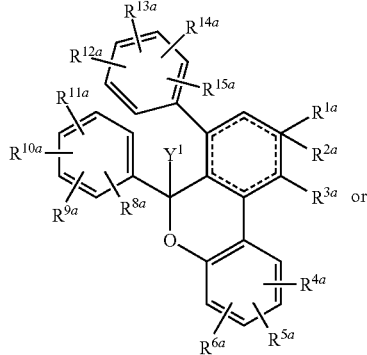

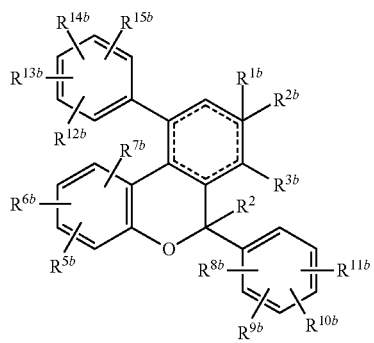

For example, in some further embodiments, the compound has one of the following structures (Ip) or (IIp):

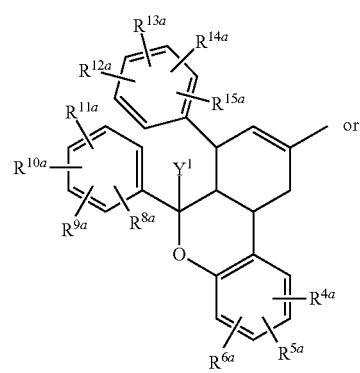

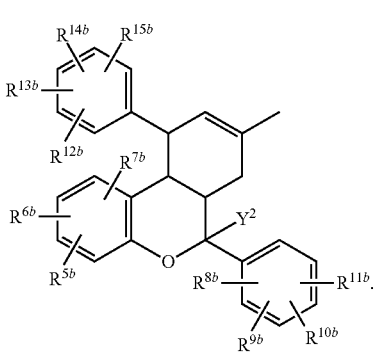

In still some other further embodiments, $Y^1$ joins with one of $R^{12a}$, $R^{13a}$, $R^{14a}$ or $R^{15a}$ to form an ether bond and the compound has one of the following structures (Iq) or (Ir):

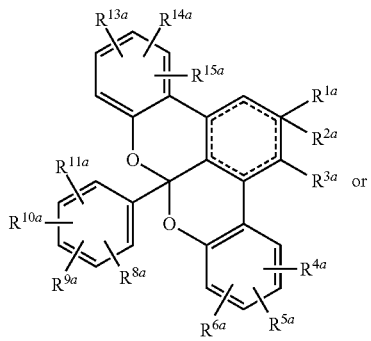

(Iq)

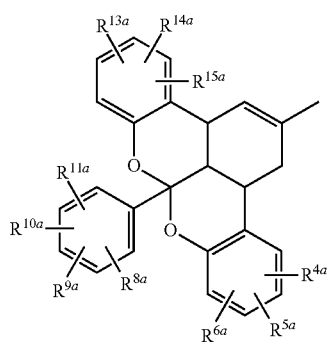

(Ir)

In some more specific embodiments, the compound is selected from any of the compounds provided in Table A.

TABLE A

List of Exemplary Compounds

| Structure | Name | Species | Molecular Formula | M.W. |
|---|---|---|---|---|
| 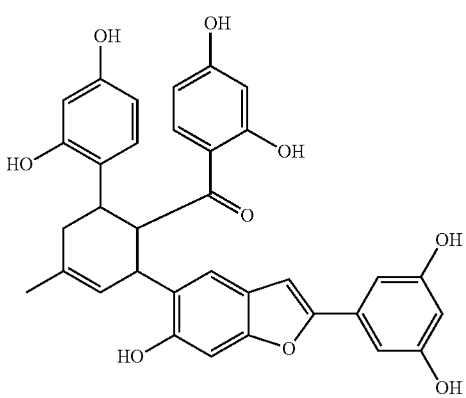 [SMILES: CC1=CC(c2cc3cc(-c4cc(O)cc(O)c4)oc3cc2O)C(C(=O)c2ccc(O)cc2O)C(c2ccc(O)cc2O)C1] | Albafuran C | *Morus alba* | $C_{34}H_{28}O_9$ | 580.590 |
| 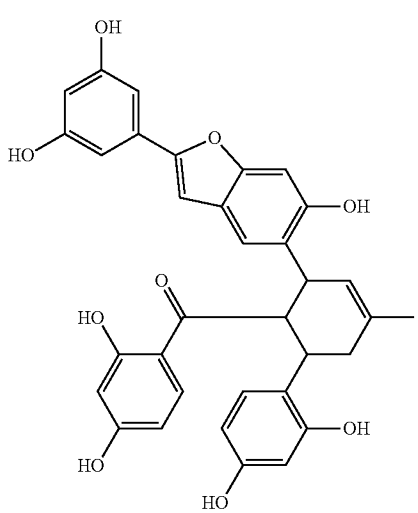 [SMILES: CC1=CC(c2cc3cc(-c4cc(O)cc(O)c4)oc3cc2O)C(C(=O)c2ccc(O)cc2O)C(c2ccc(O)cc2O)C1] | Abafuran C; 2-Epimer | *Morus australis* | $C_{34}H_{28}O_9$ | 580.590 |

TABLE A-continued

List of Exemplary Compounds

| Structure | Name | Species | Molecular Formula | M.W. |
|---|---|---|---|---|
| 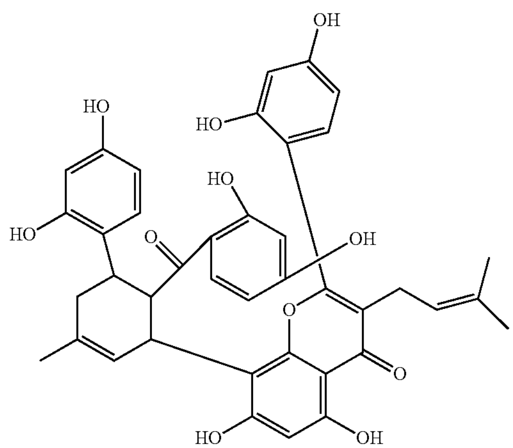 [SMILES: CC(C)=CCc1c(-c2ccc(O)cc2O)oc2c(C3C=C(C)CC(c4ccc(O)cc4O)C3C(=O)c3ccc(O)cc3O)c(O)cc(O)c2c1=O] | Albanin F | Morus alba, also from Morus australis, Morus bombycis, and Morus lhou | $C_{40}H_{36}O_{11}$ | 692.718 |
| 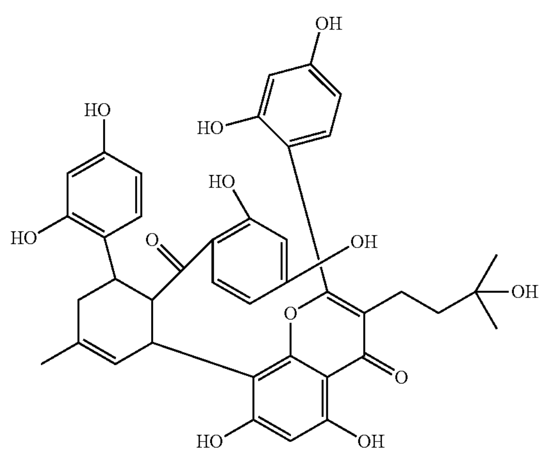 [SMILES: CC1=CC(c2c(O)cc(O)c3c(=O)c(CCC(C)(C)O)c(-c4ccc(O)cc4O)oc23)C(C(=O)c2ccc(O)cc2O)C(c2ccc(O)cc2O)C1] | Albanin F (Moracenin D); 12,13-Dihydro, 13-hydroxy | Morus sp. | $C_{40}H_{38}O_{12}$ | 710.733 |
| 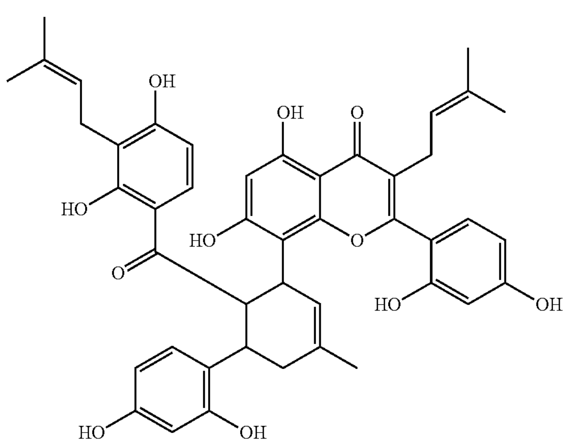 [SMILES: CC(C)=CCc1c(O)ccc(C(=O)C2C(c3c(O)cc(O)c4c(=O)c(CC=C(C)C)c(-c5ccc(O)cc5O)oc34)C=C(C)CC2c2ccc(O)cc2O)c1O] | Albanin G (Kuwanon H. Moracenin A.) | Morus alba; also isol. from Morus australis, Morus bombycis, and Morus lhou | $C_{45}H_{44}O_{11}$ | 760.836 |

TABLE A-continued

List of Exemplary Compounds

| Structure | Name | Species | Molecular Formula | M.W. |
|---|---|---|---|---|
| 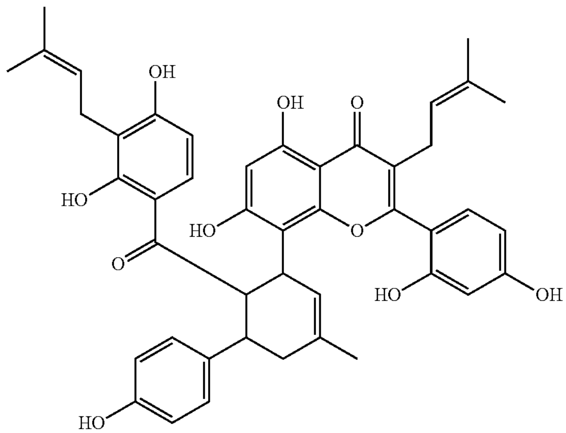 [SMILES: CC(C)=CCc1c(O)ccc(C(=O)C2C(c3c(O)cc(O)c4c(=O)c(CC=C(C)C)c(-c5ccc(O)cc5O)oc34)C=C(C)CC2c2ccc(O)cc2)c1O] | Albanin G; 2'''-Deoxy (Mongolicin D) | Morus mongolica | $C_{45}H_{44}O_{10}$ | 744.837 |
| 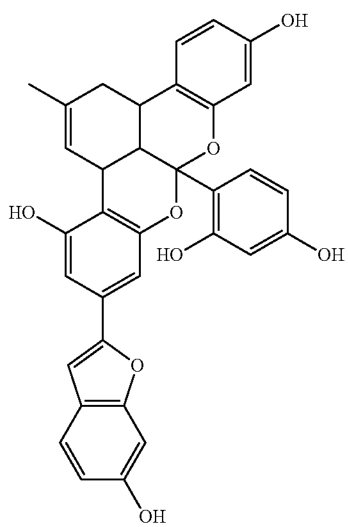 [SMILES: CC1=CC2c3c(O)cc(-c4cc5ccc(O)cc5o4)cc3OC3(c4ccc(O)cc4O)Oc4cc(O)ccc4C(C1)C23] | Albanol A (Mulberrofuran G.) | Morus lhou | $C_{34}H_{26}O_8$ | 562.575 |
| 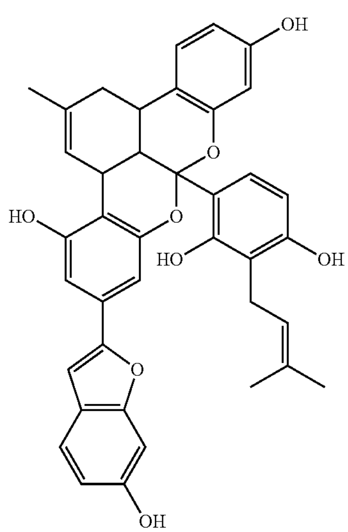 [SMILES: CC(C)=CCc1c(O)ccc(C23Oc4cc(O)ccc4C4CC(C)=CC(c5c(O)cc(-c6cc7ccc(O)cc7o6)cc5O2)C43)c1O] | Albanol A; 3''-(3-Methyl-2-butenyl), Mulberrofuran F | Morus lhou | $C_{39}H_{34}O_8$ | 630.693 |

TABLE A-continued

List of Exemplary Compounds

| Structure | Name | Species | Molecular Formula | M.W. |
|---|---|---|---|---|
| 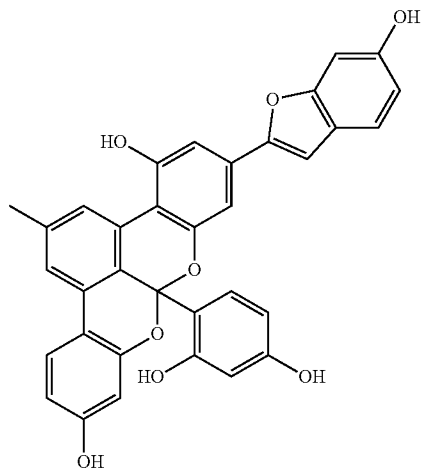 [SMILES: Cc1cc2c3c(c1)-c1c(O)cc(-c4cc5ccc(O)cc5o4)cc1OC3(c1ccc(O)cc1O)Oc1cc(O)ccc1-2] | Albanol B | *Morus alba* | $C_{34}H_{22}O_8$ | 558.543 |
| 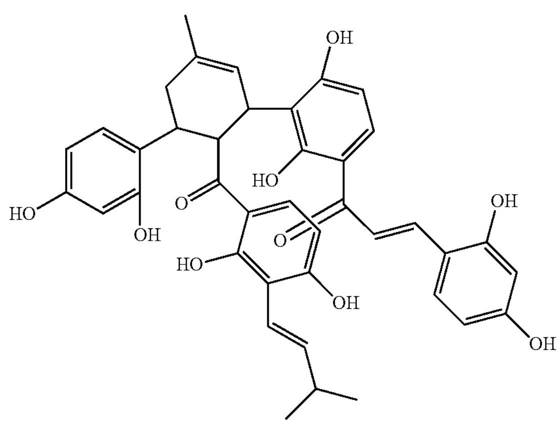 | Artonin C | *Artocarpus heterophyllus* (jackfruit) | $C_{40}H_{38}O_{10}$ | 678.734 |
| 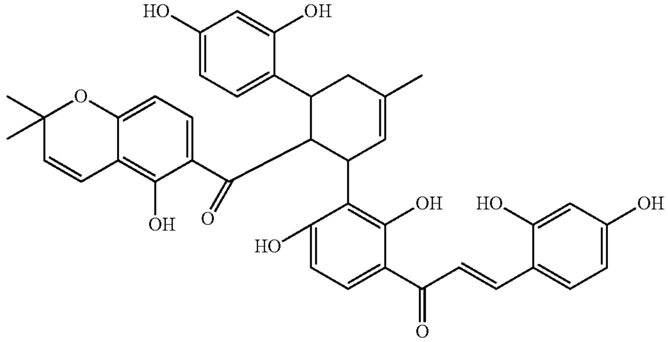 [SMILES: CC1=CC(c2c(O)ccc(C(=O)/C=C/c3ccc(O)cc3O)c2O)C(C(=O)c2ccc3c(c2O)C=CC(C)(C)O3)C(c2ccc(O)cc2O)C1] | Artonin D | *Artocarpus heterophyllus* (jackfruit) | $C_{40}H_{36}O_{10}$ | 676.718 |

TABLE A-continued
List of Exemplary Compounds
| Structure | Name | Species | Molecular Formula | M.W. |
|---|---|---|---|---|
| 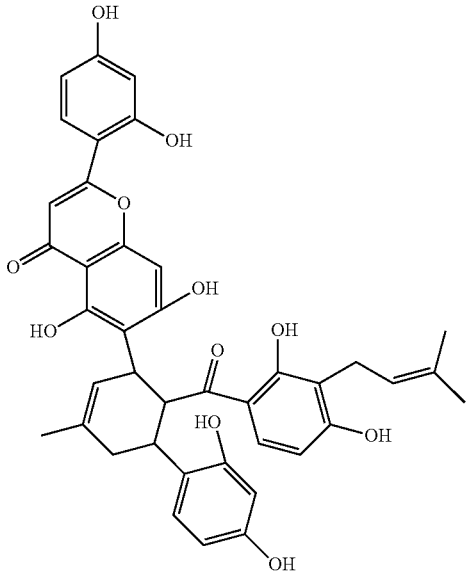 [SMILES: CC(C)=CCc1c(O)ccc(C(=O)C2C(c3c(O)cc4oc(-c5ccc(O)cc5O)cc(=O)c4c3O)C=C(C)CC2c2ccc(O)cc2O)c1O] | Artonin I | *Morus heterophyllus* | $C_{40}H_{36}O_{11}$ | 692.718 |
| 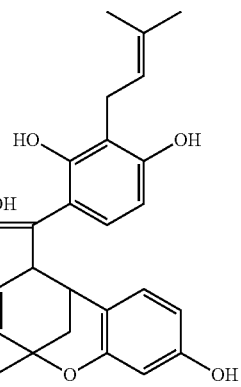 | Australisin B | *Morus australis* | $C_{39}H_{34}O_9$ | 646.692 |
| 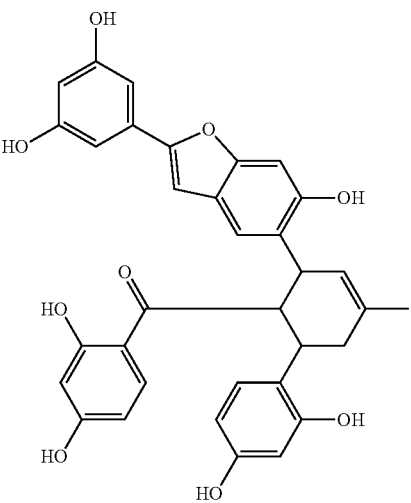 [SMILES: CC1=CC(c2cc3cc(-c4cc(O)cc(O)c4)oc3cc2O)C(C(=O)c2ccc(O)cc2O)C(c2ccc(O)cc2O)C1] | Australisin C.; 2-Epimer | *Morus australis* | $C_{34}H_{28}O_9$ | |

TABLE A-continued

List of Exemplary Compounds

| Structure | Name | Species | Molecular Formula | M.W. |
|---|---|---|---|---|
| 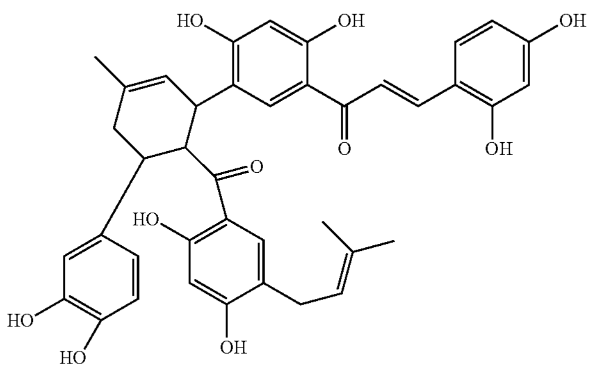 [SMILES: CC(C)=CCc1cc(C(=O)C2C(c3cc(C(=O)/C=C/c4ccc(O)cc4O)c(O)cc3O)C=C(C)CC2c2ccc(O)c(O)c2)c(O)cc1O] | Brosimone B | *Brosimopsis oblongifolia* (preferred genus name *Brosimum*) | $C_{40}H_{38}O_{10}$ | 678.734 |
| 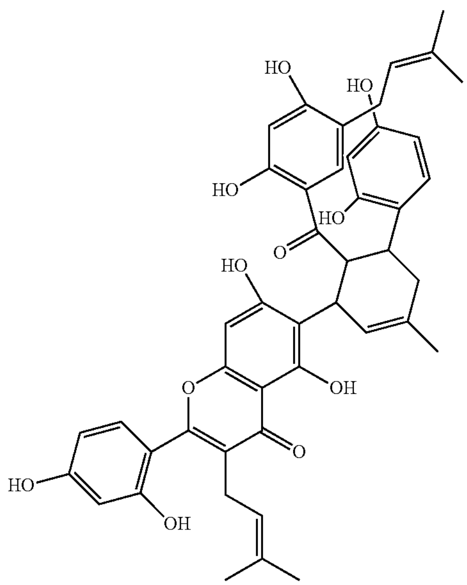 [SMILES: CC(C)=CCc1cc(C(=O)C2C(c3c(O)cc4oc(-c5ccc(O)cc5O)c(CC=C(C)C)c(=O)c4c3O)C=C(C)CC2c2ccc(O)cc2O)c(O)cc1O] | Brosimone D | *Brosimopsis oblongifolia* (preferred genus name *Brosimum*) | $C_{45}H_{44}O_{11}$ | 760.836 |
| 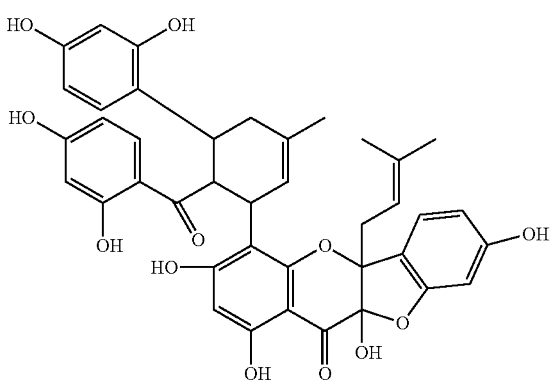 [SMILES: CC(C)=CCC12Oc3c(c(O)cc(O)c3C3C=C(C)CC(c4ccc(O)cc4O)C3C(=O)c3ccc(O)cc3O)C(=O)C1(O)Oc1cc(O)ccc12] | Cathayanon A | *Morus cathayana* | $C_{40}H_{36}O_{12}$ | 708.717 |

TABLE A-continued

List of Exemplary Compounds

| Structure | Name | Species | Molecular Formula | M.W. |
|---|---|---|---|---|
| 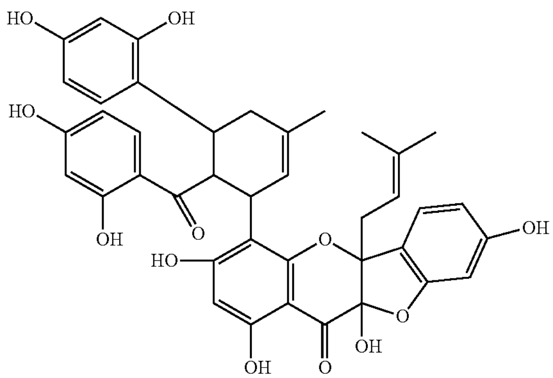 [SMILES: CC(C)=CCC12Oc3c(c(O)cc(O)c3C3C=C(C)CC(c4ccc(O)cc4O)C3C(=O)c3ccc(O)cc3O)C(=O)C1(O)Oc1cc(O)ccc12] | Cathayanon A; 14-Epimer | Morus cathayana | $C_{40}H_{36}O_{12}$ | 708.717 |
| 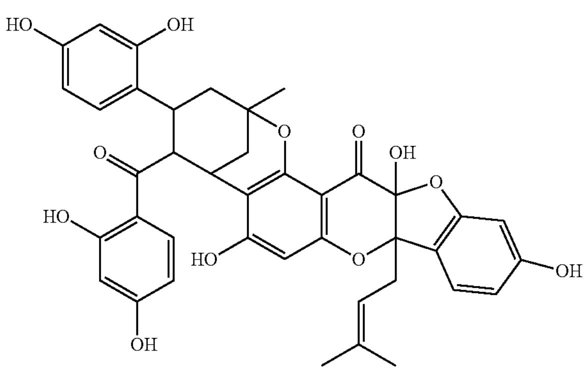 [SMILES: CC(C)=CCC12Oc3cc(O)c4c(c3C(=O)C1(O)Oc1cc(O)ccc12)OC1(C)CC(c2ccc(O)cc2O)C(C(=O)c2ccc(O)cc2O)C4C1] | Cathayanon E | Morus cathayana | $C_{40}H_{36}O_{12}$ | 708.717 |
| 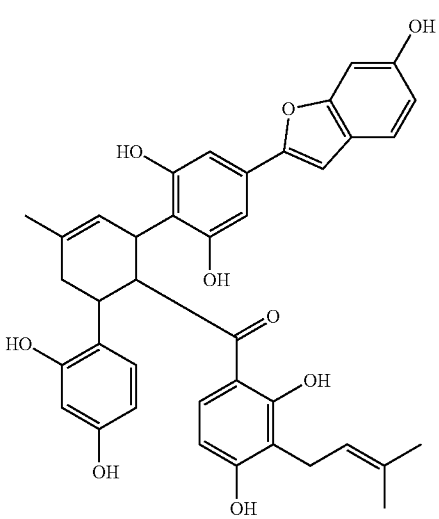 [SMILES: CC(C)=CCc1c(O)ccc(C(=O)C2C(c3c(O)cc(-c4cc5ccc(O)cc5o4)cc3O)C=C(C)CC2c2ccc(O)cc2O)c1O] | Chalcomoracin | Morus alba and Morus mongolica | $C_{39}H_{36}O_{9}$ | 648.708 |

TABLE A-continued
List of Exemplary Compounds
| Structure | Name | Species | Molecular Formula | M.W. |
|---|---|---|---|---|
| 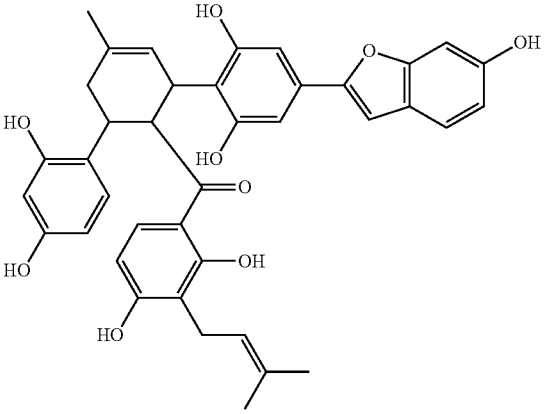 [SMILES: CC(C)=CCc1c(O)ccc(C(=O)C2C(c3c(O)cc(-c4cc5ccc(O)cc5o4)cc3O)C=C(C)CC2c2ccc(O)cc2O)c1O] | Chalcomoracin; 3",5"-Diepimer | *Sorocea muriculata* | $C_{39}H_{36}O_9$ | 648.708 |
| 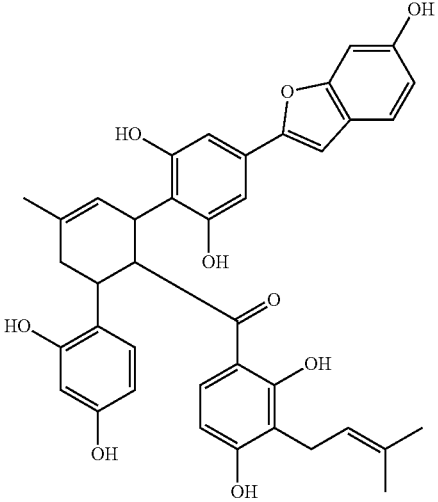 [SMILES: CC(C)=CCc1c(O)ccc(C(=O)C2C(c3c(O)cc(-c4cc5ccc(O)cc5o4)cc3O)C=C(C)CC2c2ccc(O)cc2O)c1O] | Chalcomoracin; 3"-Epimer | *Morus mongolica* | $C_{39}H_{36}O_9$ | 648.708 |
| 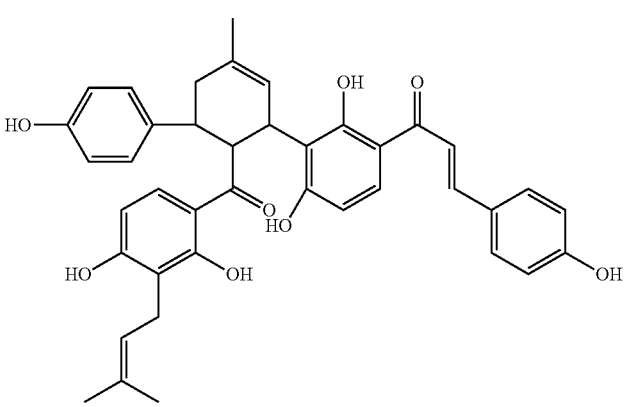 [SMILES: CC(C)=CCc1c(O)ccc(C(=O)C2C(c3c(O)ccc(C(=O)/C=C/c4ccc(O)cc4)c3O)C=C(C)CC2c2ccc(O)cc2)c1O] | Dorstenone | *Dorstenia barteri* | $C_{40}H_{38}O_8$ | 646.735 |

TABLE A-continued
List of Exemplary Compounds
| Structure | Name | Species | Molecular Formula | M.W. |
|---|---|---|---|---|
| 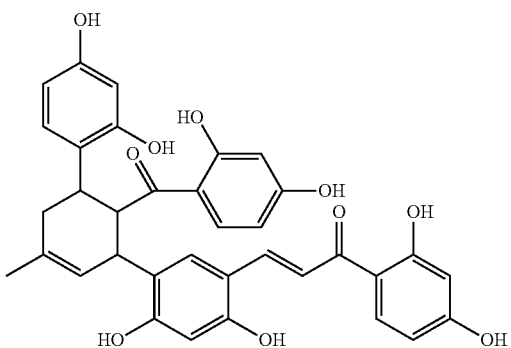 [SMILES: CC1=CC(c2cc(/C=C/C(=O)c3ccc(O)cc3O)c(O)cc2O)C(C(=O)c2ccc(O)cc2O)C(c2ccc(O)cc2O)C1] | Guangsangon C | *Morus macroura* | $C_{35}H_{30}O_{10}$ | 610.616 |
| 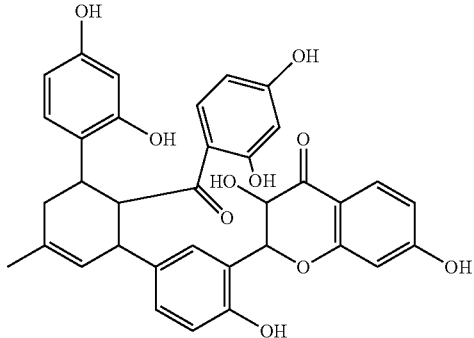 [SMILES: CC1=CC(c2ccc(O)c(C3Oc4cc(O)ccc4C(=O)C3O)c2)C(C(=O)c2ccc(O)cc2O)C(c2ccc(O)cc2O)C1] | Guangsangon D | *Morus macroura* | $C_{35}H_{30}O_{10}$ | 610.616 |
| 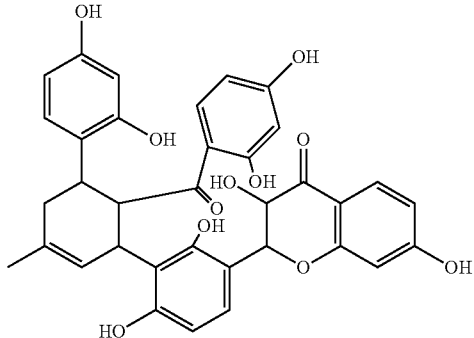 [SMILES: CC1=CC(c2c(O)ccc(C3Oc4cc(O)ccc4C(=O)C3O)c2O)C(C(=O)c2ccc(O)cc2O)C(c2ccc(O)cc2O)C1] | Guangsangon D; 2'-Deoxy, 4',6'-dihydroxy | *Morus macroura* | $C_{35}H_{30}O_{11}$ | 626.615 |
| 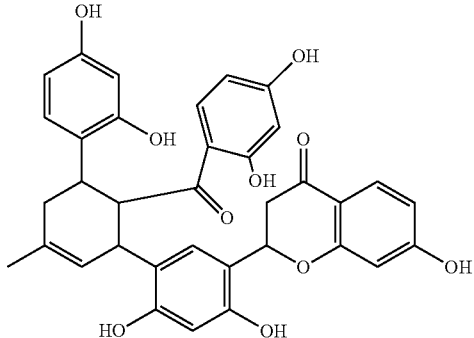 [SMILES: CC1=CC(c2cc(C3CC(=O)c4ccc(O)cc4O3)c(O)cc2O)C(C(=O)c2ccc(O)cc2O)C(c2ccc(O)cc2O)C1] | Guangsangon D; 3-Deoxy, 4'-hydroxy | *Morus macroura* and *Morus wittiorum* | $C_{35}H_{30}O_{10}$ | 610.616 |

TABLE A-continued
List of Exemplary Compounds
| Structure | Name | Species | Molecular Formula | M.W. |
|---|---|---|---|---|
| 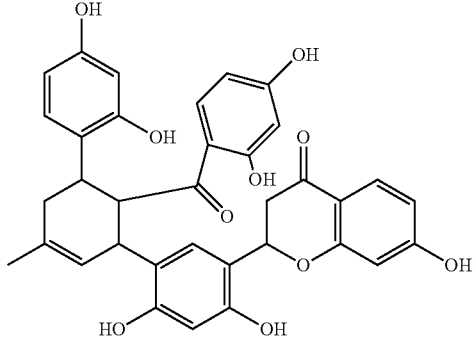 [SMILES: CC1=CC(c2cc(C3CC(=O)c4ccc(O)cc4O3)c(O)cc2O)C(C(=O)c2ccc(O)cc2O)C(c2ccc(O)cc2O)C1] | Guangsangon D; 2-Epimer, 3-deoxy, 4'-hydroxy | *Morus macroura* | $C_{35}H_{30}O_{10}$ | 610.616 |
| 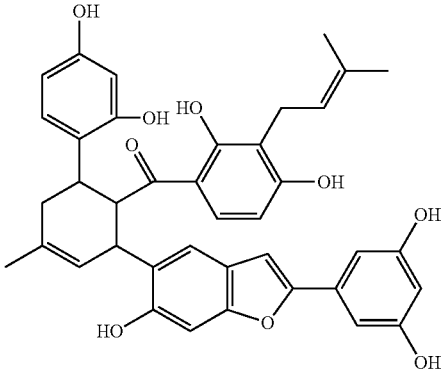 [SMILES: CC(C)=CCc1c(O)ccc(C(=O)C2C(c3cc4cc(-c5cc(O)cc(O)c5)oc4cc3O)C=C(C)CC2c2ccc(O)cc2O)c1O] | Guangsangon E | *Morus macroura* | $C_{39}H_{36}O_9$ | 648.708 |
| 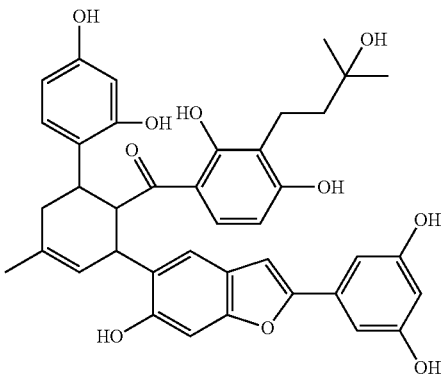 [SMILES: CC1=CC(c2cc3cc(-c4cc(O)cc(O)c4)oc3cc2O)C(C(=O)c2ccc(O)c(CCC(C)(C)O)c2O)C(c2ccc(O)cc2O)C1] | Guangsangon E; 3''-Epimer, 2'''',3''''-dihydro, 3''''-hydroxy | *Morus macroura* | $C_{39}H_{38}O_{10}$ | 666.723 |

TABLE A-continued

List of Exemplary Compounds

| Structure | Name | Species | Molecular Formula | M.W. |
|---|---|---|---|---|
| 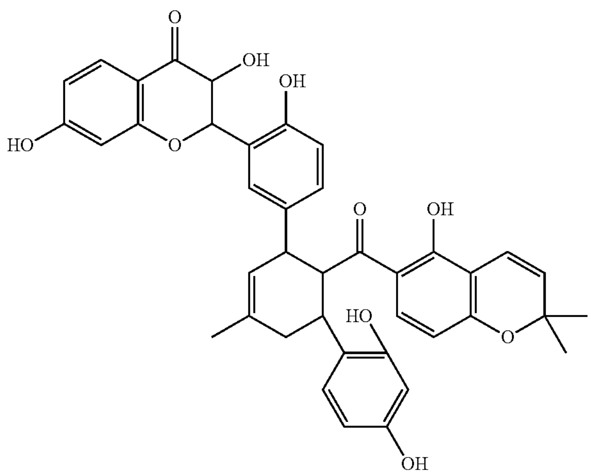 [SMILES: CC1=CC(c2ccc(O)c(C3Oc4cc(O)ccc4C(=O)C3O)c2)C(C(=O)c2ccc3c(c2O)C=CC(C)(C)O3)C(c2ccc(O)cc2O)C1] | Guangsangon F | *Morus macroura* | $C_{40}H_{36}O_{10}$ | 676.718 |
| 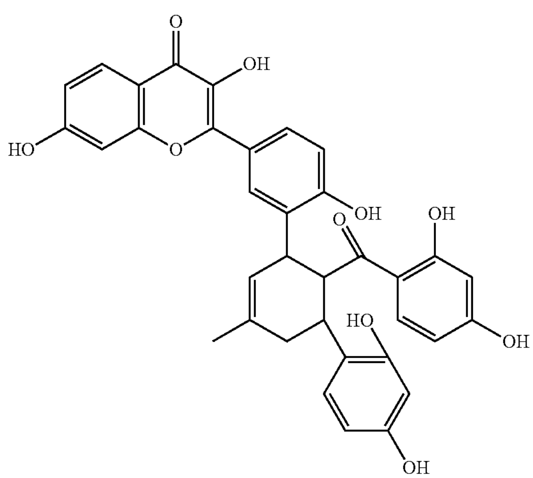 [SMILES: CC1=CC(c2cc(-c3oc4cc(O)ccc4c(=O)c3O)ccc2O)C(C(=O)c2ccc(O)cc2O)C(c2ccc(O)cc2O)C1] | Guangsangon G | *Morus macroura* | $C_{35}H_{28}O_{10}$ | 608.600 |
| 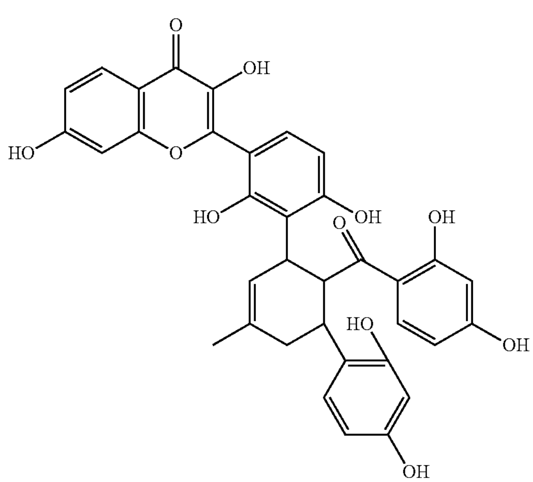 [SMILES: CC1=CC(c2c(O)ccc(-c3oc4cc(O)ccc4c(=O)c3O)c2O)C(C(=O)c2ccc(O)cc2O)C(c2ccc(O)cc2O)C1] | Guangsangon G; 1''-Epimer, 2'-hydroxy | *Morus macroura* | $C_{35}H_{28}O_{11}$ | 624.600 |

TABLE A-continued

List of Exemplary Compounds

| Structure | Name | Species | Molecular Formula | M.W. |
|---|---|---|---|---|
| 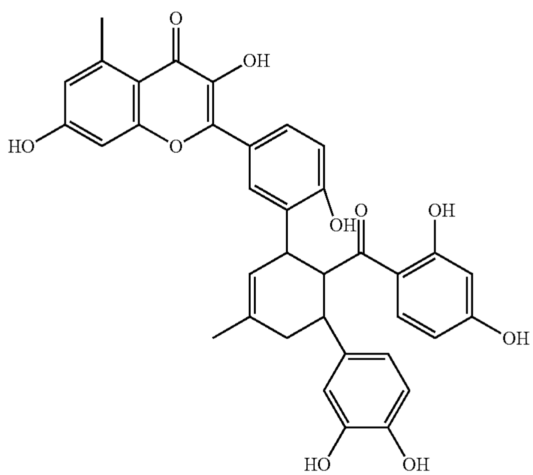 [SMILES: CC1=CC(c2cc(-c3oc4cc(O)cc(C)c4c(=O)c3O)ccc2O)C(C(=O)c2ccc(O)cc2O)C(c2ccc(O)c(O)c2)C1] | Guangsangon G; 2'-Hydroxy | Morus macroura | $C_{35}H_{28}O_{11}$ | 624.600 |
| 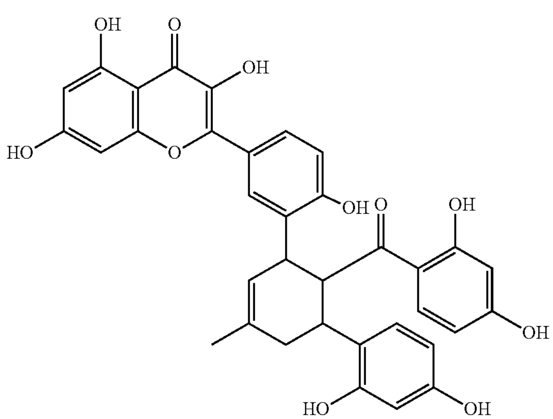 [SMILES: CC1=CC(c2cc(-c3oc4cc(O)cc(O)c4c(=O)c3O)ccc2O)C(C(=O)c2ccc(O)cc2O)C(c2ccc(O)cc2O)C1] | Guangsangon G; 5-Hydroxy | Morus wittiorum | $C_{35}H_{28}O_{11}$ | 625.600 |
| 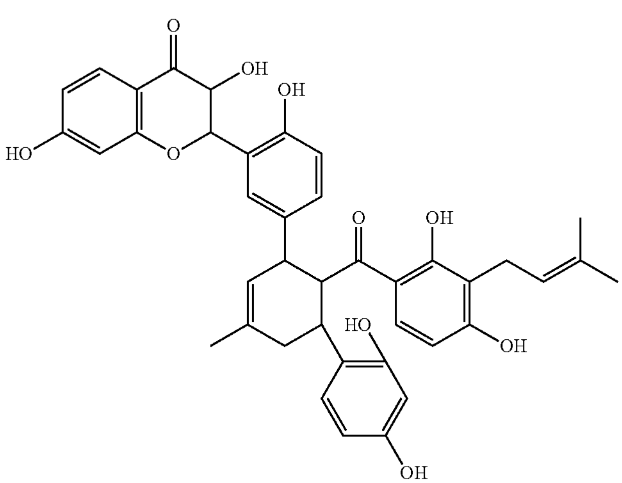 [SMILES: CC(C)=CCc1c(O)ccc(C(=O)C2C(c3ccc(O)c(C4Oc5cc(O)ccc5C(=O)C4O)c3)C=C(C)CC2c2ccc(O)cc2O)c1O] | Guangsangon H | Morus macroura | $C_{40}H_{38}O_{10}$ | 678.734 |

TABLE A-continued

List of Exemplary Compounds

| Structure | Name | Species | Molecular Formula | M.W. |
|---|---|---|---|---|
| 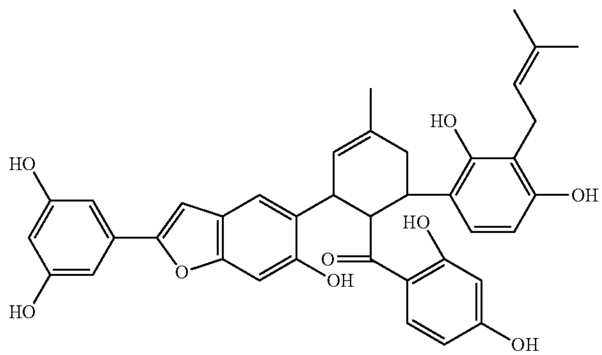 [SMILES: CC(C)=CCc1c(O)ccc(C2CC(C)=CC(c3cc4cc(-c5cc(O)cc(O)c5)oc4cc3O)C2C(=O)c2ccc(O)cc2O)c1O] | Guangsangon J | *Morus macroura* | $C_{39}H_{36}O_9$ | 648.708 |
| 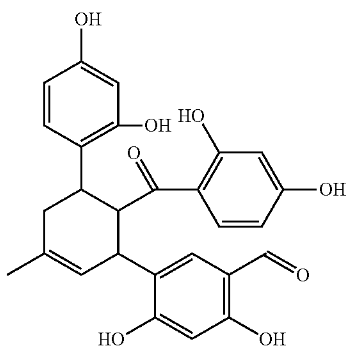 [SMILES: CC1=CC(c2cc(C=O)c(O)cc2O)C(C(=O)c2ccc(O)cc2O)C(c2ccc(O)cc2O)C1] | Guangsangon L | *Morus alba* | $C_{27}H_{24}O_8$ | 476.482 |
| 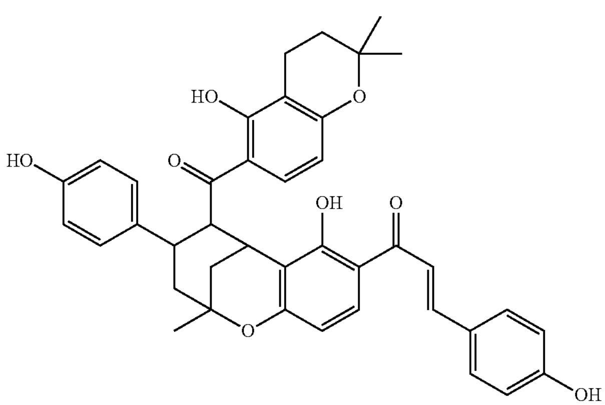 [SMILES: CC1(C)CCc2c(ccc(C(=O)C3C(c4ccc(O)cc4)CC4(C)CC3c3c(ccc(C(=O)/C=C/c5ccc(O)cc5)c3O)O4)c2O)O1] | Isobavachromene dimer | *Dorstenia zenkeri* | $C_{40}H_{38}O_8$ | 646.735 |
| 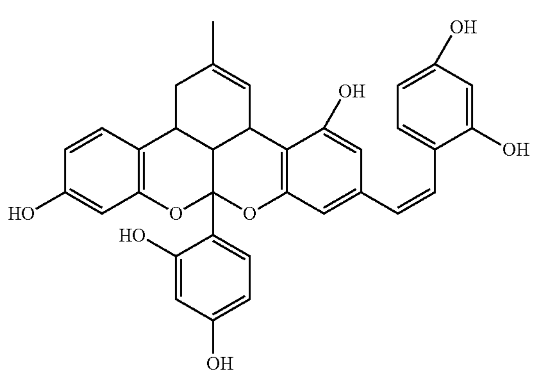 [SMILES: CC1=CC2c3c(O)cc(/C=C\c4ccc(O)cc4O)cc3OC3(c4ccc(O)cc4O)Oc4cc(O)ccc4C(C1)C23] | Kuwanol A | *Morus bombycis* | $C_{34}H_{28}O_8$ | 564.590 |

TABLE A-continued
List of Exemplary Compounds
| Structure | Name | Species | Molecular Formula | M.W. |
|---|---|---|---|---|
| 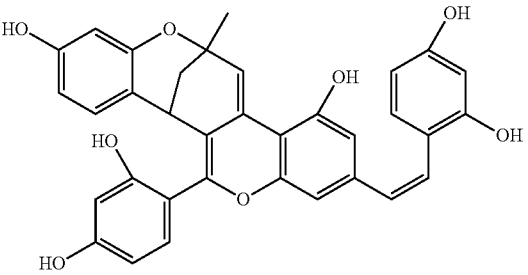 [SMILES: CC12C=C3C(=C(c4ccc(O)cc4O)Oc4cc(/C=C\c5ccc(O)cc5O)cc(O)c43)C(C1)c1ccc(O)cc1O2] | Kuwanol B | *Morus bombycis* | $C_{34}H_{26}O_8$ | 562.575 |
| 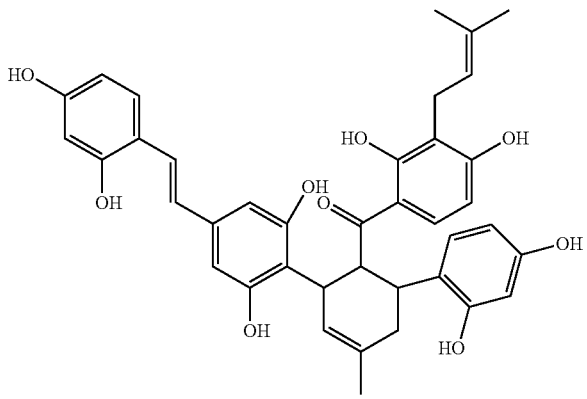 [SMILES: CC(C)=CCc1c(O)ccc(C(=O)C2C(c3c(O)cc(/C=C/c4ccc(O)cc4O)cc3O)C=C(C)CC2c2ccc(O)cc2O)c1O] | Kuwanol E | *Morus alba* (white mulberry) | $C_{39}H_{38}O_9$ | 650.724 |
| 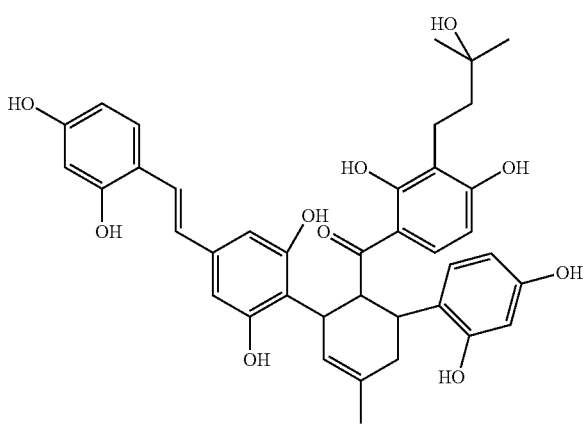 [SMILES: CC1=CC(c2c(O)cc(/C=C/c3ccc(O)cc3O)cc2O)C(C(=O)c2ccc(O)c(CCC(C)(C)O)c2O)C(c2ccc(O)cc2O)C1] | Kuwanol E; 2'''',3''''-Dihydro, 3''''-hydroxy | *Sorocea ilicifolia* | $C_{39}H_{40}O_{10}$ | 668.739 |

TABLE A-continued

List of Exemplary Compounds

| Structure | Name | Species | Molecular Formula | M.W. |
|---|---|---|---|---|
| 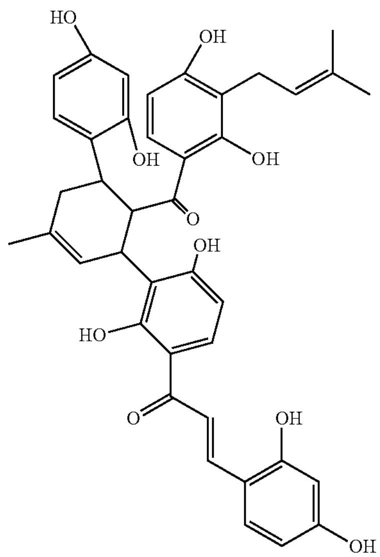 [SMILES: CC(C)=CCc1c(O)ccc(C(=O)C2C(c3c(O)ccc(C(=O)/C=C/c4ccc(O)cc4O)c3O)C=C(C)CC2c2ccc(O)cc2O)c1O] | Kuwanon J | Morus alba and from Morus bombycus and Morus nigra | $C_{40}H_{38}O_{10}$ | 678.734 |
| | Kuwanon J; 16″-Deoxy | Morus alba (white mulberry) | $C_{40}H_{38}O_{9}$ | 662.735 |

TABLE A-continued

List of Exemplary Compounds

| Structure | Name | Species | Molecular Formula | M.W. |
|---|---|---|---|---|
| 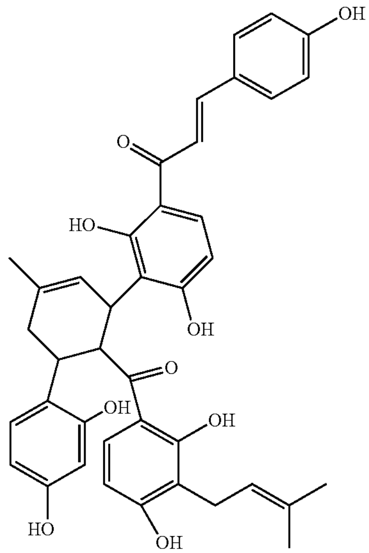 [SMILES: CC(C)=CCc1c(O)ccc(C(=O)C2C(c3c(O)ccc(C(=O)/C=C/c4ccc(O)cc4)c3O)C=C(C)CC2c2ccc(O)cc2O)c1O] | Kuwanon J; 2-Deoxy | *Morus alba* (white mulberry) | $C_{40}H_{38}O_9$ | 662.735 |
| | Kuwanon J, Δ21″,22″-Isomer, 2-deoxy | *Morus alba* (white mulberry) | $C_{40}H_{38}O_9$ | 662.735 |

TABLE A-continued

List of Exemplary Compounds

| Structure | Name | Species | Molecular Formula | M.W. |
|---|---|---|---|---|
| | Kuwanon J; 2,16″-Dideoxy | *Morus alba* (white mulberry) | $C_{40}H_{38}O_8$ | 646.735 |
| | Kuwanon J; 2′,3′-Dihydro | *Morus mangolica* | $C_{40}H_{40}O_{10}$ | 680.750 |

TABLE A-continued

List of Exemplary Compounds

| Structure | Name | Species | Molecular Formula | M.W. |
|---|---|---|---|---|
| | Kuwanon J; 1''-Epimer | *Morus alba* and *Morus bombycus* | $C_{40}H_{38}O_{10}$ | 678.734 |
| | Kuwanon J; Δ21'',22''-Isomer, 2-deoxy (Artonin X.) | *Artocarpus heterophyllus* (jackfruit) | $C_{40}H_{38}O_9$ | 662.735 |

TABLE A-continued
List of Exemplary Compounds
| Structure | Name | Species | Molecular Formula | M.W. |
|---|---|---|---|---|
| 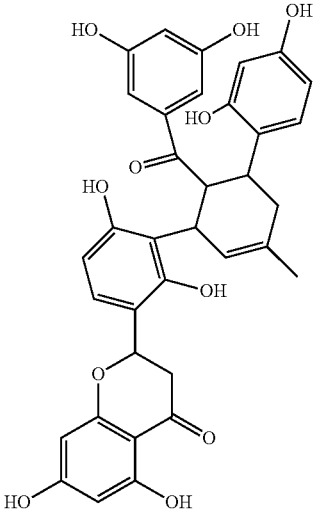 [SMILES: CC1=CC(c2c(O)ccc(C3CC(=O)c4c(O)cc(O)cc4O3)c2O)C(C(=O)c2cc(O)cc(O)c2)C(c2ccc(O)cc2O)C1] | Kuwanon L | *Morus alba* (white mulberry) | $C_{35}H_{30}O_{11}$ | 626.615 |
| 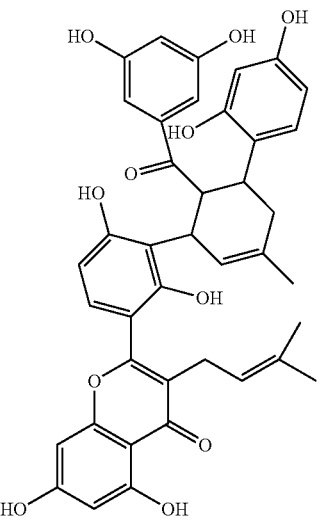 [SMILES: CC(C)=CCc1c(-c2ccc(O)c(C3C=C(C)CC(c4ccc(O)cc4O)C3C(=O)c3cc(O)cc(O)c3)c2O)oc2cc(O)cc(O)c2c1=O] | Kuwanon L; 2,3-Didehydro, 3-(3-methyl-2-butenyl) | *Morus alba* (white mulberry) | $C_{40}H_{36}O_{11}$ | 692.718 |

TABLE A-continued
List of Exemplary Compounds
| Structure | Name | Species | Molecular Formula | M.W. |
|---|---|---|---|---|
| 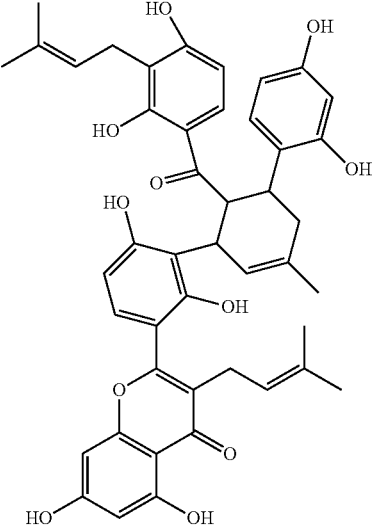 [SMILES: CC(C)=CCc1c(O)ccc(C(=O)C2C(c3c(O)ccc(-c4oc5cc(O)cc(O)c5c(=O)c4CC=C(C)C)c3O)C=C(C)CC2c2ccc(O)cc2O)c1O] | Kuwanon N | *Morus lhou* | $C_{45}H_{44}O_{11}$ | 760.836 |
| 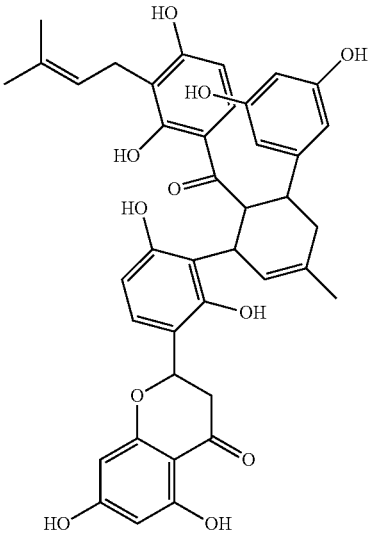 | Kuwanon O | *Morus lhou* | $C_{40}H_{38}O_{11}$ | 694.734 |

TABLE A-continued

List of Exemplary Compounds

| Structure | Name | Species | Molecular Formula | M.W. |
|---|---|---|---|---|
| 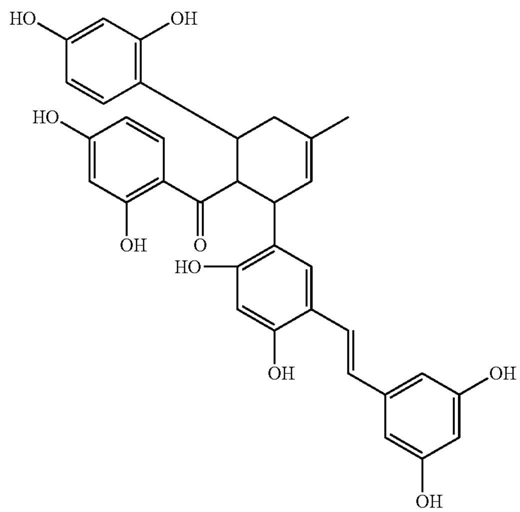 [SMILES: CC1=CC(c2cc(/C=C/c3cc(O)cc(O)c3)c(O)cc2O)C(C(=O)c2ccc(O)cc2O)C(c2ccc(O)cc2O)C1] | Kuwanon P | *Morus lhou* | $C_{34}H_{30}O_9$ | 582.606 |
| 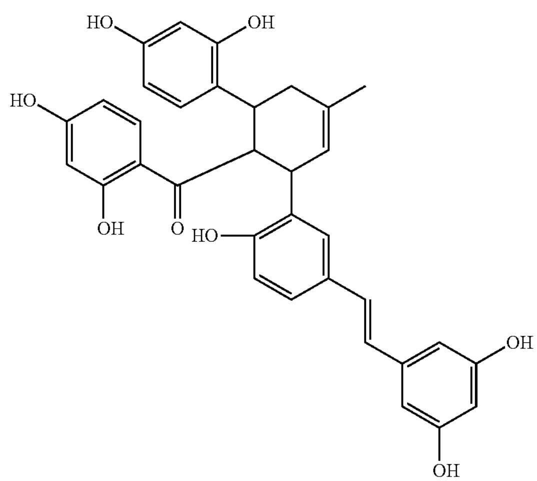 [SMILES: CC1=CC(c2cc(/C=C/c3cc(O)cc(O)c3)ccc2O)C(C(=O)c2ccc(O)cc2O)C(c2ccc(O)cc2O)C1] | Kuwanon P; 2-Deoxy | *Morus macroura* | $C_{34}H_{30}O_8$ | |
| 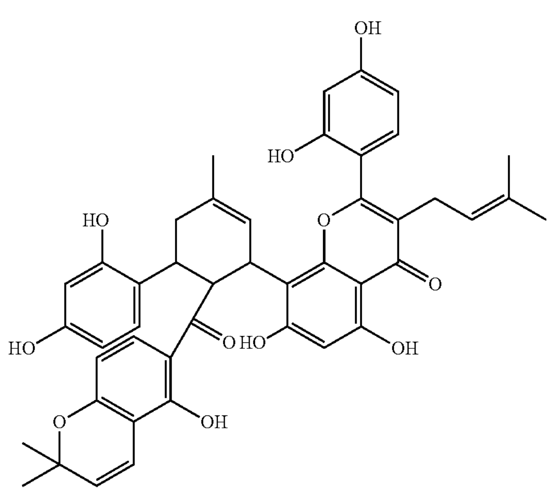 [SMILES: CC(C)=CCc1c(-c2ccc(O)cc2O)oc2c(C3C=C(C)CC(c4ccc(O)cc4O)C3C(=O)c3ccc4c(c3O)C=CC(C)(C)O4)c(O)cc(O)c2c1=O] | Kuwanon W | *Morus lhou* | $C_{45}H_{42}O_{11}$ | 758.820 |

TABLE A-continued
List of Exemplary Compounds
| Structure | Name | Species | Molecular Formula | M.W. |
|---|---|---|---|---|
| 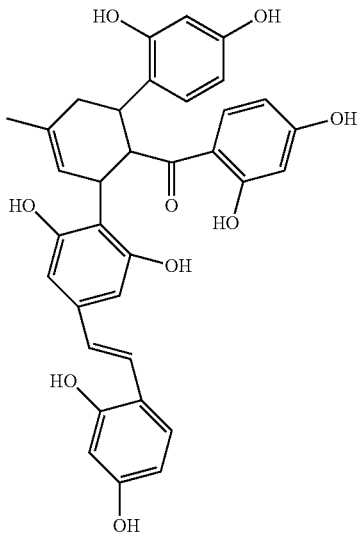 [SMILES: CC1=CC(c2c(O)cc(/C=C/c3ccc(O)cc3O)cc2O)C(C(=O)c2ccc(O)cc2O)C(c2ccc(O)cc2O)C1] | Kuwanon X | *Morus lhou* | $C_{34}H_{30}O_9$ | 582.606 |
| 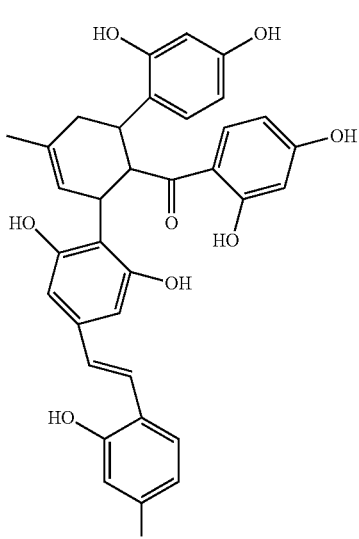 | Kuwanon X; 3″-Epimer | *Morus alba* (white mulberry) | $C_{34}H_{30}O_9$ | 582.606 |
| 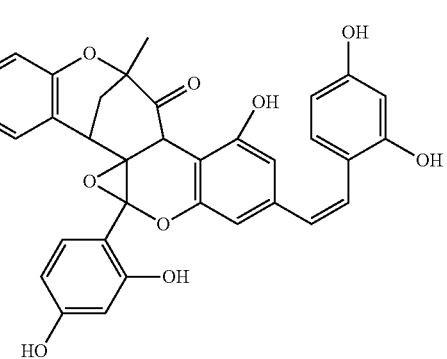 | Kuwanon Z | *Morus alba* (white mulberry) | $C_{34}H_{26}O_{10}$ | 594.573 |

TABLE A-continued

List of Exemplary Compounds

| Structure | Name | Species | Molecular Formula | M.W. |
|---|---|---|---|---|
| 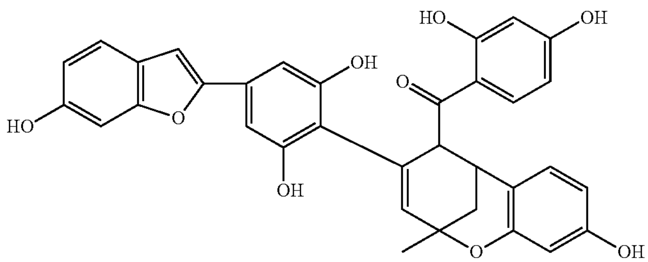 [SMILES: CC12C=C(c3c(O)cc(-c4cc5ccc(O)cc5o4)cc3O)C(C(=O)c3ccc(O)cc3O)C(C1)c1ccc(O)cc1O2] | Mongolicin C | *Morus mongolica* | $C_{34}H_{26}O_9$ | 578.574 |
| 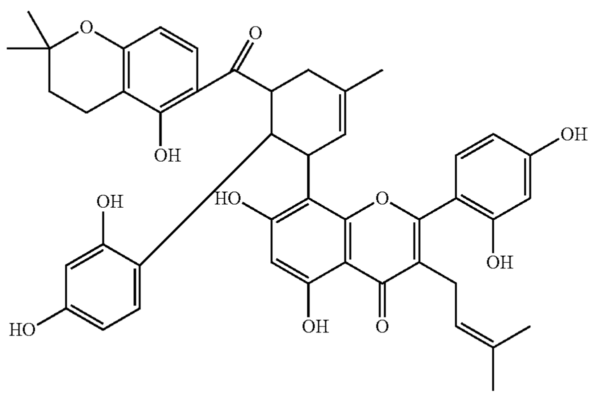 [SMILES: CC(C)=CCc1c(-c2ccc(O)cc2O)oc2c(C3C=C(C)CC(C(=O)c4ccc5c(c4O)CCC(C)(C)O5)C3c3ccc(O)cc3O)c(O)cc(O)c2c1=O] | Moracenin C | *Morus* sp. | $C_{45}H_{44}O_{11}$ | 760.836 |
| 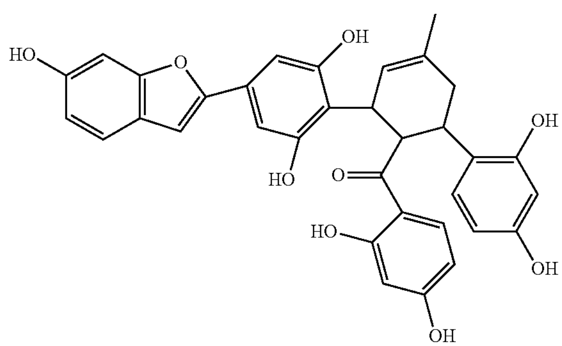 [SMILES: CC1=CC(c2c(O)cc(-c3cc4ccc(O)cc4o3)cc2O)C(C(=O)c2ccc(O)cc2O)C(c2ccc(O)cc2O)C1] | Mulberrofuran C | *Morus bombycis* (Moraceae) | | |
| 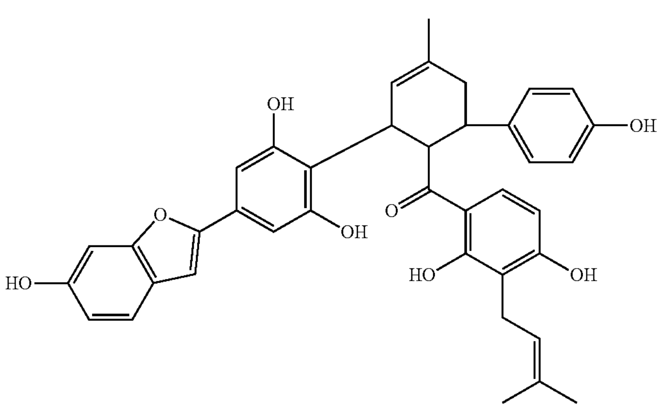 [SMILES: CC(C)=CCc1c(O)ccc(C(=O)C2C(c3c(O)cc(-c4cc5ccc(O)cc5o4)cc3O)C=C(C)CC2c2ccc(O)cc2)c1O] | Mulberrofuran E | *Morus alba* (white mulberry) (Moraceae) | $C_{39}H_{36}O_8$ | 632.709 |

TABLE A-continued
List of Exemplary Compounds
| Structure | Name | Species | Molecular Formula | M.W. |
|---|---|---|---|---|
| 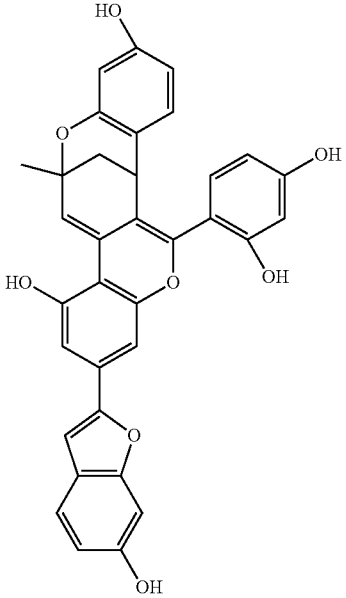 [SMILES: CC12C=C3C(=C(c4ccc(O)cc4O)Oc4cc(-c5cc6ccc(O)cc6o5)cc(O)c43)C(C1)c1ccc(O)cc1O2] | Mulberrofuran I | Morus bombycis | $C_{34}H_{24}O_8$ | 560.559 |
| 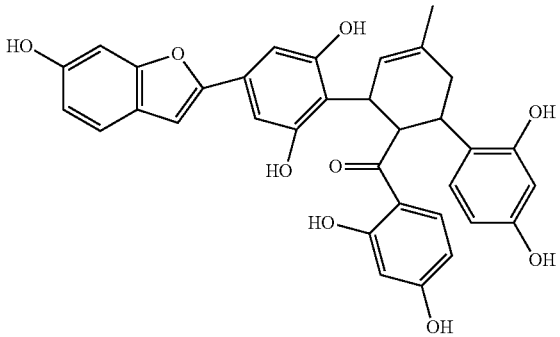 [SMILES: CC1=CC(c2c(O)cc(-c3cc4ccc(O)cc4o3)cc2O)C(C(=O)c2ccc(O)cc2O)C(c2ccc(O)cc2O)C1] | Mulberrofuran J | Morus lhou | $C_{34}H_{28}O_9$ | 580.590 |
| 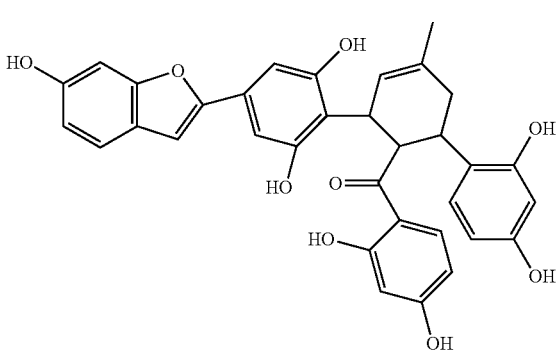 [SMILES: CC1=CC(c2c(O)cc(-c3cc4ccc(O)cc4o3)cc2O)C(C(=O)c2ccc(O)cc2O)C(c2ccc(O)cc2O)C1] | Mulberrofuran J, 2-Epimer | Morus bombycis | | |

//
TABLE A-continued
List of Exemplary Compounds
| Structure | Name | Species | Molecular Formula | M.W. |
|---|---|---|---|---|
| 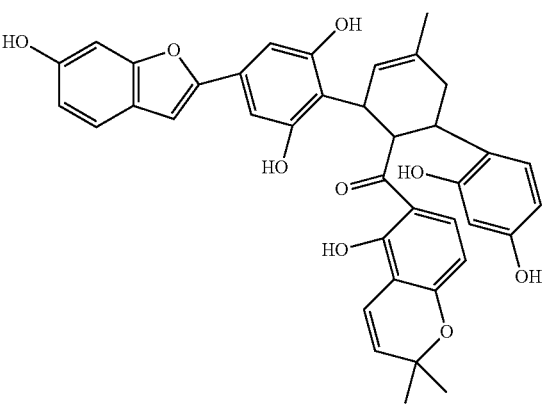 [SMILES: CC1=CC(c2c(O)cc(-c3cc4ccc(O)cc4o3)cc2O)C(C(=O)c2ccc3c(c2O)C=CC(C)(C)O3)C(c2ccc(O)cc2O)C1] | Mulberrofuran O | *Morus alba* | | 646.692 |
| 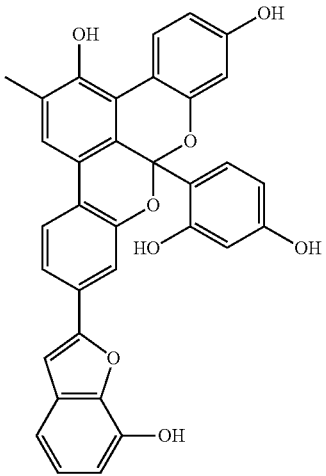 [SMILES: Cc1cc2c3c(c1O)-c1ccc(O)cc1OC3(c1ccc(O)cc1O)Oc1cc(-c3cc4cccc(O)c4o3)ccc1-2] | Mulberrofuran P | *Morus alba* (white mulberry) | $C_{34}H_{22}O_9$ | 574.542 |
| 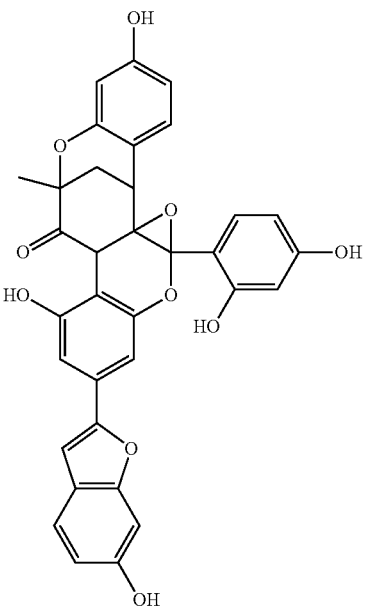 [SMILES: CC12CC(c3ccc(O)cc3O1)C13OC1(c1ccc(O)cc1O)Oc1cc(-c4cc5ccc(O)cc5o4)cc(O)c1C3C2=O] | Mulberrofuran Q | *Morus alba* (white mulberry) | $C_{34}H_{24}O_{10}$ | 592.558 |

TABLE A-continued
List of Exemplary Compounds
| Structure | Name | Species | Molecular Formula | M.W. |
|---|---|---|---|---|
| 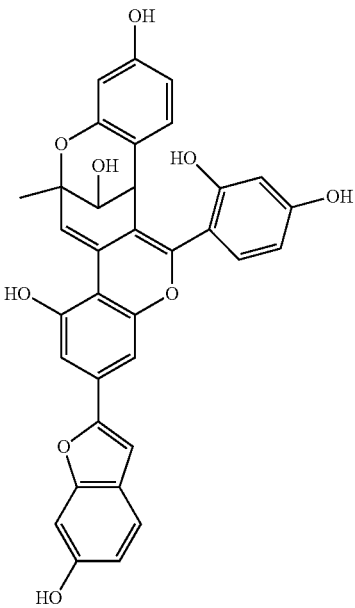 [SMILES: CC12C=C3C(=C(c4ccc(O)cc4O)Oc4cc(-c5cc6ccc(O)cc6o5)cc(O)c43)C(c3ccc(O)cc3O1)C2O] | Mulberrofuran S | Morus alba (white mulberry) | $C_{34}H_{24}O_9$ | 576.558 |
| 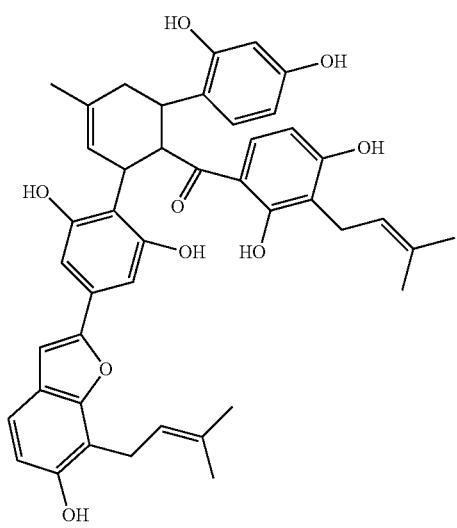 [SMILES: CC(C)=CCc1c(O)ccc(C(=O)C2C(c3c(O)cc(-c4cc5ccc(O)c(CC=C(C)C)c5o4)cc3O)C=C(C)CC2c2ccc(O)cc2O)c1O] | Mulberrofuran T | Morus alba (white mulberry) | $C_{44}H_{44}O_9$ | 716.826 |

TABLE A-continued
List of Exemplary Compounds
| Structure | Name | Species | Molecular Formula | M.W. |
|---|---|---|---|---|
| 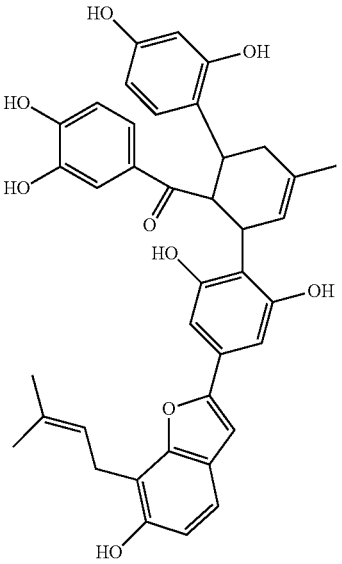 [SMILES: CC(C)=CCc1c(O)ccc2cc(-c3cc(O)c(C4C=C(C)CC(c5ccc(O)cc5O)C4C(=O)c4ccc(O)c(O)c4)c(O)c3)oc12] | Mulberrofuran U | *Morus insignis* | $C_{39}H_{36}O_9$ | 648.708 |
| 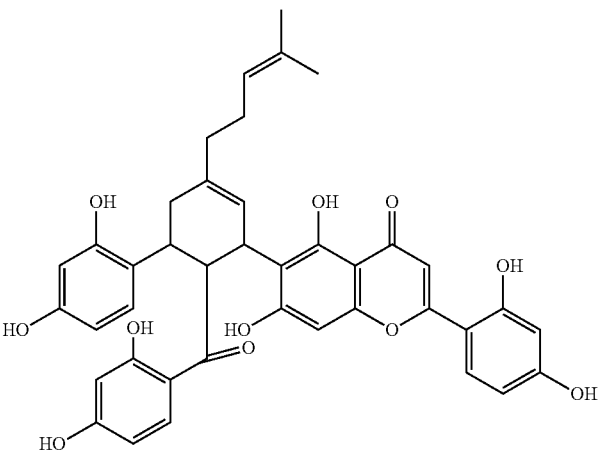 [SMILES: CC(C)=CCCC1=CC(c2c(O)cc3oc(-c4ccc(O)cc4O)cc(=O)c3c2O)C(C(=O)c2ccc(O)cc2O)C(c2ccc(O)cc2O)C1] | Multicaulisin | *Morus multicaulis* | $C_{40}H_{36}O_{11}$ | 692.718 |
| 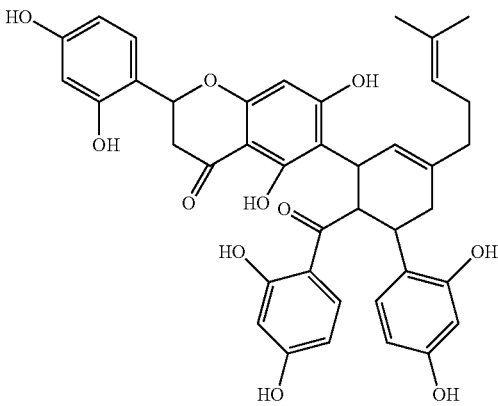 [SMILES: CC(C)=CCCC1=CC(c2c(O)cc3c(c2O)C(=O)CC(c2ccc(O)cc2O)O3)C(C(=O)c2ccc(O)cc2O)C(c2ccc(O)cc2O)C1] | Sanggenol G | *Morus cathayana* | $C_{30}H_{34}O_7$ | 694.734 |

TABLE A-continued

List of Exemplary Compounds

| Structure | Name | Species | Molecular Formula | M.W. |
|---|---|---|---|---|
| 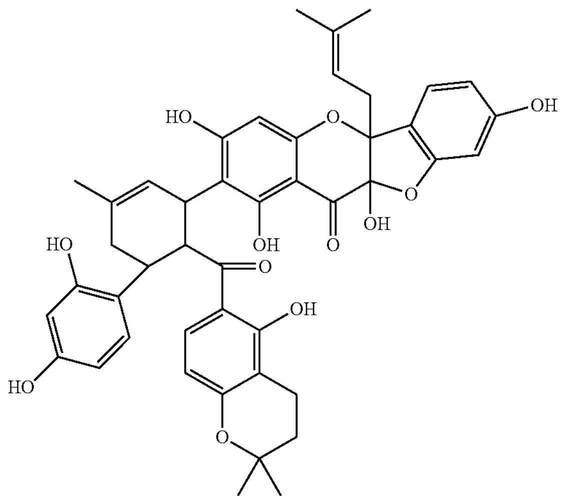 [SMILES: CC(C)=CCC12Oc3cc(O)c(C4C=C(C)CC(c5ccc(O)cc5O)C4C(=O)c4ccc5c(c4O)CCC(C)(C)O5)c(O)c3C(=O)C1(O)Oc1cc(O)ccc12] | Sanggenol J | Morus cathayana | $C_{45}H_{44}O_{12}$ | 776.835 |
| 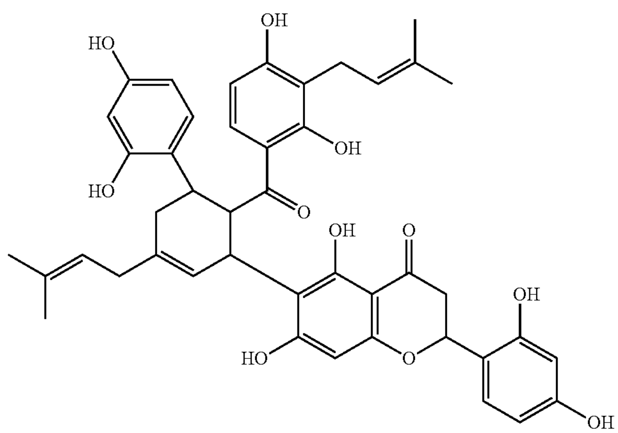 [SMILES: CC(C)=CCC1=CC(c2c(O)cc3c(c2O)C(=O)CC(c2ccc(O)cc2O)O3)C(C(=O)c2ccc(O)c(CC=C(C)C)c2O)C(c2ccc(O)cc2O)C1] | Sanggenol M | Morus mongolica | $C_{44}H_{44}O_{11}$ | 748.825 |
| 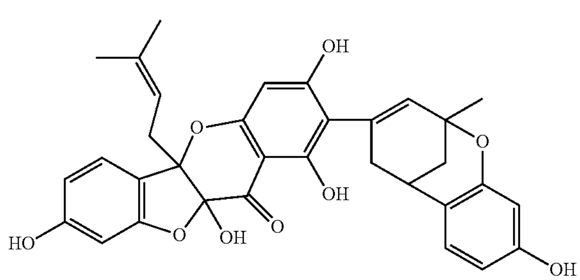 [SMILES: CC(C)=CCC12Oc3cc(O)c(C4=CC5(C)CC(C4)c4ccc(O)cc4O5)c(O)c3C(=O)C1(O)Oc1cc(O)ccc12] | Sanggenon B | Morus | $C_{33}H_{30}O_9$ | 570.595 |

TABLE A-continued
List of Exemplary Compounds
| Structure | Name | Species | Molecular Formula | M.W. |
|---|---|---|---|---|
| 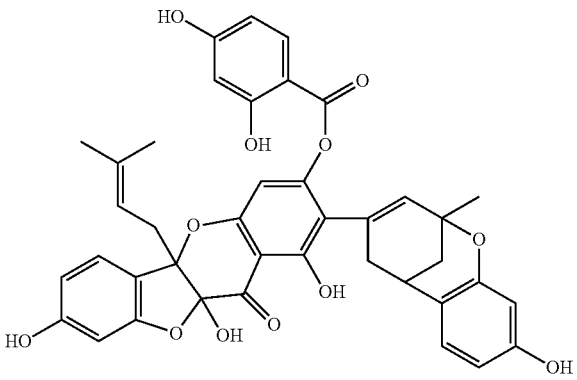 [SMILES: CC(C)=CCC12Oc3cc(OC(=O)c4ccc(O)cc4O)c(C4=CC5(C)CC(C4)c4ccc(O)cc4O5)c(O)c3C(=O)C1(O)Oc1cc(O)ccc12] | Sanggenon B; 7-O-(2,4-Dihydroxy-benzoyl) (Sanggenon S) | *Morus* sp | $C_{40}H_{34}O_{12}$ | 706.701 |
| 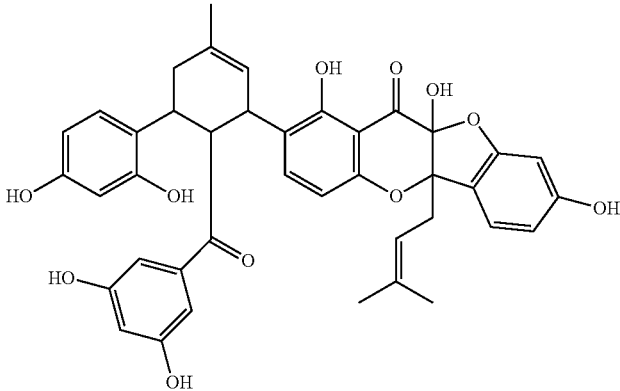 [SMILES: CC(C)=CCC12Oc3ccc(C4C=C(C)CC(c5ccc(O)cc5O)C4C(=O)c4cc(O)cc(O)c4)c(O)c3C(=O)C1(O)Oc1cc(O)ccc12] | Sanggenon D | *Morus cathayana* | $C_{40}H_{36}O_{12}$ | 708.717 |
| 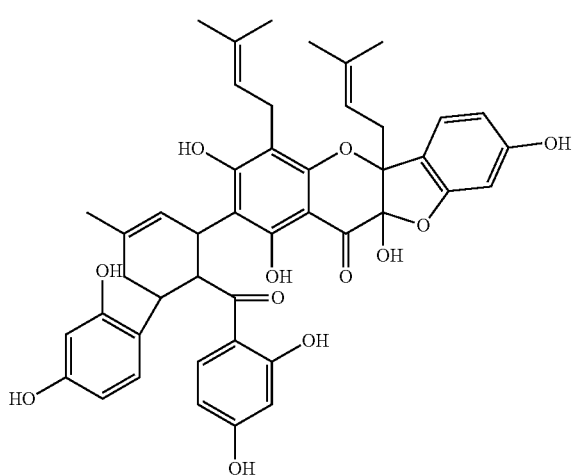 [SMILES: CC(C)=CCc1c(O)c(C2C=C(C)CC(c3ccc(O)cc3O)C2C(=O)c2ccc(O)cc2O)c(O)c2c1OC1(CC=C(C)C)c3ccc(O)cc3OC1(O)C2=O] | Sanggenon E | *Morus* Spp. | $C_{45}H_{44}O_{12}$ | 776.835 |

TABLE A-continued

List of Exemplary Compounds

| Structure | Name | Species | Molecular Formula | M.W. |
|---|---|---|---|---|
| 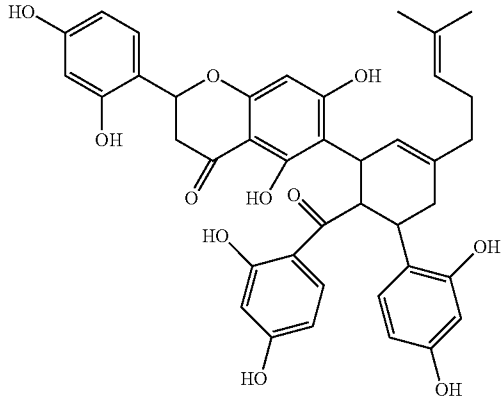 [SMILES: CC(C)=CCCC1=CC(c2c(O)cc3c(c2O)C(=O)CC(c2ccc(O)cc2O)O3)C(C(=O)c2ccc(O)cc2O)C(c2ccc(O)cc2O)C1] | Sanggenon G | *Morus alba* | $C_{40}H_{38}O_{11}$ | 694.734 |
| 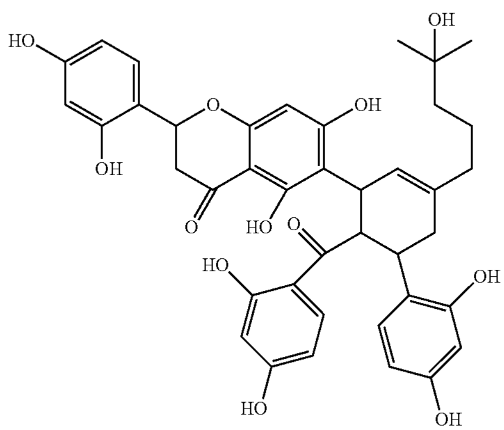 [SMILES: CC(C)(O)CCCC1=CC(c2c(O)cc3c(c2O)C(=O)CC(c2ccc(O)cc2O)O3)C(C(=O)c2ccc(O)cc2O)C(c2ccc(O)cc2O)C1] | Sanggenon G; 14,15-Dihydro, 15-hydroxy | *Morus* sp. | $C_{40}H_{40}O_{12}$ | 712.749 |
| 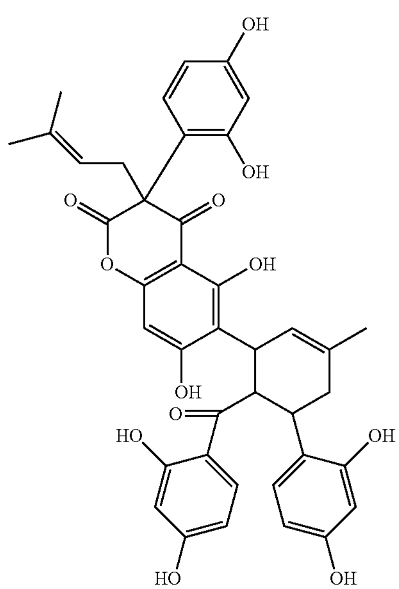 [SMILES: CC(C)=CCC1(c2ccc(O)cc2O)C(=O)Oc2cc(O)c(C3C=C(C)CC(c4ccc(O)cc4O)C3C(=O)c3ccc(O)cc3O)c(O)c2C1=O] | Sanggenon Q | *Morus mongolica* | $C_{40}H_{36}O_{12}$ | 708.717 |

TABLE A-continued

List of Exemplary Compounds

| Structure | Name | Species | Molecular Formula | M.W. |
|---|---|---|---|---|
| 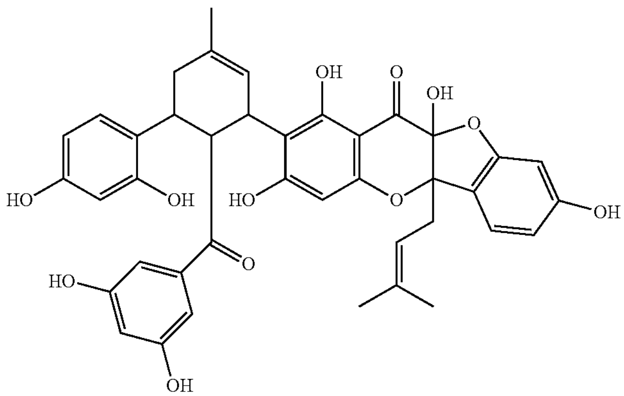 [SMILES: CC(C)=CCC12Oc3cc(O)c(C4C=C(C)CC(c5ccc(O)cc5O)C4C(=O)c4cc(O)cc(O)c4)c(O)c3C(=O)C1(O)Oc1cc(O)ccc12] | Sanggenon D; 3'-Epimer | Morus cathayana | $C_{40}H_{36}O_{12}$ | 708.717 |
| 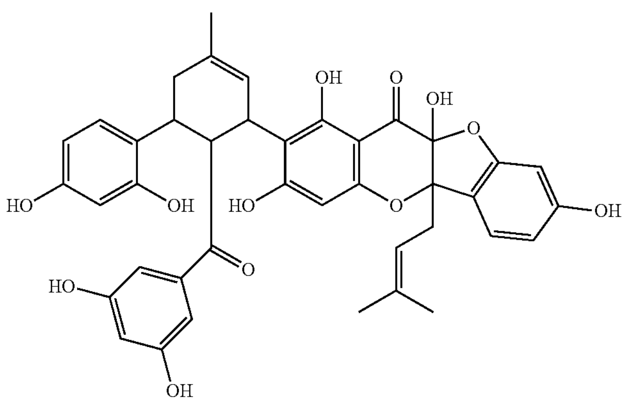 [SMILES: CC(C)=CCC12Oc3cc(O)c(C4C=C(C)CC(c5ccc(O)cc5O)C4C(=O)c4cc(O)cc(O)c4)c(O)c3C(=O)C1(O)Oc1cc(O)ccc12] | Sanggenon D; 2,3,3'-Triepimer | Morus cathayana | $C_{40}H_{36}O_{12}$ | 708.717 |
| 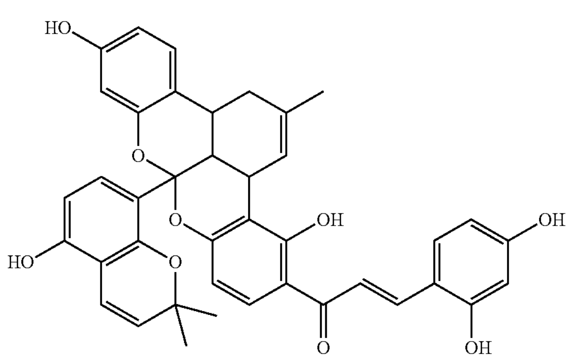 [SMILES: CC1=CC2c3c(ccc(C(=O)/C=C/c4ccc(O)cc4O)c3O)OC3(c4ccc(O)c5c4OC(C)(C)C=C5)Oc4cc(O)ccc4C(C1)C23] | Sorocein B | Sorocea bonplandii | $C_{40}H_{34}O_9$ | 658.703 |

TABLE A-continued

List of Exemplary Compounds

| Structure | Name | Species | Molecular Formula | M.W. |
|---|---|---|---|---|
| 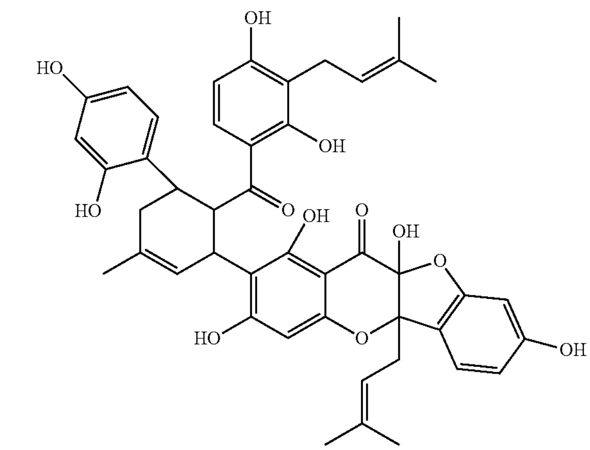 [SMILES: CC(C)=CCc1c(O)ccc(C(=O)C2C(c3c(O)cc4c(c3O)C(=O)C3(O)Oc5cc(O)ccc5C3(CC=C(C)C)O4)C=C(C)CC2c2ccc(O)cc2O)c1O] | Sorocein H | *Sorocea bonplandii* (Moraceae) and *Morus* spp. | $C_{45}H_{44}O_{12}$ | 776.835 |
| 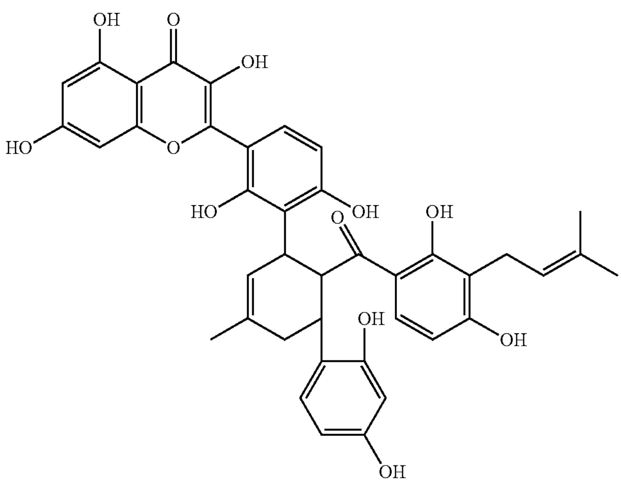 [SMILES: CC(C)=CCc1c(O)ccc(C(=O)C2C(c3c(O)ccc(-c4oc5cc(O)cc(O)c5c(=O)c4O)c3O)C=C(C)CC2c2ccc(O)cc2O)c1O] | Wittiorumin B | *Morus wittorum* | $C_{40}H_{36}O_{12}$ | 708.717 |
| 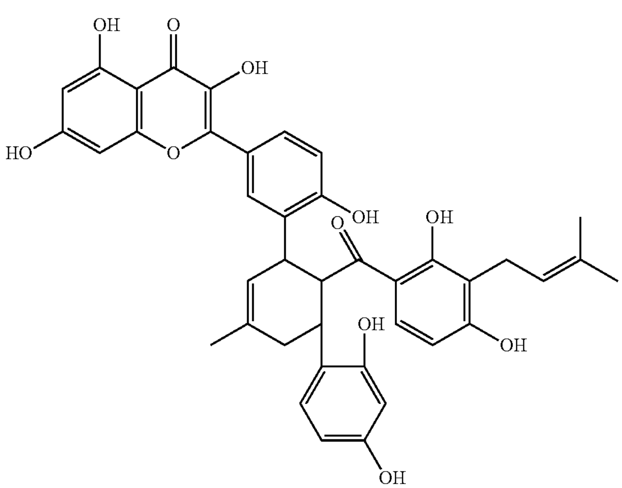 [SMILES: CC(C)=CCc1c(O)ccc(C(=O)C2C(c3cc(-c4oc5cc(O)cc(O)c5c(=O)c4O)ccc3O)C=C(C)CC2c2ccc(O)cc2O)c1O] | Wittiorumin B; 1''-Epimer, 2'-deoxy | *Morus wittiorum* | $C_{40}H_{36}O_{11}$ | 692.718 |

TABLE A-continued
List of Exemplary Compounds
| Structure | Name | Species | Molecular Formula | M.W. |
|---|---|---|---|---|
| 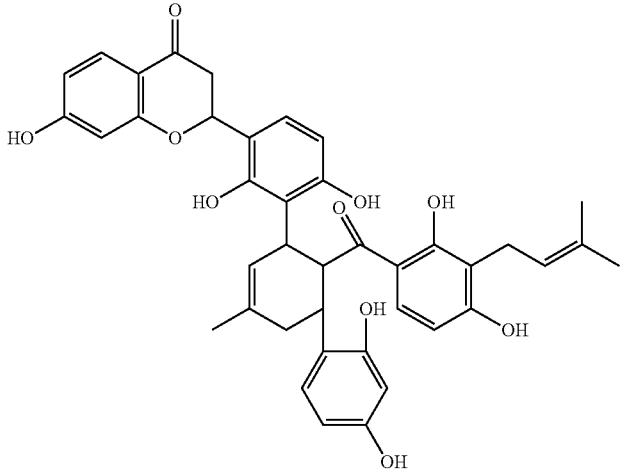 [SMILES: CC(C)=CCc1c(O)ccc(C(=O)C2C(c3c(O)ccc(C4CC(=O)c5ccc(O)cc5O4)c3O)C=C(C)CC2c2ccc(O)cc2O)c1O] | Wittiorumin E | Morus wittiorum | $C_{40}H_{38}O_{10}$ | 678.734 |
| 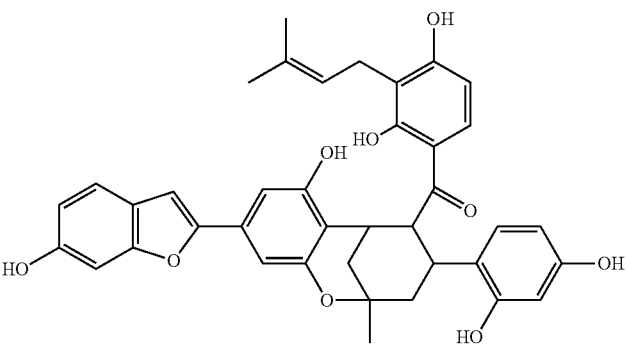 [SMILES: CC(C)=CCc1c(O)ccc(C(=O)C2C(c3ccc(O)cc3O)CC3(C)CC2c2c(O)cc(-c4cc5ccc(O)cc5o4)cc2O3)c1O] | Wittiorumin F | Morus wittiorum | $C_{39}H_{36}O_9$ | 648.708 |
| 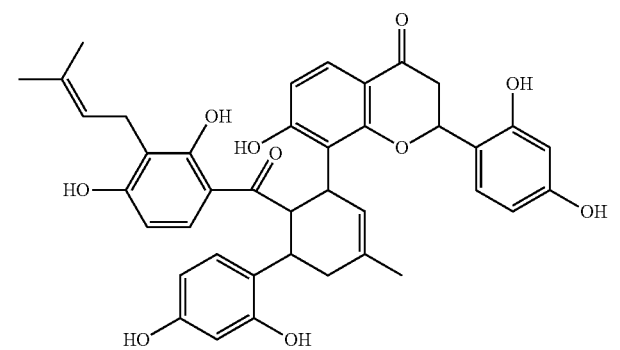 [SMILES: CC(C)=CCc1c(O)ccc(C(=O)C2C(c3c(O)ccc4c3OC(c3ccc(O)cc3O)CC4=O)C=C(C)CC2c2ccc(O)cc2O)c1O] | Wittiorumin G | Morus wittiorum | $C_{40}H_{38}O_{10}$ | 678.734 |

TABLE A-continued

List of Exemplary Compounds

| Structure | Name | Species | Molecular Formula | M.W. |
|---|---|---|---|---|
| 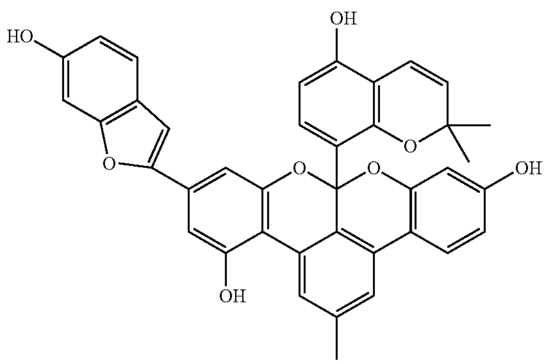 [SMILES: Cc1cc2c3c(c1)-c1c(O)cc(-c4cc5ccc(O)cc5o4)cc1OC3(c1ccc(O)c3c1OC(C)(C)C=C3)Oc1cc(O)ccc1-2] | Yunanensin A | *Morus yunnanensis* | $C_{39}H_{28}O_8$ | 624.645 |

Compounds in Table A can be extracted, isolated or purified from the indicated plant species or certain plant parts (e.g., from the bark, trunk, trunk bark, stem bark, root, root bark, bark surface, leaves, fruits, flowers, other plant parts, or any combination thereof) or can be prepared synthetically or semi-synthetically as described in more detail below. In certain embodiments, one or more compounds of Table A are enriched for or are the major active ingredients in an extract of the indicated plant species, wherein the enriched extract is obtained from a whole plant or certain plant parts, such as leaves, bark, trunk, trunk bark, stem, stem bark, twigs, tubers, root, root bark, bark surface, young shoots, rhizomes, seed, fruit, androecium, gynoecium, calyx, stamen, petal, sepal, carpel (pistil), flower, or any combination thereof.

It is understood that any embodiment of the compounds of structure (I) or (II), as set forth above, and any specific substituent set forth herein for the compounds of structure (I) or (II), as set forth above, may be independently combined with other embodiments or substituents of compounds of structure (I) or (II) to form embodiments of this disclosure not specifically set forth above. In addition, in the event that a list of substituents is listed for any particular R group in a particular embodiment or claim, it is understood that each individual substituent may be deleted from the particular embodiment or claim and that the remaining list of substituents will be considered to be within the scope of this disclosure.

For the purposes of administration, the compounds of the present invention may be administered as a raw chemical or may be formulated as pharmaceutical or nutraceutical compositions. Pharmaceutical or nutraceutical compositions of the present invention comprise a compound of structure (I) or (II) and a pharmaceutically or nutraceutically acceptable carrier, diluent or excipient. The compound of structure (I) or (II) is present in the composition in an amount which is effective to treat a particular disease or condition of interest—that is, in an amount sufficient promote weight loss or any of the other associated indications described herein, and generally with acceptable toxicity to a patient. Weight loss and other activity of compounds of structure (I) or (II) can be determined by one skilled in the art, for example, as described in the Examples below. Appropriate concentrations and dosages can be readily determined by one skilled in the art.

Administration of the compounds of this disclosure, or their pharmaceutically or nutraceutically acceptable salts, in pure form or in an appropriate pharmaceutical or nutraceutical composition, can be carried out via any of the accepted modes of administration of agents for serving similar utilities. The pharmaceutical or nutraceutical compositions of this disclosure can be prepared by combining a compound of this disclosure with an appropriate pharmaceutically or nutraceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical or nutraceutical compositions include oral, topical, transdermal, inhalation, parenteral, sublingual, buccal, rectal, vaginal, or intranasal. The term parenteral as used herein includes subcutaneous injections, intravenous, intramuscular, intrasternal injection or infusion techniques. Pharmaceutical or nutraceutical compositions of this disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of this disclosure in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of this disclosure, or a pharmaceutically or nutraceutically acceptable salt thereof, for treatment of a disease or condition of interest in accordance with the teachings of this invention.

A pharmaceutical or nutraceutical composition of this disclosure may be in the form of a solid or liquid. In one aspect, the carrier(s) are particulate, so that the compositions are, for example, in tablet or powder form. The carrier(s)

may be liquid, with the compositions being, for example, oral syrup, injectable liquid or an aerosol, which is useful in, for example, inhalatory administration.

When intended for oral administration, the pharmaceutical or nutraceutical composition is in either solid or liquid form, where semi-solid, semi-liquid, suspension and gel forms are included within the forms considered herein as either solid or liquid.

As a solid composition for oral administration, the pharmaceutical or nutraceutical composition may be formulated into a powder, granule, compressed tablet, pill, capsule, chewing gum, wafer, bar, or like form. Such a solid composition will typically contain one or more inert diluents or edible carriers. In addition, one or more of the following may be present: binders such as carboxymethylcellulose, ethyl cellulose, cyclodextrin, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical or nutraceutical composition is in the form of a capsule, for example, a gelatin capsule, it may contain, in addition to materials of the above type, a liquid carrier such as polyethylene glycol or oil.

The pharmaceutical or nutraceutical composition may be in the form of a liquid, for example, an elixir, syrup, solution, emulsion or suspension. The liquid may be for oral administration or for delivery by injection, as two examples. When intended for oral administration, a useful composition contains, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical or nutraceutical compositions of this disclosure, whether they be solutions, suspensions or other like form, may include one or more of the following adjuvants: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a generally useful adjuvant. An injectable pharmaceutical or nutraceutical composition is sterile.

A liquid pharmaceutical or nutraceutical composition of this disclosure intended for either parenteral or oral administration should contain an amount of a compound of this disclosure such that a suitable dosage will be obtained.

The pharmaceutical or nutraceutical composition of this disclosure may be intended for topical administration, in which case the carrier may suitably comprise a solution, emulsion, cream, lotion, ointment, or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical or nutraceutical composition for topical administration. If intended for transdermal administration, the composition may include a transdermal patch or iontophoresis device.

The pharmaceutical or nutraceutical composition of this disclosure may be intended for rectal administration, in the form, for example, of a suppository, which will melt in the rectum and release the drug. The composition for rectal administration may contain an oleaginous base as a suitable nonirritating excipient. Such bases include lanolin, cocoa butter and polyethylene glycol.

The pharmaceutical or nutraceutical composition of this disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical or nutraceutical composition of this disclosure in solid or liquid form may include an agent that binds to the compound of this disclosure and thereby assists in the delivery of the compound. Suitable agents that may act in this capacity include a monoclonal or polyclonal antibody, a protein or a liposome.

The pharmaceutical or nutraceutical composition of this disclosure in solid or liquid form may include reducing the size of a particle to, for example, improve bioavailability. The size of a powder, granule, particle, microsphere, or the like in a composition, with or without an excipient, can be macro (e.g., visible to the eye or at least 100 μm in size), micro (e.g., may range from about 100 μm to about 100 nm in size), nano (e.g., may no more than 100 nm in size), and any size in between or any combination thereof to improve size and bulk density.

The pharmaceutical or nutraceutical composition of this disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation, may determine the most appropriate aerosol(s).

The pharmaceutical or nutraceutical compositions of this disclosure may be prepared by methodology well known in the pharmaceutical or nutraceutical art. For example, a pharmaceutical or nutraceutical composition intended to be administered by injection can be prepared by combining a compound of this disclosure with sterile, distilled water so as to form a solution. A surfactant may be added to facilitate the formation of a homogeneous solution or suspension. Surfactants are compounds that non-covalently interact with the compound of this disclosure so as to facilitate dissolution or homogeneous suspension of the compound in the aqueous delivery system.

The compounds of this disclosure, or their pharmaceutically or nutraceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of this disclosure, or pharmaceutically or nutraceutically acceptable derivatives thereof, may also be administered simultaneously with, prior to, or after administration of one or more other therapeutic agents. Such combination therapy includes administration of a single pharmaceutical or nutraceutical dosage formulation which contains a compound of this disclosure and one or more additional active agents, as well as administration of the compound of this disclosure and each active agent in its own separate pharmaceutical or nutraceutical dosage formulation. For example, a compound of this disclosure and another active agent can be administered to the patient together in a single oral dosage composition, such as a tablet or capsule, or each agent can be administered in separate oral dosage formulations. Where separate dosage formulations are used, the compounds of this disclosure and one or more additional active agents can be administered at essentially the same time, i.e., concurrently, or at separately staggered times, i.e., sequentially; combination therapy is understood to include all these regimens.

It is understood that in the present description, combinations of substituents or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of this disclosure which are pharmacologically active. Such derivatives may therefore be described as "prodrugs". All prodrugs of compounds of this invention are included within the scope of this disclosure.

Furthermore, all compounds of this disclosure which exist in free base or acid form can be converted to their pharmaceutically or nutraceutically acceptable salts by treatment with the appropriate inorganic or organic base or acid by methods known to one skilled in the art. Salts of the compounds of this disclosure can be converted to their free base or acid form by standard techniques.

In some embodiments, compounds of the present disclosure can be isolated from plant sources, for example, from those plants included in Table A and elsewhere throughout the present application. Suitable plant parts for isolation of the compounds include leaves, bark, trunk, trunk bark, stem, stem bark, twigs, tubers, root, root bark, bark surface, young shoots, rhizomes, seed, fruit, androecium, gynoecium, calyx, stamen, petal, sepal, carpel (pistil), flower, or any combination thereof. In some related embodiments, the compounds are isolated from plant sources and synthetically modified to contain any of the recited substituents. In this regard, synthetic modification of the compound isolated from plants can be accomplished using any number of techniques which are known in the art and are well within the knowledge of one of ordinay skill in the art.

As noted above, the compounds of the present invention are Diels-Alder adducts of a chalcone and prenylphenyl moiety. While not wishing to be bound by theory, it is believed that the Diels-Alder reaction occurs as part of the biosynthetic pathway in various plants, and thus certain embodiments of this disclosure include isolating the compounds from plants and using as is or performing various synthetic modifications. However, in other embodiments the compounds are prepared synthetically. For example, the following Reaction Scheme illustrates a method of making compounds of this invention, i.e., compound of structure (I) of (II) using synthetic techniques:

Reaction Scheme 1

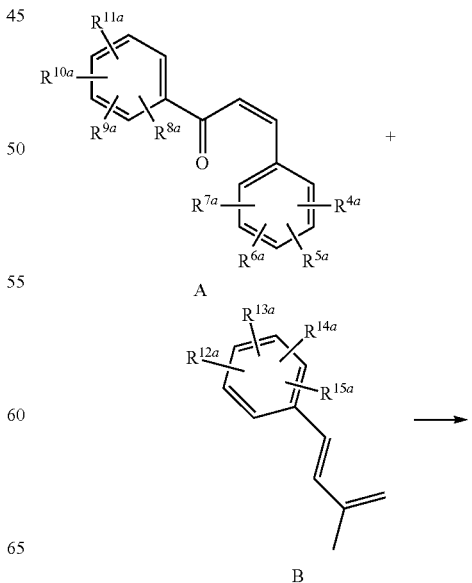

-continued

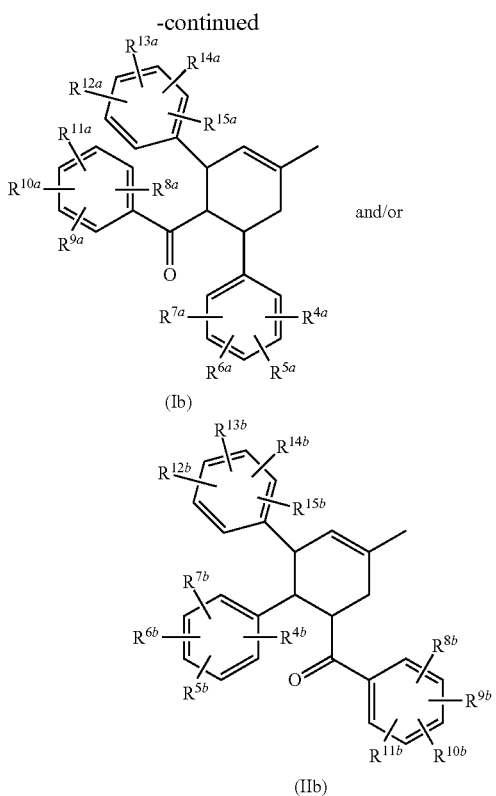

(Ib)

and/or (IIb)

Representative compounds of structure (I) or (II) (e.g., (Ib) or (IIb)) can be prepared synthetically according to the general procedure illustrated in Reaction Scheme 1. Chalcone A and isoprenylphenyl B may be purchased from commercial sources, isolated from plant sources or prepared according to procedures known in the art. Reaction of chalcone A with isoprenylphenyl B under appropriate Diels-Alder conditions (which are known in the art) results in compounds of structure (I) or (II). Compounds of structure (I) and (II) are regioisomers as a result of the asymmetry of chalcone A. The various substituents (i.e., the "R" groups) can be installed prior to Diels-Alder cyclization as depicted in Reaction Scheme 1 or installed after cyclization. Methods for modification of the above method and for adding various R groups are well known in the art and within the grasp of one of ordinary skill in the art.

It is understood that one skilled in the art may be able to make these compounds by similar methods or by combining other methods known to one skilled in the art. It is also understood that one skilled in the art would be able to make, in a similar manner as described below, other compounds of structure (I) or (II) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

In further embodiments, at least one Diels-Alder adduct of a chalcone and prenylphenyl moiety of the present disclosure may be combined with one or more weight management agents. A "weight management agent," as used herein, refers to a biologically active compound, molecule, or composition that allows a subject to manage their weight, which may involve maintaining a particular weight level, reducing weight gain or reducing weight. The biological activity of the weight management agents may include reducing or suppressing appetite, altering metabolic levels, altering lipid metabolism, decreasing caloric intake, or the like. Exemplary weight management agents include anorectic agents, lipase inhibitors, cannabinoid receptor modulators, psychotropic agents, insulin sensitizers, stimulants, satiety agents, or combinations thereof.

In certain embodiments, Diels-Alder adducts of a chalcone and prenylphenyl moiety of the present disclosure are used with at least one other weight management agent, such as an anorectic agent, a lipase inhibitor, a cannabinoid receptor modulator, a psychotropic agent, an insulin sensitizer, a stimulant, or a satiety agent. The weight management agents and the Diels-Alder adducts of a chalcone and prenylphenyl moiety of the present disclosure may be formulated together or separately. In addition, the Diels-Alder adducts of a chalcone and prenylphenyl moiety of the present disclosure may be administered or taken by a subject simultaneously with, prior to, or after administration of the at least one other weight management agent.

In certain embodiments, the anorectic agent is sibutramine, diethylpropion, benzphetamine, phendimetrazine, or catecholamine. In further embodiments, the lipase inhibitor is a Mutamba extract, a Rosemary extract, carnosic acid, carnosol, lipostatin, tetrahydrolipostatin, *Punica granatum* pericarp extract, *Marchantia polymorphs* whole plant extract, Panax japonicas extract or Platycodi radix extract.

In still further embodiments, the cannabinoid receptor modulator is a cannabinoid receptor agonist, antagonist, or inverse agonist. In yet further embodiments, the cannabinoid receptor modulator is specific for cannabinoid receptor 1 (CB1), cannabinoid receptor 2 (CB2), or both CB1 and CB2, such as a CB1 antagonist or inverse agonist. Exemplary cannabinoid receptor modulators include rimonabant, N-(piperidin-1-yl)-5-(4-iodophenyl)-1-(2,4-dichlorophenyl)-4-methyl-1H-pyrazole-3-carboxamide (AM 251), 1-(2,4-Dichlorophenyl)-5-(4-iodophenyl)-4-methyl-N-4-morpholinyl-1H-pyrazole-3-carboxamide (AM281), 4-[6-methoxy-2-(4-methoxypheyl)1-benzofuran-3-carbonyl] benzonitrile (LY 320135), *Magnolia* extract, magnolol, honokiol, magnolol and honokiol, purinol, or *Piper Longum* seed extract. In certain embodiments, Diels-Alder adducts of a chalcone and prenylphenyl moiety of the present disclosure may be used with a second, third, fourth, or fifth Diels-Alder adduct of a chalcone and a prenylphenyl moiety. In certain embodiments, the weight management agents includes two, three, four, five, six, seven, eight, nine, or ten Diels-Alder adducts of a chalcone and a prenylphenyl moiety.

For example, certain embodiments Diels-Alder adducts of a chalcone and prenylphenyl moiety of the present disclosure may be used with an anorectic agent and a lipase inhibitor, or an anorectic agent and a cannabinoid receptor modulator, or an anorectic agent and a psychotropic agent, an anorectic agent and an insulin sensitizer, or an anorectic agent and a stimulant, or an anorectic agent and a satiety agent. In still further embodiments, Diels-Alder adducts of a chalcone and prenylphenyl moiety of the present disclosure may be used with a lipase inhibitor and a stimulant, or a cannabinoid receptor modulator and a stimulant, or a cannabinoid receptor modulator and a lipase inhibitor. Any of the aforementioned compositions may further comprise a satiety agent or a psychotropic agent or an insulin sensitizer.

In certain embodiments, Diels-Alder adducts of a chalcone and prenylphenyl moieties used alone, in combination, or with another weight management agent have a prenylphenyl moiety that is a prenylated phenol, an isoprenylated flavonoid, a prenylated flavonoid, a prenylated flavoinoid dimer, or a combination thereof. In certain embodiments, the Diels-Alder adducts of a chalcone and a prenylphenyl moiety have a prenylphenyl moiety that is an isoprenylated flavonoid such as an isoprenylated flavone, flavonol, flavanone, chalcone, isoflavone, isoflavanone, aurone, or stilbene. In certain embodiments, Diels-Alder adducts of a chalcone and a prenylphenyl moiety have a prenylated flavonoid that is a prenylated flavone, flavonol, flavanone, chalcone, isoflavone, isoflavanone, aurone, or stilbene. In further embodiments, Diels-Alder adducts of a chalcone and a prenylphenyl moiety used alone, in combination, or with one or more other weight management agents purified from, isolated from, enriched for, or contained in a *Morus* extract or a *Milicia excelsa* extract, such as Albanin G, Kuwanon G, Kuwanon M, Cathayanon A, Morusin, Morusinol, Sanggenon C, Sanggenon D, Sanggenon O, or any combination thereof.

In further embodiments, the weight management agent used with Diels-Alder adducts of a chalcone and a prenylphenyl moiety is a psychotropic agent such as a mood stabilizer, anti-depressant, or anti-convulsant. In still further embodiments, the weight management agent used with Diels-Alder adducts of a chalcone and a prenylphenyl moiety is a stimulant such as caffeine, dicaffeoylquinic acid or dextroamphetamine, or one or more stimulant purified from, isolated from, enriched for, or contained in a Yerba Mate extract, green tea extract, green coffee bean extract, *Cola nut* extract, *Citrus* aurantium fruit extract, Gacinia extract, *Areca* catechu fruit/seed extract or dextroamphetamine. In even further embodiments, the weight management agent used with Diels-Alder adducts of a chalcone and a prenylphenyl moiety is an insulin sensitizer such as thiazolidinediones (e.g., rosiglitazone, pioglitazone), oxazolidinediones, isoxazolidinediones, biguanides (e.g., metformin), selective mTOT (mitochondrial Target of Thiazolidinediones) modulators, cinnamon extract, banaba extract, chromium, fish oil, acetic acid, D-chiro-inositol, or α-lipoic acid. In yet further embodiments, the weight management agent used with Diels-Alder adducts of a chalcone and a prenylphenyl moiety is a satiety agent such as dodecanoic acid, glyceryl dodecanoate, glyceryl 1,3-didodecanoate, glyceryl tridodecanoate, and derivatives or mixtures thereof, or one or more satiety agent purified from, isolated from, enriched for, or contained in a hoodia extract, a pine nut extract, or a fiber supplement.

As noted herein, compounds of a Diels-Alder adduct of a chalcone and a prenylphenyl moiety may be obtained by chemical synthesis or from a plant extract, such as a *Morus* or *Milicia* extract. For example, *Morus* is a genus of flowering trees in the family Moraceae, which comprises more than 30 species (known as mulberries) that grow wild or under cultivation in many countries. Exemplary *Morus* species include *Morus alba L., Morus australis Poir, Morus celtidifolia Kunth, Morus insignis, Morus mesozygia Stapf, Morus microphylla, Morus nigra L., Morus rubra L., Morus atropurpurea, Morus bombycis, Morus cathayana, Morus indica, Morus lhou, Morus japonica, Morus kagayamae, Morus laevigata, Morus latifolia, Morus liboensis, Morus macroura, Morus mongolica, Morus multicaulis, Morus notabilis, Morus rotundiloba, Morus serrate, Morus heterophyllus, Morus tillaefolia, Morus trilobata, Morus yunnanensis*, and *Morus wittiorum*. In certain embodiments, a *Morus* extract is from *Morus alba*, or a *Morus* extract is a mixture of extracts from one, two, three, four, or five different *Morus* species. A mixture of extracts may include extracts from two or more *Morus* species listed in Table A.

*Magnolia* includes about 210 flowering plant species in the subfamily Magnolioideae of the family Magnoliaceae. *Magnolia*, known as Hou Pu, can grow wild or under cultivation in many countries. Exemplary *Magnolia* species includes *Magnolia obovata Thunb., Magnolia officinalis* Rehd. & Wilson, *Magnolia rostrata* W. W. Smith, *Magnolia tripetala, Magnolia globosa* Hook f & Thoms, *Magnolia sieboldii* K. Koch, *Magnolia wilsonii* (Finet. & Gagnep.) Rehd., *Magnolia fraseri* Walt. *Magnolia macrophylla* Michx, *Magnolia decidua* (Q. Y. Zheng) V. S. Kumar, *Magnolia dolichogyna* (Dandy ex Noot) Figlar & Noot., *Magnolia duclouxii* Finet & Gagnep., *Magnolia figlarii* V. S. Kumar, *Magnolia fordiana, Magnolia emarginata* Urb. & Ekman, *Magnolia hamorii* Howard, *Magnolia pallescens* Urb. & Ekman, *Magnolia mahechae* (Lozano) Govaerts. *Magnolia ptaritepuiana* Steyermark, *Magnolia striatifolia* Little, *Magnolia mexicana* DC., *Magnolia minor* (Urb.) Govaerts, *Magnolia morii* (Lozano) Govaerts, *Magnolia narinensis* (Lozano) Govaerts, *Magnolia neillii* (Lozano) Govaerts, *Magnolia ovata* (A.St.-Hil.) Spreng, *Magnolia polyhypsophilla* (Lozano) Govaerts, *Magnolia quetzal, Magnolia rimachii* (Lozano) Govaerts, *Magnolia sambuensis, Magnolia delavayi* Franchet, *Magnolia fistulosa* (Finet & Gagnep) Dandy, *Magnolia henryi* Dunn, *Magnolia nana* Dandy, *Magnolia odoratissima, Magnolia grandiflora* L, and *Magnolia guatemalensis*. In certain embodiments, a *Magnolia* extract is from *Magnolia officinalis*, or a *Magnolia* extract is a mixture of extracts from one, two, three, four, or five different *Magnolia* species.

*Rosmarinus* officinalis, commonly known as Rosemary, is a woody, perennial herb with fragrant, evergreen, needle-like leaves and white, pink, purple, or blue flowers, native to the Mediterranean region. Rosemary is a member of the mint family Lamiaceae, which includes many other herbs. Other exemplary Rosemary species include *Rosmarinus tomentosus, Rosmarinus eriocalyx*, and *Rosmarinus palaui*. In certain embodiments, a Rosemary extract is from *Rosmarinus* officinalis, or a Rosemary extract is a mixture of extracts from one, two, or three Rosemary species.

The plant origin for most commonly utilized Yerba Mate is *Ilex paraguariensis*, which is a species of holly (family Aquifoliaceae) well known as a source of the beverage called mate. Yerba Mate is native to subtropical South America in northeastern Argentina, Bolivia, southern Brazil, Uruguay and Paraguay. The genus is distributed throughout the world's different climates. Exemplary *Ilex* species includes American Holly (*Ilex opaca*), Carolina Holly (*Ilex ambigua*), Chinese Holly (*Ilex cornuta*), Common Winterberry (*Ilex verticillate*), Dahoon (*Ilex cassine*), Deciduous Holly (*Ilex decidua*), English Holly (*Ilex aquifolium*), Australia Holly (*Ilex arnhemensis*). Inkberry (*Ilex glabra*), Japanese Holly (*Ilex crenata*), Large Gallberry (*Ilex coriacea*), Smooth Winterberry (*Ilex laevigata*), Yaupon (*Ilex vomitoria*), Africa species (*Ilex mitis*), and *Ilex canariensis* Macaronesia, *Ilex aquifolium*). *Ilex mucronate*, formerly the type species of Nemopanthus, is native to eastern North America. Nemopanthus was treated as a monotypic genus with eight species of the family Aquifoliaceae, now transferred to *Ilex* based on molecular data (closely related to *Ilex amelanchier*). In certain embodiments, a Yerba Mate extract is from *Ilex paraguariensis*, or a Yerba Mate extract is a mixture of extracts from one, two, three, four, or five *Ilex* species.

*Guazuma*, a genus of flowering trees in the family Malvaceae, is widely found in the Caribbean, South American, Central America and Mexico. Mutamba is a common name of *Guazuma* plant with various medicinal values in traditional herbal medicine. Exemplary condensed tannins of this disclosure maybe extracted from different species of *Guazuma* plant, including *Guazuma commersoniopsis, Guazuma euguazuma, Guazuma gynophoricola, Guazuma blumei, Guazuma bubroma, Guazuma burbroma, Guazuma coriacea, Guazuma crinita, Guazuma grandiflora, Guazuma guazuma, Guazuma invira, Guazuma iuvira, Guazuma longipedicellata, Guazuma parvifolia, Guazuma polybotra, Guazuma polybotrya, Guazuma rosea, Guazuma tomentosa, Guazuma ulmifolia*, and *Guazuma utilis*. In certain embodiments, a Mutamba extract is from *Guazuma ulmifolia*, or a Mutamba extract is a mixture of extracts from one, two, three, four, or five *Guazuma* species.

In certain embodiments, a composition comprising a Diels-Alder adduct of a chalcone and a prenylphenyl moiety comprises a *Morus* extract containing or enriched for at least one Diels-Alder adduct of a chalcone and a prenylphenyl moiety, a *Magnolia* extract, and a Yerba mate extract, which extracts can be mixed or used together in a 2:1:5 weight ratio to a 2:1:10 weight ratio, respectively. In further embodiments, a composition comprising a Diels-Alder adduct of a chalcone and a prenylphenyl moiety and a weight management agent comprises a *Morus* extract containing or enriched for at least one Diels-Alder adduct of a chalcone and a prenylphenyl moiety, a *Magnolia* extract, and a Yerba Mate extract, which extracts can be mixed or used together in a 2:1:5 weight ratio to a 2:1:10 weight ratio, respectively. In any of the aforementioned embodiments, a *Morus* extract is a *Morus alba* extract or extract enriched for Kuwanon G, Albanin G, Morusin, or any combination thereof; a *Magnolia* extract is a *Magnolia* officinalis extract or extract enriched for magnolol, honkiol, both, or a high purity mixture of both; and a Yerba Mate extract is an *Ilex paraguayensis* extract is enriched for caffeine, dicaffeoylquinic acid, or both. In related embodiments, a weight management agent is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In certain embodiments, a composition comprising a Diels-Alder adduct of a chalcone and a prenylphenyl moiety comprises a Diels-Alder adduct of a chalcone and a prenylphenyl moiety, Purinol (a high purity, such as at least 90% purity, or at least 91%, 92%, 93%. 94%, or 95% purity, magnolol and honokiol mixture isolated from *Magnolia* plant extract), and Yerba mate extract, wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O or any combination thereof. In further embodiments, a composition comprising a Diels-Alder adduct of a chalcone and a prenylphenyl moiety and a weight management agent comprises a Diels-Alder adduct of a chalcone and a prenylphenyl moiety, Purinol (a high purity, such as at least 90% purity, or at least 91%, 92%, 93%. 94%, or 95% purity) magnolol and honokiol mixture isolated from *Magnolia* plant extract), and Yerba Mate extract, wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O, or any combination thereof, and the Yerba Mate extract is an *Ilex paraguayensis* extract enriched for caffeine, dicaffeoylquinic acid, or both.

In certain embodiments, a composition comprising a Diels-Alder adduct of a chalcone and a prenylphenyl moiety comprises a *Morus* extract containing or enriched for at least one Diels-Alder adduct of a chalcone and a prenylphenyl moiety, a *Magnolia* extract, and a Mutamba extract, which can be mixed or used together in a 2:1:5 weight ratio to a 2:1:10 weight ratio, respectively. In further embodiments, a composition comprising a Diels-Alder adduct of a chalcone and a prenylphenyl moiety and a weight management agent comprises a *Morus* extract containing or enriched for at least one Diels-Alder adduct of a chalcone and a prenylphenyl moiety, a *Magnolia* extract, and a Mutamba extract, which extracts can be mixed or used together in a 2:1:5 weight ratio to a 2:1:10 weight ratio, respectively. In any of the aforementioned embodiments, a *Morus* extract is a *Morus alba* extract or extract enriched for Kuwanon G, Albanin G, Morusin, or any combination thereof, and a *Magnolia* extract is a *Magnolia* officinalis extract or extract enriched for magnolol, honkiol, both, or a high purity mixture of both. In related embodiments, a weight management agent is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In certain embodiments, a composition comprising a Diels-Alder adduct of a chalcone and a prenylphenyl moiety comprises a Diels-Alder adduct of a chalcone and a prenylphenyl moiety, purinol, and Mutamba extract, wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O, or any combination thereof. In further embodiments, a composition comprising a Diels-Alder adduct of a chalcone and a prenylphenyl moiety and a weight management agent comprises a Diels-Alder adduct of a chalcone and a prenylphenyl moiety, purinol, and Mutamba extract, wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O, or any combination thereof.

In certain embodiments, a composition comprising a Diels-Alder adduct of a chalcone and a prenylphenyl moiety comprises a *Morus* extract containing or enriched for at least one Diels-Alder adduct of a chalcone and a prenylphenyl moiety, a Rosemary extract, and a Yerba mate extract, which can be mixed or used together in a 2:5:5 weight ratio to a 2:5:10 weight ratio, respectively. In further embodiments, a composition comprising a Diels-Alder adduct of a chalcone and a prenylphenyl moiety and a weight management agent comprises a *Morus* extract containing or enriched for at least one Diels-Alder adduct of a chalcone and a prenylphenyl moiety, a Rosemary extract, and a Yerba Mate extract, which extracts can be mixed or used together in a 2:5:5 weight ratio to a 2:5:10 weight ratio, respectively. In any of the aforementioned embodiments, a *Morus* extract is a *Morus alba* extract or extract enriched for Kuwanon G, Albanin G, Morusin, or any combination thereof. In related embodiments, a weight management agent is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In certain embodiments, a composition comprising a Diels-Alder adduct of a chalcone and a prenylphenyl moiety comprises (1) a Diels-Alder adduct of a chalcone and a prenylphenyl moiety, carnosol, and Yerba Mate extract or (2) a Diels-Alder adduct of a chalcone and a prenylphenyl moiety, carnosic acid, and Yerba Mate extract; wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O or any combination thereof, and the Yerba Mate extract is an *Ilex paraguayensis* extract is enriched for caffeine, dicaffeoylquinic acid, or both. In further embodiments, a composition comprising a Diels-Alder adduct of a chalcone and a prenylphenyl moiety and a weight management agent comprises (1) a Diels-Alder adduct of a chalcone and a prenylphenyl moiety, carnosol, and Yerba Mate extract or (2) a Diels-Alder adduct of a chalcone and a prenylphenyl moiety, carnosic acid, and Yerba Mate extract; wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O or any combination thereof, and the Yerba Mate extract is an *Ilex paraguayensis* extract is enriched for caffeine, dicaffeoylquinic acid, or both.

In certain embodiments, a composition comprising a Diels-Alder adduct of a chalcone and a prenylphenyl moiety comprises a *Morus* extract containing or enriched for at least one Diels-Alder adduct of a chalcone and a prenylphenyl moiety, a Rosemary extract, and a mutamba extract, which can be mixed or used together in a 2:5:5 weight ratio to a 2:5:10 weight ratio, respectively. In further embodiments, a composition comprising a Diels-Alder adduct of a chalcone and a prenylphenyl moiety and a weight management agent comprises a *Morus* extract containing or enriched for at least one Diels-Alder adduct of a chalcone and a prenylphenyl moiety, a Rosemary extract, and a mutamba extract, which extracts can be mixed or used together in a 2:5:5 weight ratio to a 2:5:10 weight ratio, respectively. In any of the aforementioned embodiments, a *Morus* extract is a *Morus alba* extract or extract enriched for Kuwanon G, Albanin G, Morusin, or any combination thereof. In related embodiments, a weight management agent is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In certain embodiments, a composition comprising a Diels-Alder adduct of a chalcone and a prenylphenyl moiety comprises a (1) a Diels-Alder adduct of a chalcone and a prenylphenyl moiety, carnosol, and mutamba extract or (2) a Diels-Alder adduct of a chalcone and a prenylphenyl moiety, carnosic acid, and mutamba extract; wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O or any combination thereof. In further embodiments, a composition comprising a Diels-Alder adduct of a chalcone and a prenylphenyl moiety and a weight management agent comprises a (1) a Diels-Alder adduct of a chalcone and a prenylphenyl moiety, carnosol, and mutamba extract or (2) a Diels-Alder adduct of a chalcone and a prenylphenyl moiety, carnosic acid, and mutamba extract; wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O or any combination thereof.

In certain embodiments, a composition comprising a Diels-Alder adduct of a chalcone and a prenylphenyl moiety comprises a *Morus* extract containing or enriched for at least one Diels-Alder adduct of a chalcone and a prenylphenyl moiety, a Rosemary extract, and an *Areca* extract, which can be mixed or used together in a 2:5:5 weight ratio to a 2:5:10 weight ratio, respectively. In further embodiments, a composition comprising a Diels-Alder adduct of a chalcone and a prenylphenyl moiety and a weight management agent comprises a *Morus* extract containing or enriched for at least one Diels-Alder adduct of a chalcone and a prenylphenyl moiety, a Rosemary extract, and an *Areca* extract, which extracts can be mixed or used together in a 2:5:5 weight ratio to a 2:5:10 weight ratio, respectively. In any of the aforementioned embodiments, a *Morus* extract is a *Morus alba* extract or extract enriched for Kuwanon G, Albanin G, Morusin, or any combination thereof. In related embodiments, a weight management agent is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In certain embodiments, a composition comprising a Diels-Alder adduct of a chalcone and a prenylphenyl moiety comprises a (1) a Diels-Alder adduct of a chalcone and a prenylphenyl moiety, carnosol, and *Areca* extract or (2) a Diels-Alder adduct of a chalcone and a prenylphenyl moiety, carnosic acid, and *Areca* extract; wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O or any combination thereof. In further embodiments, a composition comprising a Diels-Alder adduct of a chalcone and a prenylphenyl moiety and a weight management agent comprises a (1) a Diels-Alder adduct of a chalcone and a prenylphenyl moiety, carnosol, and *Areca* extract or (2) a Diels-Alder adduct of a chalcone and a prenylphenyl moiety, carnosic acid, and *Areca* extract; wherein the Diels-Alder adduct of a chalcone and a prenylphenyl moiety is Albanin G, Kuwanon G, Kuwanon M, Cathayanon A, Morusin, Morusinol, Sanggenon C, Sanggenon D, Sanggenon O or any combination thereof.

In any of the aforementioned embodiments, a composition comprising an extract mixture (optionally including a weight management agent) can be formulated with a pharmaceutically or nutraceutically acceptable carrier, diluent or excipient. In further embodiments, the pharmaceutical or nutraceutical formulation comprises from about 0.5 weight percent (wt %) to about 90 wt %, about 0.5 wt % to about 80 wt %, about 0.5 wt % to about 75 wt %, about 0.5 wt % to about 70 wt %, about 0.5 wt % to about 50 wt %, about 1.0 wt % to about 40 wt %, about 1.0 wt % to about 20 wt %, about 1.0 wt % to about 10 wt %, about 3.0 wt % to about 9.0 wt %, about 5.0 wt % to about 10 wt %, about 3.0 wt % to about 6.5 wt % of the major active ingredients in an extract mixture, or the like. In any of these embodiments, the pharmaceutical or nutraceutical composition is formulated as a tablet, a capsule, a powder, or granule. In related embodiments, a weight management agent is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In any of the aforementioned embodiments, a composition comprising an extract mixture (optionally including a weight management agent) wherein one of the extracts is a *Morus* extract enriched for one or more major active ingredients, such as Kuwanon G, Albanin G, Morusin, or any combination thereof. In certain embodiments, a *Morus* extract is a *Morus alba* extract enriched for Kuwanon G, Albanin G, Morusin, or any combination thereof. In further embodiments, a pharmaceutical or nutraceutical formulation comprising an extract mixture as described herein comprises from about 0.5 weight percent (wt %) to about 5.0 wt % of the major active ingredients, such as Kuwanon G, Albanin G, Morusin, or any combination thereof, in a *Morus* extract, such as a *Morus alba* extract or extract enriched for Kuwanon G, Albanin G, Morusin, or any combination thereof.

In any of the aforementioned embodiments, a composition comprising an extract mixture (optionally including a weight management agent) wherein one of the extracts is a *Guazuma ulmifolia* (Mutamba) extract enriched for one or more major active ingredients. In certain embodiments, a *Guazuma ulmifolia* (Mutamba) extract is enriched for a procyanidin, procyanidin B2, procyanidin B5, procyanidin C1, procyanidin dimers, procyanidin trimers, procyanidin tetramers, procyanidin pentamers, procyanidin hexamers, condensed tannins, an oligomer of catechin or epicatechin, epicatechin, or any combination thereof. In further embodiments, a pharmaceutical or nutraceutical formulation comprising an extract mixture as described herein comprises from about 0.5 weight percent (wt %) to about 50 wt % of the major active ingredients in a *Guazuma ulmifolia* (Mutamba) extract, such as a procyanidin, procyanidin B2, procyanidin B5, procyanidin C1, procyanidin dimers, procyanidin trimers, procyanidin tetramers, procyanidin pentamers, procyanidin hexamers, condensed tannins, an oligomer of catechin or epicatechin, epicatechin, or any combination thereof.

In any of the aforementioned embodiments, a composition comprising an extract mixture (optionally including a weight management agent) wherein one of the extracts is a *Magnolia* extract enriched for one or more major active ingredients, such as magnolol, honokiol, or both, or a high purity magnolol, honokiol, or mixture thereof. In certain embodiments, the *Magnolia* extract is a *Magnolia officinalis* extract enriched for magnolol, honokiol, or both, or a high purity magnolol, honokiol, or mixture thereof isolated from *Magnolia* plant extract that has at least about 90%, 91%, 92%, 93%. 94%, or 95% purity. In certain embodiments, a pharmaceutical or nutraceutical formulation comprising an extract mixture as described herein comprises from about 5.0 weight percent (wt %) to about 10 wt % of the major active ingredients in a *Magnolia officinalis* (*Magnolia*) extract, such as magnolol, honokiol, both, or a high purity mixture of both.

In any of the aforementioned embodiments, a composition comprising an extract mixture (optionally including a weight management agent) wherein one of the extracts is a Yerba Mate extract enriched for one or more major active ingredients. In certain embodiments, a Yerba Mate extract is an *Ilex paraguayensis* extract is enriched for caffeine, dicaffeoylquinic acid, or both. In further embodiments, a pharmaceutical or nutraceutical formulation comprising an extract mixture as described herein comprises from about 0.5 weight percent (wt %) to about 5.0 wt % of the major active ingredients in an *Ilex paraguayensis* (Yerba Mate) extract, such as caffeine, dicaffeoylquinic acid, or both.

In any of the aforementioned embodiments, a composition comprising an extract mixture (optionally including a weight management agent) wherein one of the extracts is a *Rosmarinus officinalis* (Rosemary) extract enriched for one or more major active ingredients. In certain embodiments, a *Rosmarinus officinalis* (Rosemary) extract is enriched for a carnosol, carnosoic acid, ursolic acid, or any combination thereof. In further embodiments, a pharmaceutical or nutraceutical formulation comprising an extract mixture as described herein comprises from about 1.0 weight percent (wt %) to about 10 wt % of the major active ingredients in a *Rosmarinus* officinalis (Rosemary) extract, such as carnosol, carnosoic acid, ursolic acid, or any combination thereof.

In any of the aforementioned embodiments, a pharmaceutical or nutraceutical formulation comprising an extract mixture (optionally including a weight management agent) of a *Morus* extract, a *Magnolia* extract, and an *Ilex paraguayensis* (Yerba Mate) extract, will include from about 0.5 weight percent (wt %) to about 5.0 wt % of the major active ingredients in a *Morus* extract, from about 5.0 wt % to about 10 wt % of the major active ingredients in a *Magnolia* extract, and from about 0.5 wt % to about 5.0 wt % of the major active ingredients in Yerba Mate extract. In certain embodiments, a pharmaceutical or nutraceutical formulation comprises about 1% of the major active ingredients in a

*Morus* extract (such as Kuwanon G, Albanin G, Morusin, or any combination thereof), about 7% of the major active ingredients in a *Magnolia* extract (such as magnolol, honokiol, both, or a high purity mixture of both), and about 1% of the major active ingredients in a Yerba Mate extract (such as caffeine, dicaffeoylquinic acid, or both). In any of the aforementioned embodiments, a *Morus* extract is a *Morus alba* extract or extract enriched for Kuwanon G, Albanin G, Morusin, or any combination thereof, and a *Magnolia* extract is a *Magnolia* officinalis extract or extract enriched for magnolol, honokiol, both, or a high purity mixture of both. In any of these embodiments, the pharmaceutical or nutraceutical composition is formulated as a tablet, a capsule, a powder, or granule.

In any of the aforementioned embodiments, a pharmaceutical or nutraceutical formulation comprising an extract mixture (optionally including a weight management agent) of a *Morus* extract, a *Magnolia* extract, and a *Guazuma ulmifolia* (Mutamba) extract, will include from about 0.5 weight percent (wt %) to about 5.0 wt % of the major active ingredients in a Morus extract, from about 5.0 wt % to about 10 wt % of the major active ingredients in a *Magnolia* extract, and from about 0.5 wt % to about 50 wt % of the major active ingredients in a Mutamba extract. In certain embodiments, a pharmaceutical or nutraceutical formulation comprises about 1% of the major active ingredients in a *Morus* extract (such as Kuwanon G, Albanin G, Morusin, or any combination thereof), about 7% of the major active ingredients in a *Magnolia* extract (such as magnolol, honokiol, both, or a high purity mixture of both), and about 1% of the major active ingredients in a Mutamba extract (such as a procyanidin, procyanidin B2, procyanidin B5, procyanidin C1, procyanidin dimers, procyanidin trimers, procyanidin tetramers, procyanidin pentamers, procyanidin hexamers, condensed tannins, an oligomer of catechin or epicatechin, epicatechin, or any combination thereof). In any of the aforementioned embodiments, a *Morus* extract is a *Morus alba* extract or extract enriched for Kuwanon G, Albanin G, Morusin, or any combination thereof, and a *Magnolia* extract is a *Magnolia* officinalis extract or extract enriched for magnolol, honokiol, both, or a high purity mixture of both. In any of these embodiments, the pharmaceutical or nutraceutical composition is formulated as a tablet, a capsule, a powder, or granule. In related embodiments, a weight management agent is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In any of the aforementioned embodiments, a pharmaceutical or nutraceutical formulation comprising an extract mixture (optionally including a weight management agent) of a *Morus* extract, a *Rosmarinus* officinalis (Rosemary) extract, and an *Ilex paraguayensis* (Yerba mate) extract, will include from about 0.5 weight percent (wt %) to about 5.0 wt % of the major active ingredients in a *Morus* extract, from about 1.0 wt % to about 10 wt % of the major active ingredients in a Rosemary extract, and from about 0.5 wt % to about 5.0 wt % of the major active ingredients in a Yerba Mate extract. In certain embodiments, a pharmaceutical or nutraceutical formulation comprises about 1% of the major active ingredients in a *Morus* extract (such as Kuwanon G, Albanin G, Morusin, or any combination thereof), about 4.5% of the major active ingredients in a Rosemary extract (such as carnosol, carnosoic acid, ursolic acid, or any combination thereof), and about 1% of the major active ingredients in a Yerba Mate extract (such as caffeine, dicaffeoylquinic acid, or both). In any of the aforementioned embodiments, a *Morus* extract is a *Morus alba* extract or enriched extract. In any of these embodiments, the pharmaceutical or nutraceutical composition is formulated as a tablet, a capsule, a powder, or granule. In related embodiments, a weight management agent is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In further embodiments, a composition comprising a Diels-Alder adduct of a chalcone and a prenylphenyl moiety as provided herein (optionally including a weight management agent) may be used in a method for treating or preventing weight gain or obesity, promoting weight loss, appetite suppression, modifying satiety, modifying fat uptake, increasing metabolism to promote weight loss or prevent weight gain, maintaining body weight, reducing body fat or fatty tissues, increasing muscle or lean body mass, reducing hepatosteatosis, improving fatty liver, improving one or more liver NASH scores, enhancing fatty acid metabolism in liver, promoting a healthy lipid profile (by, e.g., lowering LDL cholesterol, lowering total cholesterol, lowering triglyceride, or increasing HDL), promoting glucose metabolism, reducing fasting glucose levels, maintaining healthy glucose levels, reducing caloric intake, improving caloric efficiency, reducing food intake, reducing visceral fat, reducing waist circumference, reducing body-to-mass index (BMI), increasing energy, increasing stamina, maintaining energy level while dieting, promoting thermogenesis reducing excess fluids, reducing water retention while maintaining normal hydration, increasing muscle mass, improving fat-to-muscle mass ratio, optimizing or improving body composition, optimizing or improving hormonal balance for appitite control, maintaining normal insulin, leptin, ghrelin, PYY, GIP or enterostatin levels or functions, optimizing, managing or improving hormonal balance to control satiety, maintaining or managing healthy CCK peptide, GLP-1, bombesin, or somatostatin levels or functions, maintaining healthy flora of intestinal tract, optimizing, improving or managing digestion, inducing lipolysis, reducing intracellular triglyceride accumulation, reducing fat accumulation in adipose tissue or an adipocyte, maintaining healthy adiponectin levels, managing or reducing lipogenesis or weight gain associated with metabolism of fructose, glucose or both, reducing or controlling oxidative stress associated with an overweight or obese mammal (e.g., by reducing reactive oxygen species or oxidative free radicals; improving ORAC (Oxygen Radical Absorption Capacity) values; maintaining a healthy level of glutathione, superoxide dismutase, catalase, peroxidase or endogenous antioxidants; maintaining healthy oxidative homeostasis), controlling or managing systemic inflammation associated with an overweight or obese mammal (e.g., by promoting normal metabolism of arachidonic acid, maintaining a normal level of pro-inflammatory cytokines), managing mood stress or other mental disorders associated with an overweight or obese mammal, or any combination thereof.

In related embodiments, a weight management agent for use with the compositions to treat or improve the various weight-related conditions is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In certain embodiments, provided herein is an isolated oligomer or a composition (e.g., for weight management or weight loss) comprising a pharmaceutically acceptable excipient and an oligomer, wherein the oligomer comprises from two to thirty subunits, wherein the subunits have, at each occurrence, independently the following structure (III):

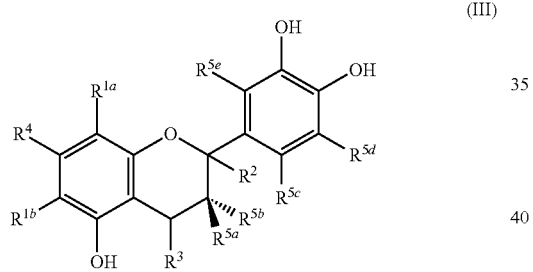

(III)

or a pharmaceutically acceptable salt, stereoisomer or tautomer thereof, wherein $R^{1a}$ and $R^{1b}$ are, at each occurrence, independently H, hydroxyl, halo, a gallic acid ester, a glycoside, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl, aralkylcarbonyl, or a direct bond to an adjacent subunit; $R^2$ is, at each occurrence, independently H or an ether bond to an adjacent subunit; $R^3$ is, at each occurrence, independently H or a direct bond to an adjacent subunit; $R^4$ is, at each occurrence, OH or an ether bond to an adjacent subunit; and $R^{5a}$, $R^{5b}$, $R^{5c}$, $R^{5d}$ and $R^{5e}$ are, at each occurrence, independently H, hydroxyl, halo, a gallic acid ester, a glycoside, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl or aralkylcarbonyl, wherein at least one of $R^{1a}$, $R^{1b}$, $R^2$, $R^3$ or $R^4$ is a direct bond or ether bond to an adjacent subunit. In certain embodiments, oligomers of flavan-3-ol, with subunits as set forth in structure (III) and wherein at least one of $R^{1a}$, $R^{1b}$, $R^2$, $R^3$ or $R^4$ is a direct bond or ether bond to an adjacent subunit, are dimers, trimers, tetramers, pentamers, hexamers, heptamers, octamers, nonamers, decamers, or up to 30 flavan-3-ol subunits (such a 30-mer would have a total molecular weight of about $10^3$ Da).

In further embodiments, two adjacent subunits may have one of the following structures (IIIa), (IIIb) or (IIIc):

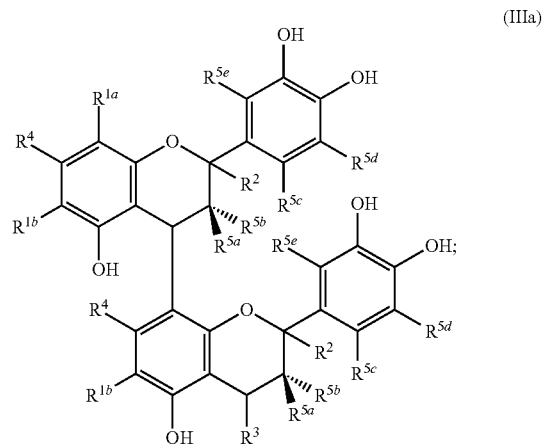

(IIIa)

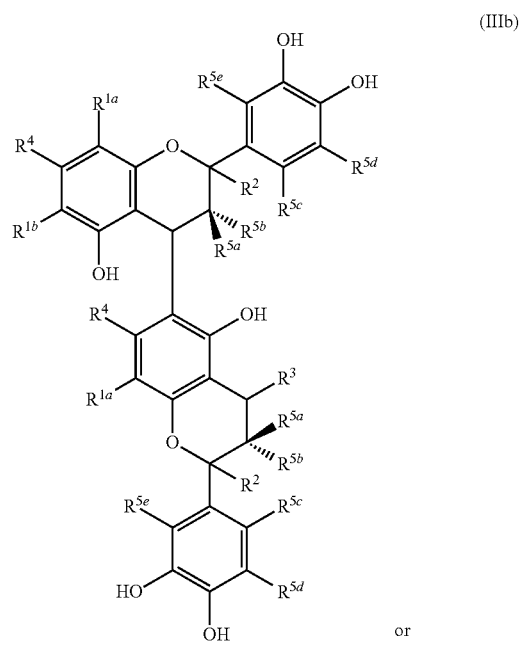

(IIIb)

or

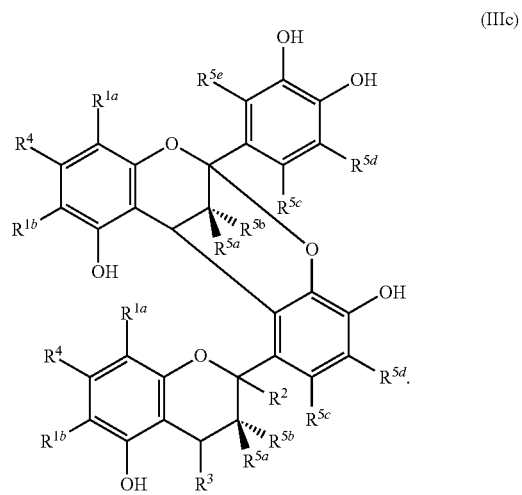

(IIIc)

In any of the aforementioned embodiments, each of $R^{1a}$ and $R^{1b}$ is, at each occurrence, H or a direct bond to an adjacent subunit. In a further embodiment, $R^{5a}$ is, at each occurrence, H and $R^{5b}$ is, at each occurrence, hydroxyl; or $R^{5a}$ is, at each occurrence, hydroxyl and $R^{5b}$ is, at each occurrence, H. In still further embodiments, each of $R^{5c}$, $R^{5d}$ and $R^{5e}$ is, at each occurrence, H. In certain embodiments, oligomers of flavan-3-ol, with subunits as set forth in structure (IIIa), (IIIb), or (IIIc) are dimers, trimers, tetramers, pentamers, hexamers, heptamers, octamers, nonamers, decamers, or up to 30 flavan-3-ol subunits (such a 30-mer would have a total molecular weight of about $10^3$ Da).

In certain embodiments, provided herein is an isolated oligomer or a composition (e.g., for weight management or weight loss) comprising a pharmaceutically acceptable excipient and an oligomer, wherein the oligomer comprises from two to thirty subunits, wherein the subunits have, at each occurrence, independently the following structure (IIId):

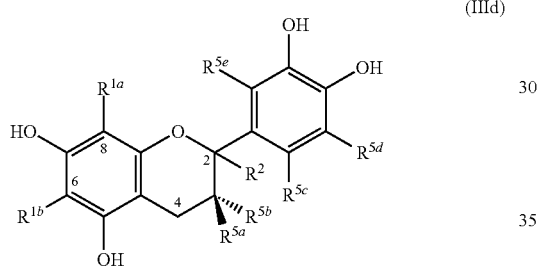

(IIId)

or a pharmaceutically acceptable salt, stereoisomer or tautomer thereof, wherein $R^{1a}$ and $R^{1b}$ are, at each occurrence, independently H, hydroxyl, halo, a gallic acid ester, a glycoside, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl, aralkylcarbonyl, or a direct bond to an adjacent subunit; and $R^{5a}$, $R^{5b}$, $R^{5c}$, $R^{5d}$ and $R^{5e}$ are, at each occurrence, independently H, hydroxyl, halo, a gallic acid ester, a glycoside, sulfhydryl, amino, aldehyde, $C_{1-12}$ alkyl, $C_{1-12}$ alkoxy, $C_{1-12}$ alkthio, $C_{1-12}$ alkyamino, aryl, heteroaryl, aralkyl, alkyl carbonyl or aralkylcarbonyl, wherein at least one of $R^{1a}$, $R^{1b}$, position 2, or position 4 is a direct bond or ether bond to an adjacent subunit. In certain embodiments, oligomers of flavan-3-ol, with subunits as set forth in structure (IIId) and wherein at least one of $R^{1a}$, $R^{1b}$, position 2, or position 4 is a direct bond or ether bond to an adjacent subunit, are dimers, trimers, tetramers, pentamers, hexamers, heptamers, octamers, nonamers, decamers, or up to 30 flavan-3-ol subunits (such a 30-mer would have a total molecular weight of about $10^3$ Da).

In further embodiments, two adjacent subunits may have one of the following structures (IIIe), (IIIf) or (IIIg):

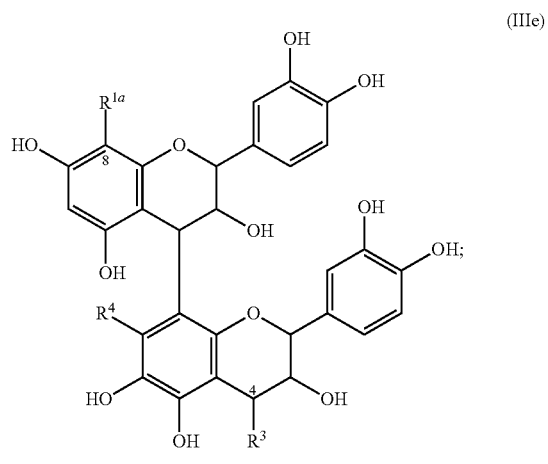

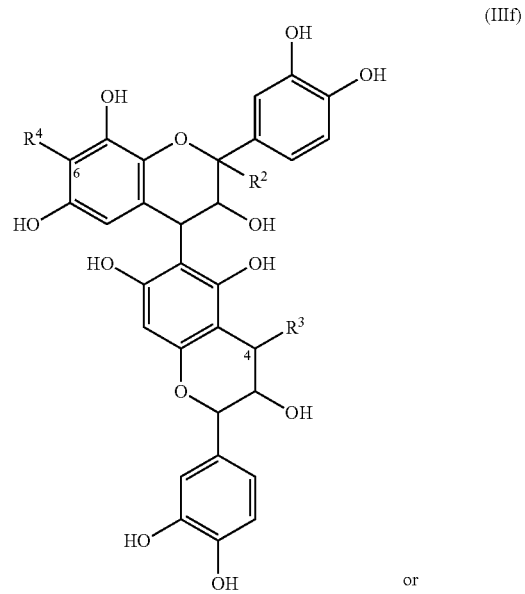

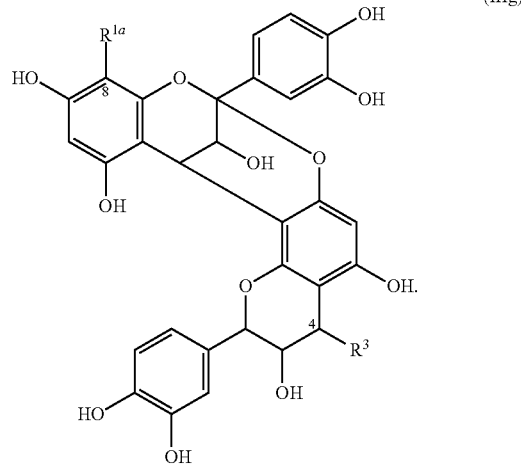

Structures (IIIe) and (IIIf) are exemplary B-type linkages and Structure (IIIg) is an example of an A-type linkage. More specifically, Structure (IIIe) is a 4→8 linkage, wherein $R^{1a}$, $R^3$ or both are available as a direct bond or ether bond to one or more adjacent subunits up to total of 30 subunits, and Structure (IIIe) is a 4→6 linkage, wherein $R^3$, $R^4$ or both are available as a direct bond or ether bond to one or more adjacent subunits up to total of 30 subunits.

In certain embodiments, the present disclosure provides a composition comprising any of the aforementioned oligomers of flavan-3-ol and at least one other weight management agent, such as an anorectic agent, lipase inhibitor, cannabinoid receptor modulator, psychotropic agent, insulin sensitizer, stimulant, or satiety agent. In further embodiments, the anorectic agent is sibutramine, diethylpropion, benzphetamine, phendimetrazine, or catecholamine. In still further embodiments, the lipase inhibitor is a Rosemary extract, carnosic acid, carnosol, lipostatin, tetrahydrolipostatin, *Punica* granatum pericarp extract, *Marchantia* polymorpha whole plant extract, *Panax* japonicas extract or Platycodi radix extract. In yet further embodiments, the cannabinoid receptor modulator is a cannabinoid receptor agonist, antagonist, or inverse agonist, which may be specific for cannabinoid receptor 1 (CB1), cannabinoid receptor 2 (CB2), or both CB1 and CB2 (e.g., a a cannabinoid receptor 1 (CB1) antagonist or inverse agonist). In further embodiments, the cannabinoid receptor modulator is rimonabant, N-(piperidin-1-yl)-5-(4-iodophenyl)-1-(2,4-dichlorophenyl)-4-methyl-1H-pyrazole-3-carboxamide (AM 251), 1-(2, 4-Dichlorophenyl)-5-(4-iodophenyl)-4-methyl-$N^4$-morpholinyl-1H-pyrazole-3-carboxamide (AM281), 4-[6-methoxy-2-(4-methoxypheyl)1-benzofuran-3-carbonyl] benzonitrile (LY 320135), a *Morus* extract, Diels-Alder adduct of a chalcone and a prenylphenyl moiety from plants (e.g., isolated from or contained in a *Morus alba* extract, a *Milicia excelsa* extract, or is Albanin G, Kuwanon G, Kuwanon M, Cathayanon A, Morusin, Morusinol, Sanggenon C, Sanggenon D, Sanggenon O or a combination thereof), *Magnolia* extract, magnolol, honokiol, magnolol and honokiol, purinol, or *Piper* Longum seed extract. In still further embodiments, the psychotropic agent is a mood stabilizer, anti-depressant, or anti-convulsant. In even further embodiments, the insulin sensitizer is a thiazolidinedione (e.g., rosiglitazone, pioglitazone), a biguanide (e.g., metformin), or a selective mTOT modulator. In yet further embodiments, the stimulant is a Yerba Mate extract, caffeine, green tea extract, green coffee bean extract, *Cola nut* extract, *Citrus* aurantium fruit extract, *Gacinia* extract, *Areca* catechu fruit/seed extract or dextroamphetamine. In further embodiments, the satiety agent is dodecanoic acid, glyceryl dodecanoate, glyceryl 1,3-didodecanoate, glyceryl tridodecanoate and derivatives and mixtures thereof, or hoodia extract, pine nut extract, or a fiber supplement.

In certain embodiments, a composition comprises a Mutamba extract containing or enriched for one or more oligomers of flavan-3-ol as described herein, a *Morus* extract containing or enriched for at least one Diels-Alder adduct of a chalcone and a prenylphenyl moiety, and a *Magnolia* extract, which can be mixed or used together in a 5:2:1 weight ratio to a 10:2:1 weight ratio, respectively. In any of the aforementioned embodiments, a *Morus* extract is a *Morus alba* extract or extract enriched for Kuwanon G, Albanin G, Morusin, or any combination thereof, and a *Magnolia* extract is a *Magnolia* officinalis extract or extract enriched for magnolol, honokiol, both, or a high purity mixture of both.

In certain embodiments, a composition comprises a Mutamba extract containing or enriched for one or more oligomers of flavan-3-ol as described herein, a Rosemary extract, and a Yerba Mate extract, which can be mixed or used together in a 2:1:2 weight ratio to a 1:1:1 weight ratio, respectively.

In still further embodiments, one or more oligomers of flavan-3-ol or compositions of such oligomers of flavan-3-ol compounds as described herein, (optionally including a weight management agent) may be used in a method for treating or preventing weight gain or obesity, promoting weight loss, appetite suppression, modifying satiety, modifying fat uptake, increasing metabolism to promote weight loss or prevent weight gain, maintaining body weight, reducing body fat or fatty tissues, increasing muscle or lean body mass, reducing hepatosteatosis, improving fatty liver, improving one or more liver NASH scores, enhancing fatty acid metabolism in liver, promoting a healthy lipid profile (by, e.g., lowering LDL cholesterol, lowering total cholesterol, lowering triglyceride, or increasing HDL), promoting glucose metabolism, reducing fasting glucose levels, maintaining healthy glucose levels, reducing caloric intake, improving caloric efficiency, reducing food intake, reducing visceral fat, reducing waist circumference, reducing body-to-mass index (BMI), increasing energy, increasing stamina, maintaining energy level while dieting, promoting thermogenesis reducing excess fluids, reducing water retention while maintaining normal hydration, increasing muscle mass, improving fat-to-muscle mass ratio, optimizing or improving body composition, optimizing or improving hormonal balance for appitite control, maintaining normal insulin, leptin, ghrelin, PYY, GIP or enterostatin levels or functions, optimizing, managing or improving hormonal balance to control satiety, maintaining or managing healthy CCK peptide, GLP-1, bombesin, or somatostatin levels or functions, maintaining healthy flora of intestinal tract, optimizing, improving or managing digestion, inducing lipolysis, reducing intracellular triglyceride accumulation, reducing fat accumulation in adipose tissue or an adipocyte, maintaining healthy adiponectin levels, managing or reducing lipogenesis or weight gain associated with metabolism of fructose, glucose or both, reducing or controlling oxidative stress associated with an overweight or obese mammal (e.g., by reducing reactive oxygen species or oxidative free radicals; improving ORAC (Oxygen Radical Absorption Capacity) values; maintaining a healthy level of glutathione, superoxide dismutase, catalase, peroxidase or endogenous antioxidants; maintaining healthy oxidative homeostasis), controlling or managing systemic inflammation associated with an overweight or obese mammal (e.g., by promoting normal metabolism of arachidonic acid, maintaining a normal level of pro-inflammatory cytokines), managing mood stress or other mental disorders associated with an overweight or obese mammal, or any combination thereof.

In related embodiments, a weight management agent for use with the compositions to treat or improve the various weight-related conditions is an anorectic agent, lipase inhibitor, cannabinoid receptor modulator, psychotropic agent, insulin sensitizer, stimulant, satiety agent, or any combination thereof. In any of these embodiments, a weight management agent is an anorectic agent. In any of these embodiments, a weight management agent is a lipase inhibitor. In any of these embodiments, a weight management agent is a cannabinoid receptor modulator. In any of these embodiments, a weight management agent is a psychotropic agent. In any of these embodiments, a weight management agent is an insulin sensitizer. In any of these embodiments, a weight management agent is a stimulant. In any of these embodiments, a weight management agent is a satiety agent.

In any of the aforementioned method of use embodiments, a composition comprising an extract mixture (optionally including a weight management agent) can be formulated with a pharmaceutically or nutraceutically acceptable carrier, diluent or excipient. In further embodiments, the pharmaceutical or nutraceutical formulation comprises from about 0.5 weight percent (wt %) to about 90 wt %, about 0.5 wt % to about 80 wt %, about 0.5 wt % to about 75 wt %, about 0.5 wt % to about 70 wt %, about 0.5 wt % to about 50 wt %, about 1.0 wt % to about 40 wt %, about 1.0 wt % to about 20 wt %, about 1.0 wt % to about 10 wt %, about 3.0 wt % to about 9.0 wt %, about 5.0 wt % to about 10 wt %, about 3.0 wt % to about 6.5 wt % of the major active ingredients in an extract mixture, or the like. In any of these embodiments, the pharmaceutical or nutraceutical composition is formulated as a tablet, a capsule, a powder, or granule.

In any of the aforementioned method of use embodiments, a composition comprising an extract mixture (optionally including a weight management agent) wherein one of the extracts is a *Morus* extract enriched for one or more major active ingredients. In further embodiments, a pharmaceutical or nutraceutical formulation comprising an extract mixture as described herein comprises from about 0.5 weight percent (wt %) to about 5.0 wt % of the major active ingredients in a *Morus* extract enriched for, for example, Kuwanon G, Albanin G, Morusin, or any combination thereof. In certain of these embodiments, a *Morus* extract is a *Morus alba* extract enriched for Kuwanon G, Albanin G, Morusin, or any combination thereof.

In any of the aforementioned method of use embodiments, a composition comprising an extract mixture (optionally including a weight management agent) wherein one of the extracts is a *Guazuma ulmifolia* (Mutamba) extract enriched for one or more major active ingredients. In certain embodiments, a *Guazuma ulmifolia* (Mutamba) extract is enriched for a procyanidin procyanidin B2, procyanidin B5, procyanidin C1, procyanidin dimers, procyanidin trimers, procyanidin tetramers, procyanidin pentamers, procyanidin hexamers, condensed tannins, an oligomer of catechin or epicatechin, epicatechin, or any combination thereof. In further embodiments, a pharmaceutical or nutraceutical formulation comprising an extract mixture as described herein comprises from about 0.5 weight percent (wt %) to about 50 wt % of the major active ingredients in a *Guazuma ulmifolia* (Mutamba) extract, such as a procyanidin procyanidin B2, procyanidin B5, procyanidin C1, procyanidin dimers, procyanidin trimers, procyanidin tetramers, procyanidin pentamers, procyanidin hexamers, condensed tannins, an oligomer of catechin or epicatechin, epicatechin, or any combination thereof.

In any of the aforementioned method of use embodiments, a composition comprising an extract mixture (optionally including a weight management agent) wherein one of the extracts is a *Magnolia* extract enriched for one or more major active ingredients. In further embodiments, a pharmaceutical or nutraceutical formulation comprising an extract mixture as described herein comprises from about 5.0 weight percent (wt %) to about 10 wt % of the major active ingredients in a *Magnolia* extract, such as magnolol, honokiol, both, or a high purity mixture of both. In certain of these embodiments, a *Magnolia* extract is a *Magnolia* officinalis extract enriched for magnolol, honokiol, or both, or a high purity magnolol, honokiol, or mixture thereof isolated from a *Magnolia* officinalis plant extract having at least 90%, 91%, 92%, 93%. 94%, or 95% purity.

In any of the aforementioned method of use embodiments, a composition comprising an extract mixture (optionally including a weight management agent) wherein one of the extracts is a *Ilex paraguayensis* (Yerba Mate) extract enriched for one or more major active ingredients. In certain embodiments, an *Ilex paraguayensis* (Yerba Mate) extract is enriched for caffeine, dicaffeoylquinic acid, or both. In further embodiments, a pharmaceutical or nutraceutical formulation comprising an extract mixture as described herein comprises from about 0.5 weight percent (wt %) to about 5.0 wt % of the major active ingredients in an *Ilex paraguayensis* (Yerba mate) extract, such as caffeine, dicaffeoylquinic acid, or both.

In any of the aforementioned method of use embodiments, a composition comprising an extract mixture (optionally including a weight management agent) wherein one of the extracts is a *Rosmarinus* officinalis (Rosemary) extract enriched for one or more major active ingredients. In certain embodiments, a *Rosmarinus officinalis* (Rosemary) extract is enriched for a carnosol, carnosoic acid, ursolic acid, or any combination thereof. In further embodiments, a pharmaceutical or nutraceutical formulation comprising an extract mixture as described herein comprises from about 1.0 weight percent (wt %) to about 10 wt % of the major active ingredients in a *Rosmarinus officinalis* (Rosemary) extract, such as carnosol, carnosoic acid, ursolic acid, or any combination thereof.

In any of the aforementioned method of use embodiments, a pharmaceutical or nutraceutical formulation comprising an extract mixture (optionally including a weight management agent) of a *Morus* extract, a *Magnolia* extract, and a *Ilex paraguayensis* (Yerba mate) extract, will include from about 0.5 weight percent (wt %) to about 5.0 wt % of the major active ingredients in a *Morus* extract, from about 5.0 wt % to about 10 wt % of the major active ingredients in a *Magnolia* extract, and from about 0.5 wt % to about 5.0 wt % of the major active ingredients in Yerba Mate extract. In certain embodiments, a pharmaceutical or nutraceutical formulation comprises about 1% of the major active ingredients in a *Morus* extract (such as Kuwanon G, Albanin G, Morusin, or any combination thereof), about 7% of the major active ingredients in a *Magnolia* extract (such as magnolol, honokiol, both, or a high purity mixture of both), and about 1% of the major active ingredients in a Yerba Mate extract (such as caffeine, dicaffeoylquinic acid, or both). In any of the aforementioned embodiments, a *Morus* extract is a *Morus alba* extract or extract enriched for Kuwanon G, Albanin G, Morusin, or any combination thereof, and a *Magnolia* extract is a *Magnolia* officinalis extract or extract enriched for magnolol, honokiol, both, or a high purity mixture of both. In any of these embodiments, the pharmaceutical or nutraceutical composition is formulated as a tablet, a capsule, a powder, or granule.

In any of the aforementioned method of use embodiments, a pharmaceutical or nutraceutical formulation comprising an extract mixture (optionally including a weight management agent) of a *Morus* extract, a *Magnolia* extract, and a *Guazuma ulmifolia* (Mutamba) extract, will include from about 0.5 weight percent (wt %) to about 5.0 wt % of the major active ingredients in a *Morus* extract, from about 5.0 wt % to about 10 wt % of the major active ingredients in a *Magnolia* extract, and from about 0.5 wt % to about 50 wt % of the major active ingredients in a Mutamba extract. In certain embodiments, a pharmaceutical or nutraceutical formulation comprises about 1% of the major active ingredients in a *Morus* extract (such as Kuwanon G, Albanin G, Morusin, or any combination thereof), about 7% of the major active ingredients in a *Magnolia* extract (such as magnolol, honokiol, both, or a high purity mixture of both), and about 1% of the major active ingredients in a Mutamba extract (such as a procyanidin procyanidin B2, procyanidin B5, procyanidin C1, procyanidin dimers, procyanidin trimers, procyanidin tetramers, procyanidin pentamers, procyanidin hexamers, condensed tannins, an oligomer of catechin or epicatechin, epicatechin, or any combination thereof). In any of the aforementioned embodiments, a *Morus* extract is a *Morus alba* extract or extract enriched for Kuwanon G, Albanin G, Morusin, or any combination thereof, and a *Magnolia* extract is a *Magnolia officinalis* extract or extract enriched for magnolol, honokiol, both, or a high purity mixture of both. In any of these embodiments, the pharmaceutical or nutraceutical composition is formulated as a tablet, a capsule, a powder, or granule.

In any of the aforementioned method of use embodiments, a pharmaceutical or nutraceutical formulation comprising an extract mixture (optionally including a weight management agent) of a *Morus* extract, a *Rosmarinus officinalis* (Rosemary) extract, and a *Ilex paraguayensis* (Yerba Mate) extract, will include from about 0.5 weight percent (wt %) to about 5.0 wt % of the major active ingredients in a *Morus* extract, from about 1.0 wt % to about 10 wt % of the major active ingredients in a Rosemary extract, and from about 0.5 wt % to about 5.0 wt % of the major active ingredients in a Yerba Mate extract. In certain embodiments, a pharmaceutical or nutraceutical formulation comprises about 1% of the major active ingredients in a *Morus* extract (such as Kuwanon G, Albanin G, Morusin, or any combination thereof), about 4.5% of the major active ingredients in a Rosemary extract (such as carnosol, carnosoic acid, ursolic acid, or any combination thereof), and about 1% of the major active ingredients in a Yerba Mate extract (such as caffeine, dicaffeoylquinic acid, or both). In any of the aforementioned embodiments, a *Morus* extract is a *Morus alba* extract or extract enriched for Kuwanon G, Albanin G, Morusin, or any combination thereof, and a *Magnolia* extract is a *Magnolia officinalis* extract or extract enriched for magnolol, honokiol, both, or a high purity mixture of both. In any of these embodiments, the pharmaceutical or nutraceutical composition is formulated as a tablet, a capsule, a powder, or granule.

EXAMPLES

Example 1

Preparation of Organic and Aqueous Extracts from *Morus alba*

Plant material from *Morus alba* L. root barks was ground to a particle size of no larger than two millimeters (mm). Dried ground plant material (60 grams (g)) was then transferred to an Erlenmeyer flask and Methanol:Dichloromethane (1:1 volume ratio) (600 milliliters (mL)) was added. The mixture was shaken for one hour, filtered and the biomass was extracted again with Methanol:Dichloromethane (1:1 volume ratio) (600 mL). These organic extracts were combined and evaporated under vacuum to provide 3.55 g of organic extract (OE). After organic extraction, the biomass was air dried and extracted once with ultrapure water (600 mL). The aqueous solution was filtered and freeze-dried to provide 4.44 g of aqueous extract (AE).

Similar results were obtained using the same procedure, but with the organic solvent being replaced with methanol or ethanol to provide a methanol extract (ME) or ethanol extract (EE), respectively. Other species and parts of plants and marine sample were extracted using this same procedure.

Example 2

CB1 Binding Activity by Plant Extracts

Cannabinoid receptor binding assays were used as a primary screening method to identify CB1 antagonist compounds. The assays were performed using methods adapted from by Reggio et al., *J. Med. Chem.* 41:5177, 1998 (CB1 receptor assay) and Munro et al., *Nature* 365:61, 1993 (CB2 receptor assay). Briefly, human cannabinoid receptor protein bound to Chem-1 membrane was used in modified HEPES (pH 7.4) buffer. A 10 microgram (μg) aliquot of Chem-1 membrane, radioactively labeled [$^3$H] CB1-ligand SR141716A (2 nanomolar (nM)) (CB1 receptor antagonist) and test extracts or positive control R(+)-WIN-55, 212-2 (10 μM) (CB1 receptor agonist) were incubated in Incubation Buffer (50 mM HEPES (pH 7.4), 5 mM $MgCl_2$, 1 mM CaCl2, 0.2% BSA) for 90 minutes at 37° C. After incubation, the membranes were filtered and washed four times and then the filters were counted to determine amount of [$^3$H] WIN-55,212-2 specifically bound to the CB1-membrane.

Table 1 presents the CB1 binding assay results from the OE and AEs obtained from different plant parts of *Morus alba*: root barks, fruits, leaves, stem barks and stem. The greatest inhibition of CB1-ligand binding activity was found in OE obtained from root barks with 91% inhibition at testing concentration of 100 μg/mL and 82% at testing concentration of 10 μg/mL.

TABLE 1

Inhibition of CB1 ligand binding activity by Extracts from Various *Morus alba* Plant Parts

| Plant Source | Tested Extract | Active Extract | CB1 Inhibition* |
|---|---|---|---|
| *Morus alba* (root barks) | OE†, AE‡ | OE | 91% (100 μg/mL) 82% (10 μg/mL) |
| *Morus alba* (fruits) | EE | — | — |
| *Morus alba* (leaves) | EE#, OE, AE, ME‡ | — | — |
| *Morus alba* (stem barks) | AE | — | — |
| *Morus alba* (stems) | ME | — | — |

*Results are expressed as a percent inhibition relative to control radiolabeled SR141716A ligand.
†OE means ground plant material extracted with Methanol:Dichloromethane (1:1 volume ratio) as described in Example 1.
‡AE means OE extracted material that was air dried and extracted once with ultrapure water, filtered and freeze-dried to provide aqueous extract material as described in Example 1.
EE means that the ground plant material was extracted with only ethanol.
‡ME means that the ground plant material was extracted with only methanol.

These data show that organic extracts of *Morus alba* root bark contain moderately high levels of a component that block the binding of the labeled CB1-ligand to a human CB1 receptor protein. In contrast, the other *Morus alba* plant tissues tested in this experiment (fruits, leaves, stem bark, and stems) all had undetectable levels of inhibition of CB1-ligand binding to CB1 receptor.

The CB1 Binding assay also detected inhibition activity from other species of plants listed in Table 2. The common chemical components in those Moraceae and Fabaceae plants are Diels-Alder adducts of a chalcone and prenylphenyl moiety. The existence of Diels-Alder adducts of a chalcone and prenylphenyl moiety is detectable in different plant tissues, such as roots, stems, rhizomes or whole plants.

TABLE 2

CB1 binding activity from plant extracts containing prenylated flavonoids

| Family | Latin Name | CB1 Binding activity | Plant parts |
|---|---|---|---|
| Moraceae | *Morus alba* | 82% at 10 µg/ml<br>91% at 100 µg/ml | Root barks |
| Moraceae | *Milicia excelsa* | 29% at 10 µg/ml<br>113% at 100 µg/ml | Stem barks |
| Fabaceae | *Glycyrrhize glabra* | 48% at 10 µg/ml<br>67% at 100 µg/ml | Rhizome |

Example 3

High Throughput Purification (HTP) of Active Plant Extracts

Organic extract material (400 mg) from the *Morus alba* root bark extract obtained in Example 1 was loaded onto a prepacked (2 cm ID×8.2 cm, 10 g silica gel) column. The column was then eluted using a Hitachi® High Throughput Purification (HTP) system with a gradient mobile phase of (A) 50:50 volume ratio of EtOAc:Hexane and (B) Methanol from 100% A to 100% B in 30 minutes at a flow rate of 5 mL/min. The separation was monitored using a broadband wavelength UV detector and the fractions were collected in a 96-deep-well plate at 1.9 mL/well using a Gilson fraction collector. The sample plate was dried under low vacuum and centrifugation and then the samples were dissolved with 1.5 mL dimethyl sulfoxide (DMSO) per well. A portion (100 µL) was taken and combined (based on UV trace) for the CB1 inhibition assay. Column fractions having significant CB1 binding activity were retained for further testing.

Example 4

Inhibition of CB1 Activity by Combined HTP Fractions from *Morus alba*

Organic extract of *Morus alba* root bark from Example 3 was further investigated by examining the combined HTP fractions for inhibition of CB1 binding activity by labeled CB1-ligand. The activity profile of combined HTP fractions indicates that more than one component in the fractionated *Morus alba* organic extract might contribute to the inhibition of CB1-ligand binding activity.

Table 3 presents the CB1 binding assay results from the combined HTP fractions of *Morus alba* root bark extract.

TABLE 3

CB1-ligand binding inhibition of combined *Morus alba* HTP fractions

| HTP Fraction Pools | % CB1 Binding Activity Inhibition |
|---|---|
| Fraction 1 to 4 | 46% |
| Fraction 5 to 36 | 88% |
| Fraction 37 to 46 | −55% |
| Fraction 47 to 84 | 85% |
| Fraction 85 to 95 | 78% |
| Fraction 96 | 67% |

Example 5

Isolation, Purification, and Identification of CB1-Binding Inhibitors from *Morus alba* Extracts An organic extract (11 g) from the root barks of *Morus alba*, obtained as described in Example 1, was divided and loaded separately onto two pre-packed flash columns (120 g silica, particle size 32-60 µm, 4 cm×19 cm), and then eluted with Hexane, EtOAc and Methanol (as the mobile phase) at a flow rate of 20 mL/minutes. The gradients started with 95% Hexane/EtOAC for 5 minutes, then increased EtOAC from 5% to 100% over the duration of 25 minutes, and then held at 100% EtOAc for additional five minutes, before increasing MeOH from 0% to 50% MeOH/EtOAC over a next period of 15 minutes, finally changed the elution solution to 100% MeOH and eluted the column for another 16 minutes. The total run time was 66 minutes and 88 fractions were generated for each column. The fractions were analyzed by silica gel thin layer chromatography (TLC) and pooled together to generate eight column eluent pools. Each of the eight eluent pools was then tested using the CB1 binding assay described in Example 2. The resulting CB1 binding assay data are shown in Table 4.

TABLE 4

CB1 activity by Silica Fraction Pools

| Eluent Pool Number | % CB1 Binding Activity Inhibition |
|---|---|
| 1 | −43% |
| 2 | −36% |
| 3 | −5% |
| 4 | 64% |
| 5 | 71% |
| 6 | 29% |
| 7 | 29% |
| 8 | 35% |

These data show that the highest level of inhibition of CB1-ligand binding was in pool 4 (containing 1.4 g of material) and pool 5 (1.7 g of material) when tested in the CB1 binding assay at a concentration of 20 µg/mL.

The resulting best active best pool (containing 300 mg of material) was fractionated on a preparative C18 column (30 cm×250 cm) with a gradient mobile phase of water (A) and methanol (B) over 60 minutes at a flow rate of 20 mL/minute to generate 22 fraction pools. Mass Spectrometry (MS) analysis showed that these pooled fractions of material contain three related compounds, described in more detail below, all of which had inhibitory activity in the CB1-binding assay described in Example 2.

Compound 1 (28.2 mg) was identified as a Diels-Alder adduct of a chalcone and prenylphenyl moiety called Kuwanon G, also known as Moracenin B or Albanin F, by High Resolution Electron Spray Ionization Mass Spectroscopy (HRESIMS) (m/z) [M+H]$^-$=693.2329; UV $\lambda_{max}$ (MeOH): 265, 320 nm; $^1$H NMR (600 MHz, DMSO-d$_6$, 100° C.) δ ppm 1.44 (s, 3 H) 1.52 (br. s., 3 H) 1.58 (s, 3 H) 1.92 (m, 2 H) 3.08 (d, 3 H) 3.56 (m, 2 H) 4.29 (d, J=10.02 Hz, 1 H) 4.48 (m, 1 H) 5.07 (m, 1 H) 5.14 (br. s, 1 H) 5.93 (s, 2 H) 5.96 (dd, J=8.35, 2.23 Hz, 1 H) 6.02 (br s, 1 H) 6.11 (d, J=2.23 Hz, 1 H) 6.41 (dd, J=8.35, 2.23 Hz, 1 H) 6.51 (s, 1 H) 6.60 (m, 1 H) 7.13 (d, J=8.35 Hz, 1 H) 7.28 (br s, 1 H); $^{13}$C NMR (126 MHz, METHANOL-d$_4$) δ ppm 16.35 (1 C) 21.78 (1 C) 23.35 (1 C) 24.53 (1 C) 37.72 (1 C) 97.14 (1 C) 101.57 (1 C) 102.22 (1 C) 102.33 (1 C) 104.28 (1 C) 106.55 (2 C) 107.00 (1 C) 107.21 (1 C) 112.37 (1 C) 114.47 (1 C) 120.27 (1 C) 121.62 (2 C) 123.27 (1 C) 131.05 (1 C) 131.35 (2 C) 132.62 (1 C) 132.99 (1 C) 155.16 (1 C) 155.56 (1 C) 156.38 (1 C) 159.66 (1 C) 160.39 (2 C) 161.13 (1 C) 161.88 (1 C) 164.51 (1 C) 164.63 (1 C) 182.46 (1 C) 208.68 (1 C).

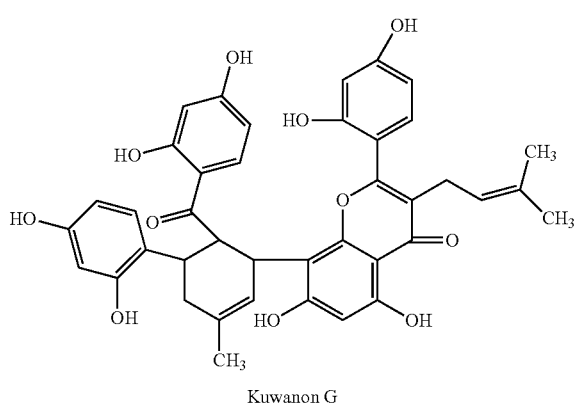 [SMILES: CC(C)=CCc1c(-c2ccc(O)cc2O)oc2c(C3C=C(C)CC(c4ccc(O)cc4O)C3C(=O)c3ccc(O)cc3O)c(O)cc(O)c2c1=O]

Kuwanon G

Compound 2 (10.5 mg) was identified as Albanin G, also known as Kuwanon H or Moracenin A, another Diels-Alder adduct of a chalcone and prenylphenyl moiety by HRESIMS (m/z) [M−H]⁻=759; UV $\lambda_{max}$ (MeOH): 265, 320 nm; $^{13}$C NMR (126 MHz, METHANOL-$d_4$) ppm 16.35 (1 C) 16.47 (1 C) 20.96 (1 C) 21.79 (1 C) 23.32 (1 C) 24.51 (1 C) 24.53 (1 C) 33.74 (1 C) 35.61 (1 C) 36.81 (1 C) 37.77 (1 C) 97.19 (1 C) 102.27 (1 C) 102.33 (1 C) 104.24 (1 C) 106.07 (1 C) 106.53 (2 C) 107.34 (1 C) 112.37 (1 C) 113.94 (1 C) 114.35 (1 C) 120.17 (1 C) 121.60 (2 C) 122.31 (2 C) 123.25 (1 C) 130.21 (2 C) 131.33 (2 C) 132.96 (1 C) 156.37 (3 C) 157.07 (1 C) 159.59 (1 C) 160.37 (1 C) 161.23 (1 C) 161.77 (1 C) 161.96 (1 C) 162.21 (1 C) 182.45 (1 C) 208.82 (1 C).

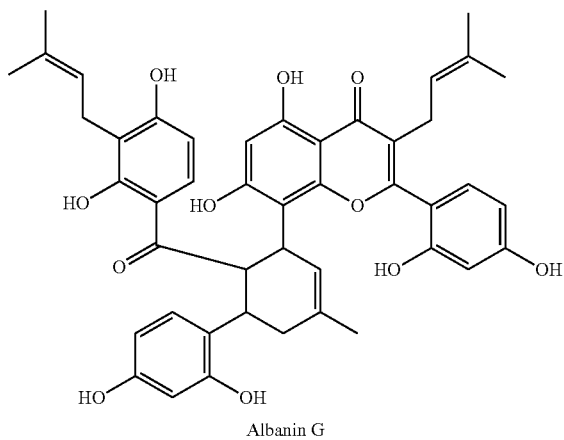 [SMILES: CC(C)=CCc1c(O)ccc(C(=O)C2C(c3c(O)cc(O)c4c(=O)c(CC=C(C)C)c(-c5ccc(O)cc5O)oc34)C=C(C)CC2c2ccc(O)cc2O)c1O]

Albanin G

Example 6

Inhibition of CB1, CB2 and α-Glucosidase by Kuwanon G and Albanin G Purified from *Morus alba*

The CB1 binding assay, described in Example 2, was used to test the Kuwanon G and Albanin G compounds isolated and identified in Example 5. The Kuwanon G Albanin G compounds were tested at concentrations ranging between 0.04 μg/mL and 20 μg/mL, to obtain a dose-response curve for each compound. The sample concentration was plotted against the percent inhibition and the $IC_{50}$ (defined as the concentration at which 50% inhibition of binding activity is achieved in relation to the control) was determined. CB1 assay data for each compound are shown in Table 5.

Inhibition of CB2 receptor-ligand binding activity of the purified Kuwanon G and Albanin G compounds was also examined using methods similar to those described in Example 2 for the CB1 receptor, with some modifications. Briefly, human cannabinoid CB2 receptor protein expressed in CHO-K1 cells were used in modified HEPES buffer (pH 7.0). A 30 μg aliquot of CB2-membrane was mixed with tritium labeled nonspecific CB1 agonist [$^3$H] WIN-55,212-2 (2.4 nM) and test samples of Kuwanon G and Albanin G compounds, or just the non-specific ligand R (+)-WIN-55, 212-2 (10 μM) (positive control) were incubated in incubation buffer (20 mM HEPES (pH 7.0), 0.5 mg/ml BSA) for 90 minutes at 37° C. After incubation, the membranes were filtered and washed; the filters were then counted to determine the amount of radiolabeled [$^3$H] WIN-55, 212-2 that was specifically bound to the CB2-membrane. The CB2 assay data for each compound are shown in Table 5.

Inhibition of rice α-glucosidase activity by each of the purified Kuwanon G and Albanin G compounds was measured as follows. Rice α-Glucosidase inhibition assay: the test compound or vehicle was pre-incubated with 77 mU/ml enzyme Rice α-glucosidase in MES buffer pH 6.3 for 15 minutes at 25° C. The reaction was initiated with addition of 2 mM p-nitrophenyl α-D-glucopyanoside, incubated for another 90 minute at 70° C., and then terminated by adding of 1 M sodium carbonate. The end-product p-nitrophenol was measured by spectrophotometer. The rice α-glucosidase assay data for each *Morus alba* compound is shown in Table 5.

TABLE 5

Inhibition of CB1, CB2 and α-glucosidase by Kuwanon G and Albanin G

| Compound | % Inhibition Rice α-glucosidase (100 μg/ml) | % Inhibition CB1-Binding (20 μg/ml) | CB1 $IC_{50}$ (μM) | CB2 $IC_{50}$ (μM) |
|---|---|---|---|---|
| Kuwanon G | −22% | 92% | 10.1 | 28.9 |
| Albanin G | 66% | 96% | 0.1 | 6.6 |

These data demonstrate that the two major active compounds—Kuwanon G and Albanin G—are CB1 selective inhibitors and that the extract is free from any significant α-glucosidase inhibition.

Example 7

CB1 and CB2 Binding Inhibition by Compounds Purified from *Milicia excelsa* (African Teak)

The organic extract (8 g) from the stem barks of *Milicia excelsa*, obtained using the methods described in Example 1, was divided and loaded separately onto two pre-packed flash columns (120 g silica, particle size 32-60 μm, 4 cm×19 cm), then the column was eluted with the gradient as described in Example 5. A Diels-Alder adduct of a chalcone and prenylphenyl moiety was isolated from one of the active fractions and identified as Sanggenon C/D/O. The structure and spectroscopy data were as follows: ESIMS (m/z) [M−2H]⁻ 706; UV $\lambda_{max}$ (MeOH): 265, 320 nm; $^1$H NMR (500 MHz, METHANOL-$d_4$) ppm 1.55 (s, $CH_3$, 3 H) 1.58 (s, $CH_3$, 3 H) 1.82 (m, $CH_3$, 3 H) 2.28 (dd, J=18.65, 5.09 Hz, 1 H) 2.39 (dd, J=17.80, 5.09 Hz, 1 H) 2.69 (m, 1H) 2.94 (m, 1 H) 3.87 (d, J=6.78 Hz, CH, 1 H) 4.16 (br. s., CH, 1 H) 4.49 (br. s., CH, 1 H) 5.19 (br. s., 1 H) 5.45 (br. s., 1 H) 5.64 (s, 1 H) 6.11 (d, J=2.26 Hz, 1 H) 6.17 (dd, J=8.48, 2.26 Hz, 1H) 6.23-6.34

(m, 3 H) 6.42 (dd, J=8.20, 1.70 Hz, 1 H) 6.86 (d, J=8.19 Hz, 1 H) 7.21 (d, J=8.48 Hz, 1 H) 8.08 (d, J=8.76 Hz, 1 H).

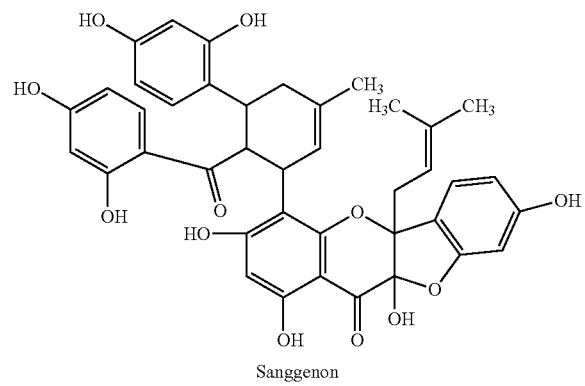 [SMILES: CC(C)=CCC12Oc3c(c(O)cc(O)c3C3C=C(C)CC(c4ccc(O)cc4O)C3C(=O)c3ccc(O)cc3O)C(=O)C1(O)Oc1cc(O)ccc12]

Sanggenon

Sanggenon was tested in the CB1 binding inhibition activity assay as described in Example 2. The activity data are set forth in Table 6.

TABLE 6

Inhibition of CB1 and CB2 by Sanggenon isolated from Milicia excelsa

| Compound | CB1 (20 µg/ml) | CB1 IC$_{50}$ (µM) | CB2 IC$_{50}$ (µM) |
|---|---|---|---|
| Sanggenon | 96% | 3.5 | 24 |

These data show that Sanggenon is a potent inhibitor of CB1 ligand binding with CB1 selectivity over the CB2 receptor protein.

Example 8

Preparation of Various Milicia excelsa Extracts

Milicia EtOAc extract 8 was produced as follows: 5 kg of dried Milicia excelsa stem barks were cut, crushed, and extracted with approximately 4-fold volume (20 L) of ethyl alcohol (Food grade, Korea Ethanol Supplies Company, Korea) in water (v/v). The extraction solvent was treated at 80° C., for 4 hrs and the resulting extraction was filtered to obtain a supernatant that was concentrated with evaporator at 40° C. The above-described extraction procedure was repeated two times. The resulting extraction solutions were combined together and concentrated until the volume become 1/25 of the original volumes. The concentrated solution was then dried by vacuum freeze-drying to obtain 200 g of crude Milicia excelsa EtOH extract powder. 196 g of crude Milicia excelsa EtOH extract powder prepared in the above procedure was suspended in 2 L of distilled water and the suspension was vigorously mixed with 2 L of n-hexane to obtain an n-hexane soluble fraction and water-soluble fraction. The n-hexane soluble fraction was collected and the residual solution was subjected to a second n-hexane extraction. The above-described procedure was repeated four times and the resulting n-hexane soluble fractions were combined and evaporated under vacuum to obtain 74.8 g of n-hexane soluble extract 8-1 of Milicia excelsa stem bark.

The water-soluble fraction of Milicia excelsa stem bark prepared in above procedure was vigorously mixed with an equivalent volume of ethyl acetate to obtain an ethyl acetate soluble fraction and a water-soluble fraction. The ethyl acetate soluble fraction was collected and the residual solution was subjected to the ethyl acetate extraction again. This procedure was repeated four times. The ethyl acetate soluble fractions and water-soluble fractions were respectively evaporated under vacuum to obtain 63.9 g of ethyl acetate soluble extract 8 and 35.34 g of water-soluble extract 8-2 of Milicia excelsa stem bark.

Example 9

Test of α-Glucosidase and CB1 Activity in Morus alba Extracts

The Morus abla 70% EtOH extract and its enriched EtOAc fraction generated from water/EtOAc partition were evaluated for the activity against α-glucosidase in the assay described in Example 6. These data are displayed in Table 7.

TABLE 7

CB1 and α-Glucosidase Inhibition Activity of Morus alba Extracts

| Sample | α-Glucosidase Inhibition (100 µg/ml) | CB1 Inhibition |
|---|---|---|
| 70% EtOH | 99% | 64% (20 µg/ml) |
| EtOAc Fraction | −18% | 58% (5 µg/ml) |

These data show that after EtOAc enrichment of Morus alba ethanol extract, the α-glucosidase inhibition activity of the ethanol extract was eliminated, while the binding inhibition activity of the extract (i.e., prenylated flavonoids) in the CB1 receptor binding assay was retained.

Example 10

In Vitro Study of CB1 Functional Activity of Compounds Isolated from Morus alba and Other Plants In vitro efficacy and CB1 binding specificity of compounds isolated from Morus alba and Milicia excelsa were tested in the human CB1 receptor binding assay, and the agonist or antagonist function of the compounds was determined by measuring the effect on cAMP or agonist-induced cAMP modulation. Assays were performed by Ricerca Biosciences LLC, (Concord, Ohio) on plant extract samples essentially as described by Breivogel et al., J. Biol. Chem. 273:16865, 1998 and Gonsiorek et al., Mol. Pharmacol. 57:1045, 2000.

CB1 Agonist Effect GPCR Functional Assay

Briefly, CHO-K1 cells were suspended in HBSS buffer complemented with HEPES 20 mM (pH 7.4), then distributed in microplates at a density of $10^4$ cells/well in the presence of one of the following: HBSS (basal control), a reference agonist at 100 nM (stimulated control), a reference agonist (EC$_{50}$ determination) or a plant extract test compound. Thereafter, the adenylyl cyclase activator NKH 477 is added at a final concentration of 3 µM. Following a 10 minute incubation at 37° C., the cells are lysed and the fluorescence acceptor (D2-labeled cAMP) and fluorescence donor (anti-cAMP antibody labeled with europium cryptate) were added. After 60 min at room temperature, the fluorescence transfer is measured at λex=337 nm and λem=620 nm and 665 nm using a microplate reader (Rubystar, BMG). The cAMP concentration is determined by dividing the signal measured at 665 nm by that measured at 620 nm (ratio). The results are expressed as a percent of the control response to 100 nM CP 55940 (full CB1 agonist). The standard reference agonist is CP 55940, which is tested in each experiment at several concentrations to generate a concentration-response curve from which its $EC_{50}$ value is calculated.

CB1 Antagonist Effect GPCR Functional Assay

The CHO-K1 cells are suspended in HBSS buffer complemented with HEPES 20 mM (pH 7.4), then distributed in microplates at a density of $10^4$ cells/well and preincubated for five min at room temperature in the presence of one of the following: the reference antagonist, AM 281, at 3 µM (basal control), HBSS (stimulated control), the reference antagonist, for $IC_{50}$ determination, or the test plant extract compounds. The reference agonist CP 55940 is also present at a final concentration of 10 nM or is omitted from the reaction mixture for the basal control. Thereafter, the adenylyl cyclase activator NKH 477 is added at final concentration of 3 µM. Following 10 min incubation at 37° C., the cells are lysed and the fluorescence acceptor (D2-labeled cAMP) and fluorescence donor (anti-cAMP antibody labeled with europium cryptate) are added. After 60 min at room temperature, the fluorescence transfer is measured at $\lambda_{ex}$=337 nm and $\lambda_{em}$=620 nm and 665 nm using a microplate reader (Rubystar, BMG). The cAMP concentration is determined by dividing the signal measured at 665 nm by that measured at 620 nm (ratio). The results are expressed as a percent inhibition of the control response to 10 nM CP 55940. The standard reference antagonist is AM 281, which is tested in each experiment at several concentrations to generate a concentration-response curve from which its $IC_{50}$ value is calculated. The compounds were tested at six different concentrations (0.3, 1, 3, 10, 30, and 150 µM) to generate a dose curve. The results are set forth in Table 8 below.

TABLE 8

CB1 Agonist and Antagonist Activity

| Compound | CB1 Agonist $EC_{50}$ (µM) | CB1 Antagonist Inhibition (at 100 µM) |
|---|---|---|
| Kuwanon G | 85 | −1% |
| Albanin G | ND | 17% |
| Sanggenon | 31 | −14% |

The data presented in Table 7, suggest that the Kuwanon G and Sanggenon compounds are affecting the CB1 receptor activity with agonist-like behavior instead of antagonist. In contrast, Albanin G appears to have a modest antagonist-like activity with the CB1 receptor.

Example 11

HPLC Quantification of Active Extracts from *Morus alba*

Extracts for raw materials were produced as follows: 20 grams of plant powder mixed with Diatomaceous earth was put into a 100 mL extraction cell. It was extracted with solvent (100% EtOH or MeOH/$CH_2Cl_2$ at 1:1) using ASE 350 (Extraction condition: Heat=5 minutes, Static=5 minutes, Flush=80 volume, Purge=900 seconds, Cycles=3, Pressure=1500 psi, Temperature=80° C., Solvent C=100% Ethanol). After extraction, the solution was filtered and collected, then concentrated with evaporator at 50° C. to produce a solid extract.

Agilent HPLC/PDA system was used for the detection and quantification of the Diels-Alder adducts of a chalcone and prenylphenyl moiety Kuwanon G and Albanin in the Morus extracts. The C18 reversed-phase column (Phenomenex, USA) was utilized as Luna 5 um, 50 mm long and 4.6 mm in diameter. A binary Purified water (mobile phase A) and acetonitrile (mobile phase B) gradient was used for elution. The flow rate was set to 1 ml/min passing through the Luna C18 column with a column temperature of 40° C. The UV detector was set to read absorbance at 270 nm.

TABLE 9

Gradient Table of HPLC Analytical Method

| Time (min) | Mobile phase A | Mobile phase B |
|---|---|---|
| 0.0 | 50 | 50 |
| 5.0 | 50 | 50 |
| 30.0 | 20 | 80 |
| 30.5 | 50 | 50 |
| 35.0 | 50 | 50 |

Pure Kuwanon G, pure Albanin G, and Reference Standard Material (RSM, Morus EtOAc fraction 17) were utilized as quantification standards. All extract samples were prepared in a concentration range from 3 mg/ml to 1 mg/ml after sonicating for approximately 15 minutes. The sample solution was cooled in a flask to room temperature and filtered through a 0.45 um nylon syringe filter and 10 µl of the sample was injected into HPLC.

*Morus* plants were collected from China and South Korea from different geological locations in both countries. The HPLC quantification of Kuwanon G and Albanin G content in different species, different plant parts, collected from different locations, and at different age of plants, are listed in Table 10 through Table 14.

TABLE 10

Kuwanon G and Albanin G Content in Two Species of *Morus* Plants

| | % of Extract | | Extraction |
|---|---|---|---|
| Sample | Kuwanon G | AlbaninG | Yield (%) |
| *Morus alba* | 5.13 | 3.98 | 15.8 |
| | 4.6 | 3.09 | 14.1 |
| *Morus catayana* | 0.4 | ND | 9.7 |

TABLE 11

Kuwanon G and Albanin G Contents in Different Parts of *Morus* Plants

| | | The content (%) of extract | | Extraction |
|---|---|---|---|---|
| *Morus alba* | Part | Kuwanon G | AlbaninG | Yield (%) |
| 1 | Leaf | 0.06 | N.D | 7.9 |
| 2 | Fruit | N.D | N.D | 23.1 |
| 3 | Branch | 0.20 | 0.25 | 7.4 |
| 4 | Leaf, Branch | N.D | N.D | 7.3 |
| | Root bark | 3.90 | 2.51 | 17.8 |
| | Root wood | 0.15 | N.D | 5.4 |
| | Fine root | 3.52 | 2.98 | 15.4 |
| | Stem bark | 0.97 | 0.61 | 10.2 |
| | Stem wood | N.D | N.D | 3.2 |
| 5 | Bark | 3.48 | 1.26 | 24.6 |
| | Periderm | 0.09 | ND | 21.5 |

TABLE 12

Kuwanon G and Albanin G Content in *Morus alba* Root Barks from Different Geological Locations in Korea

| Vendor Name | Active content (%) | | Extraction Yield (%) |
|---|---|---|---|
| | Kuwanon G | Albanin G | |
| Kyoungdong | 5.13 | 3.98 | 15.8 |
| Kyoundong | 1.23 | 0.82 | 17.4 |
| Asan | 3.11 | 1.81 | 19.2 |
| Seon-il mulsan | 1.99 | 0.59 | 10.2 |
| Kyoungdong | 0.80 | N.D | 11.05 |

TABLE 13

Kuwanon G and Albanin G Content in *Morus alba* Root Barks purchased from Different Geological Locations in China.

| Vendor Name | The content (%)/Extract | | Extraction Yield (%) |
|---|---|---|---|
| | Kuwanon G | Albanin G | |
| Sichuan | 3.64 | 2.82 | 14.1 |
| Hubei | 0.64 | 0.13 | 6 |
| Hunan | 0.14 | 0.18 | 5.65 |
| Guizhou | 4.60 | 3.09 | 14.1 |
| Yunnan | 0.67 | 0.33 | 8 |
| Sichuan/Xichang | 0.85 | N.D | 12.1 |
| Sichuan/Mian Yang | 4.66 | 2.74 | 11 |
| Sichuan | 3.41 | 2.73 | 14.5 |
| Sichuan | 3.44 | 2.67 | 15.1 |
| Hunan | 4.60 | 2.30 | 11.05 |

TABLE 14

Kuwanon G and Albanin G Content in Different Age of *Morus alba* Root Barks.

| Location | Years old | Content % Extract | | Extraction Yield (%) |
|---|---|---|---|---|
| | | Kuwanon G | Albanin G | |
| A | 2 | 8.85 | 6.12 | 12 |
| | 3 | 3.49 | 2.40 | 8.9 |
| B | 2 | 2.49 | 1.00 | 8.6 |

Example 12

Preparation of *Morus Alba* 70% EtOH Extract 12

Dried *Morus alba* roots and root barks (93.3 kg) were cut, crushed, and then extracted with approximately seven-fold volume (700 L) of 70% ethyl alcohol in water (v/v); the extraction was carried out at 100° C. for 4 hrs. The ethanol solution was filtered to obtain the supernatant, which was then concentrated with an evaporator under vacuum at 40° C. This extraction and concentration procedure was repeated two times. The extraction solutions were then combined together and concentrated until the volume become 1/25 of the original volume. The concentrated solution was dried by vacuum freeze-drying to obtain 18.3 kg of *Morus alba* 70% EtOH extract powder 12. The extraction yield was about 19.6% (w/w). The major active component content is listed in Table 16 of Example 20.

Example 13

Preparation of *Morus alba* EtOAc Fraction 13

*Morus alba* EtOH extract 12 from Example 12 (15 kg) was extracted with approximately two-fold volume (300 L) of ethyl acetate (EP grade, Ducksan Chemical, Korea). Extraction was performed by homogenization of the extraction solution at 15,000 rpm for five minutes with homogenizer (IKA T25D, Germany). The well homogenized extraction solution was then separated by centrifuge (Beckman J-20xP, Germany) at 3,000 rpm (rotor# JLA 8.1000) for five minutes. The upper layer (EtOAc soluble layer) was filtered by filter paper (Hyundai Micro, No. 20, Korea) and the EtOAc solution was collected. The residue (precipitate material) collected from the centrifugation was re-extracted with two-fold volume (300 L) of ethyl acetate (EP grade, Ducksan Chemical, Korea). The re-extracted solution was agitated at 150 rpm for 2 hours. The resulting mixture was then filtered (Hyundai Micro, No. 20, Korea) to obtain an additional EtOAc extract solution. The above-described procedure was repeated two times. The resulting three EtOAc extract solutions were then combined and concentrated by evaporator at 40° C. to obtain the final EtOAc extract 13. The yield was 3.04 kg from 15 kg of 70% EtOH extract. The major active component content is listed in Table 16 of Example 20.

Example 14

Preparation of *Morus alba* EtOAc Fraction 14

*Morus alba* EtOAc fraction 14 was produced from EtOH extract using the extraction methods described in Example 12. 4.5 kg of dried *Morus alba* roots and roots barks yielded 715 g of crude *Morus alba* EtOH extract powder. Corresponding n-hexane soluble and water soluble extracts were prepared from 691.4 g of the crude *Morus alba* EtOH powder after solvent partition. This resulted in production of 95.9 g of the n-hexane soluble extract and 263.8 g of the water-soluble extract of *Morus alba*. The water soluble extract was further partitioned with an equivalent amount of ethyl acetate (EtOAc) to produce an EtOAc extract. The final amount of *Morus alba* EtOAc fraction 14 obtained from this process was 331.8 g. The major active component content is listed in Table 16 of Example 20.

Example 15

Preparation of *Morus alba* EtOAc Fraction 15

Morus EtOAc fraction 15 was produced using the extraction methods described in Examples 12 and 14. Dried *Morus alba* roots and root barks (2.0 kg) yielded 283.5 g of crude *Morus alba* EtOAc extract powder. Corresponding n-hexane soluble and water soluble extracts were prepared from 100 g of the crude *Morus alba* EtOH powder according to the method of Example 14. This resulted in production of 13.7 g of the n-hexane soluble extract and 38 g of the water-soluble extract of *Morus alba*. After solvent partition with EtOAc, the final amount of *Morus alba* EtOAc fraction 15 obtained from this process was 47.6 g. The major active component content is listed in Table 16 of Example 20.

Example 16

Preparation of *Morus alba* EtOAc Fraction 16

Morus EtOAc fraction 16 was produced using the extraction methods described in Examples 12 and 14. 3 kg of dried *Morus alba* roots and root bark yielded 428 g of crude *Morus alba* EtOAc extract powder. Corresponding n-hexane soluble and water soluble extracts were prepared from 300 g of the crude *Morus alba* EtOH powder according to the methods of Example 14. This resulted in production of 40.8 g of the n-hexane soluble extract and 92.7 g of the water-soluble extract of *Morus alba*. After solvent partition with EtOAc, the final amount of *Morus alba* EtOAc fraction 16 obtained from this process was 150.1 g. The major active component content is listed in Table 16 of Example 20.

Example 17

Preparation of *Morus alba* EtOAc Fraction 17

Morus EtOAc fraction 17 was produced using the extraction methods described in Examples 12 and 14. 4 kg of dried *Morus alba* roots and root bark yielded 570 g of crude *Morus alba* EtOH extract powder. Corresponding n-hexane soluble and water soluble extracts were prepared from 570 g of the crude *Morus alba* EtOH powder according to the methods of Example 14. This resulted in production of 80.5 g of the n-hexane soluble extract and 156 g of the water-soluble extract of *Morus alba*. After solvent partition with EtOAc, the final amount of *Morus alba* EtOAc fraction 17, obtained from this process was 327 g. The major active component content is listed in Table 16 of Example 20.

Example 18

Preparation of *Morus alba* 70% EtOH Precipitate Extract 18

*Morus alba* EtOH precipitate extract 18 was produced by follows; 634 kilograms (KG) of dried *Morus alba* roots and root barks were cut, crushed and extracted with approximately 7 fold volume (3600 liters (L)) of 70% ethyl alcohol in water (v/v); the extraction solvent was treated at 80° C., for 4 hrs; the residue was filtered to obtain the supernatant which was then concentrated with an evaporator at 40° C. The above-described procedure was repeated three times. The extraction solutions were then concentrated until the volume become about 1/30 the original starting volumes. Then the concentrated solutions were combined to evaporate again in order to reduce volume of concentrated solution until 1/90 volume of the original extraction solution. The concentrated solution was rested at room temperature for 24 hours (hr) to allow separation into two layers (supernatant and precipitate-layer). The precipitate was filtered and dried by vacuum freeze-drying to obtain M alba 70% EtOH precipitate powder. A total of 24 kg of the resulting product was obtained from 634 kg of raw plant material. The extraction yield was about 3.79% (w/w). The major active component content is listed in Table 16 of Example 20.

Example 19

Preparation of *Morus alba* 70% EtOH Precipitate (19-1), EtOH Combination (19-2), and EtOH Supernatant (19-3) Extracts

*Morus alba* EtOH precipitate extract was produced as follows: 465 kg of dried *Morus alba* roots and root bark were cut, crushed, and extracted with approximately 10-fold volume (4500 L) of 70% ethyl alcohol in water (v/v); the extraction solvent was treated at 80° C. for 4 hrs; the residue was filtered to obtain the supernatant which was concentrated with an evaporator at 40° C. Above-described procedure was repeated three times. The extraction solutions were concentrated until the volume become 1/30 the original volume. The concentrated solutions were then combined and evaporated again to reduce the volume of the concentrated solution until 1/90 volume of the original extraction solution was achieved. The concentrated solution was left at room temperature for 24 hr to allow separation into a supernatant and precipitate layer. The precipitate layer was then dried by vacuum to obtain 12 kg of *Morus alba* 70% EtOH precipitate extract powder. The extraction yield was about 2.6% (w/w). The supernatant layer was dried by vacuum drying to obtain 24 kg *Morus alba* 70% EtOH supernatant extract powder. The extraction yield for the supernatant extract was about 5.2%.

*Morus alba* 70% EtOH combination extract 19-2 was obtained by blending 2 kg of precipitate extract 19-1 and 4 kg of supernatant extract 19-3. The major active component content in both *Morus alba* EtOH precipitate 19-1 and combination extract 19-2 is listed in Table 16 of Example 20.

Example 20

HPLC Quantification of Active Content in Different *Morus alba* Extracts

The detailed HPLC quantification method for Kuwanon G and Albanin G was described in Example 11. With the complexity of crude extracts, different elution solvents, such as the following, could also be utilized: a binary 0.1% phosphoric acid in purified water (mobile phase A) and acetonitrile (mobile phase B) gradient was used for elution (Table 15).

TABLE 15

Gradient table of HPLC Analytical Method

| Time (min) | Mobile phase A | Mobile phase B |
|---|---|---|
| 0 | 33 | 67 |
| 5 | 33 | 67 |
| 55 | 24 | 76 |
| 59 | 0 | 100 |
| 65 | 0 | 100 |
| 66 | 33 | 67 |
| 75 | 33 | 67 |

The flow rate 0.8 ml/min passing through the Luna C18 column with column temperature 35° C. The UV detector was set up at 275 nm. The reference standard material (RSM, Morus EtOAc fraction 17) was extracted with DMSO and utilized for calculation. Table 16 lists the major active components of Kuwanon G and Albanin G in the pilot and production grade Mortis alba root bark extracts and fractions described in Examples 12-19.

TABLE 16

Kuwanon G and Albanin G in Different *Morus alba* Root Bark Extracts and Fractions

| Sample Extract | % Kuwanon G | % Albanin G | % Total Active |
|---|---|---|---|
| 12 | 2.88 | 1.64 | 4.51 |
| 13 | 8.80 | 5.80 | 14.60 |
| 14 | 13.53 | 8.32 | 21.85 |
| 15 | 10.51 | 6.95 | 17.46 |
| 16 | 10.93 | 7.38 | 18.31 |
| 17 (RSM) | 9.95 | 6.65 | 16.60 |
| 18 | 5.30 | 4.16 | 9.46 |
| 19-1 | 6.21 | 4.33 | 10.54 |
| 19-2 | 3.30 | 1.81 | 5.11 |

Example 21

Preparation of Rosemary Steam Distillated EtOH Extract

Dried Rosemary leaf (2.6 kg) was distillated with approximately 6 fold volume (15 L) of water to remove essential oils and volatile components at 100° C. for 5 hrs. After steam distillation the retained residue was filtered to remove the water distillated solution from the residue and then, the residue was re-extracted with 6-fold volume (15 L) of ethyl alcohol (95%) at 80° C. for 5 hrs. The resulting extraction was filtered to obtain a supernatant that was concentrated using an evaporator at 40° C. The above-described extraction procedure was repeated twice. The resulting supernatants were combined together and then concentrated with an evaporator at 40° C. The resulting concentrated solution was then dried by vacuum freeze-drying to obtain 357.1 g of Rosemary steam distillated EtOH extract powder 21. The extraction yield was about 13.7% (w/w). Chemical analysis showed that Rosemary extract 21 contained the following compounds (percent weight): Carnosol: 2.97%; Carnosic Acid: 2.00% and Ursolic acid: 18.49%; total actives of these three compounds 23.80%.

Example 22

Preparation of Rosemary EtOH Extracts 22 and 22-1

Rosemary EtOH extract 22 was produced using essentially the methods described in Example 21. 29 kg of dried Rosemary leaf was distillated with approximately 10-fold volume (300 L) of water to remove essential oils and volatile components at 100° C. for 2 hrs. The residue was next filtered to remove water distillated solution from the residue and then the residue was re-extracted with 10 fold volume (300 L) of 95% ethyl alcohol at room temperature (20° C.) for 2 hrs. The resulting residue was filtered to obtain supernatant that was concentrated with an evaporator at 40° C. The resulting residue was extracted again with a 10-fold volume (300 L) of 70% ethyl alcohol (v/v) at room temperature (20° C.) for 2 hrs. The resulting extract residue was filtered and the supernatants retained and combined. The resulting supernatant was then concentrated with an evaporator at 40° C. The resulting concentrated solution was finally dried by vacuum freeze-drying to obtain 2.5 kg of Rosemary water distillated EtOH extract powder 22. The extraction yield was about 8.6% (w/w). HPLC Actives profile for Carnosol, Carnosic acid and Ursolic acid of this extract are provided in Example 25, Table 18.

Rosemary EtOH extract 22-1 was produced as follows: 58.68 kg of dried Rosemary leaf was distillated with approximately 10 fold volume (600 L) water to remove essential oils and volatile components at 100° C. for 2 hrs; the residue was removed from the water distillated solution by filtration and then the residue was re-extracted with 10 fold volume (600 L) 95% ethyl alcohol at room temperature (20° C.) for 2 hrs. The residue was filtered to obtain supernatant. The residue was then extracted again with 10 fold volume (600 L) 70% ethyl alcohol (v/v) at room temperature (20° C.) for 2 hrs. The doubly extracted residue was filtered to obtain supernatant. Both supernatants were combined and concentrated with an evaporator at 40° C. Concentrated supernatants were dried by vacuum freeze-drying to obtain Rosemary water distillated EtOH extract powder 22-1. The yield was 5.0 kg Rosemary extract powder 22-1 obtained from 58.68 kg of raw material. The extraction yield was about 8.5% (w/w).

Example 23

Preparation of Rosemary Water Distillated EtOH Extract 23

Rosemary EtOH extract was produced essentially as described in Example 22. 62 kg of dried Rosemary leaf yielded 5.9 kg water distillated extract powder. The extraction yield was about 9.5% (w/w). HPLC Actives profile for Carnosol, Carnosic acid and Ursolic acid in this extract 23 are provided in Example 25, Table 10.

Example 24

Preparation of Rosemary Steam Distillated EtOH Extract 24

Rosemary steam distillated EtOH extract was produced essentially as described in Example 21. 2 kg of dried Rosemary leaf yielded 317.7 g of water distillated extract powder designated lot# RN348-3201. The extraction yield was about 15.8% (w/w). HPLC Actives profile for Carnosol, Carnosic acid and Ursolic acid in this extract are provided in Example 22, Table 10.

Example 25

Analytical Results for Rosemary Leaf Extract

The following analytical method was used to determine the amount of Carnosol, Carnosic acid and Ursolic acid in Rosemary steam distillated ethanol extract 24 and water distillated ethanol extracts 22 and 23. An Agilent HPLC/PDA system was used with a C18 reversed-phase column (Phenomenex, USA, Luna 5 um, 250 mm×4.6 mm), for detection and quantitation of Carnosol, Carnosic acid and Ursolic acid. A binary 0.1% phosphoric acid in purified water (mobile phase A) and acetonitrile (mobile phase B) gradient was used for elution as set forth in Table 9. The column flow rate was set at 1 ml/min passing through the Luna C18 column with a column temperature of 40° C. The UV detector was set up to read absorbance at 210 nm.

TABLE 17

Rosemary Gradient Elution Scheme

| Time (min) | Mobile phase A | Mobile phase B |
|---|---|---|
| 0 | 40 | 60 |
| 5 | 20 | 80 |
| 30 | 0 | 100 |
| 34 | 0 | 100 |
| 35 | 40 | 60 |
| 40 | 40 | 60 |

Carnosol, Carnosic acid and Ursolic acid standards were purchase from Sigma and dissolved in DMSO. Highest level control concentration of carnosol and carnosic acid was made to 0.1 mg/ml. The highest level control concentration of ursolic acid was made to 0.3 mg/ml and diluted to (0.065 mg/ml or 0.02 mg/ml) using methanol. The test sample concentration were adjusted to about 1 mg/ml in methanol in a volumetric flask and sonicated until the sample dissolved (approximately 20 minutes). The sample flask was then cooled to room temperature, mixed well and filtered through a 0.45 um nylon syringe filter and then 10 ul of sample was injected into HPLC. HPLC results showed the Table 10.

TABLE 18

HPLC Results of Rosemary Leaf Extracts

| Sample Extract | Carnosol % | Carnosic acid % | Ursolic acid % | Total % |
|---|---|---|---|---|
| 22 | 8.84 | 4.37 | 7.83 | 21.04 |
| 23 | 6.52 | 5.32 | 10.47 | 22.31 |
| 24 | 4.07 | 2.69 | 14.53 | 21.30 |

Example 26

Preparation of Yerba Mate Ethyl Alcohol Extract 26

Yerba Mate (*Ilex paraguariensis*) EtOH extract was produced as follows: 1 kg of dried *Ilex paraguariensis* leaf, was cut, crushed, and extracted with a 20-fold volume (20 L) of 95% ethyl alcohol at 85° C. for 4 hrs. The resulting residue was filtered to obtain a supernatant that was concentrated with an evaporator at 40° C. The resulting residue was extracted a second time with 20-fold volume (20 L) of 95% ethyl alcohol (v/v) at 85° C. for 4 hrs and filtered to obtain a second supernatant which was concentrated with an evaporator at 40° C. The resulting concentrated cake was dried under vacuum to obtain 260 g of Yerba Mate EtOH extract powder. The extraction yield was about 26% (w/w).

Example 27

Preparation of Yerba Mate Ethyl Alcohol Extract 27

Yerba Mate EtOH extract was produced as follows: 150 kg of dried Yerba Mate (*Ilex paraguayensis*) leaf were cut, crushed, and extracted with approximately 7-fold volume (1050 L) of 70% ethyl alcohol in water (v/v) and the extraction solvent held at 100° C. for 4 hrs. The residue was filtered to obtain a supernatant that was concentrated with an evaporator at 40° C. The above-described procedure was repeated twice. The extraction solutions were then combined together and concentrated until the volume become 1/25 of the original volume. The concentrated solution was dried by vacuum freeze-drying to obtain 26.7 kg of *Mate* 70% EtOH extract powder. The extraction yield is about 17.8% (w/w). HPLC analysis, as described in Example 29, determined that the amount of Caffeine in Yerba Mate extract 27 was 2.44% by weight.

Example 28

Quantification of Caffeine in Yerba Mate Leaf Extract

The following analytical method was used to determine the amount of Caffeine in the Yerba Mate leaf extracts. The same Agilent HPLC/PDA system, including the C18 reversed-phase column (Phenomenex, USA) described in Example 25 was used for the detection of Caffeine and minor components. A binary 0.1% phosphoric acid in purified water (mobile phase A) and methanol (mobile phase B) gradient was used for elution of Mate sample components as described in Table 11. The flow rate was set to 1 ml/min passing through the Luna C18 column with a column temperature of 35° C. The UV detector was set to read absorbance at 275 nm.

TABLE 19

Yerba Mate Gradient Elution Scheme

| Time (min) | Mobile phase A | Mobile phase B |
|---|---|---|
| 0 | 95 | 5 |
| 5 | 95 | 5 |
| 65 | 0 | 100 |
| 75 | 0 | 100 |
| 80 | 95 | 5 |
| 90 | 95 | 5 |

The quantification standard—Caffeine was purchased from Sigma. Dicaffeoylquinic acid (DCYA) standards were purchased from Chengdu Biopurify Phytohemicals Ltd., and dissolved in DMSO. The highest concentration level of caffeine and 4,5-DCYA was 0.05 mg/ml and diluted to L5 from L1 (0.0031 mg/ml) using methanol. The highest concentration level of 3,4-DCYA was 0.02 mg/ml and diluted to L5 from L1 (0.00125 mg/ml) using methanol. The highest concentration level of 3,5-DCYA was 0.025 mg/ml and diluted to L5 from L1 (0.0016 mg/ml) using methanol. Concentration of Yerba Mate leaf extract samples were adjusted to about 1 mg/ml in methanol in a volumetric flask and sonicated until dissolved (approximately 20 minutes), and then cooled to room temperature, mixed well and filtered through a 0.45 um nylon syringe filter. 10 μl of sample was examined by HPLC. HPLC actives quantification results for Yerba Mate extract 27 and weight loss Compositions 1 and 3 (exemplified in Examples 38 and 39, respectively) are provided in Table 20.

TABLE 20

HPLC Quantification of Yerba Mate Extract and Weight Loss Compositions

| Sample | Caffeine | 3-4 DCYA | 3-5 DCYA | 4-5 DCYA | Total % |
|---|---|---|---|---|---|
| 27 | 2.44 | 0.77 | 1.24 | 2.09 | 6.55 |
| Composition 1 | 1.80 | 0.58 | 0.94 | 1.56 | 4.88 |
| Composition 3 | 1.29 | 0.41 | 0.69 | 1.43 | 3.82 |

Example 29

Preparation of *Magnolia* Extracts 29 and 29A

*Magnolia* (*Magnolia officinalis*) extract 29 was produced as follows. 70 kg of dried stem barks of *Magnolia* officinalis was cut, crushed, and extracted with 70% ethyl alcohol and the extraction solvent treated at 80° C. for 4 hrs. The resulting the residue was filtered to obtain a supernatant that was concentrated with an evaporator at 40° C. The above-described procedure was repeated two times. The extraction solutions were then combined together and concentrated until the volume become 1/25 of the original volume. Sodium hydroxide (NaOH) was added into the concentrated solution to obtain a final concentration of 1% NaOH. After saponification at 80° C. for 30 min, the solution was extracted with 2-fold volume of Hexane with agitator for 1 hour. The resulting Hexane soluble fraction was then collected and above-described procedure repeated three times.

The n-hexane soluble fractions were combined and evaporated under vacuum until the volume become 1/6 of the original volume. High purity *Magnolia* extract was obtained after re-crystallization vacuum drying. 70 kg of dried stem barks of *Magnolia officinalis* yielded 652 g of high purity *Magnolia* extract. The extraction yield is 0.93%. A second batch of *Magnolia* extract (29A) was also produced according to the same procedure. Quantification of the active content in both extracts is provided in the following example.

Example 30

Analytical Method for Analysis of *Magnolia* stem bark Extracts

The following analytical method was used to determine the amount of Magnolol and Honokiol in *Magnolia* stem bark extracts. The same Agilent HPLC/PDA system, including the C18 reversed-phase column (Phenomenex, USA) described in Example 25 was used for the detection of Magnolol and Honokiol. A binary purified water (mobile phase A) and acetonitrile (mobile phase B) gradient was used for detection of Magnolol and Honokiol as described in Table 13. The flow rate was set to 1 ml/min passing through the Luna C18 column with a column temperature of 35° C. and absorbance was read at 290 nm.

TABLE 21

*Magnolia* Gradient Elution Scheme

| Time (min) | Mobile phase A | Mobile phase B |
|---|---|---|
| 0.0 | 23 | 77 |
| 18.0 | 23 | 77 |
| 18.1 | 0 | 100 |
| 25.0 | 0 | 100 |
| 25.1 | 23 | 77 |
| 30.0 | 23 | 77 |

Magnolol and Honokiol standards were purchased from Guangzhou Honsea Sunshine Bio Science and Technology co., Ltd. and extracted with methanol. The highest standard concentration of Honokiol and Magnolol was 0.2 mg/ml and diluted to L3 from L1 (0.05 mg/ml) using methanol. The *Magnolia* stem bark extract sample concentration was adjusted to about 0.2 mg/ml and combination sample concentration was 2 mg/ml in methanol. A volumetric flask was used in sample preparation and sonicated until dissolved (approximately 10 minutes), flask was cooled to room temperature and QS with extraction method, mixed well and filtered through a 0.45 um nylon syringe filter and 20 μl sample was analyzed by HPLC. The HPLC quantification results are provided in Table 22.

TABLE 22

HPLC Results of Magnolol and Honokiol in *Magnolia* Stem Bark Extracts

| Sample | Honokiol % | Magnolol % | Total % (by weight) |
|---|---|---|---|
| 29A | 46.23 | 51.54 | 97.77 |
| 29 | 51.20 | 47.20 | 98.40 |

Example 31

Preparation of *Areca catechu* 70% EtOH Extract 31

Ground *Areca catechu* seed (7 kg) was divided into two portions of 3 kg and 4 kg, crushed and place into two extraction units and extracted with about an 8-fold volume (about 240 L and 320 L) of 70% ethyl alcohol in water (v/v) and the extraction solvent held at 90° C. for 4 hrs. After filtering the extract solution, the filtrate was concentrated with an evaporator at 50° C. until only a water solution remained, which was then collected and frozen at −70° C. The remaining crushed seed material was then extracted again as before. The $1^{st}$ and $2^{nd}$ frozen extract solutions were then dried in a freeze dryer device. The dried extracts were combined and ground into a fine powder to obtain 930 g. The final extraction yield was about 13.2% (w/w).

Example 32

Preparation of *Mutamba* (*Guazuma ulmifoila*) stem bark EtOH Extract 32

Mutamba EtOH extract 32 was produced as follows: 500 g of dried Mutamba (*Guazuma ulmifolia*) stem bark was cut, crushed and extracted with 20-fold volume (10 L) of 95% ethyl alcohol at 85° C. for 4 hrs. The residue was filtered to obtain a supernatant. The residue was then extracted a second time as before and the two EtOH supernatants combined together and concentrated with evaporator at 40° C. The concentrated cake was dried by vacuum drying to obtain 70 g of *Mutamba stem bark* EtOH extract powder. The extraction yield was about 14% (w/w). HPLC analysis showed that this extract contained 1.31% Procyanidin B2 and 0.86% Epicatechin.

Example 33

Preparation of Mutamba Extracts 33, 33-1, and 33-2

Mutamba EtOH extract 33 was produced as follows: two different batches of 2.3 kg of dried *Mutamba stem bark* were cut, crushed and then each batch was extracted with 15-fold volume (30 L) of 95% ethyl alcohol at 85° C. for 4 hrs. The residue was filtered to obtain two batch supernatants. The two supernatants were combined and concentrated with an evaporator at 40° C. The resulting concentrated cake was then dried by vacuum to obtain 370 g of Mutamba EtOH extract powder 33. The extraction yield is about 8.04% (w/w).

The two residues from the above-extraction were then extracted again with about a 15-fold volume (30 L) of 95% ethyl alcohol (v/v) at 85° C. for 4 hrs. The residue was filtered to obtain a supernatant that was concentrated with an evaporator at 40° C. The resulting concentrated cake was dried by vacuum drying to obtain 290 g of Mutamba EtOH extract powder 33-1 and the extraction yield was about 6.3% (w/w).

The Mutamba EtOH extract 33-2 was produced as follows: Mutamba EtOH powder extracts 33 and 33-1 were combined together and pulverized resulting in 660 g of Mutamba EtOH extract 33-2. The final extraction yield was about 14.34% (w/w). HPLC analysis showed that this extract contained 0.96% Procyanidin B2 and 0.62% Epicatechin.

Example 34

Preparation of Mutamba EtOH Extract Fractions 34, 34-1, and 34-2

Mutamba EtOH extract derived fractions 34, 34-1, and 34-2 were produced as follows: 500 g of *Mutamba stem bark* EtOH extract 33-2 from Example 33, was suspended in 5 L of distilled water and the suspension was mixed with 5 L of ethylacetate vigorously to divide into an ethylacetate soluble fraction and a water-soluble fraction. The ethylacetate soluble fraction was collected and the residual solution was subjected to a second ethylacetate extraction. The above-described procedure was repeated three times. The collected ethylacetate soluble fractions were pooled and then evaporated in vacuo to give 117 g of ethylacetate soluble extract of Mutamba stem bark 34. HPLC analysis showed that this extract contained 2.57% Procyanidin B2 and 2.24% Epicatechin.

A water-soluble fraction of Mutamba stem bark EtOH extract 33-2 prepared in Example 33 was vigorously mixed with an equivalent volume of butyl alcohol and water, and allowed to separate into a butyl alcohol soluble fraction and water-soluble fraction. The butyl alcohol soluble fraction was collected and the residual solution was subjected to the butyl alcohol extraction again. This procedure was repeated three times. The respective fractions were pooled and evaporated in vacuo to obtain 260 g of butyl alcohol soluble extract 34-1 and 130 g of water-soluble extract 34-2 of Mutamba stem bark. HPLC analysis showed that Mutamba extract fraction 34-1 contained: 1.31% Procyanidin B2 and 0.86% Epicatechin. HPLC analysis was not performed on Mutamba extract fraction 34-2.

Example 35

Preparation of Mutamba EtOH Extract 35

Mutamba EtOH extract 35 was produced by follows: 920 g of dried Mutamba stem bark was cut, crushed, and extracted with 20-fold volume (20 L) of 95% ethyl alcohol at 85° C. for 4 hrs. The residue was filtered to obtain a supernatant and the retained residue was then again extracted with 20 L of 95% ethyl alcohol (v/v) and filtered as before. The resulting supernatants were combined together and concentrated with an evaporator at 40° C. The resulting concentrated cake was dried under vacuum to obtain 132 g of Mutamba EtOH extract powder 35. The extraction yield was about 14.34% (w/w). HPLC analysis showed that extract 35 contained 1.03% Procyanidin B2 and 0.60% Epicatechin.

Example 36

Preparation of Mutamba EtOH Extract 36

Mutamba EtOH extract 36 was produced as follows: 85.7 kg of dried Mutamba stem bark was cut, crushed, and extracted with approximately 8-fold volume (720 L) of 70% ethyl alcohol in water (v/v) after incubation in the extraction solvent at 100 C for 4 hrs. The residue was filtered to obtain a retained supernatant and the residue was then re-extracted twice more using the same extraction procedure. The retained supernatants were then were combined together and concentrated until the volume was 1/25 of the original starting volume. This concentrated solution was then dried by vacuum freeze-drying to obtain 13.9 Kg of Mutamba stem bark 70% EtOH extract powder 36. The extraction yield was about 16.2% (w/w). The extraction yield was about 14.34% (w/w). HPLC analysis showed that extract 36 contained 1.03% Procyanidin B2 and 0.60% Epicatechin.

Example 37

HPLC Quantification of Various Mutamba Extracts

An Agilent HPLC/PDA system was used for the detection and quantitation of procyanidin B2 and epicatechin compounds in Mutamba plant extracts obtained from trees grown in different locations, using different tree parts, different tree sexes and different tree ages. A C18 reversed-phase column (Agilent, USA) was used (Zorbax eclipse XDB-C18, 3.5 um, 150 mm×4.6 mm. A binary column gradient was used for elution of material from the column. Mobile Phase A: 0.01% trifluoroacetic acid in purified water, and Mobile Phase B: acetonitrile gradient was used for elution (Table 23). The flow rate was set to 0.8 ml/min passing through the Luna C18 column with a column temperature of 35° C. The UV detector was set to record absorbance at 275 nm.

TABLE 23

Gradient Table of HPLC Analytical Method

| Time (min) | Mobile Phase A | Mobile Phase B |
|---|---|---|
| 0 | 92 | 8 |
| 10 | 83 | 17 |
| 20 | 80.6 | 19.4 |
| 25 | 77.4 | 22.6 |
| 28 | 70.0 | 29.8 |
| 30 | 35 | 65 |
| 38 | 0 | 100 |
| 40 | 0 | 100 |
| 42 | 92 | 8 |
| 45 | 92 | 8 |

Pure epicatechin reference sample was purchased from Sigma. Pure procyanidin B2 was purchased from Chengdu Biopurify Phytohemicals, Ltd. Both reference samples were dissolved in DMSO. Highest level concentration range of epicatechin was 0.05 mg/ml and diluted to L5 from L1 (0.003 mg/ml) using 50% methanol in water. Highest level concentration of procyanidin B2 was 0.05 mg/ml and diluted to L5 from L1 (0.003 mg/ml) using 50% methanol in water. Concentration of the Mutamba extract samples were adjusted to 2 mg/ml in 50% methanol in water in a volumetric flask and sonicated until dissolved (approximately 20 minutes), and then cooled to room temperature, mixed well and filtered through a 0.45 um nylon syringe filter. HPLC analysis was performed by injecting a 10 μl sample into the HPLC.

1. Belize

All plant materials were cut, crushed, and extracted with 70% EtOH and the procyanidin B2 and epicatechin contents analyzed by HPLC as described above. The HPLC results are presented in Table 24.

TABLE 24

Procyanidin B2 and Epicatechin Content in Mutamba Trees from Belize

| Mutamba | | | Content (%) of Extract | | | Extraction |
|---|---|---|---|---|---|---|
| Tree Sample | Ext ID | Tree Part | Procyanidin B2 | Epicatechin | Total | Yield (%) |
| One year old female tree | B1 | Stem | 0.67 | 0.94 | 1.61 | 8.9 |
| | B2 | Bark | 1.18 | 1.06 | 2.24 | 17.1 |
| Mature female tree | B3 | Stem | 0.99 | 1.04 | 2.03 | 6.5 |
| | B4 | Bark | 1.92 | 1.54 | 3.45 | 12.4 |
| Female tree (3 m height) | B5 | Bark | 4.49 | 2.21 | 6.70 | 17.1 |
| | B6 | Stem | 1.02 | 1.03 | 2.05 | 7.5 |
| Female tree (3-4 m height) | B7 | Bark | 2.98 | 1.55 | 4.52 | 20.4 |
| | B8 | Stem | 1.01 | 1.03 | 2.03 | 9.3 |
| Mature male tree | B9 | Bark | 3.97 | 2.00 | 5.97 | 15.1 |
| | B10 | Stem | 0.31 | 0.70 | 1.01 | 7.2 |

2. India

Five different Mutamba samples from different tree parts were purchased from a vendor in India. The plant materials were cut, crushed, and extracted with MeOH/$CH_2Cl_2$ (1:1 volume ratio) and the procyanidin B2 and epicatechin contents analyzed by HPLC as described above. The HPLC results are presented in Table 25.

TABLE 25

Procyanidin B2 and Epicatechin Content in Mutamba Trees from India

| Extract | | Content (%) of Extract | | | Extraction |
|---|---|---|---|---|---|
| No. | PART | Procyanidin B2 | Epicatechin | Total | Yield (%) |
| I1-1 | Leaf | 0 | 0 | 0 | 13.4 |
| I1-2 | Fruit | 0 | 0 | 0 | 12.7 |
| I1-3 | Fine stem | 0 | 0 | 0 | 8.2 |
| I1-4 | Stem bark | 0 | 0 | 0 | 5.6 |
| I1-5 | Stem wood | 0 | 0 | 0 | 2.2 |

3. Six Different Countries.

Mutamba stem bark samples from six different countries were purchased from a vendor. The plant materials were cut, crushed, and extracted with 100% EtOH (E) or 70% EtOH (70E) or MeOH/$CH_2Cl_2$ (1:1 volume ratio)(OE) and the procyanidin B2 and epicatechin contents analyzed by HPLC as described herein. The HPLC results are presented in Table 26.

TABLE 26

Procyanidin B2 and Epicatechin Content in Mutamba Stem Bark from Different Countries

| Extract | | % Content/Extract | | | Extraction | |
|---|---|---|---|---|---|---|
| No. | Country | Procyanidin B2 | Epicatechin | Total | Yield (%) | Solvent |
| U1 | Peru | 1.14 | 0.62 | 1.76 | 28 | 70E |
| M2 | Mexico | 0.98 | 0.36 | 1.33 | 3 | 70E |
| B11 | Belize | 1.31 | 0.75 | 2.06 | 13 | 70E |
| P99 | Panama | 1.31 | 0.86 | 2.17 | | E |
| E10 | England | 0.31 | 0.05 | 0.36 | 8.1 | 70E |
| I1-4 | India | 0 | 0 | 0 | 5.6 | OE |

Example 38

Preparation of Magnolia:Morus:Yerba Mate Composition 1

Three component (Magnolia:Morus:Yerba Mate) Composition 1 was produced by from the following three plant extract components: 1.02 kg of dried *Magnolia* extract powder 29, 2.01 kg of *Morus alba* root bark extract powder 18, and 10.08 kg of Yerba Mate extract powder 27 were blended with v-type blender (Seo-kang Engineering, Korea) at 30 rpm for 1 hour. The final blending weight ratio was Magnolia:Morus:Yerba Mate of 1:2:10 and resulted in production of 12.65 kg of weight loss combination Composition 1. The major active compound profile in Composition 1 was determined by HPLC analysis as described in Examples 11, 20, 25, 28 and 30. The quantification results are shown in the Table 27.

TABLE 27

Summary of Active Components in Composition 1

| | *Magnolia* | | *Morus* | | Yerba Mate |
|---|---|---|---|---|---|
| Sample | Honokiol % | Magnolol % | Kuwanon G % | Albanin G % | Caffeine % |
| Composition 1 | 3.88 | 3.91 | 1.09 | 0.77 | 1.80 |

Example 39

Preparation of Morus:Rosemary:Yerba Mate Composition 3

Three component (Morus:Rosemary:Yerba Mate) Composition 3 was produced as follows: 2.4 kg of dried Morus root bark extract powder 18, 6.0 kg of dried Rosemary extract powder 23, and 12.04 kg of dried Yerba Mate extract powder 27 were blended with v-type blender (Seo-kang Engineering, Korea) at 30 rpm for 1 hour. The final blending weight ratio was *Morus:Rosemary:Mate* at 2:5:10 and resulted in 20.4 kg of Composition 3. The active contents in the composition were quantified with the HPLC illustrated in Examples 11, 20, 25, 28 and 30. The quantification results are shown in the Table 28.

TABLE 28

Summary of Active Content of Composition 3

| | Rosemary | | | *Morus* | | Mate |
|---|---|---|---|---|---|---|
| Sample | % Carnosol | % Carnosic acid | % Ursolic acid | % Kuwanon G | % Albanin G | % Caffeine |
| Composition 3 | 1.59 | 0.44 | 3.45 | 0.77 | 0.53 | 1.29 |

Example 40

Preparation of Morus:Acceleris:Loesyn:Bakutrol Composition 6

Four component (Morus:Acceleris:Loesyn:Bakutrol) composition 6 was produced as follows: 968.6 g of *Morus alba* root bark extract 20, 484.3 g of *Panax ginseng* extract (Acceleris), and 387.4 g of standardized Aloe chromones in Aloe vera inner leaf gel powder (Loesyn) were combined in a capped one-gallon jar, then shaken and turned in the jar to produce a uniform powder (Powder 1). 96.9 g of *Psoralea seed* extract (Bakutrol) was placed in a 2-liter beaker, and gradually one-half of Powder 1 was added to the *Bakutrol* liquid until a granule-like mixture was achieved. This mixture was then added to the remaining half of Powder 1 and mixed thoroughly. Finally, the complete mixture was put into a blender for pulverizing. The final combination composition 6 had a blending weight ratio of *Morus:Acceleris: Loesyn:Bakutrol* at 10:5:4:1. The active contents of Composition 6 are shown in Table 29.

TABLE 29

Summary of Active Contents in Composition 6

| Sample | Acceleris Total Ginsenoside (Rd, Rg3, Rk1, Rg5) | Loesyn % Aloesin | *Morus alba* root bark extract % Kuwanon G | *Morus alba* root bark extract % Albanin G | Bakutrol % Bakuchiol |
|---|---|---|---|---|---|
| Composition 6 | 10.02 | 0.80 | 1.57 | 0.88 | 3.34 |

Example 41

Preparation of Morus:Rosemary:Areca Composition 9

Three component (Morus:Rosemary:Areca) composition 9 was produced as follows: 153.2 g of dry *Morus alba* root bark extract 18, 382.2 g of Rosemary extract powder 22-1, and 765.8 g of *Areca catechu* fruit extract powder 31, were blended together with a ribbon blender (Hankook P. M. EMG, Korea) at 30 rpm for 1 hour to obtain 1.301 kg of UP609. The blending ratio of Morus:Rosemary:Areca was 2:5:10 (weight ratio). The active contents of Composition 9 are shown in Table 30.

TABLE 30

Summary of Active Content in Composition 9

| Sample | Rosemary Carnosol % | Rosemary Carnosic acid % | Rosemary Ursolic acid % | Morus Kuwanon G % | Morus Albanin G % | Areca |
|---|---|---|---|---|---|---|
| Composition 9 | 2.14 | 2.01 | 5.12 | 0.63 | 0.45 | — |

Example 42

Preparation of Magnolia:Morus:Mutamba Composition 2

Three component (Magnolia:Morus:Mutamba) Composition 2 was produced as follows: 1.02 Kg of dry *Magnolia* extract powder 29, 2.04 Kg of dry *Morus alba* root bark extract powder 18, and 10.05 Kg of dry Mutamba stem bark extract powder 36, were blended together with a v-type blender (Seo-kang Engineering, Korea) at 30 rpm for 1 hour to obtain 13.05 Kg of Composition 2. The blending ratio of *Magnolia:Morus:Mutamba* was 1:2:10 (weight ratio).

TABLE 31

Summary of Active Ingredients for Composition 2

| Sample | Magnolia Honokiol % | Magnolia Magnolol % | Morus Kuwanon G % | Morus Albanin G % | Mutamba Procyanidin B2 | Mutamba Epicatechin |
|---|---|---|---|---|---|---|
| Composition 2 | 4.06 | 4.19 | 1.01 | 0.71 | 1.10 | 0.81 |

Example 43

Preparation of Mutamba:Rosemary:Mate Composition 4

Three component (Mutamba:Rosemary:Mate) Composition 4 was produced as follows: 352.3 g of Mutamba stem bark extract powder 36, 352.1 g of Rosemary extract powder 22, and 352.1 g of Mate extract powder 27, were blended with a ribbon-style blender (Seo-kang Engineering, Korea) at 30 rpm for 1 hour to obtain 1.04 Kg of combination Composition 4. The blending ratio of Mutamba:Rosemary: Mate was 1:1:1 (weight ratio).

TABLE 32

Summary of Active ingredients for Composition 4

| Sample | Rosemary Carnosol % | Rosemary Carnosic acid % | Rosemary Ursolic acid % | Mutamba Procyanidin B2 | Mutamba Epicatechin | Mate Caffeine % |
|---|---|---|---|---|---|---|
| Composition 4 | 2.11 | 1.79 | 2.30 | 0.47 | 0.32 | 0.71 |

Example 44

Preparation of Mutamba:Rosemary:Mate Composition 8

Three component (Mutamba:Rosemary:Mate) Composition 8 was produced as follows: 640.2 g of Mutamba stem bark extract powder 36, 320.1 g of Rosemary extract powder 22, and 640.2 g of Mate extract powder 27, were blended with a ribbon-style blender (Seo-kang Engineering, Korea) at 30 rpm for 1 hour to obtain 1.52 Kg of combination Composition 8. The blending ratio of Mutamba:Rosemary:Mate was 2:1:2 (weight ratio).

TABLE 33

Summary of Active Ingredients for Composition 8

| Sample | Rosemary | | | Mutamba | | Mate |
| --- | --- | --- | --- | --- | --- | --- |
| | Carnosol % | Carnosic acid % | Ursolic acid % | Procyanidin B2 | Epicatechin | Caffeine % |
| Composition 8 | 1.64 | 0.94 | 3.56 | 0.53 | 0.45 | 2.44 |

Example 45

Acute Food Intake in Sprague-Dawley Rats as a Measure of Appetite Suppression This example describes the acute food intake rat animal model for evaluation of the effects of diet and test compounds on amount and rate of food intake of rats after a fasting period.

Method:

Male Sprague-Dawley (SD) rats (Koatech, Korea), eight weeks of age at the beginning of the experiment, were used in this study. During acclimation periods the animals were maintained on a regular rat chow diet (2018S, Harlan, USA). The rats were housed in a climate-controlled room maintained on a 12 hr/12 hr reverse light/dark cycle. Rats were administered 0.5% CMC (carboxymethyl cellulose) aqueous solution as vehicle or in combination with a test composition 30 minutes prior to the start of the dark-phase feeding cycle. Experimental testing commenced at the onset of the 12 hr dark cycle. Prior to initiation of a test cycle the rats were fasted overnight (less than about 16 hours) to enhance their hunger. Otherwise the animals had unlimited access to 45% high fat diet (Harlan, USA) and tap water. Food intake was measured at 0, 1, 2, 4, 6, 8, 10 and 24 hours from the start of the experiment to determine the acute food intake of each animal in a study, and total body weight was also measured at 2, 8, and 24 hours.

Example 46

Acute Food Intake Study of *Morus Alba* Extract in Sprague-Dawley (SD) Rats

This Example presents a 24-hour food intake test carried according to the Example 45 to determine the effect of administration of *Morus alba* plant extract 15 on rat food intake. SD rats were administered *Morus alba* extract 15 produced according to Example 15, in a solution of 0.5% CMC (carboxymethyl cellulose) 30 minutes prior to the start of dark-phase feeding cycle. The *Morus alba* extract was administered at a dose of 250, 500 and 1000 mg/kg of animal weight, 7 animals per group.

Table 34 shows the food intake test results for rats treated with a single dose of *Morus alba* extract 15 at three different amounts compared to control animals.

TABLE 34

Cumulative Food Intake in Non-Obese Fasting Rats Fed a High Fat Diet

| Group | Dose (mg/kg) | | Cumulative Food Intake (hour) | | | | | | |
| --- | --- | --- | --- | --- | --- | --- | --- | --- | --- |
| | | | 1 | 2 | 4 | 6 | 8 | 10 | 24 |
| Control | — | Mean | 3.45 | 5.33 | 8.73 | 15.35 | 20.57 | 22.99 | 26.85 |
| | | SD | 1.20 | 1.00 | 1.12 | 1.92 | 1.47 | 1.49 | 2.20 |
| *Morus alba* | 250 | Mean | 1.43 | 2.94 | 5.86 | 9.77 | 13.56 | 16.68 | 24.16 |
| | | SD | 0.98 | 1.50 | 3.13 | 5.47 | 6.15 | 6.55 | 4.63 |
| | | p value | 0.0067 | 0.0098 | 0.0763 | 0.0544 | 0.0376 | 0.0648 | 0.2338 |
| | 500 | Mean | 1.72 | 2.97 | 5.23 | 8.37 | 12.28 | 14.01 | 19.93 |
| | | SD | 0.96 | 0.80 | 1.21 | 2.71 | 2.98 | 3.35 | 2.72 |
| | | p value | 0.0315 | 0.0029 | 0.0033 | 0.0070 | 0.0071 | 0.0087 | 0.0065 |
| | 1,000 | Mean | 0.74 | 1.26 | 3.12 | 6.06 | 9.95 | 15.11 | 19.48 |
| | | SD | 0.31 | 1.00 | 2.12 | 2.97 | 1.57 | 2.41 | 3.06 |
| | | p value | 0.0007 | 0.0005 | 0.0080 | 0.0035 | 0.0000 | 0.0031 | 0.0088 |

The data presented in Table 34 shows that all of the *Morus alba* treatment groups exhibited a statistically significant reduction in cumulative food intake. Further, a dose dependent reduction in food intake was observed in the first hour of food intake measurement through to completion of the study. These results demonstrate that *Morus alba* extract has a statistically significant effect on food intake in rats, which indicates that *Morus alba* extract can be used as a body weight control composition via inhibition of food intake. Also, the reduced food intake from a single oral dose of *Morus alba* extract lasted more than 10 hours. Thus, it is feasible to achieve a reduced appetite, enhanced satiety, or reduced food or caloric intake by once or twice per day oral administration of *Morus alba* extract.

Example 47

Acute Food Intake Study of *Milicia excelsa* Extract 8 in SD Rats

This 24-hour food intake study was conducted according to the Example 45. SD rats were administered *Milicia excelsa* extract 8 produced according to Example 8, at a dosage of 1000 mg/kg of animal weight, in 0.5% CMC (carboxymethyl cellulose solution) solution 30 min prior to the start of the dark-phase feeding cycle.

As shown the Table 35 and Table 36, body weight and body weight gain were reduced significantly at the 8 hr and 24 hour study time points. Body weight gain was determined by measurement of the weight difference for each study group between each successive sample time point of the study. *Milicia excelsa* extract treatment groups also exhibited reduced food intake at the 1 hr, 4 hr, 6 hr and 8 hr time points (Table 37). Treatment SD rats fed the *Milicia excelsa* extracts were also reduced significantly in cumulative food intake for 24 hour (Table 38).

TABLE 35

Body Weight in Non-Obese Fasting Rats Fed a High Fat Diet

| Group | Dose (mg/kg) | | Body weight (g) | | | |
|---|---|---|---|---|---|---|
| | | | 0 h | 2 h | 8 h | 24 h |
| Control | — | Mean | 203.34 | 209.74 | 219.06 | 217.22 |
| | | SD | 5.27 | 4.26 | 6.79 | 5.26 |
| *Milicia excelsa* | 1,000 | Mean | 202.69 | 207.01 | 205.04 | 205.96 |
| | | SD | 8.15 | 7.34 | 7.03 | 12.49 |
| | | p value | 0.8680 | 0.4610 | 0.0050 | 0.0309 |

TABLE 36

Change in Body Weight Gain in Non-Obese Fasting Rats Fed High Fat Diet

| Group | Dose (mg/kg) | | Body weight gain (g) | | |
|---|---|---|---|---|---|
| | | | 2 h | 8 h | 24 h |
| Control | — | Mean | 6.41 | 15.73 | 13.88 |
| | | SD | 1.69 | 4.36 | 1.92 |
| *Milicia excelsa* | 1,000 | Mean | 4.32 | 2.35 | 3.27 |
| | | SD | 2.46 | 6.44 | 11.00 |
| | | p value | 0.1028 | 0.0001 | 0.0144 |

TABLE 37

Food Intake per Time Point in Non-Obese Fasting Rats Fed a High Fat Diet

| Group | Dose (mg/kg) | | Food Intake (g) per Time Point | | | | | | |
|---|---|---|---|---|---|---|---|---|---|
| | | | 1 h | 2 h | 4 h | 6 h | 8 | 10 h | 24 h |
| Control | — | Mean | 3.09 | 2.07 | 2.76 | 4.19 | 3.51 | 1.33 | 6.34 |
| | | SD | 1.24 | 1.54 | 1.64 | 1.02 | 2.64 | 1.60 | 2.83 |
| *Milicia excelsa* | 1000 | Mean | 0.80 | 0.94 | 0.35 | 0.70 | 0.98 | 1.05 | 6.44 |
| | | SD | 0.41 | 0.75 | 0.50 | 1.07 | 1.81 | 1.78 | 5.09 |
| | | p value | 0.0002 | 0.0570 | 0.0011 | 0.0000 | 0.0236 | 0.7210 | 0.9562 |

TABLE 38

Cumulative Food Intake in Non-Obese Fasting Rats Fed High Fat Diet

| Group | Dose (mg/kg) | | Cumulative food intake (g) | | | | | | |
|---|---|---|---|---|---|---|---|---|---|
| | | | 1 h | 2 h | 4 h | 6 h | 8 | 10 h | 24 h |
| Control | — | Mean | 3.09 | 5.15 | 7.91 | 12.10 | 15.61 | 16.93 | 23.27 |
| | | SD | 1.24 | 1.96 | 1.57 | 2.01 | 3.75 | 3.23 | 1.57 |
| *Milicia excelsa* | 1000 | Mean | 0.80 | 1.74 | 2.09 | 2.79 | 3.77 | 4.82 | 11.26 |
| | | SD | 0.41 | 0.80 | 1.05 | 2.04 | 3.50 | 4.46 | 8.06 |
| | | p value | 0.0002 | 0.0003 | 0.0000 | 0.0000 | 0.0000 | 0.0000 | 0.0010 |

These data show that *Milicia excelsa* extracts were effective in significantly reducing body weight and body weight gain. In addition, SD rats fed a normal chow diet after fasting had reduced intake of food. Therefore, the present result suggests that *Milicia excelsa* extract can be used as a body weight controller via inhibition of food intake.

Example 48

High Fat Diet Induced Obesity (DIO) Mouse Model

C57CL/6J mice aged 4-6 weeks (Korea Research Institute of Bioscience & Biotechnology, Ohchang, Korea) were housed in Polycarbonate cages (five mice per cage) in a room with a 12 hr:12 hr light-dark cycle and an ambient temperature of 24° C. All the mice were fed a commercial chow diet for 1 week after arrival in the animal facility. Mice were then divided into normal and obesity groups and fed with normal diet (ND) and high fat diets (HFD) respectively. The HFD group was divided into multiple treatment groups: a high fat diet vehicle group (HFD), an orlistat (purchased as OTC drug Alli®) positive control treatment group (ORI, 40 mg/kg of animal weight, 2 times/day) and optionally a sibutramine positive control treatment group (10 mg/kg, 1 time/day). The HFD contained 340 g of fat/kg of HFD (310 g lard plus 30 g soybean oil; Harlan Laboratories, USA). The HFD was formulated to provide 60% of the total energy generated by the diet from fat by replacing carbohydrate energy with lard and soybean oil, whereas the normal diet (ND) group was fed a diet providing only 18% of the total diet energy from fat(Harlan Laboratories, USA).

Body weight was measured once each week and feed intake was measured twice per week. At the end of the experimental period, following a 12 hr. fasting period, the animals were anesthetized with ether, and blood was drawn from the abdominal vein. Liver and kidney and adipose tissues (epididymal, retroperitoneal, perirenal adipose tissues) were removed from each animal, rinsed with physiological saline, and weighed. Serum concentrations of glucose, total cholesterol, triglycerides, and LDL-cholesterol were determined using automatic analyzer (INTEGRA 400, Roche, Germany). Statistical significance of test results was measured using the Student's t-test.

Example 49

High Fat Diet Induced Obesity (DIO) Rat Model

Male Spraue-Dawley rats, age 4-6 weeks (OrientBio, Inc.; Seongnam, Korea) were housed individually in Polycarbonate cages in a room with a 12 hr:12 hr light-dark cycle and an ambient temperature of 24° C. All the rats were fed a commercial chow diet for 1 week after arrival in the animal facility. Rats were then divided into normal and obesity groups and fed with normal diet (ND) and high fat diets (HFD) respectively. The HFD group was divided into multiple treatment groups: a high fat diet vehicle group (HFD), an orlistat (purchased as OTC drug Alli®) positive control treatment group (ORI, 80 mg/kg of animal weight, 2 times/day). In some examples, sibutramine was used as a positive control (SIB, 3 mg/kg for rat studies and 10 mg/ml for mice studies).

Body weight was measured once or twice per week and feed intake was measured twice per week. Body weight gain was determined for each study group by measurement of the body weight difference for each study group between each successive week of the study. At the end of the experimental period, following a 12-h fasting period, the animals were anesthetized with ether, and blood was drawn from the abdominal vein. Liver and kidney and adipose tissues (epididymal, retroperitoneal, perirenal adipose tissues) were removed from each animal, rinsed with physiological saline, and weighted. Serum concentrations of glucose, total cholesterol and LDL-cholesterol were determined using automatic analyzer (INTEGRA 400, Roche, Germany). Statistical significance of test results was performed by Student's t-test.

Example 50

Effect of *Morus alba* Ethanol Extract 19-2 on DIO Mice

*Morus alba* 70% ethanol extract 19-2 produced according to the Example 19 was orally administrated to DIO mice as described in the Example 48. The *Morus alba* extract was administered at two dose levels: the G1 group at 500 mg/kg of animal weight and the G2 group at 1000 mg/kg of animal weight. Animals were given an oral dose by gavage two times per day. Study results for measurement of animal body weight are shown in Table 39.

TABLE 39

Effect of *Morus alba* extract 19-2 on Total Body Weight in DIO mice

| Group | | Weeks | | | | | | | |
|---|---|---|---|---|---|---|---|---|---|
| | | 0 | 1 | 2 | 3 | 4 | 5 | 6 | 7 |
| ND (Normal Diet) | Mean | 28.21 | 28.34 | 28.45 | 28.50 | 28.29 | 28.31 | 28.43 | 28.66 |
| | SD | 2.032 | 2.006 | 2.277 | 2.417 | 2.414 | 2.449 | 2.425 | 2.413 |
| | p value | 0.0000 | 0.0000 | 0.0000 | 0.0000 | 0.0000 | 0.0000 | 0.0000 | 0.0000 |
| HFD (High Fat Diet) | Mean | 43.36 | 41.24 | 40.29 | 41.26 | 42.64 | 43.32 | 45.05 | 46.23 |
| | SD | 2.414 | 2.118 | 2.712 | 3.496 | 3.796 | 4.081 | 4.515 | 4.550 |
| ORI (40 mg/kg) | Mean | 42.76 | 38.73 | 35.09 | 35.66 | 37.28 | 38.57 | 40.03 | 40.91 |
| | SD | 3.226 | 3.286 | 3.330 | 3.542 | 3.896 | 4.508 | 4.617 | 4.127 |
| | p value | 0.6889 | 0.0987 | 0.0054 | 0.0088 | 0.0185 | 0.0516 | 0.0530 | 0.0346 |
| G1 (500 mg/kg) | Mean | 42.86 | 40.58 | 38.76 | 39.55 | 40.82 | 42.44 | 44.10 | 45.22 |
| | SD | 2.921 | 2.492 | 3.219 | 3.662 | 4.658 | 5.306 | 5.949 | 6.166 |
| | p value | 0.7200 | 0.5917 | 0.3548 | 0.3909 | 0.4375 | 0.7321 | 0.7385 | 0.7281 |
| G2 (1 g/kg) | Mean | 43.07 | 40.05 | 38.02 | 36.98 | 37.56 | 38.29 | 39.18 | 39.66 |
| | SD | 0.835 | 0.287 | 0.094 | 0.014 | 0.012 | 0.024 | 0.021 | 0.017 |
| | p value | 0.8353 | 0.2868 | 0.0942 | 0.0136 | 0.0124 | 0.0242 | 0.0214 | 0.0171 | p value: compare to HFD by t-test

The data in Table 39 shows that the G1 group (low dosage of *Morus alba* extract 19-2) did not exhibit a significant difference body weight compared to the HFD group. In contrast, the G2 group (high dosage of *Morus alba* extract 19-2) exhibited statistically significant reductions in body weight at weeks 3, 4, 5, 6 and 7 when compared with the HFD group. The positive control group (ORI, treated with orlistat at 40 mg/kg of body weight) showed statistically significant reductions in body weight at weeks 2, 3, 4, and 7 when compared with the HFD group.

Table 40 shows the effects on body weight gain of each group.

TABLE 40

Effect of *Morus alba* on Body Weight Gain in Mice Fed High Fat Diet

| Group | | Weeks | | | | | | |
|---|---|---|---|---|---|---|---|---|
| | | 1 | 2 | 3 | 4 | 5 | 6 | 7 |
| ND (Normal Diet) | Mean | 0.13 | 0.24 | 0.29 | 0.08 | 0.10 | 0.22 | 0.45 |
| | SD | 0.387 | 0.567 | 0.736 | 0.810 | 0.959 | 0.839 | 0.929 |
| | p value | 0.0000 | 0.0000 | 0.0002 | 0.1790 | 0.8322 | 0.1256 | 0.0302 |
| HFD (High Fat Diet) | Mean | -2.05 | -3.37 | -3.41 | -2.14 | -1.82 | -0.22 | 1.24 |
| | SD | 0.990 | 0.266 | 0.548 | 1.214 | 1.145 | 2.417 | 3.030 |
| ORI 40 mg/kg | Mean | -4.00 | -7.38 | -6.70 | -5.01 | -3.81 | -2.36 | -1.42 |
| | SD | 0.571 | 0.839 | 1.227 | 1.409 | 1.609 | 1.175 | 1.259 |
| | p value | 0.0004 | 0.0000 | 0.0001 | 0.0005 | 0.0032 | 0.0059 | 0.0041 |
| G1 500 mg/kg | Mean | -2.27 | -4.28 | -3.49 | -2.22 | -0.60 | 1.06 | 2.18 |
| | SD | 0.921 | 1.316 | 1.429 | 2.075 | 2.660 | 3.240 | 3.383 |
| | p value | 0.7247 | 0.0621 | 0.0887 | 0.1522 | 0.6745 | 0.6957 | 0.6660 |
| G2 1000 mg/kg | Mean | -3.02 | -5.05 | -6.09 | -5.51 | -4.78 | -3.89 | -3.41 |
| | SD | 0.936 | 1.076 | 1.244 | 0.728 | 1.084 | 1.511 | 2.136 |
| | p value | 0.0521 | 0.0018 | 0.0001 | 0.0000 | 0.0001 | 0.0001 | 0.0002 | p value: compare to HFD by t-test

The data in Table 40 show that the change in weight gain for the high dosage group (G2) and the positive control group (ORI) both showed the greatest change in weight gain between week 2 and week 3 with the rate of weight loss relative to the HFD group dropping from week 4 to week 7.

Table 41 shows the effects of the *Morus alba* extract on body weight gain, food intake, and the food efficiency ratio (FER), which is the average body weight gain per day over the study period, divided by the average food intake per day over the study period.

TABLE 41

Effect of *Morus alba* on Mice Fed a High Fat Diet

| Group | | Average Body Weight Gain (g/day) | Average Food Intake (g/day) | Food Efficiency Ratio (FER) |
|---|---|---|---|---|
| ND (Normal Diet) | Mean | 0.010 | 2.973 | 0.003 |
| | SD | 0.020 | 0.334 | 0.007 |
| | p value | 0.0302 | 0.0000 | 0.0255 |
| HFD (High Fat Diet) | Mean | 0.027 | 2.390 | 0.011 |
| | SD | 0.066 | 0.580 | 0.028 |
| ORI (40 mg/kg) | Mean | -0.031 | 2.711 | -0.011 |
| | SD | 0.040 | 0.721 | 0.015 |
| | p value | 0.0041 | 0.0293 | 0.0043 |
| G1 (500 mg/kg) | Mean | 0.047 | 2.332 | 0.017 |
| | SD | 0.074 | 0.611 | 0.030 |
| | p value | 0.6660 | 0.6909 | 0.5321 |
| G2 (1000 mg/kg) | Mean | -0.074 | 1.934 | -0.038 |
| | SD | 0.046 | 0.508 | 0.024 |
| | p value | 0.0002 | 0.0013 | 0.0001 |

FER (Feed efficacy ratio) = Body weight gain(g/day)/Food intake(g/day)
p value: compare to HFD by t-test The data presented in Table 41 show that the high dose *Morus alba* treatment group (G2) and the positive control treatment group (ORI) both showed a statistically significant decrease in body weight gain per day of the study compared to the HFD group. In addition, both the G2 and ORI groups also showed a statistically significant decrease in FER as compared to the HFD group. Interestingly, the ORI and G2 groups also showed statistically significant changes in food intake per day of the study, with the ORI showing an increase in food intake compared to the HFD group, while the G2 group showed a decrease in average food intake per day of the study compared to the HFD group, suggesting that the mechanism of action is different between the two compositions.

Taken together, the data presented in this example indicate that the *Morus alba* 70% ethanol extract 19-2 when taken at a dose of 1000 mg/kg of subject body weight, twice per day, is effective in helping to control food intake and body weight for subjects on a high fat diet.

Example 51

Effect of *Morus alba* Extract Precipitate 19-1 on DIO Mice

*Morus alba* precipitate 19-1, produced by precipitation from a concentrated 70% ethanol extract of Example 189, was orally administered to DIO mice using the methods described in Example 48. The *Morus alba* extract precipitate was administered at two dose levels: the G1 group at 250 mg/kg of animal weight and the G2 group at 500 mg/kg of animal weight. Animals were given an oral dose by gavage two times per day. Study results for measurement of animal body weight are shown in Table 42.

TABLE 42

Effect of *Morus alba* extract precipitate 19-1 on Total Body Weight

| Group | | Weeks | | | | | | | |
|---|---|---|---|---|---|---|---|---|---|
| | | 0 | 1 | 2 | 3 | 4 | 5 | 6 | 7 |
| ND | Mean | 28.21 | 28.34 | 28.45 | 28.50 | 28.29 | 28.31 | 28.43 | 28.66 |
| | SD | 2.032 | 2.006 | 2.277 | 2.417 | 2.414 | 2.449 | 2.425 | 2.413 |
| | p value | 0.0000 | 0.0000 | 0.0000 | 0.0000 | 0.0000 | 0.0000 | 0.0000 | 0.0000 |
| HFD | Mean | 43.36 | 41.24 | 40.29 | 41.26 | 42.64 | 43.32 | 45.05 | 46.23 |
| | SD | 2.414 | 2.118 | 2.712 | 3.496 | 3.796 | 4.081 | 4.515 | 4.550 |
| ORI | Mean | 42.76 | 38.73 | 35.09 | 35.66 | 37.28 | 38.57 | 40.03 | 40.91 |
| 40 mg/kg | SD | 3.226 | 3.286 | 3.330 | 3.542 | 3.896 | 4.508 | 4.617 | 4.127 |
| | p value | 0.6889 | 0.0987 | 0.0054 | 0.0088 | 0.0185 | 0.0516 | 0.0530 | 0.0346 |
| G1 | Mean | 43.10 | 39.97 | 37.09 | 36.78 | 39.00 | 40.83 | 41.77 | 42.82 |
| 250 mg/kg | SD | 2.990 | 2.678 | 2.290 | 2.576 | 2.788 | 3.162 | 3.383 | 3.930 |
| | p value | 0.8566 | 0.3250 | 0.0294 | 0.0153 | 0.0572 | 0.2155 | 0.1394 | 0.1473 |
| G2 | Mean | 42.92 | 38.48 | 34.67 | 34.35 | 35.21 | 35.65 | 35.22 | 35.85 |
| 500 mg/kg | SD | 3.028 | 2.365 | 1.806 | 1.523 | 1.688 | 2.011 | 2.189 | 2.101 |
| | p value | 0.7591 | 0.0330 | 0.0005 | 0.0003 | 0.0004 | 0.0006 | 0.0002 | 0.0001 | p value: compared to HFD by t-test

As shown the Table 42, body weight was significantly decreased in a dose dependent manner in the *Morus alba* treatment groups. In particular, the G1 group (low dosage of *Morus alba* extract precipitate 19-1) exhibited a significant difference in body weight compared to the HFD group for week 2 and week 3. Further the weight gain trend, as compared to the HFD group suggests a lowered rate of weight gain compared to the HFD group even if the numbers for weeks 4, 5, 6 and 7 failed to achieve statistical significance. Whereas the G2 group (high dosage of *Morus alba* extract precipitate 19-1) exhibited statistically significant reductions in body weight at weeks 2 through week 7, when compared with the HFD group. The positive control group, ORI, (treated with orlistat) showed statistically significant reductions in body weight at weeks 2, 3, 4, and 7 when compared with the HFD group.

Table 43 shows the effects on body weight gain in each study group.

The data in Table 43 show that both of the *Morus alba* treatment groups and the positive control ORI group exhibited statistically significant decreases in body weight gains each week after the first week of treatment of as compared to the HFD group. In addition, the data also show the weight loss effect of the *Morus alba* treatment groups is dose dependent.

Table 44 shows the effects of the *Morus alba* extract precipitate 19-1 on body weight gain, food intake, and the food efficiency ratio (FER), which is the average body weight gain per day over the study period, divided by the average food intake per day over the study period.

TABLE 44

Effect of *Morus alba* extract precipitate 19-1 on Mice Fed a High Fat Diet

| Group | | Average Body Weight Gain (g/day) | Average Food Intake (g/day) | Food Efficiency Ratio (FER) |
|---|---|---|---|---|
| ND | Mean | 0.010 | 2.973 | 0.003 |
| (Normal | SD | 0.020 | 0.334 | 0.007 |
| Diet) | p value | 0.0302 | 0.0000 | 0.0255 |

TABLE 43

Effect of *Morus alba* Extract Precipitate 19-1 on Mice Fed a High Fat Diet

| Group | | Weeks | | | | | | |
|---|---|---|---|---|---|---|---|---|
| | | 1 | 2 | 3 | 4 | 5 | 6 | 7 |
| ND | Mean | 0.13 | 0.24 | 0.29 | 0.08 | 0.10 | 0.22 | 0.45 |
| | SD | 0.387 | 0.567 | 0.736 | 0.810 | 0.959 | 0.839 | 0.929 |
| | p value | 0.0000 | 0.0000 | 0.0002 | 0.1790 | 0.8322 | 0.1256 | 0.0302 |
| HFD | Mean | −2.12 | −3.08 | −2.10 | −0.73 | −0.04 | 1.69 | 2.87 |
| | SD | 0.689 | 0.880 | 1.365 | 1.583 | 1.897 | 2.339 | 2.504 |
| ORI | Mean | −4.00 | −7.38 | −6.70 | −5.01 | −3.81 | −2.36 | −1.42 |
| 40 mg/kg | SD | 0.571 | 0.839 | 1.227 | 1.409 | 1.609 | 1.175 | 1.259 |
| | p value | 0.0004 | 0.0000 | 0.0001 | 0.0005 | 0.0032 | 0.0059 | 0.0041 |
| G1 | Mean | −3.13 | −6.02 | −6.33 | −4.11 | −2.27 | −1.34 | −0.28 |
| 250 mg/kg | SD | 1.272 | 1.916 | 2.678 | 2.375 | 2.316 | 2.654 | 2.757 |
| | p value | 0.0732 | 0.0018 | 0.0017 | 0.0059 | 0.0614 | 0.0352 | 0.0372 |
| G2 | Mean | −4.44 | −8.25 | −8.57 | −7.71 | −7.27 | −7.70 | −7.07 |
| 500 mg/kg | SD | 1.399 | 1.600 | 1.665 | 1.594 | 1.315 | 1.414 | 1.582 |
| | p value | 0.0011 | 0.0000 | 0.0000 | 0.0000 | 0.0000 | 0.0000 | 0.0000 | p value: compare to HFD by t-test

TABLE 44-continued

Effect of *Morus alba* extract precipitate 19-1 on Mice Fed a High Fat Diet

| Group | | Average Body Weight Gain (g/day) | Average Food Intake (g/day) | Food Efficiency Ratio (FER) |
|---|---|---|---|---|
| HFD (High Fat Diet) | Mean | 0.062 | 2.390 | 0.026 |
| | SD | 0.054 | 0.580 | 0.023 |
| ORI (40 mg/kg) | Mean | −0.031 | 2.711 | −0.011 |
| | SD | 0.040 | 0.721 | 0.015 |
| | p value | 0.0041 | 0.0293 | 0.0043 |
| G1 (250 mg/kg) | Mean | −0.006 | 2.468 | −0.002 |
| | SD | 0.060 | 0.682 | 0.024 |
| | p value | 0.0372 | 0.5874 | 0.0351 |
| G2 (500 mg/kg) | Mean | −0.154 | 1.937 | −0.079 |
| | SD | 0.034 | 0.542 | 0.018 |
| | p value | 0.0000 | 0.0016 | 0.0000 |

Feed efficacy ratio (FER) = Body weight gain (g/day)/Food intake(g/day)
p value: compare to HFD by t-test The data presented in Table 44 show that both of the *Morus alba* treatment groups (G1 and G2) and the positive control treatment group (ORI) all showed statistically significant decreases in body weight gain per day of the study. The ORI and G2 treatment groups also showed a statistically significant decrease in the average amount of food intake per day as compared to the HFD group. In addition, the G1, G2, and ORI treatment groups also showed a statistically significant decrease in FER as compared to the HFD group.

Table 45 shows the effects of the *Morus alba* extract precipitate 19-1 on several specific tissues that are known to have increased fat content in subjects on a high fat diet.

TABLE 45

Effects of *Morus alba* extract precipitate 19-1 on Organ Weight

| Group | | Liver | Epididymal Fat | Retroperitoneal Fat | Perirenal Fat | Total Fat[1] |
|---|---|---|---|---|---|---|
| ND (Normal Diet) | Mean | 0.87 | 0.58 | 0.14 | 0.09 | 0.81 |
| | SD | 0.102 | 0.189 | 0.070 | 0.032 | 0.280 |
| | p value | 0.0051 | 0.0000 | 0.0000 | 0.0001 | 0.0000 |
| HFD (High Fat Diet) | Mean | 1.44 | 1.98 | 0.54 | 0.43 | 2.95 |
| | SD | 0.406 | 0.464 | 0.085 | 0.134 | 0.478 |
| ORI (40 mg/kg) | Mean | 1.12 | 1.92 | 0.47 | 0.33 | 2.73 |
| | SD | 0.204 | 0.359 | 0.055 | 0.094 | 0.433 |
| | p value | 0.0842 | 0.8036 | 0.0791 | 0.1376 | 0.3649 |
| G1 (250 mg/kg) | Mean | 1.26 | 2.24 | 0.57 | 0.36 | 3.17 |
| | SD | 0.247 | 0.237 | 0.075 | 0.121 | 0.252 |
| | p value | 0.3216 | 0.2006 | 0.5206 | 0.3072 | 0.2958 |
| G2 (500 mg/kg) | Mean | 1.06 | 1.42 | 0.35 | 0.19 | 1.97 |
| | SD | 0.115 | 0.062 | 0.043 | 0.036 | 0.117 |
| | p value | 0.0347 | 0.0118 | 0.0001 | 0.0014 | 0.0005 | p value: compare to HFD by t-test

The data in Table 45 show that there is a statistically significant difference between liver weight, epididymal fat, retroperitoneal fat, perirenal fat and total fat between the ND control group (fed a normal nutritional diet having a moderate caloric intact of fat) and the HFD group. Interestingly, the high dosage *Morus alba* extract precipitate group (G2) showed statistically significant decreases in all categories of fat measurement as compared with the HFD group, whereas the ORI treatment group showed no statistically significant changes in any of the measured values.

Table 46 shows the effects of the *Morus alba* extract precipitate 19-1 on fasting glucose (F-Glu), total cholesterol (T-chol) and LDL-cholesterol (LDL-C) as measure in blood samples obtained at the end of the study.

TABLE 46

Effect of *Morus alba* extract precipitate 19-1 on Biochemistry Parameters

| Group | | F-Glu (mg/dL) | T-Chol (mg/dL) | LDL-C (mg/dL) |
|---|---|---|---|---|
| ND | Mean | 125.40 | 107.00 | 5.00 |
| | SD | 29.628 | 20.347 | 1.793 |
| | p value | 0.0016 | 0.0085 | 0.0060 |
| HFD | Mean | 253.20 | 193.60 | 9.08 |
| | SD | 53.867 | 52.003 | 1.689 |
| ORI | Mean | 222.43 | 134.57 | 4.27 |
| | SD | 51.006 | 31.627 | 0.896 |
| | p value | 0.3375 | 0.0338 | 0.0001 |
| G1 | Mean | 280.14 | 173.57 | 5.59 |
| | SD | 39.015 | 29.580 | 1.608 |
| | p value | 0.3361 | 0.4134 | 0.0046 |
| G2 | Mean | 188.29 | 136.14 | 4.24 |
| | SD | 36.523 | 37.936 | 1.664 |
| | p value | 0.0313 | 0.0503 | 0.0006 | p value: compare to HFD by t-test

The data in Table 46 show that low dosage *Morus alba* extract precipitate group (G1) had statistically significant decrease in LDL-cholesterol compared to the HFD group. The high dosage *Morus alba* extract precipitate group (G2) had statistically significant decreases in total glucose, cholesterol, and LDL-cholesterol as compared to the HFD group.

Taken together, the data presented in this example indicate that the *Morus alba* precipitate extract 19-1 when taken at a dose of 500 mg/kg of subject body weight, twice per day, is effective in helping to control food intake and body weight for subjects eating a high fat diet. In addition, subjects taking the 500 mg/kg dose of *Morus alba* precipitate extract 19-1 also exhibited statistically significant improvements in blood chemistry end points and tissue fat levels as compared to control subjects in the HFD group. These results demonstrate that *Morus alba* extracts enriched in the Diels-Alder adducts of a chalcone and prenylphenyl moiety Kuwanon G, and Albanin G can be used to control body weight, lower food intake, lower tissue fat content, lower blood glucose levels, decrease total cholesterol and decrease LDL-cholesterol.

Example 52

Effect of *Morus alba* Ethyl Acetate Extract 16 on DIO Rats

*Morus alba* ethyl acetate extract 16 produced as described in Example 16 was orally administered to DIO rats using the methods described in Example 40. Study time period was 42 days. The *Morus alba* extract was administered to group G1 using a dose of 500 mg/kg of animal weight. Study animals were given an oral dose by gavage two times per day. Study results for measurement of total animal body weight for all study groups are shown in Table 47. Table 48 shows the effects on body weight gain when calculated as the difference between a subject animal weighed on day 0 of the study compared to the body weight measured at the end of each time point day of the study.

The data presented in Table 47 show that *Morus alba* ethyl acetate extract 16 when dosed at 500 mg/kg of animal body weight, produced a statistically significant decrease in body weight from day 2 to day 14, day 21, and day 28 as compared to the HFD group. The positive control SIB (Sibutramine dosed at 3 mg/kg) group, produced a statistically significant reduction in body weight at day 2 through the remainder of the study (day 42).

TABLE 47

Effect of *Morus alba* Extract 16 (500 mg/kg of total subject weight) on Total Body Weight of DIO Rats

| Group | | 0 | 1 | 2 | 3 | 4 | 7 | 10 | 14 |
|---|---|---|---|---|---|---|---|---|---|
| ND (Normal Diet) | Mean | 325.08 | 332.10 | 336.67 | 339.58 | 340.88 | 353.66 | 360.07 | 371.43 |
| | SD | 12.82 | 12.98 | 14.15 | 14.35 | 14.96 | 18.07 | 18.48 | 19.63 |
| | p value | 0.000 | 0.000 | 0.000 | 0.000 | 0.000 | 0.000 | 0.000 | 0.000 |
| HFD (High Fat Diet) | Mean | 364.82 | 368.90 | 374.50 | 378.61 | 381.19 | 391.61 | 400.99 | 411.04 |
| | SD | 7.46 | 8.74 | 7.87 | 8.52 | 9.22 | 9.25 | 10.64 | 11.51 |
| SIB (Sibutramine 3 mg/kg) | Mean | 364.15 | 368.06 | 356.78 | 357.21 | 358.78 | 368.11 | 377.69 | 388.70 |
| | SD | 10.40 | 10.28 | 11.60 | 13.06 | 13.82 | 15.94 | 17.24 | 19.19 |
| | p value | 0.870 | 0.848 | 0.001 | 0.001 | 0.001 | 0.001 | 0.002 | 0.007 |
| G1 (500 g/Kg) | Mean | 364.35 | 366.90 | 366.10 | 364.73 | 362.01 | 373.26 | 385.46 | 393.89 |
| | SD | 9.34 | 8.58 | 8.71 | 10.97 | 18.12 | 18.56 | 14.42 | 15.84 |
| | p value | 0.901 | 0.612 | 0.036 | 0.006 | 0.010 | 0.015 | 0.014 | 0.013 |

| Group | | 18 | 21 | 24 | 28 | 31 | 35 | 38 | 42 |
|---|---|---|---|---|---|---|---|---|---|
| ND (Normal Diet) | Mean | 379.57 | 388.12 | 396.23 | 405.93 | 412.33 | 424.10 | 431.21 | 439.27 |
| | SD | 20.17 | 20.99 | 22.32 | 22.64 | 22.42 | 21.69 | 22.59 | 21.27 |
| | p value | 0.000 | 0.000 | 0.000 | 0.00 | 00.000 | 0.000 | 0.000 | 0.000 |
| HFD (High Fat Diet) | Mean | 420.30 | 428.30 | 436.77 | 448.90 | 455.75 | 465.73 | 471.56 | 483.09 |
| | SD | 12.00 | 14.51 | 15.62 | 16.93 | 17.48 | 16.38 | 16.59 | 16.34 |
| SIB (Sibtramine 3 mg/kg) | Mean | 395.38 | 407.06 | 414.91 | 425.99 | 432.32 | 442.55 | 447.66 | 454.96 |
| | SD | 19.05 | 21.34 | 20.48 | 20.94 | 22.49 | 23.56 | 25.53 | 25.35 |
| | p value | 0.003 | 0.019 | 0.016 | 0.015 | 0.019 | 0.021 | 0.025 | 0.010 |
| G1 (500 g/Kg) | Mean | 407.12 | 413.32 | 423.76 | 430.11 | 442.06 | 450.60 | 460.19 | 466.34 |
| | SD | 16.21 | 16.56 | 22.10 | 21.32 | 21.65 | 22.69 | 25.42 | 23.37 |
| | p value | 0.055 | 0.045 | 0.148 | 0.043 | 0.138 | 0.106 | 0.254 | 0.082 | p value: Compared to HFD group

TABLE 48

Effect of *Morus alba* Extract 16 (500 mg/kg of total subject weight) on Weight Gain in DIO Rats

| Group | | 1 | 2 | 3 | 4 | 7 | 10 | 14 | 18 |
|---|---|---|---|---|---|---|---|---|---|
| ND (Normal Diet) | Mean | 7.02 | 11.58 | 14.50 | 15.80 | 28.57 | 34.99 | 46.34 | 54.49 |
| | SD | 3.08 | 3.32 | 3.42 | 3.78 | 7.31 | 8.42 | 9.79 | 11.09 |
| | p value | 0.021 | 0.163 | 0.650 | 0.720 | 0.502 | 0.712 | 0.974 | 0.817 |
| HFD (High Fat Diet) | Mean | 4.07 | 9.67 | 13.78 | 16.37 | 26.79 | 36.16 | 46.21 | 55.48 |
| | SD | 1.93 | 2.48 | 3.55 | 3.16 | 3.65 | 5.10 | 7.36 | 7.20 |
| SIB (Sibutramine | Mean | 3.91 | −7.37 | −6.94 | −5.37 | 3.96 | 13.54 | 24.55 | 31.23 |
| | SD | 1.89 | 3.49 | 6.76 | 6.91 | 9.81 | 10.77 | 12.83 | 12.49 |

TABLE 48-continued

Effect of Morus alba Extract 16 (500 mg/kg of total subject weight) on Weight Gain in DIO Rats

| 3 mg/kg) | p value | 0.855 | 0.000 | 0.000 | 0.000 | 0.000 | 0.000 | 0.000 | 0.000 |
|---|---|---|---|---|---|---|---|---|---|
| G1 | Mean | 2.55 | 1.76 | 0.38 | -2.34 | 8.92 | 21.11 | 29.54 | 42.77 |
| (500 g/Kg)) | SD | 3.17 | 5.89 | 9.54 | 17.57 | 18.29 | 13.92 | 16.59 | 16.33 |
| | p value | 0.214 | 0.002 | 0.001 | 0.008 | 0.013 | 0.008 | 0.013 | 0.043 |

| | | Days | | | | | |
|---|---|---|---|---|---|---|---|
| Group | | 21 | 24 | 28 | 31 | 35 | 38 | 42 |
| ND | Mean | 63.04 | 71.15 | 80.84 | 87.25 | 99.02 | 106.13 | 114.19 |
| (Normal | SD | 11.64 | 13.71 | 14.31 | 14.17 | 13.46 | 14.72 | 14.88 |
| Diet) | p value | 0.930 | 0.889 | 0.604 | 0.559 | 0.757 | 0.925 | 0.531 |
| HFD | Mean | 63.48 | 71.95 | 84.07 | 90.93 | 100.90 | 106.73 | 118.26 |
| (High Fat | SD | 10.13 | 11.40 | 13.03 | 13.50 | 13.32 | 13.55 | 13.58 |
| Diet) | | | | | | | | |
| SIB | Mean | 42.91 | 50.75 | 61.84 | 68.17 | 78.40 | 83.51 | 90.81 |
| (Sibtramine | SD | 14.03 | 13.21 | 13.27 | 14.71 | 15.22 | 17.02 | 16.74 |
| 3 mg/kg) | p value | 0.002 | 0.001 | 0.001 | 0.002 | 0.003 | 0.004 | 0.001 |
| G1 | Mean | 48.97 | 59.41 | 65.76 | 77.71 | 86.25 | 95.84 | 101.99 |
| (500 g/Kg)) | SD | 18.04 | 22.91 | 22.14 | 22.76 | 23.59 | 25.92 | 23.90 |
| | p value | 0.044 | 0.145 | 0.040 | 0.136 | 0.109 | 0.259 | 0.082 | p value: Compared to HFD group

The data in Table 48 show that the G1 Morus alba ethyl acetate extract 16 treatment group exhibited statistically significant decreases in body weight gains from day 2 to day 21, and then day 28 of the study as compared to the HFD group. The positive control SIB (Sibutramine dosed at 3 mg/kg) showed statistically significant decreases in body weight gains from day 2 to completion of the study on day 42 as compared to the HFD group.

Table 49 shows the effects of Morus alba extract Ethyl Acetate Extract 16 on DIO Rats for the following end points: average body weight gain per day of the study, average food intake per day of the study, and the food efficiency ratio (FER) which is calculated as the average body weight gain per day over the study period, divided by the average food intake per day over the study period.

TABLE 49

Effect of Morus alba ethyl acetate extract 16 on Rats Fed a High Fat Diet

| Group | | Weight gain (g/day) | Food intake (g/day) | Food Efficiency Ratio (FER) |
|---|---|---|---|---|
| ND | Mean | 2.720 | 16.460 | 0.165 |
| (Normal Diet) | SD | 0.350 | 0.650 | 0.019 |
| | p value | 0.531 | 0.041 | 0.059 |
| HFD | Mean | 2.820 | 15.420 | 0.183 |
| (High Fat Diet) | SD | 0.320 | 0.700 | 0.021 |
| SIB | Mean | 2.160 | 13.880 | 0.155 |
| (Sibtramine | SD | 0.400 | 0.660 | 0.024 |
| 3 mg/kg) | p value | 0.001 | 0.007 | 0.013 |
| G1 | Mean | 2.430 | 16.300 | 0.149 |
| (500 g/Kg)) | SD | 0.570 | 0.660 | 0.033 |
| | p value | 0.082 | 0.077 | 0.015 |

Food Efficiency Ratio (FER) = (body weight gain (g/day)/food intake (g/day)
p value: Compared to HFD group The data in Table 49 show that the ethyl acetate extract of Morus alba as administered to group G1 showed a statistically significantly lower Food Efficiency Ratio as compared to the HFD group. The SIB positive control treatment group showed statically lower values than the HFD group for Weight Gain per day, Food Intake per day, and Food Efficiency Ratio.

TABLE 50

Effects of Morus alba extract 16 on Fat Deposit Weight in Rats Fed a High Fat Diet

| Group | | Epididymal Fat | Retro-peritoneal Fat | Perirenal Fat | Total Fat |
|---|---|---|---|---|---|
| ND | Mean | 5.556 | 2.397 | 1.468 | 9.420 |
| (Normal Diet) | SD | 1.300 | 0.593 | 0.389 | 2.207 |
| | p value | 0.001 | 0.001 | 0.007 | 0.001 |
| HFD | Mean | 8.636 | 4.637 | 2.370 | 15.643 |
| (High Fat Diet) | SD | 1.986 | 1.463 | 0.799 | 4.179 |
| SIB | Mean | 6.698 | 3.190 | 1.562 | 11.450 |
| (Sibtramine | SD | 1.064 | 0.701 | 0.399 | 1.999 |
| 3 mg/kg) | p value | 0.017 | 0.015 | 0.013 | 0.013 |
| G1 | Mean | 5.911 | 2.648 | 1.405 | 9.964 |
| (500 g/Kg)) | SD | 0.404 | 0.624 | 0.242 | 1.183 |
| | p value | 0.002 | 0.002 | 0.004 | 0.002 | p value: Compared to HFD group

The data in Table 50 show that there is a statistically significant difference between Epididymal Fat, Retroperitoneal Fat, Perirenal Fat and Total Fat between the ND control group, fed a normal diet having a moderate caloric intact of fat, and the HFD group. Morus alba extract treated group (G1) and the positive control treatment group (SIB) showed statistically significant decreases in all categories of fat measurement as compared with the HFD group, demonstrating that the Morus alba extract 16 is effective in reducing the amount of fat present in DIO rats.

Table 51 shows the effects of the Morus alba extract 16 on fasting glucose (F-Glu), total cholesterol (T-chol) and LDL-cholesterol (LDL-C) as measure in blood samples obtained at the end of the study.

TABLE 51

Effects of Morus alba extract 16 on Biochemistry Parameters in DIO Rats

| Group | | T-Chol (mg/dL) | Triglyceride (mg/dL) | Fasting Glucose (mg/dL) |
|---|---|---|---|---|
| ND | Mean | 98.67 | 40.89 | 112.67 |
| (Normal Diet) | SD | 10.89 | 17.61 | 10.57 |
| | p value | 0.027 | 0.753 | 0.001 |

TABLE 51-continued

Effects of *Morus alba* extract 16 on Biochemistry Parameters in DIO Rats

| Group | | T-Chol (mg/dL) | Triglyceride (mg/dL) | Fasting Glucose (mg/dL) |
|---|---|---|---|---|
| HFD | Mean | 113.40 | 44.50 | 135.70 |
| (High Fat Diet) | SD | 15.36 | 30.37 | 13.85 |
| SIB | Mean | 106.60 | 41.10 | 136.00 |
| (Sibtramine | SD | 10.83 | 23.50 | 12.01 |
| 3 mg/kg) | p value | 0.269 | 0.783 | 0.959 |
| G1 | Mean | 90.40 | 32.20 | 113.80 |
| (500 g/Kg)) | SD | 9.29 | 14.28 | 11.33 |
| | p value | 0.001 | 0.268 | 0.001 | p value: Compared to HFD group

The data in Table 51 show that *Morus alba* extract 16 treatment group had statistically significant decrease in Total-Cholesterol and Fasting Glucose as compared to the HFD group. The SIB treatment group showed no statistically significant changes compared to the HFD group for any of the measured endpoints.

These data show that the *Morus alba* extract 16 when taken at a dose of 500 mg/kg of body weight, twice per day, is effective in lowering the rate of body weight gain in rats fed a high fat diet. In addition, subjects taking the 500 mg/kg dose of extract 16 also exhibited statistically significant improvements in blood chemistry end points (Table 51) and tissue fat levels (Table 50) as compared to control subjects in the HFD group. These results demonstrate that *Morus alba* extracts enriched in Kuwanon G and Albanin G can be used to control body weight gain, lower tissue fat content, lower fasting blood glucose levels, and decrease total cholesterol levels.

Example 53

Effect of Mutamba Ethanol Extract 32 on DIO Mice

Mutamba ethanol extract 32, produced according to the Example 32, was orally administrated to DIO mouse model as illustrated in the Example 48. The Mutamba extract was administered to treatment group G1 at 1000 mg/kg of animal weight per day. G1 treatment group animals were given an oral dose of 500 mg/kg by gavage two times per day. Study results for measurement of animal body weight are shown in Table 52.

TABLE 52

Effect of Mutamba Extract 32 on Total Body Weight in DIO Mice

| Group | | Weeks | | | | | | | | |
|---|---|---|---|---|---|---|---|---|---|---|
| | | 0 | 1 | 2 | 3 | 4 | 5 | 6 | 7 | 8 |
| ND | Mean | 27.98 | 28.04 | 28.12 | 28.56 | 27.99 | 28.05 | 28.37 | 28.67 | 29.39 |
| (Normal | SD | 1.657 | 1.561 | 1.602 | 1.982 | 1.467 | 1.517 | 1.493 | 1.513 | 1.977 |
| Diet) | p value | 0.0000 | 0.0028 | 0.0014 | 0.000 | 0.000 | 0.0005 | 0.0003 | 0.000 | 0.000 |
| HFD | Mean | 39.72 | 38.80 | 39.56 | 40.78 | 41.80 | 43.21 | 44.69 | 46.10 | 46.74 |
| (High | SD | 3.576 | 4.005 | 3.672 | 3.301 | 3.178 | 3.776 | 3.612 | 3.085 | 3.144 |
| Fat Diet) | | | | | | | | | | |
| SIB | Mean | 39.70 | 34.24 | 33.96 | 36.05 | 36.64 | 37.42 | 38.54 | 38.74 | 39.95 |
| 10 mg/ | SD | 3.575 | 1.812 | 1.948 | 1.579 | 3.568 | 4.384 | 5.499 | 5.556 | 5.766 |
| kg | p value | 0.990 | 0.049 | 0.029 | 0.0348 | 0.0552 | 0.070 | 0.082 | 0.039 | 0.058 |
| ORI | Mean | 39.96 | 37.37 | 37.05 | 37.41 | 37.60 | 38.12 | 40.04 | 41.77 | 42.06 |
| 40 mg/ | SD | 3.489 | 4.190 | 4.401 | 4.659 | 4.860 | 5.563 | 6.028 | 5.998 | 6.246 |
| kg | p value | 0.920 | 0.596 | 0.357 | 0.223 | 0.145 | 0.129 | 0.1769 | 0.1889 | 0.1730 |
| G1 | Mean | 39.79 | 34.93 | 36.51 | 35.78 | 36.06 | 37.75 | 37.41 | 39.70 | 41.53 |
| 1000 mg/ | SD | 3.771 | 3.548 | 4.453 | 2.564 | 2.706 | 3.213 | 3.465 | 4.039 | 4.074 |
| kg | p value | 0.978 | 0.1448 | 0.271 | 0.0281 | 0.0152 | 0.0393 | 0.0116 | 0.0226 | 0.0535 | p value: compare to HFD by t-test

The data in Table 52 show that the Mutamba ethanol extract 32, 1000 mg/kg/day treatment group showed statistically significant decreases in body weight from week 3 through to week 7 of the study as compared to the HFD group. The positive control SIB (sibutramine dosed at 10 mg/kg) showed statistically significant decreases in total body weight from week 1, 2, 3 and 7 of the study as compared to the HFD group.

Study results for measurement of animal body weight gain are shown in Table 53.

TABLE 53

Effect of Mutamba extract 32 on Body Weight Gain in DIO Mice

| Group | | Weeks | | | | | | | |
|---|---|---|---|---|---|---|---|---|---|
| | | 1 | 2 | 3 | 4 | 5 | 6 | 7 | 8 |
| ND | Mean | 0.07 | 0.14 | 0.58 | 0.01 | 0.08 | 0.39 | 0.69 | 1.41 |
| (Normal | SD | 0.393 | 0.545 | 1.306 | 0.757 | 0.654 | 0.606 | 0.779 | 1.018 |
| Diet) | p value | 0.1193 | 0.4309 | 0.4576 | 0.0009 | 0.0000 | 0.0015 | 0.0011 | 0.0000 |

TABLE 53-continued

Effect of Mutamba extract 32 on Body Weight Gain in DIO Mice

| Group | | Weeks | | | | | | | |
|---|---|---|---|---|---|---|---|---|---|
| | | 1 | 2 | 3 | 4 | 5 | 6 | 7 | 8 |
| HFD (High Fat Diet) | Mean | −0.93 | −0.16 | 1.06 | 2.07 | 3.49 | 4.97 | 6.38 | 7.01 |
| | SD | 1.121 | 0.941 | 0.606 | 1.097 | 1.142 | 1.483 | 1.739 | 1.863 |
| SIB 10 mg/kg | Mean | −5.46 | −4.84 | −2.75 | −2.17 | −1.38 | −0.27 | −0.06 | 1.15 |
| | SD | 3.088 | 2.260 | 1.968 | 1.997 | 2.462 | 3.360 | 3.216 | 3.563 |
| | p value | 0.0150 | 0.0038 | 0.0262 | 0.0047 | 0.0054 | 0.0159 | 0.0062 | 0.0149 |
| ORI 40 mg/kg | Mean | −2.59 | −2.90 | −2.55 | −2.35 | −1.84 | 0.08 | 1.81 | 2.10 |
| | SD | 0.792 | 1.346 | 1.714 | 1.792 | 2.536 | 3.102 | 3.188 | 3.124 |
| | p value | 0.0268 | 0.0058 | 0.0022 | 0.0015 | 0.0027 | 0.0130 | 0.0228 | 0.0166 |
| G1 1000 mg/kg | Mean | −4.86 | −3.28 | −4.01 | −3.73 | −2.04 | −2.38 | −0.09 | 1.74 |
| | SD | 3.302 | 2.576 | 2.049 | 2.271 | 2.083 | 2.423 | 1.974 | 1.540 |
| | p value | 0.0357 | 0.0345 | 0.0038 | 0.0009 | 0.0008 | 0.0004 | 0.0006 | 0.0012 | p value: compare to HFD by t-test

The data in Table 53 show that the Mutamba ethanol extract 32, 1000 mg/kg/day treatment group and the positive control treatment group SIB and ORI, all showed statistically significant decreases in body weight gain across all weeks of the study.

Study results for effects of treatments on body weight gain, food intake, and the food efficiency ratio (FER) are shown in Table 54.

TABLE 54

Effect of Mutamba Extract 32 on DIO Mice

| Group | | Average Body Weight Gain (g/day) | Average Food Intake (g/day) | Food Efficiency Ratio (FER) |
|---|---|---|---|---|
| ND (Normal Diet) | Mean | 0.025 | 2.836 | 0.009 |
| | SD | 1.018 | 0.253 | 0.018 |
| | p value | 0.0013 | 0.0001 | 0.0013 |
| HFD (High Fat Diet) | Mean | 0.125 | 2.536 | 0.049 |
| | SD | 1.863 | 0.213 | 0.033 |
| SIB (10 mg/kg) | Mean | 0.021 | 2.724 | 0.008 |
| | SD | 3.563 | 0.676 | 0.064 |
| | p value | 0.0149 | 0.2868 | 0.0111 |
| ORI (40 mg/kg) | Mean | 0.038 | 2.826 | 0.013 |
| | SD | 3.124 | 0.410 | 0.056 |
| | p value | 0.0166 | 0.0162 | 0.0093 |
| G1 (1000 mg/kg) | Mean | 0.031 | 2.631 | 0.012 |
| | SD | 1.540 | 0.667 | 0.027 |
| | p value | 0.0012 | 0.5819 | 0.0010 |

Feed efficacy ratio (FER) = Body weight gain (g/day)/Food intake (g/day)
p value: compared to HFD by t-test The data presented in Table 54 show that average body weight gain per day and food efficiency ratio (FER) endpoints were significantly lowered in the Mutamba and SIB treatment groups, when compared to the high fat diet group. The ORI treatment resulted in statistically significant decreases in average body weight gain per day, average food intake per day and FER.

Study results for effects of treatments on blood biochemistry parameters are shown in Table 55.

TABLE 55

Effect of Mutamba Extract 32 on Biochemistry Parameters in DIO Mice

| Group | | ALT (U/L) | AST (U/L) | T-chol (mg/dL) | LDL-C (mg/dL) | HDL-C (mg/dL) | TG (mg/dL) |
|---|---|---|---|---|---|---|---|
| ND (Normal Diet) | Mean | 13.78 | 45.56 | 120.40 | 8.10 | 60.08 | 33.00 |
| | SD | 1.171 | 1.137 | 10.431 | 1.140 | 4.609 | 12.062 |
| | p value | 0.0571 | 0.0687 | 0.0059 | 0.0421 | 0.0560 | 0.0968 |
| HFD (High Fat Diet) | Mean | 78.62 | 87.84 | 192.00 | 11.42 | 70.78 | 48.40 |
| | SD | 54.749 | 38.225 | 32.458 | 2.853 | 9.671 | 13.777 |
| SIB (10 mg/kg) | Mean | 37.00 | 65.95 | 155.75 | 6.18 | 68.73 | 49.75 |
| | SD | 34.273 | 19.436 | 53.786 | 2.636 | 15.400 | 16.091 |
| | p value | 0.2290 | 0.3357 | 0.2483 | 0.0254 | 0.8127 | 0.8958 |
| ORI (40 mg/kg) | Mean | 40.42 | 67.96 | 184.40 | 6.78 | 78.52 | 143.60 |
| | SD | 23.183 | 14.479 | 22.030 | 0.976 | 5.498 | 102.878 |
| | p value | 0.1887 | 0.3085 | 0.6763 | 0.0088 | 0.1584 | 0.1072 |
| G1 (1000 mg/kg) | Mean | 34.34 | 55.60 | 182.60 | 5.42 | 108.30 | 34.40 |
| | SD | 11.243 | 6.784 | 8.905 | 0.672 | 51.059 | 14.029 |
| | p value | 0.1456 | 0.1326 | 0.5620 | 0.0079 | 0.1770 | 0.1500 | p value: compare to HFD by t-test

The data in Table 55 show that the *Mutamba*, ORI and SIB treatment groups, all exhibited statistically significant decrease in LDL-cholesterol compared to the HFD group.

Table 56 shows the effects of the Mutamba ethanol extract 32 treatment on measurements in DIO mice on several histopathological measures of fatty liver and the resulting calculated Non-Alcoholic Staetohepatitis (NASH) score of the liver.

TABLE 56

Effect of Mutamba Extract 32 on Liver Pathology in DIO Mice

| Group | | Steatosis (0-3) | Lobular Inflammation (0-3) | Hepatocellular Ballooning (0-2) | NASH (sum) |
|---|---|---|---|---|---|
| ND (Normal Diet) | Mean | 0.00 | 0.13 | 0.00 | 0.13 |
| | SD | 0.000 | 0.354 | 0.000 | 0.354 |
| | p value | 0.0000 | 0.0004 | 0.0000 | 0.0054 |
| HFD (HighFat Diet) | Mean | 2.50 | 1.50 | 1.00 | 5.00 |
| | SD | 1.000 | 0.577 | 0.000 | 1.414 |
| SIB (10 mg/kg) | Mean | 0.50 | 0.50 | 0.25 | 1.25 |
| | SD | 1.000 | 0.577 | 0.500 | 1.893 |
| | p value | 0.0300 | 0.0498 | 0.0240 | 0.0192 |
| ORI (40 mg/kg) | Mean | 1.20 | 1.60 | 0.60 | 3.40 |
| | SD | 0.837 | 0.894 | 0.548 | 2.074 |
| | p value | 0.0708 | 0.8529 | 0.1930 | 0.2315 |
| G1 (1000 mg/kg) | Mean | 0.80 | 1.20 | 0.00 | 2.00 |
| | SD | 0.447 | 0.447 | 0.000 | 0.707 |
| | p value | 0.0108 | 0.4071 | 0.0000 | 0.0041 | p value: compare to HFD by t-test

The data in Table 56 show that there are statistically significant differences in the amount of Steatosis, Lobular inflammation, Hepatocellular ballooning and the NASH score between the ND control group, fed a normal diet having a moderate caloric intact of fat, and the HFD group. Treatment group G1 showed statistically significant decreases in Steatosis, Hepatocellular ballooning and NASH score as compared with the HFD group. The SIB treatment group showed statistically significant decreases in Steatosis, Lobular inflammation, Hepatocellular ballooning and NASH score as compared with the HFD group. The ORI treatment group did not show any statistically significant changes compared to the HFD group. These data demonstrate that the Mutamba extract 32 was effective in reducing the amount of liver damage present in mice fed a high fat diet.

Overall, the data presented in this example show that Mutamba ethanol extract 32 was effective in lowering body weight LDL blood cholesterol and fatty liver in mice fed a high fat diet.

Example 54

Effect of Mutamba Ethanol Extract 33-2 on DIO Mice

Mutamba ethanol extract 33-2, produced according to the Example 33, was orally administrated to DIO mouse model as illustrated in the Example 48. The Mutamba extract was administered to treatment group G1 at 1000 mg/kg of animal weight per day. G1 treatment group animals were given an oral dose of *Mutamba* 33-2 at 1000 mg/kg by gavage two times per day. G2 treatment group animals were given an oral dose of Mutamba ethanol extract 33-2 at 500 mg/kg by gavage two times per day. Study results for measurement of animal body weight gain are shown in Table 57.

TABLE 57

Effect of Mutamba Extract 33-2 on Body Weight Gain in DIO Mice

| Group | | Weeks | | | | | | | |
|---|---|---|---|---|---|---|---|---|---|
| | | 1 | 2 | 3 | 4 | 5 | 6 | 7 | 8 |
| ND (Normal Diet) | Mean | 0.15 | 0.30 | 0.08 | −0.13 | −0.07 | 0.45 | −0.10 | 0.14 |
| | SD | 0.529 | 0.405 | 0.747 | 0.952 | 0.952 | 0.906 | 0.747 | 0.968 |
| | p value | 0.0590 | 0.1707 | 0.0035 | 0.0001 | 0.0000 | 0.0001 | 0.0000 | 0.0000 |
| HFD (High Fat Diet) | Mean | 0.85 | 0.81 | 2.12 | 4.11 | 5.47 | 6.79 | 7.55 | 8.21 |
| | SD | 0.374 | 0.596 | 0.642 | 0.457 | 0.349 | 0.177 | 1.046 | 1.493 |
| SIB (10 mg/kg) | Mean | −2.72 | −2.39 | −0.39 | 1.47 | 2.54 | 3.99 | 5.15 | 6.27 |
| | SD | 1.090 | 1.286 | 1.719 | 1.615 | 1.705 | 1.931 | 2.051 | 1.890 |
| | p value | 0.0004 | 0.0026 | 0.0289 | 0.0166 | 0.0167 | 0.0312 | 0.0729 | 0.1399 |
| ORI (40 mg/kg) | Mean | −3.05 | −2.81 | −2.63 | −1.28 | 0.43 | 3.52 | 3.72 | 5.13 |
| | SD | 1.312 | 1.370 | 1.786 | 1.859 | 1.706 | 1.384 | 1.445 | 1.461 |
| | p value | 0.0007 | 0.0018 | 0.0016 | 0.0021 | 0.0021 | 0.0057 | 0.0031 | 0.0172 |
| G1 (1000 mg/kg) | Mean | 0.39 | 1.02 | 2.19 | 3.13 | 3.99 | 4.29 | 5.19 | 4.78 |
| | SD | 0.397 | 0.465 | 0.833 | 1.239 | 1.187 | 1.616 | 2.104 | 1.768 |
| | p value | 0.1143 | 0.5666 | 0.8935 | 0.1815 | 0.0486 | 0.0253 | 0.0819 | 0.0177 |
| G2 (500 mg/kg) | Mean | −1.65 | −1.63 | 0.08 | 2.02 | 3.63 | 5.65 | 6.30 | 7.82 |
| | SD | 0.843 | 1.730 | 2.212 | 2.686 | 3.249 | 3.895 | 4.567 | 4.408 |
| | p value | 0.0009 | 0.0321 | 0.1221 | 0.1568 | 0.2756 | 0.5510 | 0.5829 | 0.8747 | p value: compare to HFD by t-test

The data in Table 57 show that the Mutamba ethanol extract 33-2, 1000 mg/kg/day treatment group showed statistically significant decreases in body weight gain at weeks 5, 6 and 8 of the study. The G2, 500 mg/kg/day treatment group showed statistically significant decreases in body weight gain at weeks 1, and 2 of the study.

Study results for effects of treatments on body weight gain, food intake, and the food efficiency ratio (FER) are shown in Table 58.

TABLE 58

Effect of Mutamba extract 33-2 on DIO Mice

| Group | | Body Weight Gain (g/day) | Food Intake (g/day) | Food Efficiency Ratio (FER) |
|---|---|---|---|---|
| ND (Normal Diet) | Mean | 0.003 | 2.395 | 0.001 |
| | SD | 0.018 | 0.206 | 0.007 |
| | p value | 0.0000 | 0.4282 | 0.0000 |
| HFD (High Fat Diet) | Mean | 0.149 | 2.341 | 0.064 |
| | SD | 0.027 | 0.179 | 0.012 |
| SIB (10 mg/kg) | Mean | 0.114 | 2.624 | 0.043 |
| | SD | 0.034 | 0.372 | 0.013 |
| | p value | 0.1399 | 0.0118 | 0.0458 |
| ORI (40 mg/kg) | Mean | 0.093 | 2.769 | 0.034 |
| | SD | 0.027 | 0.436 | 0.010 |
| | p value | 0.0172 | 0.0016 | 0.0037 |
| G1 (1000 mg/kg) | Mean | 0.087 | 2.337 | 0.037 |
| | SD | 0.032 | 0.249 | 0.014 |
| | p value | 0.0177 | 0.9588 | 0.0180 |
| G2 (500 mg/kg) | Mean | 0.142 | 2.503 | 0.057 |
| | SD | 0.080 | 0.642 | 0.032 |
| | p value | 0.8747 | 0.3421 | 0.6966 |

Feed efficacy ratio (FER) = Body weight gain (g/day)/Food intake (g/day)
p value: compare to HFD by t-test The data presented in Table 58 show that average body weight gain per day and food efficiency ratio (FER) endpoints were statistically significantly lowered in the Mutamba ethanol extract 33-2, 1000 mg/kg/day treatment group compared to the high fat diet group.

Study results for effects of treatments on blood biochemistry parameters are shown in Table 59.

TABLE 59

Effect of Mutamba extract 33-2 on Biochemistry Parameters in DIO Mice

| Group | | T-chol (mg/dL) | LDL-C (mg/dL) | TG (mg/dL) |
|---|---|---|---|---|
| ND (Normal Diet) | Mean | 89.60 | 7.04 | 22.00 |
| | SD | 9.659 | 2.304 | 7.071 |
| | p value | 0.0000 | 0.1018 | 0.0097 |
| HFD (High Fat Diet) | Mean | 213.25 | 10.13 | 37.00 |
| | SD | 21.639 | 2.617 | 9.487 |
| SIB (10 mg/kg) | Mean | 158.60 | 5.26 | 46.60 |
| | SD | 5.030 | 1.389 | 15.126 |
| | p value | 0.0130 | 0.0086 | 0.2631 |
| ORI (40 mg/kg) | Mean | 182.40 | 7.42 | 41.20 |
| | SD | 12.482 | 1.593 | 16.514 |
| | p value | 0.0306 | 0.0955 | 0.4616 |
| G1 (1000 mg/kg) | Mean | 168.00 | 6.14 | 22.60 |
| | SD | 35.763 | 1.191 | 5.079 |
| | p value | 0.0628 | 0.0181 | 0.5066 | p value: compare to HFD by t-test

The data in Table 59 show that Mutamba extract 33-2, 1000 mg/kg/day treatment group decreased LDL-cholesterol in a statistically significant fashion as compared to the HFD group.

The data presented in this example show that Mutamba extract 33-2 when administered at 1000 mg/kg of subject body weight showed significantly decreased body weight gain, Food Efficiency Ratio, and LDL-cholesterol. Therefore, the present results indicate that Mutamba extract 33-2 can be used as a body weight and blood cholesterol controller.

Example 55

Efficacy Study of Mutamba Fractions 34, 34-1, and 34-2 on a DIO Mouse Model

Mutamba fractions 34, 34-1, and 34-2 produced according to the example 34 was orally administered to DIO mice as described in Example 48. Three Mutamba fraction treatment groups were: G1 at 250 mg/kg of EtOA fraction 34; G2 at 250 mg/kg of BuOH fraction 34-1; and G3 at 250 mg/kg of Water fraction 34-2. The treatment article was given orally by gavaging 2 times per day.

The EtOA fraction of Mutamba treatment group (G1) didn't show any effect on body weight. However, the BuOH fraction treatment group (G2) showed significantly decreased body weight at week 4, 6, 7, and 8. The water fraction treatment group (G3) showed significantly decreased body weight at week 2 when compared to the HFD group (Table 60).

TABLE 60

Effect of Mutamba Fractions 34, 34-1, and 34-2 on Body Weight in Mice Fed a High Fat Diet

| Group | | Weeks | | | | | | | | |
|---|---|---|---|---|---|---|---|---|---|---|
| | | 0 | 1 | 2 | 3 | 4 | 5 | 6 | 7 | 8 |
| ND | Mean | 27.34 | 27.49 | 27.64 | 27.42 | 27.21 | 27.27 | 27.79 | 27.24 | 27.48 |
| | SD | 1.283 | 1.271 | 1.242 | 1.444 | 1.831 | 1.700 | 1.601 | 1.465 | 1.381 |
| | p value | 0.0000 | 0.0000 | 0.0000 | 0.0000 | 0.0000 | 0.0000 | 0.0000 | 0.0000 | 0.0000 |
| HFD | Mean | 41.07 | 41.92 | 41.88 | 43.18 | 45.18 | 46.54 | 47.85 | 48.62 | 49.27 |
| | SD | 1.955 | 2.295 | 2.486 | 2.132 | 2.295 | 2.110 | 1.834 | 1.353 | 0.933 |
| SIB | Mean | 38.41 | 35.69 | 36.03 | 38.02 | 39.89 | 40.95 | 42.40 | 43.57 | 44.69 |
| | SD | 2.522 | 3.066 | 3.200 | 3.812 | 3.817 | 4.185 | 4.412 | 4.534 | 4.322 |
| | p value | 0.1290 | 0.0121 | 0.0202 | 0.0472 | 0.0458 | 0.0466 | 0.0556 | 0.0711 | 0.0788 |

TABLE 60-continued

Effect of Mutamba Fractions 34, 34-1, and 34-2 on Body Weight in Mice Fed a High Fat Diet

| Group | | 0 | 1 | 2 | 3 | 4 | 5 | 6 | 7 | 8 |
|---|---|---|---|---|---|---|---|---|---|---|
| ORI | Mean | 39.76 | 36.71 | 36.95 | 37.14 | 38.49 | 40.19 | 43.28 | 43.49 | 44.90 |
| | SD | 3.037 | 1.792 | 1.674 | 2.110 | 2.927 | 2.871 | 2.544 | 2.674 | 2.635 |
| | p value | 0.4846 | 0.0064 | 0.0092 | 0.0038 | 0.0074 | 0.0079 | 0.0198 | 0.0105 | 0.0167 |
| G1 | Mean | 37.39 | 36.44 | 37.29 | 39.04 | 40.69 | 42.40 | 44.37 | 45.27 | 46.55 |
| | SD | 4.593 | 5.544 | 5.215 | 5.225 | 4.695 | 4.013 | 3.926 | 3.721 | 3.519 |
| | p value | 0.1823 | 0.1092 | 0.1531 | 0.1840 | 0.1263 | 0.1067 | 0.1487 | 0.1343 | 0.1807 |
| G2 | Mean | 38.00 | 38.93 | 38.73 | 38.17 | 38.32 | 40.16 | 40.92 | 41.91 | 42.36 |
| | SD | 2.719 | 4.010 | 4.241 | 5.007 | 5.136 | 5.224 | 3.599 | 3.378 | 3.001 |
| | p value | 0.1013 | 0.2294 | 0.2337 | 0.1067 | 0.0438 | 0.0572 | 0.0103 | 0.0076 | 0.0032 |
| G3 | Mean | 37.97 | 37.32 | 36.97 | 38.90 | 40.53 | 42.15 | 43.60 | 44.40 | 45.38 |
| | SD | 2.741 | 4.074 | 3.009 | 3.738 | 4.141 | 4.756 | 4.610 | 4.646 | 4.815 |
| | p value | 0.1000 | 0.0854 | 0.0346 | 0.0827 | 0.0862 | 0.1334 | 0.1293 | 0.1264 | 0.1461 | p value: compare to HFD by t-test

The BuOH fraction 34-1 treatment group (G2) body weight gain was significantly decreased at weeks 6, 7, and 8. Otherwise, the EtOA fraction 34 treatment group (G1) showed significantly decreased body weight at week 1 and the water fraction 34-2 treatment group (G3) at week 2 when compared to HFD group (Table 61).

TABLE 61

Effect of Mutamba fractions 34, 34-1, and 34-2 on Body Weight Gain in Mice Fed a High Fat Diet

| Group | | 1 | 2 | 3 | 4 | 5 | 6 | 7 | 8 |
|---|---|---|---|---|---|---|---|---|---|
| ND | Mean | 0.15 | 0.30 | 0.08 | −0.13 | −0.07 | 0.45 | −0.10 | 0.14 |
| | SD | 0.529 | 0.405 | 0.747 | 0.952 | 0.952 | 0.906 | 0.747 | 0.968 |
| | p value | 0.0590 | 0.1707 | 0.0035 | 0.0001 | 0.0000 | 0.0001 | 0.0000 | 0.0000 |
| HFD | Mean | 0.85 | 0.81 | 2.12 | 4.11 | 5.47 | 6.79 | 7.55 | 8.21 |
| | SD | 0.374 | 0.596 | 0.642 | 0.457 | 0.349 | 0.177 | 1.046 | 1.493 |
| SIB | Mean | −2.72 | −2.39 | −0.39 | 1.47 | 2.54 | 3.99 | 5.15 | 6.27 |
| | SD | 1.090 | 1.286 | 1.719 | 1.615 | 1.705 | 1.931 | 2.051 | 1.890 |
| | p value | 0.0004 | 0.0026 | 0.0289 | 0.0166 | 0.0167 | 0.0312 | 0.0729 | 0.1399 |
| ORI | Mean | −3.05 | −2.81 | −2.63 | −1.28 | 0.43 | 3.52 | 3.72 | 5.13 |
| | SD | 1.312 | 1.370 | 1.786 | 1.859 | 1.706 | 1.384 | 1.445 | 1.461 |
| | p value | 0.0007 | 0.0018 | 0.0016 | 0.0021 | 0.0021 | 0.0057 | 0.0031 | 0.0172 |
| G1 | Mean | −0.95 | −0.10 | 1.65 | 3.30 | 5.01 | 6.98 | 7.88 | 9.16 |
| | SD | 1.149 | 0.723 | 0.744 | 0.895 | 1.356 | 1.657 | 1.765 | 1.639 |
| | p value | 0.0204 | 0.0831 | 0.3539 | 0.1464 | 0.4988 | 0.8108 | 0.7554 | 0.3978 |
| G2 | Mean | 0.93 | 0.73 | 0.17 | 0.32 | 2.16 | 2.92 | 3.90 | 4.36 |
| | SD | 1.467 | 1.768 | 2.894 | 3.226 | 2.843 | 1.143 | 1.323 | 1.868 |
| | p value | 0.9170 | 0.9341 | 0.2109 | 0.0575 | 0.0589 | 0.0014 | 0.0029 | 0.0124 |
| G3 | Mean | −0.65 | −1.00 | 0.93 | 2.56 | 4.18 | 5.63 | 6.43 | 7.41 |
| | SD | 1.584 | 1.407 | 1.207 | 1.661 | 2.288 | 2.369 | 2.560 | 2.947 |
| | p value | 0.1004 | 0.0484 | 0.1225 | 0.1161 | 0.2782 | 0.3374 | 0.4428 | 0.6410 | p value: compare to HFD by t-test

There were no significant changes on FER when mice were treated with the EtOA fraction 34 and water fraction 34-1, but the BuOH fraction 34-1 treatment group showed borderline changes (Table 62).

TABLE 62

Effect of Mutamba fractions 34, 34-1, and 34-2 on Mice Fed a High Fat Diet

| Group | | Body weight gain (g/day) | Food intake (g/day) | FER (Food efficiency ratio) |
|---|---|---|---|---|
| ND | Mean | 0.003 | 2.395 | 0.001 |
| | SD | 0.018 | 0.206 | 0.007 |
| | p value | 0.0000 | 0.4282 | 0.0000 |
| HFD | Mean | 0.149 | 2.341 | 0.064 |
| | SD | 0.027 | 0.179 | 0.012 |
| SIB | Mean | 0.114 | 2.624 | 0.043 |
| | SD | 0.034 | 0.372 | 0.013 |
| | p value | 0.1399 | 0.0118 | 0.0458 |
| ORI | Mean | 0.093 | 2.769 | 0.034 |
| | SD | 0.027 | 0.436 | 0.010 |
| | p value | 0.0172 | 0.0016 | 0.0037 |
| G1 | Mean | 0.167 | 2.532 | 0.066 |
| | SD | 0.030 | 0.206 | 0.012 |
| | p value | 0.3978 | 0.0086 | 0.8046 |
| G2 | Mean | 0.079 | 1.978 | 0.040 |
| | SD | 0.034 | 0.158 | 0.017 |
| | p value | 0.0124 | 0.0000 | 0.0513 |
| G3 | Mean | 0.135 | 2.244 | 0.060 |
| | SD | 0.054 | 0.251 | 0.024 |
| | p value | 0.6410 | 0.2182 | 0.7871 |

FER (Feed efficacy ratio) = Body weight gain (g/day)/Food intake (g/day)
p value: compare to HFD by t-test In the BuOH fraction 34-1 of Mutamba treatment group (G2), ALT, HDL-C and TG showed significant changes (Table 63).

TABLE 63

Effect of Mutamba fractions 34, 34-1, and 34-2 on Biochemistry Parameters in DIO mice

| Group | | ALT (U/L) | ALP (U/L) | T-chol (mg/dL) | LDL-C (mg/dL) | HDL-C (mg/dL) | TG (mg/dL) |
|---|---|---|---|---|---|---|---|
| ND | Mean | 15.30 | 264.62 | 89.60 | 7.04 | 42.58 | 22.00 |
| | SD | 1.681 | 62.455 | 9.659 | 2.304 | 6.308 | 7.071 |
| | p value | 0.0067 | 0.0390 | 0.0000 | 0.1018 | 0.0001 | 0.0097 |
| HFD | Mean | 122.80 | 181.20 | 213.25 | 10.13 | 69.50 | 37.00 |
| | SD | 32.072 | 11.240 | 21.639 | 2.617 | 3.061 | 9.487 |
| SIB | Mean | 67.24 | 156.68 | 158.60 | 5.26 | 64.78 | 46.60 |
| | SD | 42.203 | 45.995 | 5.030 | 1.389 | 2.901 | 15.126 |
| | p value | 0.0668 | 0.3066 | 0.0130 | 0.0086 | 0.0497 | 0.2631 |
| ORI | Mean | 42.60 | 182.06 | 182.40 | 7.42 | 78.34 | 41.20 |
| | SD | 13.607 | 23.471 | 12.482 | 1.593 | 5.176 | 16.514 |
| | p value | 0.0014 | 0.9487 | 0.0306 | 0.0955 | 0.0200 | 0.4616 |
| G2 | Mean | 57.66 | 162.96 | 187.40 | 8.18 | 75.00 | 33.40 |
| | SD | 31.354 | 25.716 | 16.876 | 0.856 | 2.074 | 7.232 |
| | p value | 0.0181 | 0.2321 | 0.0830 | 0.1574 | 0.0146 | 0.0052 |
| G3 | Mean | 72.22 | 175.16 | 180.80 | 9.58 | 68.36 | 34.00 |
| | SD | 37.447 | 31.987 | 41.318 | 3.065 | 11.010 | 16.016 |
| | p value | 0.0697 | 0.7322 | 0.2013 | 0.7861 | 0.8483 | 0.1496 | p value: compare to HFD by t-test

Both the BuOH fraction 34-1 (G2) and the water fraction 34-2 (G3) treatment groups showed a significantly decreased NASH score when compared with the high fat diet (Table 64).

TABLE 64

Effect of Mutmba fractions 34, 34-1, and 34-2 on Liver Pathology in Mice Fed a High Fat Diet

| Group | | Indications | | | |
|---|---|---|---|---|---|
| | | Steatosis (0-3) | Lobular Inflammation (0-3) | Hepatocellular ballooning (0-2) | NSAH (sum) |
| ND | Mean | 0.00 | 1.00 | 0.00 | 1.00 |
| | SD | 0.000 | 0.000 | 0.000 | 0.000 |
| | p value | 0.0000 | 0.0006 | 0.0001 | 0.0000 |
| HFD | Mean | 2.75 | 2.50 | 1.75 | 7.00 |
| | SD | 0.500 | 0.577 | 0.500 | 0.816 |
| SIB | Mean | 1.20 | 1.60 | 0.40 | 3.20 |
| | SD | 0.837 | 0.548 | 0.548 | 1.304 |
| | p value | 0.0142 | 0.0479 | 0.0066 | 0.0015 |
| ORI | Mean | 1.00 | 1.60 | 0.80 | 3.40 |
| | SD | 0.707 | 0.548 | 0.837 | 1.949 |
| | p value | 0.0042 | 0.0479 | 0.0871 | 0.0111 |
| G2 | Mean | 1.40 | 1.40 | 0.80 | 3.60 |
| | SD | 0.548 | 0.548 | 0.837 | 1.871 |
| | p value | 0.0066 | 0.0222 | 0.0871 | 0.0108 |
| G3 | Mean | 1.60 | 1.60 | 0.80 | 4.00 |
| | SD | 0.548 | 0.548 | 0.837 | 1.871 |
| | p value | 0.0141 | 0.0479 | 0.0871 | 0.0212 | p value: compare to HFD by t-test

As is evident from the results, the 250 mg/kg BuOH fraction 34-1 treatment group showed significantly decreased body weight gain, FER, TG and NASH score. Therefore, the Mutamba BuOH extract 34-1 can be used as a body weight and blood cholesterol and fatty liver controller.

Example 56

Efficacy Study of Mutmaba EtOH Extract 32(in DIO Rats

Mutamba ethanol extract 32 produced according to the example 32 was orally administrated by gavage to rats in a DIO model (as described in Example 49) at a dosage of 500 mg/kg twice a day.

In the Mutamba treatment group (G3), body weight was significantly decreased at days 87, 91, 94 and 98, when compared with the high fat diet group (Table 65).

TABLE 65

Effect of Mutamba Ethanol Extract 32 on Body Weight in Rats Fed a High Fat Diet

| Group | | Days | | | | | | | | | |
|---|---|---|---|---|---|---|---|---|---|---|---|
| | | 0 | 3 | 7 | 10 | 14 | 17 | 21 | 24 | 28 | 31 |
| ND | Mean | 320.66 | 335.39 | 351.46 | 362.05 | 368.52 | 377.64 | 390.40 | 394.90 | 401.13 | 408.06 |
| | SD | 21.51 | 13.89 | 16.55 | 17.24 | 16.75 | 19.96 | 20.15 | 20.59 | 21.63 | 22.46 |
| | p value | 0.026 | 0.009 | 0.011 | 0.009 | 0.008 | 0.009 | 0.009 | 0.010 | 0.005 | 0.006 |
| HFD | Mean | 343.82 | 361.82 | 381.42 | 393.40 | 403.22 | 413.10 | 426.37 | 431.33 | 442.03 | 451.15 |
| | SD | 16.89 | 15.61 | 18.18 | 17.87 | 20.45 | 19.91 | 20.62 | 21.41 | 20.68 | 22.52 |
| G3 | Mean | 342.70 | 357.67 | 370.89 | 379.63 | 386.71 | 395.49 | 407.00 | 413.14 | 417.65 | 429.28 |
| | SD | 15.73 | 17.54 | 18.61 | 24.35 | 28.12 | 32.59 | 32.30 | 34.30 | 41.27 | 38.57 |
| | p value | 0.890 | 0.661 | 0.326 | 0.266 | 0.248 | 0.260 | 0.220 | 0.271 | 0.202 | 0.234 |

| Group | | Days | | | | | | | | |
|---|---|---|---|---|---|---|---|---|---|---|
| | | 35 | 38 | 42 | 45 | 49 | 52 | 56 | 60 | 64 | 67 |
| ND | Mean | 415.74 | 418.68 | 429.37 | 431.83 | 433.91 | 436.97 | 444.94 | 450.37 | 455.47 | 459.98 |
| | SD | 23.46 | 23.78 | 24.65 | 25.65 | 26.05 | 25.29 | 26.04 | 25.19 | 25.07 | 24.89 |
| | p value | 0.005 | 0.003 | 0.005 | 0.004 | 0.003 | 0.003 | 0.002 | 0.003 | 0.003 | 0.003 |
| HFD | Mean | 461.94 | 468.41 | 478.74 | 484.72 | 487.24 | 489.77 | 499.73 | 505.17 | 507.01 | 509.35 |
| | SD | 23.43 | 23.53 | 25.85 | 25.99 | 23.49 | 23.99 | 22.08 | 25.59 | 24.33 | 21.21 |
| G3 | Mean | 434.91 | 447.75 | 451.41 | 458.17 | 461.74 | 465.06 | 470.63 | 480.31 | 481.18 | 482.58 |
| | SD | 45.77 | 37.53 | 36.07 | 32.24 | 30.48 | 31.71 | 32.38 | 30.66 | 31.51 | 32.54 |
| | p value | 0.204 | 0.255 | 0.142 | 0.129 | 0.117 | 0.139 | 0.083 | 0.139 | 0.124 | 0.104 |

| | Group | Days | | | | | | | |
|---|---|---|---|---|---|---|---|---|---|
| | | 70 | 74 | 77 | 80 | 84 | 87 | 91 | 94 | 98 |
| ND | Mean | 462.51 | 469.00 | 473.26 | 474.59 | 481.74 | 483.20 | 488.38 | 490.31 | 493.26 |
| | SD | 25.54 | 27.48 | 26.55 | 28.19 | 27.62 | 30.18 | 30.58 | 30.68 | 31.12 |
| | p value | 0.003 | 0.003 | 0.004 | 0.003 | 0.005 | 0.004 | 0.004 | 0.003 | 0.002 |
| HFD | Mean | 512.15 | 520.72 | 523.55 | 524.71 | 528.65 | 532.17 | 539.97 | 545.50 | 553.65 |
| | SD | 22.39 | 22.28 | 24.23 | 19.80 | 19.32 | 16.34 | 19.53 | 21.76 | 22.44 |
| G3 | Mean | 488.84 | 494.84 | 497.11 | 499.54 | 497.76 | 499.07 | 504.37 | 509.43 | 512.23 |
| | SD | 34.38 | 34.29 | 36.46 | 31.10 | 35.05 | 34.15 | 35.65 | 30.19 | 25.98 |
| | p value | 0.172 | 0.132 | 0.149 | 0.107 | 0.074 | 0.049 | 0.047 | 0.030 | 0.010 | p value: Compared to HFD group

In the Mutamba treatment group, the body weight gain was decreased when compared with the high fat diet group (Table 66).

TABLE 66

Effect of Mutamba Ethanol Extract 32 on Body Weight Gain in Rats Fed a High Fat Diet

| Group | | Days | | | | | | | | | | | | | |
|---|---|---|---|---|---|---|---|---|---|---|---|---|---|---|---|
| | | 3 | 7 | 10 | 14 | 17 | 21 | 24 | 28 | 31 | 35 | 38 | 42 | 45 | 49 |
| ND | Mean | 11.51 | 27.57 | 38.17 | 44.64 | 53.76 | 66.51 | 71.02 | 77.25 | 84.18 | 91.86 | 94.80 | 105.49 | 107.95 | 110.03 |
| | SD | 2.76 | 5.38 | 7.10 | 6.59 | 10.20 | 11.04 | 11.93 | 13.25 | 14.26 | 14.55 | 16.36 | 16.70 | 18.23 | 18.63 |
| | p value | 0.130 | 0.053 | 0.036 | 0.006 | 0.028 | 0.034 | 0.041 | 0.016 | 0.015 | 0.009 | 0.005 | 0.007 | 0.005 | 0.005 |
| HFD | Mean | 13.94 | 33.54 | 45.53 | 55.34 | 65.23 | 78.49 | 83.45 | 94.16 | 103.28 | 114.06 | 120.54 | 130.87 | 136.85 | 139.36 |
| | SD | 2.59 | 4.54 | 2.95 | 4.64 | 5.13 | 6.03 | 6.70 | 7.11 | 9.02 | 10.20 | 8.38 | 10.01 | 10.78 | 8.84 |
| G3 | Mean | 12.40 | 25.62 | 34.35 | 41.43 | 50.22 | 61.73 | 67.87 | 72.37 | 84.01 | 89.63 | 102.47 | 106.14 | 112.89 | 116.47 |
| | SD | 5.57 | 7.68 | 9.81 | 14.62 | 18.93 | 18.90 | 20.62 | 27.18 | 24.16 | 32.13 | 23.10 | 22.37 | 18.58 | 17.03 |
| | p value | 0.529 | 0.044 | 0.023 | 0.047 | 0.084 | 0.060 | 0.099 | 0.081 | 0.087 | 0.097 | 0.091 | 0.028 | 0.016 | 0.012 |

TABLE 66-continued

Effect of Mutamba Ethanol Extract 32 on Body Weight Gain in Rats Fed a High Fat Diet

| | | Days | | | | | | | | | | | | |
|---|---|---|---|---|---|---|---|---|---|---|---|---|---|---|
| Group | | 52 | 56 | 60 | 64 | 67 | 70 | 74 | 77 | 80 | 84 | 87 | 91 | 94 | 98 |
| ND | Mean | 113.09 | 121.05 | 126.49 | 131.59 | 136.10 | 138.63 | 145.12 | 149.38 | 150.71 | 157.86 | 159.32 | 164.50 | 166.42 | 169.37 |
| | SD | 17.60 | 17.50 | 17.72 | 17.83 | 17.86 | 18.66 | 20.23 | 19.36 | 20.70 | 19.62 | 22.22 | 22.23 | 22.93 | 25.00 |
| | p value | 0.004 | 0.003 | 0.003 | 0.006 | 0.009 | 0.011 | 0.010 | 0.011 | 0.015 | 0.021 | 0.025 | 0.016 | 0.011 | 0.007 |
| HFD | Mean | 141.90 | 151.86 | 157.29 | 159.14 | 161.47 | 164.27 | 172.84 | 175.67 | 176.84 | 180.77 | 184.29 | 192.10 | 197.62 | 205.77 |
| | SD | 8.67 | 6.76 | 10.82 | 9.54 | 9.06 | 8.89 | 7.86 | 7.93 | 4.16 | 5.99 | 4.07 | 4.99 | 7.00 | 8.87 |
| G3 | Mean | 119.78 | 125.36 | 135.03 | 135.91 | 137.31 | 143.56 | 149.56 | 151.83 | 154.27 | 152.48 | 153.80 | 159.09 | 164.15 | 166.95 |
| | SD | 17.66 | 18.97 | 18.57 | 18.51 | 18.91 | 20.95 | 20.69 | 22.32 | 17.01 | 20.58 | 19.22 | 20.56 | 15.80 | 12.99 |
| | p value | 0.017 | 0.009 | 0.023 | 0.017 | 0.015 | 0.043 | 0.025 | 0.031 | 0.012 | 0.010 | 0.005 | 0.005 | 0.001 | 0.000 | p value: Compared to HFD group

Weight gain (g/day) and Food efficiency ratio (FER) were significantly lowered in the *Mutmaba* treatment group as compared to the high fat diet group (Table 67).

TABLE 67

Effect of Mutamba Ethanol Extract 32 on DIO Rats

| Group | | Weight gain (g/day) | Food intake (g/day) | FER (Food efficiency ratio) |
|---|---|---|---|---|
| ND | Mean | 1.728 | 16.265 | 0.107 |
| | SD | 0.255 | 0.868 | 0.018 |
| | p value | 0.007 | 0.669 | 0.010 |
| HFD | Mean | 2.100 | 15.953 | 0.132 |
| | SD | 0.090 | 0.787 | 0.005 |
| G3 | Mean | 1.704 | 15.693 | 0.109 |
| | SD | 0.133 | 0.709 | 0.006 |
| | p value | 0.000 | 0.693 | 0.000 |

FER (Food efficiency ratio) = (body weight gain (g/day)/food intake (g/day)
p value: Compared to HFD group In the Mutamba treatment group of absolute organ weight, Perirenal, Retroperitoneal and Total fat pad were significantly decrease, when compared with the high fat diet group (Table 68).

TABLE 68

Effects of Mutamba Ethanol Extract 32 on Absolute Organ Weights in Rats Fed a High Fat Diet

| Group | | Epididymal Fat | Retroperitoneal Fat | Perirenal Fat | Total Fat |
|---|---|---|---|---|---|
| ND | Mean | 0.014 | 0.008 | 0.005 | 0.027 |
| | SD | 0.004 | 0.002 | 0.001 | 0.006 |
| | p value | 0.007 | 0.001 | 0.004 | 0.002 |
| HFD | Mean | 0.020 | 0.013 | 0.007 | 0.040 |
| | SD | 0.003 | 0.002 | 0.001 | 0.005 |
| G3 | Mean | 0.017 | 0.009 | 0.005 | 0.030 |
| | SD | 0.003 | 0.002 | 0.001 | 0.006 |
| | p value | 0.054 | 0.006 | 0.010 | 0.008 | p value: Compared to HFD group

These results show that both body weight and body weight gain were significantly decreased in the Mutamba treatment groups. At treatment group, FER (food efficiency ratio) and visceral fat weights were also significantly decreased. Therefore, the present results suggest that Mutamba extract can be used as a body weight controller.

Example 57

Effect of *Morus alba* Ethyl Acetate Extract 15 Combined with *Magnolia* Extract 29 on DIO Mice

*Morus alba* ethyl acetate extract 15 produced as described in Example 15 and *Magnolia* extract 29 produced according to Example 29 were combined and blended to a ratio of 2:1 by weight. The combination composition was orally administrated to DIO mice as described in Example 48 at a dosage of 300 mg/kg of animal weight (200 mg/kg Morus and 100 mg/kg *Magnolia*). The study time period was seven weeks. Table 69 shows the shows the effects of the combination composition on body weight gain, that is, the change in body weight in each study group as measured at the beginning of the study compared to the weight measured on the day of each time point of the study.

TABLE 69

Effect of *Morus alba* extract 15 Combined with *Magnolia* extract 29 on Body Weight Gain in Mice Fed a High Fat Diet

| | | Weeks | | | | | | |
|---|---|---|---|---|---|---|---|---|
| Group | | 1 | 2 | 3 | 4 | 5 | 6 | 7 |
| ND | Mean | −0.09 | −0.25 | 0.09 | 0.35 | 0.13 | 0.56 | 0.79 |
| | SD | 0.202 | 0.513 | 0.418 | 0.408 | 0.500 | 0.528 | 0.543 |
| | p value | 0.1250 | 0.4003 | 0.2140 | 0.1935 | 0.0758 | 0.0351 | 0.0243 |
| HFD | Mean | −0.55 | 0.16 | 1.45 | 1.95 | 3.29 | 4.40 | 5.77 |
| | SD | 0.891 | 0.665 | 1.324 | 1.455 | 1.643 | 1.373 | 1.476 |

TABLE 69-continued

Effect of *Morus alba* extract 15 Combined with *Magnolia* extract 29 on Body Weight Gain in Mice Fed a High Fat Diet

| Group | | Weeks | | | | | | |
|---|---|---|---|---|---|---|---|---|
| | | 1 | 2 | 3 | 4 | 5 | 6 | 7 |
| ORI (40 mg/kg) | Mean | −3.20 | −4.88 | −3.34 | −2.61 | −2.04 | −1.65 | −0.07 |
| | SD | 0.611 | 1.463 | 1.502 | 1.859 | 1.640 | 1.526 | 1.437 |
| | p value | 0.0011 | 0.0028 | 0.0072 | 0.0174 | 0.0081 | 0.0029 | 0.0033 |
| G1 (300 mg/kg) | Mean | −1.87 | −2.78 | −2.15 | −1.62 | −1.56 | −1.48 | −0.56 |
| | SD | 1.126 | 1.369 | 1.533 | 1.546 | 1.976 | 2.316 | 2.240 |
| | p value | 0.1001 | 0.0144 | 0.0152 | 0.0180 | 0.0121 | 0.0077 | 0.0051 | p value: compare to HFD by t-test

The data in Table 69 show that the animals treated with a composition comprising *Morus alba* 15 combined with *Magnolia* extract 29 (treatment group G1) exhibited statistically significant decreases in body weight gains from week 2 through to week 7 of the study as compared to the HFD group. The positive control ORI (Orilistat) showed statistically significant decreases in body weight gains from week 1 through to week 7 of the study as compared to the HFD group.

Table 70 shows the effects of *Morus alba* extract 15 and *Magnolia* extract 29 combination composition on DOI mice for the following end points: average body weight gain per day of the study, average food intake per day of the study, and the food efficiency ratio (FER) which is calculated as the average body weight gain per day over the study period, divided by the average food intake per day over the study period.

TABLE 70

Effect of *Morus alba* extract 15 Combined with *Magnolia* Extract 29 on DIO Mice

| Group | | Body Weight Gain (g/day) | Food Intake (g/day) | Food Efficiency Ratio (FER) |
|---|---|---|---|---|
| ND | Mean | 0.018 | 3.558 | 0.005 |
| | SD | 0.012 | 0.560 | 0.003 |
| | p value | 0.0243 | 0.3067 | 0.0242 |
| HFD | Mean | 0.128 | 3.342 | 0.038 |
| | SD | 0.033 | 0.807 | 0.010 |
| ORI (40 mg/kg) | Mean | −0.002 | 3.961 | 0.000 |
| | SD | 0.032 | 2.330 | 0.007 |
| | p value | 0.0033 | 0.2661 | 0.0006 |
| G1 (300 mg/kg) | Mean | −0.012 | 2.261 | −0.006 |
| | SD | 0.050 | 0.858 | 0.022 |
| | p value | 0.0051 | 0.0010 | 0.0189 |

Feed Efficacy Ratio (FER) = Body weight gain (g/day)/Food intake (g/day)
p value: compare to HFD by t-test The data in Table 70 show that the composition having *Morus alba* extract 15 combined with *Magnolia* extract 29 (treatment group G1) showed a statistically significant effect on lowering body weight gain, food intake and lowering the Food Efficiency Ratio as compared to the HFD group. The ORI positive control treatment group showed statistically lower values than the HFD group for Body Weight Gain per day and Food Efficiency Ratio.

Table 71 shows the effects of *Morus alba* extract 15 and *Magnolia* extract 29 combination composition on DIO mice for total liver organ weight, the weights of three fatty deposits: epididymal fat, retroperitoneal fat, perirenal fat, and total fat (the sum of the previous three fatty tissues).

TABLE 71

Effect of *Morus alba* extract 15 Combined with *Magnolia* Extract 29 on Absolute Liver Weight and Weight of Fatty Deposits in DIO Mice

| Group | | Liver | Epididymal Fat | Retroperitoneal Fat | Perirenal Fat | Total Fat* |
|---|---|---|---|---|---|---|
| ND | Mean | 1.00 | 0.53 | 0.15 | 0.08 | 0.76 |
| | SD | 0.145 | 0.150 | 0.064 | 0.017 | 0.222 |
| | p value | 0.0410 | 0.0002 | 0.0000 | 0.0117 | 0.0001 |
| HFD | Mean | 1.22 | 2.60 | 0.69 | 0.31 | 3.60 |
| | SD | 0.215 | 0.424 | 0.051 | 0.118 | 0.521 |
| ORI 40 mg/kg | Mean | 1.05 | 1.92 | 0.55 | 0.21 | 2.68 |
| | SD | 0.137 | 0.230 | 0.039 | 0.055 | 0.310 |
| | p value | 0.2282 | 0.0236 | 0.0034 | 0.1729 | 0.0177 |
| G1 300 mg/kg | Mean | 1.23 | 1.73 | 0.52 | 0.20 | 2.45 |
| | SD | 0.274 | 0.466 | 0.076 | 0.110 | 0.643 |
| | p value | 0.9286 | 0.0148 | 0.0036 | 0.1649 | 0.0145 |

*Total fat is sum of the three fat deposits (epididymal, retroperitoneal and perirenal fat)
p value: compare to HFD by t-test The data in Table 71 show that there is a statistically significant difference in the weight of liver, epididymal fat, retroperitoneal fat, perirenal fat and total fat between the ND control group, fed a normal diet having a moderate caloric intact of fat, and the HFD group. In addition, treatment group G1 getting the composition of *Morus alba* extract 15 combined with *Magnolia* extract 29, along with the positive control treatment group (ORI), showed statistically significant decreases in two fat deposits (Epididymal Fat and Retroperitoneal Fat) and Total Fat as compared with the HFD group. These data, demonstrate the composition of *Morus alba* extract combined with *Magnolia* extract is effective at reducing the amount of fat present in DIO mice.

Table 72 shows the effects of the composition comprising *Morus alba* 15 combined with *Magnolia* extract 29 on measurements in DIO mice of fasting glucose (F-Glu), total cholesterol (T-chol) and LDL-cholesterol (LDL-C) as measure in blood samples obtained at the end of the study.

TABLE 72

Effect of *Morus alba* Extract 15 Combined with *Magnolia* Extract 29 on Biochemistry Parameters

| Group | | F-Glu (mg/dL) | T-Chol (mg/dL) | Triglyceride (mg/dL) | LDL-C (mg/dL) |
|---|---|---|---|---|---|
| ND (Normal Diet) | Mean | 178.67 | 105.67 | 30.56 | 4.54 |
| | SD | 56.934 | 17.349 | 11.886 | 1.705 |
| | p value | 0.0004 | 0.0000 | 0.7005 | 0.0807 |

TABLE 72-continued

Effect of *Morus alba* Extract 15 Combined with *Magnolia* Extract 29 on Biochemistry Parameters

| Group | | F-Glu (mg/dL) | T-Chol (mg/dL) | Triglyceride (mg/dL) | LDL-C (mg/dL) |
|---|---|---|---|---|---|
| HFD (High Fat Diet) | Mean | 334.50 | 176.75 | 28.00 | 6.25 |
| | SD | 30.957 | 10.996 | 6.976 | 0.480 |
| ORI (40 mg/kg) | Mean | 225.50 | 134.00 | 62.50 | 3.30 |
| | SD | 52.208 | 30.299 | 64.717 | 1.134 |
| | p value | 0.0115 | 0.0379 | 0.3653 | 0.0030 |
| G1 (300 mg/kg) | Mean | 251.20 | 145.60 | 24.00 | 2.28 |
| | SD | 51.237 | 16.652 | 7.071 | 0.965 |
| | p value | 0.0250 | 0.0150 | 0.4244 | 0.0001 |

The data in Table 46 show the combination composition treatment group G1 and the positive control treatment group (ORI) showed statistically significant decreases in total cholesterol, LDL-cholesterol, and fasting glucose. These data, demonstrate the *Morus alba* and *Magnolia* combinations composition when administered at 300 mg/kg of body weight is effective in reducing cholesterol and fasting glucose levels in DIO mice.

Example 58

Effect of *Morus alba* Ethyl Acetate Extract 15 Combined with Yerba Mate Extract 26 on DIO Mice

*Morus alba* ethyl acetate extract 15 produced as described in Example 15 and Yerba Mate extract 26 produced according to Example 26 were combined and blended to a ratio of 1:5 by weight. The combination composition was orally administered to DIO mice as described in Example 48 at a dosage of 1200 mg/kg of animal weight (200 mg/Kg Morus and 1000 mg/Kg Yerba Mate). The study time period was seven weeks. Table 73 shows the effects of the combination composition on total body weight and Table 74 shows the effects of the combination composition on body weight gain.

TABLE 73

Effect of *Morus alba* extract 15 Combined with Yerba Mate extract 26 on Total Weight in DIO Mice

| Group | | Weeks | | | | | | | |
|---|---|---|---|---|---|---|---|---|---|
| | | 0 | 1 | 2 | 3 | 4 | 5 | 6 | 7 |
| ND (Normal Diet) | Mean | 28.60 | 28.51 | 28.34 | 28.69 | 28.94 | 28.73 | 29.16 | 29.39 |
| | SD | 2.249 | 2.244 | 2.341 | 2.491 | 2.094 | 2.107 | 2.087 | 2.095 |
| | p value | 0.0000 | 0.0000 | 0.0000 | 0.0000 | 0.0000 | 0.0000 | 0.0000 | 0.0000 |
| HFD (High Fat Diet) | Mean | 37.98 | 38.18 | 38.72 | 40.01 | 40.51 | 41.85 | 42.96 | 44.32 |
| | SD | 2.3816 | 1.9830 | 2.2782 | 1.5612 | 1.9172 | 1.7894 | 1.9183 | 2.0291 |
| ORI (40 mg/kg) | Mean | 38.40 | 35.20 | 33.58 | 35.12 | 35.84 | 36.41 | 36.80 | 38.38 |
| | SD | 2.895 | 3.211 | 2.730 | 2.568 | 2.320 | 2.416 | 2.534 | 2.257 |
| | p value | 0.8094 | 0.1510 | 0.0465 | 0.0343 | 0.0371 | 0.0226 | 0.0174 | 0.0157 |
| G1 (1200 mg/kg) | Mean | 39.14 | 37.04 | 35.59 | 34.76 | 35.15 | 35.85 | 36.40 | 38.06 |
| | SD | 2.985 | 2.430 | 2.268 | 2.564 | 2.496 | 2.590 | 2.669 | 2.696 |
| | p value | 0.5169 | 0.4739 | 0.1085 | 0.0197 | 0.0195 | 0.0130 | 0.0104 | 0.0138 | p value: compare to HFD by t-test

TABLE 74

Effect of *Morus alba* extract 15 Combined with Yerba Mate extract 26 on Weight Gain in DIO Mice

| Group | | Weeks | | | | | | |
|---|---|---|---|---|---|---|---|---|
| | | 1 | 2 | 3 | 4 | 5 | 6 | 7 |
| ND (Normal Diet) | Mean | −0.09 | −0.25 | 0.09 | 0.35 | 0.13 | 0.56 | 0.79 |
| | SD | 0.202 | 0.513 | 0.418 | 0.408 | 0.500 | 0.528 | 0.543 |
| | p value | 0.1250 | 0.4003 | 0.2140 | 0.1935 | 0.0758 | 0.0351 | 0.0243 |
| HFD (High Fat Diet) | Mean | −0.55 | 0.16 | 1.45 | 1.95 | 3.29 | 4.40 | 5.77 |
| | SD | 0.891 | 0.665 | 1.324 | 1.455 | 1.643 | 1.373 | 1.476 |
| ORI (40 mg/kg) | Mean | −3.20 | −4.88 | −3.34 | −2.61 | −2.04 | −1.65 | −0.07 |
| | SD | 0.611 | 1.463 | 1.502 | 1.859 | 1.640 | 1.526 | 1.437 |
| | p value | 0.0011 | 0.0028 | 0.0072 | 0.0174 | 0.0081 | 0.0029 | 0.0033 |
| G1 (1200 mg/kg) | Mean | −2.10 | −3.55 | −4.38 | −3.99 | −3.29 | −2.74 | −1.08 |
| | SD | 0.655 | 1.671 | 2.413 | 2.464 | 2.567 | 2.878 | 2.484 |
| | p value | 0.0195 | 0.0116 | 0.0092 | 0.0097 | 0.0079 | 0.0076 | 0.0053 | p value: compare to HFD by t-test

The data in Table 73 show that the animals in the combination composition of Morus alba extract 15 and Yerba Mate extract 26 treatment group (G1) exhibited statistically significant decreases in total body weight from week 3 through to week 7 of the study as compared to the HFD group. The positive control ORI (orilistat dosed at 40 mg/kg) showed statistically significant decreases in total body weight from week 2 through to week 7 of the study as compared to the HFD group.

The data in Table 74 show that the animals in the combination composition of Morus alba extract 15 and Yerba Mate extract 26 treatment group (G1) and the positive control ORI group of animals both exhibited statistically significant decreases in body weight gains from week 1 through to week 7 of the study as compared to the HFD group.

Table 75 shows the effects of Morus alba extract 15 and Yerba Mate extract 26 combination composition on DIO mice for the following end points: average body weight gain per day of the study, average food intake per day of the study, and the food efficiency ratio (FER) which is calculated as the average body weight gain per day over the study period, divided by the average food intake per day over the study period.

TABLE 75

Effect of Morus alba extract 15 Combined with Yerba Mate extract 26 on DIO Mice

| Group | | Weight Gain (g/day) | Food Intake (g/day) | Food Efficiency Ratio (FER) |
|---|---|---|---|---|
| ND | Mean | 0.018 | 3.558 | 0.005 |
| (Normal Diet) | SD | 0.012 | 0.560 | 0.003 |
| | p value | 0.0243 | 0.3067 | 0.0242 |
| HFD | Mean | 0.128 | 3.342 | 0.038 |
| (High Fat Diet) | SD | 0.033 | 0.807 | 0.010 |
| ORI | Mean | −0.002 | 3.961 | 0.000 |
| (40 mg/kg) | SD | 0.032 | 2.330 | 0.007 |
| | p value | 0.0033 | 0.2661 | 0.0006 |
| G1 | Mean | −0.024 | 2.435 | −0.010 |
| (1200 mg/kg) | SD | 0.055 | 0.475 | 0.023 |
| | p value | 0.0053 | 0.0020 | 0.0143 |

FER (Feed efficacy ratio) = Body weight gain (g/day)/Food intake (g/day)
p value: compare to HFD by t-test The data in Table 75 show that the Morus alba extract 15 and Yerba Mate extract 26 combination composition treatment group G1 showed a statistically significant effect on lowering body weight gain, food intake and lower Food Efficiency Ratio as compared to the HFD group. The ORI positive control treatment group showed statistically lower values than the HFD group for Body Weight Gain per day and Food Efficiency Ratio.

Table 76 shows the effects of Morus alba extract 15 and Yerba Mate extract 26 combination composition on DOI mice for the weight of Retroperitoneal Fat.

TABLE 76

Effect of Morus alba and Yerba Mate Combination Composition on Retroperitoneal Fat in DIO Mice

| Group | | Retroperitoneal Fat |
|---|---|---|
| ND | Mean | 0.15 |
| (Normal Diet) | SD | 0.064 |
| | p value | 0.0000 |

TABLE 76-continued

Effect of Morus alba and Yerba Mate Combination Composition on Retroperitoneal Fat in DIO Mice

| Group | | Retroperitoneal Fat |
|---|---|---|
| HFD | Mean | 0.69 |
| (High Fat Diet) | SD | 0.051 |
| ORI | Mean | 0.55 |
| (40 mg/kg) | SD | 0.039 |
| | p value | 0.0034 |
| G1 | Mean | 0.57 |
| (1200 mg/kg) | SD | 0.080 |
| | p value | 0.0281 | p value: compare to HFD by t-test

The data in Table 76 show that there is a statistically significant difference in the weight of retroperitoneal fat, between the ND control group, fed a normal diet having a moderate caloric intact of fat, and the HFD group. In addition, the Morus alba extract 15 and Yerba Mate extract 26 combination composition treatment group G1 and the positive control treatment group (ORI) showed statistically significant decreases in Retroperitoneal Fat as compared with the HFD group. These data, demonstrate the Morus alba and Yerba Mate combinations composition is effective in reducing the amount of retroperitoneal fat present in DIO mice.

Table 77 shows the effects of the Morus alba 15 and Yerba Mate extract 26 combination composition on measurements in DIO mice of fasting glucose (F-Glu), total cholesterol (T-chol), triglyceride and LDL-cholesterol (LDL-C) as measure in blood samples obtained at the end of the study.

TABLE 77

Effect of Morus alba and Yerba Mate Combination Composition on Biochemistry Parameters in DIO Mice

| Group | | F-Glu (mg/dL) | T-Chol (mg/dL) | Triglyceride (mg/dL) | LDL-C (mg/dL) |
|---|---|---|---|---|---|
| ND | Mean | 178.67 | 105.67 | 30.56 | 4.54 |
| (Normal Diet) | SD | 56.934 | 17.349 | 11.886 | 1.705 |
| | p value | 0.0004 | 0.0000 | 0.7005 | 0.0807 |
| HFD | Mean | 334.50 | 176.75 | 28.00 | 6.25 |
| (High Fat Diet) | SD | 30.957 | 10.996 | 6.976 | 0.480 |
| ORI | Mean | 225.50 | 134.00 | 62.50 | 3.30 |
| (40 mg/kg) | SD | 52.208 | 30.299 | 64.717 | 1.134 |
| | p value | 0.0115 | 0.0379 | 0.3653 | 0.0030 |
| G1 | Mean | 279.80 | 146.60 | 10.60 | 4.50 |
| (1200 mg/kg) | SD | 42.275 | 14.170 | 3.209 | 0.667 |
| | p value | 0.0681 | 0.0102 | 0.0015 | 0.0032 | p value: compare to HFD by t-test

The data in Table 77 show the combination composition treatment group G1 and the positive control treatment group (ORI) showed statistically significant decreases in total cholesterol, LDL-cholesterol, and fasting glucose.

Overall, the data presented in this example show that the combination composition composed of Morus alba ethyl acetate extract 15 (200 mg/Kg) and Yerba Mate extract 26 (1000 mg/Kg) was effective in lowering total body weight and the rate of body weight gain in mice fed a high fat diet.

Example 59

Effect of Morus alba Ethyl Acetate Extract 14 Combined with Rosemary Extract 21 on DIO Mice Morus alba ethyl acetate extract 14 produced as described in Example 14 and Rosemary extract 21 produced according to Example 21 were combined and blended to a ratio of 2:5 by weight. The combination composition was orally administrated to DIO mice as described in Example 48 at a dosage of 700 mg/kg of animal weight (200 mg/Kg Morus and 500 mg/Kg Rosemary). The study time period was seven weeks. Table 78 shows the effects of the combination composition on total body weight gain and Table 79 shows the effects of the combination composition on body weight gain.

Table 80 shows the effects of Morus alba extract 14 combined with Rosemary extract 21 combination composition on DIO mice for the following end points: average body weight gain per day of the study, average food intake per day of the study, and the food efficiency ratio (FER) which is calculated as the average body weight gain per day over the study period, divided by the average food intake per day over the study period.

TABLE 78

Effect of Morus alba extract 14 Combined with Rosemary extract 21 on Weight

| Group | | 0 | 1 | 2 | 3 | 4 | 5 | 6 | 7 |
|---|---|---|---|---|---|---|---|---|---|
| ND (Normal Diet) | Mean | 29.01 | 29.30 | 29.42 | 29.27 | 29.25 | 29.73 | 29.82 | 30.11 |
| | SD | 2.824 | 2.881 | 2.523 | 2.315 | 2.368 | 2.739 | 2.942 | 3.113 |
| | p value | 0.0002 | 0.0002 | 0.0001 | 0.0000 | 0.0000 | 0.0000 | 0.0000 | 0.0000 |
| HFD (High Fat Diet) | Mean | 41.86 | 41.60 | 42.53 | 43.65 | 44.78 | 46.09 | 46.64 | 47.86 |
| | SD | 3.812 | 3.776 | 3.617 | 3.425 | 3.293 | 2.957 | 2.694 | 2.219 |
| ORI (40 mg/kg) | Mean | 42.39 | 38.83 | 36.64 | 36.48 | 38.57 | 40.07 | 40.95 | 42.99 |
| | SD | 3.489 | 4.433 | 4.681 | 3.948 | 4.221 | 4.690 | 4.775 | 4.910 |
| | p value | 0.8079 | 0.2718 | 0.0349 | 0.0073 | 0.0174 | 0.0238 | 0.0294 | 0.0514 |
| G1 (700 mg/kg) | Mean | 43.03 | 37.59 | 36.41 | 37.43 | 39.04 | 40.40 | 40.60 | 41.89 |
| | SD | 2.702 | 1.930 | 2.597 | 3.630 | 4.103 | 4.381 | 4.527 | 4.505 |
| | p value | 0.5340 | 0.0312 | 0.0046 | 0.0091 | 0.0189 | 0.0209 | 0.0157 | 0.0156 | p value: compare to HFD by t-test

TABLE 79

Effect of combination with Morus alba extract 14 Combined with Rosemary extract 21 on Body Weight Fain in DIO Mice

| Group | | 1 | 2 | 3 | 4 | 5 | 6 | 7 |
|---|---|---|---|---|---|---|---|---|
| ND | Mean | 0.29 | 0.41 | 0.26 | 0.23 | 0.71 | 0.81 | 1.10 |
| | SD | 0.530 | 0.704 | 0.665 | 0.875 | 0.724 | 0.723 | 0.834 |
| | p value | 0.0779 | 0.5236 | 0.0056 | 0.0007 | 0.0002 | 0.0003 | 0.0005 |
| HFD | Mean | −0.27 | 0.67 | 1.79 | 2.92 | 4.23 | 4.77 | 5.99 |
| | SD | 0.248 | 0.525 | 0.732 | 0.866 | 1.080 | 1.378 | 1.933 |
| ORI 40 mg/kg | Mean | −3.56 | −5.75 | −5.91 | −3.82 | −2.33 | −1.44 | 0.60 |
| | SD | 1.391 | 1.935 | 1.852 | 1.463 | 1.675 | 1.512 | 1.550 |
| | p value | 0.0002 | 0.0000 | 0.0000 | 0.0000 | 0.0000 | 0.0000 | 0.0003 |
| G1 700 mg/kg | Mean | −5.44 | −6.62 | −5.60 | −3.99 | −2.63 | −2.43 | −0.67 |
| | SD | 1.377 | 1.585 | 1.900 | 2.081 | 2.057 | 2.200 | 2.382 |
| | p value | 0.0000 | 0.0000 | 0.0000 | 0.0000 | 0.0000 | 0.0000 | 0.0003 | p value: compare to HFD by t-test

The data in Table 78 show that the animals treated with Morus alba extract 14 combined with Rosemary extract 21 (treatment group G1) exhibited statistically significant decreases in total body weight from week 1 through to week 7 of the study as compared to the HFD group. The positive control ORI (Orilistat dosed at 40 mg/kg) showed statistically significant decreases in total body weight from week 2 through to week 6, but not weeks 1 and 7 of the study as compared to the HFD group.

The data in Table 79 show that the animals in treatment group (G1) who received Morus alba extract 14 combined with Rosemary extract 21 and the positive control ORI group both exhibited statistically significant decreases in body weight gain from week 1 through to week 7 of the study as compared to the HFD group.

TABLE 80

Effect of Morus alba Extract 14 Combined with Rosemary Extract 21 on DIO Mice

| Group | | Body Weight Gain (g/day) | Food Intake (g/day) | Food Efficiency Ratio (FER) |
|---|---|---|---|---|
| ND | Mean | 0.023 | 3.046 | 0.007 |
| | SD | 0.017 | 0.188 | 0.006 |
| | p value | 0.0005 | 0.0000 | 0.0003 |
| HFD | Mean | 0.125 | 2.376 | 0.053 |
| | SD | 0.040 | 0.400 | 0.017 |
| ORI 40 mg/kg | Mean | 0.012 | 2.711 | 0.005 |
| | SD | 0.032 | 0.456 | 0.012 |
| | p value | 0.0003 | 0.0069 | 0.0002 |

TABLE 80-continued

Effect of *Morus alba* Extract 14 Combined with
Rosemary Extract 21 on DIO Mice

| Group | | Body Weight Gain (g/day) | Food Intake (g/day) | Food Efficiency Ratio (FER) |
|---|---|---|---|---|
| G1 | Mean | −0.014 | 2.180 | −0.006 |
| 700 mg/kg | SD | 0.050 | 0.474 | 0.023 |
| | p value | 0.0003 | 0.1126 | 0.0005 |

Feed Efficacy Ratio (FER) = Body Weight Gain (g/day)/Food Intake (g/day)
p value: compare to HFD by t-test The data in Table 80 show that the *Morus alba* extract 14 combined with Rosemary extract 21 combination composition treatment group G1 showed a statistically significant effect on lowering average weight gain per day and lower Food Efficiency Ratio as compared to the HFD group. The ORI positive control treatment group showed statically lower values than the HFD group for average weight gain per day, average Food Intake per day and Food Efficiency Ratio.

Table 81 shows the effects of *Morus alba* extract 14 combined with Rosemary extract 21 combination composition on DIO mice for the weight of Perirenal Fat.

TABLE 81

Effect of *Morus alba* 14 combined with Rosemary extract 21
on Perirenal Fat in DIO mice

| Group | | Perirenal Fat |
|---|---|---|
| ND | Mean | 0.08 |
| (Normal Diet) | SD | 0.026 |
| | p value | 0.0001 |
| HFD | Mean | 0.58 |
| (High Fat Diet) | SD | 0.127 |
| ORI | Mean | 0.43 |
| (40 mg/kg) | SD | 0.186 |
| | p value | 0.1369 |

TABLE 81-continued

Effect of *Morus alba* 14 combined with Rosemary extract 21
on Perirenal Fat in DIO mice

| Group | | Perirenal Fat |
|---|---|---|
| G1 | Mean | 0.40 |
| (700 mg/kg) | SD | 0.152 |
| | p value | 0.0479 | p value: compare to HFD by t-test

The data in Table 81 show that there is a statistically significant difference in the weight of perirenal fat, between the ND control group, fed a normal diet having a moderate caloric intact of fat, and the HFD group. In addition, the *Morus alba* extract 14 combined with Rosemary extract 21 composition treatment group G1 and the positive control treatment group (ORI) showed statistically significant decreases in Perirenal Fat as compared with the HFD group. These data demonstrate the *Morus alba* and Rosemary combination compositions are effective in reducing the amount of perirenal fat present in DIO mice.

Overall, the data presented in this example show that the combination composition composed of *Morus alba* ethyl acetate extract 14 (200 mg/Kg) and Rosemary extract 21 (500 mg/Kg) was effective in lowering total body weight and the rate of body weight gain in mice fed a high fat diet.

Example 60

Efficacy Study of Mutamba Ethanol Extract 35
Combined with *Morus alba* EtOAC Fraction of
Ethanol Extract 15 in DIO Mice Mutamba ethanol extract 35 produced according to the example 35 and *Morus alba* EtOAc fraction of ethanol extract 15 produced according to example 15 was blended in a ratio of 5:1. The combined composition was orally administrated to DIO mice as described in the Example 48 at a dosage of 1200 mg/kg (G1) twice a day by gavage.

The treatment group (G1) shoed significantly decreased weight gain was at weeks 4, 5, 6 and 7 as compared to the high fat diet group (Table 82).

TABLE 82

Effect of Mutamba Extract 35 Combined with *Morus alba* Extract 15 on Total
Body Weight in DIO Mice

| Group | | Weeks | | | | | | | |
|---|---|---|---|---|---|---|---|---|---|
| | | 0 | 1 | 2 | 3 | 4 | 5 | 6 | 7 |
| ND | Mean | 28.60 | 28.51 | 28.34 | 28.69 | 28.94 | 28.73 | 29.16 | 29.39 |
| | SD | 2.249 | 2.244 | 2.341 | 2.491 | 2.094 | 2.107 | 2.087 | 2.095 |
| | p value | 0.0000 | 0.0000 | 0.0000 | 0.0000 | 0.0000 | 0.0000 | 0.0000 | 0.0000 |
| HFD | Mean | 37.98 | 38.18 | 38.72 | 40.01 | 40.51 | 41.85 | 42.96 | 44.32 |
| | SD | 2.3816 | 1.9830 | 2.2782 | 1.5612 | 1.9172 | 1.7894 | 1.9183 | 2.0291 |
| ORI | Mean | 38.40 | 35.20 | 33.58 | 35.12 | 35.84 | 36.41 | 36.80 | 38.38 |
| | SD | 2.895 | 3.211 | 2.730 | 2.568 | 2.320 | 2.416 | 2.534 | 2.257 |
| | p value | 0.8094 | 0.1510 | 0.0465 | 0.0343 | 0.0371 | 0.0226 | 0.0174 | 0.0157 |
| G1 | Mean | 37.22 | 35.36 | 34.49 | 35.24 | 35.09 | 34.12 | 34.70 | 35.24 |
| | SD | 2.177 | 1.465 | 0.928 | 1.161 | 1.309 | 1.269 | 1.695 | 1.570 |
| | p value | 0.9374 | 0.5169 | 0.4739 | 0.1085 | 0.0197 | 0.0195 | 0.0130 | 0.0104 | p value: compare to HFD by t-test

The treatment group (G1), the body weight gain was significantly decreased after the second week treatment of the experiment (Table 83) and such effect was lasted to the end of the treatment.

TABLE 83

Effect of Mutamba Extract 35 Combined with *Morus alba* Extract 15 on Weight Gain in DIO Mice

| Group | | Weeks | | | | | | |
|---|---|---|---|---|---|---|---|---|
| | | 1 | 2 | 3 | 4 | 5 | 6 | 7 |
| ND | Mean | −0.09 | −0.25 | 0.09 | 0.35 | 0.13 | 0.56 | 0.79 |
| | SD | 0.202 | 0.513 | 0.418 | 0.408 | 0.500 | 0.528 | 0.543 |
| | p value | 0.1250 | 0.4003 | 0.2140 | 0.1935 | 0.0758 | 0.0351 | 0.0243 |
| HFD | Mean | −0.55 | 0.16 | 1.45 | 1.95 | 3.29 | 4.40 | 5.77 |
| | SD | 0.891 | 0.665 | 1.324 | 1.455 | 1.643 | 1.373 | 1.476 |
| ORI | Mean | −3.20 | −4.88 | −3.34 | −2.61 | −2.04 | −1.65 | −0.07 |
| | SD | 0.611 | 1.463 | 1.502 | 1.859 | 1.640 | 1.526 | 1.437 |
| | p value | 0.0011 | 0.0028 | 0.0072 | 0.0174 | 0.0081 | 0.0029 | 0.0033 |
| G1 | Mean | −1.86 | −2.74 | −1.98 | −2.13 | −3.10 | −2.53 | −1.98 |
| | SD | 0.973 | 1.483 | 1.258 | 0.901 | 2.036 | 1.246 | 1.068 |
| | p value | 0.1080 | 0.0378 | 0.0067 | 0.0011 | 0.0051 | 0.0005 | 0.0002 | p value: compare to HFD by t-test

The treatment group (G1) of FER was significantly decreased, when compared with the high fat diet group (Table 84)

TABLE 84

Effect of Mutamba Extract 35 Combined with *Morus alba* Extract 15 on DIO Mice

| Group | | Weight Gain (g/day) | Food intake (g/day) | FER (Food efficiency ratio) |
|---|---|---|---|---|
| ND | Mean | 0.018 | 3.558 | 0.005 |
| | SD | 0.012 | 0.560 | 0.003 |
| | p value | 0.0243 | 0.3067 | 0.0242 |
| HFD | Mean | 0.128 | 3.342 | 0.038 |
| | SD | 0.033 | 0.807 | 0.010 |
| ORI | Mean | −0.002 | 3.961 | 0.000 |
| | SD | 0.032 | 2.330 | 0.007 |
| | p value | 0.0033 | 0.2661 | 0.0006 |
| G1 | Mean | −0.044 | 2.652 | −0.017 |
| | SD | 0.024 | 0.273 | 0.009 |
| | p value | 0.0002 | 0.0004 | 0.0004 |

FER(Feed efficacy ratio) = Body weight Gain (g/day)/Food Intake (g/day)
p value: compare to HFD by t-test The treatment group (G1) of glucose, total cholesterol and LDL-C were significantly decreased as compared to the high fat diet group (Table 85).

TABLE 85

Effect of Mutamba Extract 35 Combined with *Morus alba* Extract 15 on Biochemistry Parameters

| Group | | Glu (mg/dL) | T-chol (mg/dL) | TG (mg/dL) | LDL-C (mg/dL) |
|---|---|---|---|---|---|
| ND | Mean | 178.67 | 105.67 | 30.56 | 4.54 |
| | SD | 56.934 | 17.349 | 11.886 | 1.705 |
| | p value | 0.0004 | 0.0000 | 0.7005 | 0.0807 |
| HFD | Mean | 334.50 | 176.75 | 28.00 | 6.25 |
| | SD | 30.957 | 10.996 | 6.976 | 0.480 |
| ORI | Mean | 225.50 | 134.00 | 62.50 | 3.30 |
| | SD | 52.208 | 30.299 | 64.717 | 1.134 |
| | p value | 0.0115 | 0.0379 | 0.3653 | 0.0030 |
| G1 | Mean | 194.80 | 116.20 | 14.60 | 2.76 |
| | SD | 33.596 | 33.752 | 8.173 | 0.948 |
| | p value | 0.0004 | 0.0114 | 0.0354 | 0.0003 |

Absolute weights of epididymal fat pads, retroperitoneal fat, perirenal fat and total fat pads were significantly decreased in the treatment group (G1) as compared to the high fat diet group (Table 86).

TABLE 86

Effect of Mutamba Extract 35 Combined with *Morus alba* Extract 15 on Absolute Organ Weights in DIO Mice

| Group | | Liver | Epididymal Fat | Retro-peritoneal Fat | PeriRenal Fat | Total Fat* |
|---|---|---|---|---|---|---|
| ND | Mean | 1.00 | 0.53 | 0.15 | 0.08 | 0.76 |
| | SD | 0.145 | 0.150 | 0.064 | 0.017 | 0.222 |
| | p value | 0.0410 | 0.0002 | 0.0000 | 0.0117 | 0.0001 |
| HFD | Mean | 1.22 | 2.60 | 0.69 | 0.31 | 3.60 |
| | SD | 0.215 | 0.424 | 0.051 | 0.118 | 0.521 |
| ORI | Mean | 1.05 | 1.92 | 0.55 | 0.21 | 2.68 |
| | SD | 0.137 | 0.230 | 0.039 | 0.055 | 0.310 |
| | p value | 0.2282 | 0.0236 | 0.0034 | 0.1729 | 0.0177 |
| G1 | Mean | 1.09 | 1.25 | 0.38 | 0.14 | 1.77 |
| | SD | 0.070 | 0.287 | 0.109 | 0.029 | 0.410 |
| | p value | 0.2515 | 0.0004 | 0.0004 | 0.0283 | 0.0003 |

*Total fat is sum of the three fat pads (epididymal, retroperitoneal and perirenal fat)
p value: compare to HFD by t-test Overall, the data show that body weight and body weight gain were significantly decreased in DIO mice treated with Mutamba extract 35 combined with *Morus alba* extract 15. FER (food efficiency ratio) and fat weights were also significantly decreased. Furthermore, fasting glucose, total cholesterol and LDL-cholesterol levels were significantly decreased by sample treatment. Therefore, the present example indicates that the combination of Mutamba extract with *Morus alba* extract can be used as a body weight, glucose level, and cholesterol level controller.

Example 61

Efficacy Study of Mutamba Ethanol Extract 35 Combined with Yerba Mate Extract 26 in DIO Mice Mutamba ethanol extract 35 produced according to the example 35 and Mate extract 26 produced according to example 26 were blended in a ratio of 1:1. The dual combination composition was orally administered to DIO mice as described in the example 48 at a dosage of 2000 mg/kg (G1) twice a day.

Weight gain was significantly decreased in the treatment group (G1) after the third week of treatment (Table 87) and that effect lasted to the end of the treatment.

TABLE 87

Effect of Mutamba Combined with Yerba Mate on Weight Gain in DIO Mice

| Group | | Weeks | | | | | | |
|---|---|---|---|---|---|---|---|---|
| | | 1 | 2 | 3 | 4 | 5 | 6 | 7 |
| ND | Mean | −0.09 | −0.25 | 0.09 | 0.35 | 0.13 | 0.56 | 0.79 |
| | SD | 0.202 | 0.513 | 0.418 | 0.408 | 0.500 | 0.528 | 0.543 |
| | p value | 0.1250 | 0.4003 | 0.2140 | 0.1935 | 0.0758 | 0.0351 | 0.0243 |
| HFD | Mean | −0.55 | 0.16 | 1.45 | 1.95 | 3.29 | 4.40 | 5.77 |
| | SD | 0.891 | 0.665 | 1.324 | 1.455 | 1.643 | 1.373 | 1.476 |
| SIB | Mean | −3.63 | −5.37 | −4.69 | −4.82 | −4.25 | −3.90 | −2.27 |
| | SD | 1.504 | 2.317 | 2.250 | 2.227 | 1.862 | 2.276 | 2.960 |
| | p value | 0.00885 | 0.0078 | 0.00553 | 0.00358 | 0.00119 | 0.00135 | 0.00511 |
| ORI | Mean | −3.20 | −4.88 | −3.34 | −2.61 | −2.04 | −1.65 | −0.07 |
| | SD | 0.611 | 1.463 | 1.502 | 1.859 | 1.640 | 1.526 | 1.437 |
| | p value | 0.0011 | 0.0028 | 0.0072 | 0.0174 | 0.0081 | 0.0029 | 0.0033 |
| G1 | Mean | −0.11 | −1.28 | −1.43 | −2.25 | −1.84 | −2.03 | −0.45 |
| | SD | 0.546 | 1.290 | 1.361 | 1.794 | 2.060 | 2.241 | 1.849 |
| | p value | 0.3970 | 0.0709 | 0.0373 | 0.0141 | 0.0104 | 0.0020 | 0.0031 | p value: compare to HFD by t-test

FER was significantly decreased in the treatment group (G1) as compared with the high fat diet group (Table 87).

TABLE 87

Effect of Mutamba Combined with Yerba Mate on DIO Mice

| Group | | Weight Gain (g/day) | Food Intake (g/day) | FER (Food efficiency ratio) |
|---|---|---|---|---|
| ND | Mean | 0.018 | 3.558 | 0.005 |
| | SD | 0.012 | 0.560 | 0.003 |
| | p value | 0.0243 | 0.3067 | 0.0242 |
| HFD | Mean | 0.128 | 3.342 | 0.038 |
| | SD | 0.033 | 0.807 | 0.010 |
| SIB | Mean | −0.051 | 3.564 | −0.014 |
| | SD | 0.066 | 1.671 | 0.018 |
| | p value | 0.0051 | 0.5332 | 0.0042 |

TABLE 87-continued

Effect of Mutamba Combined with Yerba Mate on DIO Mice

| Group | | Weight Gain (g/day) | Food Intake (g/day) | FER (Food efficiency ratio) |
|---|---|---|---|---|
| ORI | Mean | −0.002 | 3.961 | 0.000 |
| | SD | 0.032 | 2.330 | 0.007 |
| | p value | 0.0033 | 0.2661 | 0.0006 |
| G1 | Mean | −0.010 | 2.212 | −0.005 |
| | SD | 0.041 | 0.334 | 0.018 |
| | p value | 0.0031 | 0.0000 | 0.0038 |

FER(Feed efficacy ratio) = body weight Gain (g/day)/Food Intake (g/day)

p value: compare to HFD by t-test

These data show that weight gain and FER were significantly decreased in the treatment group (G1). Therefore, the present example indicates that the combination of Mutamba extract and Yerba Mate extract can be used as a body weight controller.

Example 62

Efficacy Study of Mutamba Ethanol Extract 35 Combined with *Magnolia* Extract 29 in DIO Mice Mutamba ethanol extract 35 produced according to the example 35 and *Magnolia* extract 29 produced according to example 29 was blended in a ratio of 10:1. The dual combination composition was orally administered to DIO mice as described in the example 48 at a dosage of 1100 mg/kg (G1) twice a day.

Weight gain was significantly decreased in the treatment group (G1) after the third week of treatment (Table 88) and such effect lasted until the end of the treatment.

TABLE 88

Effect of Mutamba Extract Combined with *Magnolia* Extract on Weight Gain in DIO Mice

| Group | | Weeks | | | | | | |
|---|---|---|---|---|---|---|---|---|
| | | 1 | 2 | 3 | 4 | 5 | 6 | 7 |
| ND | Mean | −0.09 | −0.25 | 0.09 | 0.35 | 0.13 | 0.56 | 0.79 |
| | SD | 0.202 | 0.513 | 0.418 | 0.408 | 0.500 | 0.528 | 0.543 |
| | p value | 0.1250 | 0.4003 | 0.2140 | 0.1935 | 0.0758 | 0.0351 | 0.0243 |
| HFD | Mean | −0.55 | 0.16 | 1.45 | 1.95 | 3.29 | 4.40 | 5.77 |
| | SD | 0.891 | 0.665 | 1.324 | 1.455 | 1.643 | 1.373 | 1.476 |
| SIB | Mean | −3.63 | −5.37 | −4.69 | −4.82 | −4.25 | −3.90 | −2.27 |
| | SD | 1.504 | 2.317 | 2.250 | 2.227 | 1.862 | 2.276 | 2.960 |
| | p value | 0.00885 | 0.0078 | 0.00553 | 0.00358 | 0.00119 | 0.00135 | 0.00511 |
| ORI | Mean | −3.20 | −4.88 | −3.34 | −2.61 | −2.04 | −1.65 | −0.07 |
| | SD | 0.611 | 1.463 | 1.502 | 1.859 | 1.640 | 1.526 | 1.437 |
| | p value | 0.0011 | 0.0028 | 0.0072 | 0.0174 | 0.0081 | 0.0029 | 0.0033 |
| G1 | Mean | −1.18 | −2.51 | −2.77 | −3.99 | −3.80 | −3.41 | −1.65 |
| | SD | 0.537 | 0.550 | 1.229 | 2.247 | 2.458 | 3.214 | 3.681 |
| | p value | 0.2326 | 0.0008 | 0.0038 | 0.0068 | 0.0047 | 0.0079 | 0.0175 | p value: compare to HFD by t-test

FER was changed in the treatment group (G1) as compared with the high fat diet group (Table 89).

TABLE 89

Effect of Mutamba Extract Combined with *Magnolia* Extract on DIO Mice

| Group | | Weight Gain (g/day) | Food Intake (g/day) | FER (Food efficiency ratio) |
|---|---|---|---|---|
| ND | Mean | 0.018 | 3.558 | 0.005 |
| | SD | 0.012 | 0.560 | 0.003 |
| | p value | 0.0243 | 0.3067 | 0.0242 |
| HFD | Mean | 0.128 | 3.342 | 0.038 |
| | SD | 0.033 | 0.807 | 0.010 |
| ORI | Mean | −0.002 | 3.961 | 0.000 |
| | SD | 0.032 | 2.330 | 0.007 |
| | p value | 0.0033 | 0.2661 | 0.0006 |
| G1 | Mean | −0.037 | 2.265 | −0.016 |
| | SD | 0.082 | 0.306 | 0.036 |
| | p value | 0.0175 | 0.0000 | 0.0475 |

FER(Feed efficacy ratio) = Body weight Gain (g/day)/Food Intake (g/day)
p value: compare to HFD by t-test TG was significantly decreased in the treatment group (G1) as compared with the high fat diet group (Table 90).

TABLE 90

Effect of Mutamba Extract Combined with *Magnolia* Extract on Biochemistry Parameter

| Group | | Glu (mg/dL) | T-chol (mg/dL) | TG (mg/dL) |
|---|---|---|---|---|
| ND | Mean | 178.67 | 105.67 | 30.56 |
| | SD | 56.934 | 17.349 | 11.886 |
| | p value | 0.0004 | 0.0000 | 0.7005 |
| HFD | Mean | 334.50 | 176.75 | 28.00 |
| | SD | 30.957 | 10.996 | 6.976 |
| ORI | Mean | 225.50 | 134.00 | 62.50 |
| | SD | 52.208 | 30.299 | 64.717 |
| | p value | 0.0115 | 0.0379 | 0.3653 |
| G1 | Mean | 280.50 | 164.25 | 15.75 |
| | SD | 34.933 | 13.200 | 3.202 |
| | p value | 0.0600 | 0.1959 | 0.0188 |

The NASH score was significantly decreased in the treatment group (G1) as compared with the high fat diet group (Table 91).

TABLE 91

Effect of the treatment group (G1) of Liver Pathology in DIO Mice

| Group | | Indications | | | |
|---|---|---|---|---|---|
| | | Steatosis (0-3) | Lobular Inflammation (0-3) | Hepatocellular ballooning (0-2) | NASH (sum) |
| ND | Mean | 0.00 | 1.33 | 0.00 | 1.20 |
| | SD | 0.000 | 0.707 | 0.000 | 0.789 |
| | p value | 0.0000 | 0.8816 | 0.0000 | 0.0000 |
| HFD | Mean | 1.86 | 1.29 | 1.29 | 4.43 |
| | SD | 0.900 | 0.488 | 0.488 | 1.272 |
| ORI | Mean | 1.00 | 1.40 | 1.00 | 3.40 |
| | SD | 0.000 | 0.548 | 0.000 | 0.548 |
| | p value | 0.0620 | 0.7114 | 0.2258 | 0.1236 |
| G1 | Mean | 1.00 | 1.00 | 0.80 | 2.80 |
| | SD | 0.000 | 0.000 | 0.837 | 0.837 |
| | p value | 0.0620 | 0.2258 | 0.2309 | 0.0322 | p value: compare to HFD by t-test

These data show that body weight gain and FER were significantly decreased in the treatment groups (G1). Furthermore, TG and NASH score were also significantly decreased in the treatment groups. Therefore, the present example shows that Mutamba extract combined with *Magnolia* extract can be used as a body weight, cholesterol level, and fatty liver controller.

Example 63

Efficacy Study of *Morus alba* Ethyl Acetate Extract 17 Combined with *Magnolia* Extract 29 and Yerba Mate Extract 26 on DIO Mice

*Morus alba* ethyl acetate fraction 17 produced according to Example 17, *Magnolia* extract 29 produced according to Example 29, Yerba Mate extract 26 produced according to Example 26, and Rosemary extract 21 produced according to the Example 21 were tested individually or combined on DIO mouse model as described in Example 48. The combination of *Morus, Magnolia,* and Yerba Mate extracts were blended to a blend ratio of 2:1:5 by weight to make combination Composition 1A.

DIO mice were divided to eight treatment groups; HFD (high fat diet group), ORI (orlistat, 40 mg/kg/day, twice daily), the combination composition treatment group G1

(*Morus, Magnolia,* Mate Composition 1A at 800 mg/kg/day), treatment group G2 (*Magnolia* extract 29, 100 mg/kg/day), treatment group G3 (Yerba Mate extract 26, 500 mg/kg/day), treatment group G4 (*Morus* extract, 200 mg/kg/day) and two Rosemary extract 21 treatment groups (G5, 500 mg/kg/day and G6, 1000 mg/kg/day). All test samples were orally administrated to DIO mice as described in the Example 48. The daily dosage for each treatment group was divided in half and administrated twice daily. The study time period was eight weeks. The effects of these treatments in DIO mice are shown in Table 92 for total body weight and Table 93 for weight gain.

TABLE 92

Effect of Various Individual or Combined Extracts on Total Body Weight in DIO Mice

| Group | | Weeks | | | | | | | | |
|---|---|---|---|---|---|---|---|---|---|---|
| | | 0 | 1 | 2 | 3 | 4 | 5 | 6 | 7 | 8 |
| ND | Mean | 29.24 | 29.11 | 29.03 | 29.47 | 29.36 | 29.51 | 29.75 | 29.76 | 30.14 |
| | SD | 1.020 | 0.967 | 1.201 | 1.166 | 1.428 | 1.309 | 1.509 | 1.270 | 1.321 |
| | p value | 0.0001 | 0.0001 | 0.000 | 0.000 | 0.000 | 0.000 | 0.000 | 0.000 | 0.000 |
| HFD | Mean | 41.31 | 41.73 | 42.12 | 43.64 | 44.94 | 46.25 | 47.78 | 48.43 | 49.29 |
| | SD | 2.932 | 2.771 | 2.856 | 2.884 | 2.870 | 3.172 | 3.247 | 3.224 | 2.783 |
| ORI | Mean | 40.22 | 37.98 | 34.08 | 35.32 | 36.38 | 37.65 | 38.75 | 39.96 | 39.99 |
| | SD | 2.816 | 2.547 | 1.277 | 1.186 | 1.867 | 2.284 | 2.931 | 3.235 | 3.633 |
| | p value | 0.528 | 0.035 | 0.0001 | 0.0001 | 0.0001 | 0.0003 | 0.0005 | 0.0011 | 0.0006 |
| G1 | Mean | 39.33 | 36.75 | 32.50 | 33.96 | 35.06 | 35.42 | 34.61 | 36.44 | 37.50 |
| (Combo) | SD | 1.591 | 1.623 | 1.554 | 1.035 | 1.145 | 1.736 | 1.180 | 1.271 | 1.474 |
| | p value | 0.2118 | 0.0064 | 0.0001 | 0.0001 | 0.0001 | 0.0001 | 0.0000 | 0.0000 | 0.000 |
| G2 | Mean | 40.13 | 39.50 | 38.12 | 39.05 | 39.92 | 40.72 | 41.43 | 42.76 | 43.63 |
| *Magnolia* | SD | 2.687 | 2.362 | 2.324 | 1.832 | 1.428 | 1.612 | 1.907 | 2.253 | 2.869 |
| | p value | 0.4852 | 0.1641 | 0.0239 | 0.0081 | 0.0033 | 0.0035 | 0.0020 | 0.0054 | 0.006 |
| G3 | Mean | 40.78 | 41.32 | 42.33 | 43.36 | 43.83 | 44.38 | 45.48 | 46.16 | 47.34 |
| Yerba | SD | 2.806 | 2.856 | 3.702 | 3.909 | 4.013 | 4.355 | 4.578 | 4.112 | 4.200 |
| Mate | p value | 0.755 | 0.807 | 0.915 | 0.887 | 0.592 | 0.415 | 0.340 | 0.311 | 0.366 |
| G4 *Morus* | Mean | 40.57 | 40.23 | 38.41 | 39.82 | 40.84 | 42.59 | 44.28 | 45.78 | 47.87 |
| | SD | 2.591 | 2.264 | 2.989 | 2.904 | 2.703 | 2.277 | 2.693 | 2.945 | 2.799 |
| | p value | 0.6524 | 0.3307 | 0.0526 | 0.0450 | 0.0288 | 0.0448 | 0.0698 | 0.1672 | 0.3989 |
| G5 | Mean | 40.52 | 40.71 | 39.41 | 40.65 | 41.38 | 42.20 | 43.52 | 44.89 | 45.82 |
| Rosemary | SD | 2.625 | 2.905 | 3.246 | 3.714 | 4.467 | 4.669 | 4.836 | 4.440 | 4.661 |
| (low) | p value | 0.6342 | 0.5476 | 0.1562 | 0.1504 | 0.1311 | 0.1099 | 0.1036 | 0.1446 | 0.1494 |
| G6 | Mean | 41.47 | 42.24 | 40.35 | 40.12 | 38.17 | 39.07 | 39.57 | 40.42 | 42.06 |
| Rosemary | SD | 2.516 | 2.274 | 3.554 | 3.795 | 2.765 | 2.915 | 3.509 | 4.526 | 5.173 |
| (high) | p value | 0.9287 | 0.7660 | 0.4067 | 0.1317 | 0.0060 | 0.0069 | 0.0053 | 0.0109 | 0.0198 | p value: compare to HFD by t-test

TABLE 93

Effect of Various Individual or Combined Extracts on Weight Gain in DIO Mice

| Group | | Weeks | | | | | | | |
|---|---|---|---|---|---|---|---|---|---|
| | | 1 | 2 | 3 | 4 | 5 | 6 | 7 | 8 |
| ND | Mean | −0.13 | −0.22 | 0.22 | 0.11 | 0.27 | 0.50 | 0.52 | 0.89 |
| | SD | 0.367 | 0.377 | 0.238 | 0.463 | 0.390 | 0.635 | 0.447 | 0.562 |
| | p value | 0.0057 | 0.0011 | 0.0080 | 0.0010 | 0.0005 | 0.0004 | 0.0002 | 0.0002 |
| HFD | Mean | 0.42 | 0.81 | 2.34 | 3.64 | 4.94 | 6.47 | 7.13 | 7.98 |
| | SD | 0.238 | 0.636 | 1.229 | 1.343 | 1.526 | 1.873 | 1.815 | 1.904 |
| ORI | Mean | −2.24 | −6.14 | −4.91 | −3.84 | −2.57 | −1.47 | −0.26 | −0.23 |
| | SD | 1.123 | 2.286 | 1.286 | 1.228 | 1.355 | 1.507 | 1.728 | 2.055 |
| | p value | 0.0018 | 0.0005 | 0.0000 | 0.0000 | 0.0000 | 0.0000 | 0.0001 | 0.0000 |
| G1 | Mean | −2.58 | −6.83 | −5.37 | −4.27 | −3.91 | −4.72 | −2.89 | −1.83 |
| (Combo) | SD | 1.466 | 0.942 | 0.729 | 2.160 | 2.740 | 1.320 | 1.880 | 2.089 |
| | p value | 0.0096 | 0.0000 | 0.0000 | 0.0000 | 0.0001 | 0.0000 | 0.0000 | 0.0000 |
| G2 | Mean | −0.63 | −2.01 | −1.08 | −0.22 | 0.59 | 1.30 | 2.63 | 3.50 |
| *Magnolia* | SD | 0.394 | 1.150 | 1.555 | 1.999 | 2.263 | 3.241 | 3.197 | 4.010 |
| | p value | 0.0005 | 0.0008 | 0.0018 | 0.0029 | 0.0030 | 0.0070 | 0.0134 | 0.0329 |
| G3 | Mean | 0.54 | 1.56 | 2.58 | 3.05 | 3.60 | 4.71 | 5.38 | 6.56 |
| Yerba | SD | 0.345 | 1.020 | 1.627 | 1.825 | 2.189 | 2.356 | 2.120 | 2.236 |
| Mate | p value | 0.4874 | 0.1617 | 0.7760 | 0.5424 | 0.2474 | 0.1822 | 0.1570 | 0.2647 |
| G4 | Mean | −0.33 | −2.16 | −0.75 | 0.27 | 2.03 | 3.71 | 5.21 | 7.30 |
| *Morus* | SD | 0.430 | 2.722 | 2.368 | 1.877 | 1.476 | 1.358 | 1.976 | 2.020 |
| | p value | 0.0038 | 0.0437 | 0.0178 | 0.0051 | 0.0072 | 0.0154 | 0.1112 | 0.5628 |
| G5 | Mean | 0.19 | −1.11 | 0.14 | 0.86 | 1.68 | 3.00 | 4.37 | 5.31 |
| Rosemary | SD | 0.314 | 1.009 | 1.435 | 1.960 | 2.165 | 2.330 | 2.011 | 2.276 |
| (low) | p value | 0.1801 | 0.0028 | 0.0171 | 0.0169 | 0.0131 | 0.0175 | 0.0318 | 0.0519 |

TABLE 93-continued

Effect of Various Individual or Combined Extracts on Weight Gain in DIO Mice

| Group | | 1 | 2 | 3 | 4 | 5 | 6 | 7 | 8 |
|---|---|---|---|---|---|---|---|---|---|
| | | | | | Weeks | | | | |
| G6 Rosemary (high) | Mean | 0.77 | −1.13 | −1.36 | −3.30 | −2.41 | −1.90 | −1.05 | 0.58 |
| | SD | 0.713 | 1.428 | 1.598 | 1.861 | 0.961 | 2.206 | 3.400 | 4.129 |
| | p value | 0.4048 | 0.0177 | 0.0032 | 0.0001 | 0.0000 | 0.0002 | 0.0010 | 0.0046 | p value: compare to HFD by t-test

Table 92 shows that mice treated with *Morus-Magnolia-Mate* Composition 1A (treatment group G1) and the positive control ORI all exhibited statistically significant decreases in total weight from week 2 through to week 8 as compared to the HFD group. The *Magnolia* treatment group (G2) exhibited statistically significant decreases in weight from week 3 through to week 8 as compared to the HFD group. The Morus treatment group (G4) exhibited statistically significant decreases in weight from week 4 through to week 5 as compared to the HFD group. The high dose Rosemary (1000 mg/Kg/day) treatment group (G6) exhibited statistically significant decreases in weight from week 4 through to week 8 as compared to the HFD group. The Yerba Mate treatment group (G3) and the low dose Rosemary (500 mg/Kg/day) treatment group (G5) did not exhibit any statistically significant decreases in weight during the study as compared to the HFD group.

Table 93 shows that the animals in the *Morus-Magnolia-Mate* combination composition 1A (treatment group G1), *Magnolia* treatment group (G2), Rosemary (1000 mg/Kg/day) treatment group G6, and the positive control ORI group all exhibited statistically significant decreases in weight gain from week 1 through to week 8 as compared to the HFD group. The Morus treatment group (G4) exhibited statistically significant decreases in weight gain from week 1 through week 6 as compared to the HFD group. The low dose Rosemary (500 mg/Kg/day) treatment group (G5) exhibited statistically significant decreases in weight gain from week 2 through to week 7 as compared to the HFD group. The Yerba Mate treatment group (G3) did not exhibit any statistically significant decreases in weight gain during the study as compared to the HFD group.

Table 94 shows that the individual extracts as well as the combination animals appear to induce more of a reduced food intake at the beginning of treatment.

TABLE 94

Effect of Various Individual or Combined Extracts on Feed Intake Change (g/day) in DIO Mice

| Group | | 4 | 7 | 11 | 14 | 21 | 25 | 28 | 32 | 35 | 39 | 42 | 46 | 49 | 53 |
|---|---|---|---|---|---|---|---|---|---|---|---|---|---|---|---|
| | | | | | | | Days | | | | | | | | |
| ND | Mean | 3.81 | 3.34 | 3.58 | 3.55 | 2.88 | 2.54 | 3.58 | 3.27 | 3.18 | 3.36 | 1.36 | 3.45 | 3.64 | 3.03 |
| | SD | 0.062 | 0.020 | 0.171 | 0.424 | 0.742 | 1.336 | 0.034 | 0.342 | 0.663 | 0.115 | 2.964 | 0.151 | 0.382 | 0.141 |
| | p value | 0.0145 | 0.0820 | 0.0157 | 0.1165 | 0.9279 | 0.9527 | 0.0086 | 0.1326 | 0.4491 | 0.0170 | 0.5610 | 0.0830 | 0.1256 | 0.3868 |
| HFD | Mean | 2.71 | 2.93 | 2.57 | 2.73 | 2.82 | 2.60 | 2.92 | 2.65 | 2.70 | 2.49 | 2.81 | 2.89 | 2.92 | 2.80 |
| | SD | 0.179 | 0.177 | 0.061 | 0.085 | 0.165 | 0.068 | 0.080 | 0.090 | 0.280 | 0.113 | 0.125 | 0.191 | 0.106 | 0.257 |
| ORI | Mean | 2.23 | 2.56 | 3.01 | 3.18 | 3.27 | 3.27 | 3.44 | 3.27 | 3.35 | 3.17 | 3.43 | 3.18 | 3.54 | 3.17 |
| | SD | 0.035 | 0.009 | 0.245 | 0.226 | 0.365 | 0.189 | 0.229 | 0.024 | 0.127 | 0.057 | 0.222 | 0.255 | 0.078 | 0.019 |
| | p value | 0.0649 | 0.0987 | 0.1312 | 0.1205 | 0.2570 | 0.0418 | 0.0930 | 0.0111 | 0.0959 | 0.0169 | 0.0759 | 0.3243 | 0.0222 | 0.1757 |
| G1 | Mean | 1.35 | 2.06 | 2.48 | 2.91 | 2.68 | 2.48 | 2.15 | 3.23 | 3.30 | 2.88 | 3.23 | 3.12 | 3.01 | 2.92 |
| | SD | 0.139 | 0.054 | 0.231 | 0.022 | 0.594 | 0.349 | 0.052 | 0.614 | 0.563 | 0.659 | 0.431 | 0.589 | 0.185 | 0.227 |
| | p value | 0.0137 | 0.0220 | 0.6476 | 0.1019 | 0.7735 | 0.6762 | 0.0076 | 0.3187 | 0.3099 | 0.5001 | 0.3228 | 0.6409 | 0.6021 | 0.6557 |
| G2 | Mean | 2.33 | 2.69 | 2.50 | 2.44 | 2.68 | 2.90 | 2.65 | 2.67 | 2.98 | 2.32 | 2.85 | 2.36 | 2.93 | 2.85 |
| | SD | 0.127 | 0.379 | 0.309 | 0.245 | 0.514 | 0.099 | 0.031 | 0.002 | 0.325 | 0.500 | 0.054 | 0.907 | 0.570 | 0.276 |
| | p value | 0.1362 | 0.4975 | 0.7879 | 0.2547 | 0.7489 | 0.0697 | 0.0486 | 0.8840 | 0.4516 | 0.6851 | 0.7622 | 0.5085 | 0.9799 | 0.8771 |
| G3 | Mean | 2.32 | 2.73 | 2.66 | 2.42 | 2.26 | 2.42 | 2.37 | 2.47 | 2.69 | 2.52 | 2.82 | 2.43 | 2.65 | 2.59 |
| | SD | 0.351 | 0.252 | 0.276 | 0.082 | 0.002 | 0.118 | 0.971 | 0.299 | 0.057 | 0.139 | 0.090 | 0.123 | 0.040 | 0.104 |
| | p value | 0.2983 | 0.4618 | 0.6914 | 0.0639 | 0.1311 | 0.2054 | 0.5107 | 0.4838 | 0.9709 | 0.8800 | 0.9459 | 0.1064 | 0.0780 | 0.3990 |
| G4 | Mean | 1.78 | 2.47 | 2.32 | 2.69 | 3.03 | 3.06 | 3.07 | 2.99 | 3.03 | 2.85 | 2.99 | 3.02 | 3.03 | 2.87 |
| | SD | 0.436 | 0.087 | 0.222 | 0.007 | 0.075 | 0.151 | 0.012 | 0.134 | 0.177 | 0.179 | 0.276 | 0.118 | 0.042 | 0.212 |
| | p value | 0.1090 | 0.0808 | 0.2639 | 0.5327 | 0.2382 | 0.0580 | 0.1179 | 0.0975 | 0.2945 | 0.1382 | 0.5031 | 0.4844 | 0.3010 | 0.7991 |
| G5 | Mean | 2.22 | 1.90 | 2.19 | 2.39 | 2.33 | 2.47 | 2.65 | 2.65 | 2.74 | 2.46 | 1.73 | 2.25 | 2.61 | 2.32 |
| | SD | 0.349 | 0.288 | 0.144 | 0.054 | 0.311 | 0.365 | 0.028 | 0.240 | 0.245 | 0.151 | 1.445 | 0.031 | 0.337 | 0.104 |
| | p value | 0.2234 | 0.0499 | 0.0758 | 0.0408 | 0.1899 | 0.6774 | 0.0472 | 0.9740 | 0.8976 | 0.8429 | 0.4015 | 0.0432 | 0.3326 | 0.1332 |
| G6 | Mean | 3.22 | 2.07 | 3.12 | 2.59 | 1.61 | 1.51 | 1.85 | 2.95 | 2.62 | 2.65 | 6.70 | 2.81 | 3.00 | 2.64 |
| | SD | 0.686 | 0.759 | 0.469 | 0.066 | 0.702 | 0.945 | 1.414 | 0.104 | 0.179 | 0.236 | 5.610 | 0.302 | 0.191 | 0.054 |
| | p value | 0.4173 | 0.2583 | 0.2389 | 0.2000 | 0.1411 | 0.2463 | 0.3996 | 0.0940 | 0.7709 | 0.4780 | 0.5060 | 0.7857 | 0.6817 | 0.4876 | p value: compare to HFD by t-test

Table 95 shows that the animals in the *Morus-Magnolia-Mate* combination composition 1A (treatment group G1), *Magnolia* treatment group (G2), high dose Rosemary (1000 mg/Kg/day) treatment group G6, and the positive control ORI group of animals, all exhibited statistically significant decreases in average weight gain and FER as compared to the HFD group. The Yerba Mate treatment group (G3) and the low dose of Rosemary (500 mg/Kg/day) treatment group (G5) exhibited statistically significant decreases in food intake as compared to the HFD group. The Morus treatment group (G4) did not exhibit any statistically significant decreases in average daily weight gain, FER, or food intake as compared to the HFD group.

TABLE 95

Effect of Various Individual or Mixed Extracts on Average Weight Gain

| Group | | Weight Gain (g/day) | Food Intake (g/day) | Food Efficiency Ratio (FER) |
|---|---|---|---|---|
| ND | Mean | 0.017 | 3.181 | 0.005 |
| (Normal Diet) | SD | 0.011 | 0.906 | 0.003 |
| | p value | 0.0002 | 0.0202 | 0.0002 |
| HFD | Mean | 0.153 | 2.752 | 0.056 |
| (High Fat Diet) | SD | 0.037 | 0.178 | 0.013 |
| ORI | Mean | −0.004 | 3.147 | −0.001 |
| (40 mg/Kg/day) | SD | 0.040 | 0.371 | 0.013 |
| | p value | 0.0000 | 0.0000 | 0.0000 |
| G1 | Mean | −0.035 | 2.700 | −0.013 |
| Composition 1A | SD | 0.040 | 0.615 | 0.015 |
| (800 mg/Kg/day) | p value | 0.0000 | 0.6676 | 0.0000 |
| G2 | Mean | 0.067 | 2.653 | 0.025 |
| Magnolia | SD | 0.077 | 0.363 | 0.029 |
| (100 mg/Kg/day) | p value | 0.0329 | 0.2023 | 0.0422 |
| G3 | Mean | 0.126 | 2.525 | 0.050 |
| Mate | SD | 0.043 | 0.279 | 0.017 |
| (500 mg/Kg/day) | p value | 0.2647 | 0.0007 | 0.5321 |
| G4 | Mean | 0.140 | 2.800 | 0.050 |
| Morus | SD | 0.039 | 0.392 | 0.014 |
| (200 mg/Kg/day) | p value | 0.5628 | 0.5614 | 0.4879 |
| G5 | Mean | 0.102 | 2.350 | 0.043 |
| Rosemary | SD | 0.044 | 0.428 | 0.019 |
| (500 mg/Kg/day) | p value | 0.0519 | 0.0001 | 0.2149 |
| G6 | Mean | 0.011 | 2.810 | 0.004 |
| Rosemary | SD | 0.079 | 1.686 | 0.028 |
| (1000 mg/Kg/day) | p value | 0.0046 | 0.8592 | 0.0042 |

FER(Feed efficacy ratio) = Body weight Gain (g/day)/Food Intake (g/day)
p value: compare to HFD by t-test Table 96 shows that absolute weights of epididymal fat pads, retroperitoneal fat, and perirenal fat were significantly decreased in the Morus treatment group (G4) and *Magnolia* treatment group (G2) as compared to the high fat diet group. Absolute weights of perirenal fat were also significantly reduced in the *Morus-Magnolia*-Mate Composition 1A treatment group (G1) and the low dose Rosemary (500 mg/Kg/day) treatment group (G5) as compared to the high fat diet group. Absolute liver weights of were significantly reduced in the *Morus-Magnolia*-Mate Composition 1A treatment group (G1), *Magnolia* treatment group (G2), and the positive control ORI group as compared to the high fat diet group.

TABLE 96

Effect of Various Individual or Combined Extracts on Absolute Organ Weight in DIO Mice

| Group | | Liver | Epididymal Fat | Retroperitoneal Fat | PeriRenal Fat | Total Fat* |
|---|---|---|---|---|---|---|
| ND | Mean | 1.07 | 0.46 | 0.11 | 0.06 | 0.63 |
| (Normal Diet) | SD | 0.062 | 0.126 | 0.042 | 0.017 | 0.181 |
| | p value | 0.0009 | 0.0001 | 0.0000 | 0.0001 | 0.0000 |
| HFD | Mean | 2.11 | 2.30 | 0.57 | 0.68 | 3.56 |
| (High Fat Diet) | SD | 0.368 | 0.400 | 0.090 | 0.141 | 0.454 |
| ORI | Mean | 1.19 | 2.03 | 0.50 | 0.29 | 2.82 |
| (40 mg/Kg/day) | SD | 0.093 | 0.831 | 0.191 | 0.129 | 1.137 |
| | p value | 0.0013 | 0.4854 | 0.4229 | 0.0005 | 0.1700 |
| G1 | Mean | 1.38 | 2.12 | 0.56 | 0.25 | 2.92 |
| Composition 1A | SD | 0.026 | 0.411 | 0.147 | 0.063 | 0.603 |
| (800 mg/Kg/day) | p value | 0.0046 | 0.4730 | 0.7973 | 0.0001 | 0.0771 |
| G2 | Mean | 1.36 | 2.77 | 0.69 | 0.43 | 3.88 |
| Magnolia | SD | 0.238 | 0.320 | 0.067 | 0.111 | 0.420 |
| (100 mg/Kg/day) | p value | 0.0018 | 0.0496 | 0.0328 | 0.0057 | 0.2287 |
| G3 | Mean | 1.80 | 2.44 | 0.60 | 0.58 | 3.63 |
| Mate | SD | 0.487 | 0.302 | 0.071 | 0.132 | 0.233 |
| (500 mg/Kg/day) | p value | 0.2394 | 0.5014 | 0.5729 | 0.2404 | 0.7381 |
| G4 | Mean | 1.82 | 2.86 | 0.69 | 0.49 | 4.04 |
| Morus | SD | 0.375 | 0.322 | 0.080 | 0.090 | 0.339 |
| (200 mg/Kg/day) | p value | 0.2112 | 0.0242 | 0.0384 | 0.0201 | 0.0628 |
| G5 | Mean | 1.81 | 2.80 | 0.64 | 0.50 | 3.94 |
| Rosemary | SD | 0.617 | 0.305 | 0.107 | 0.132 | 0.279 |
| (500 mg/Kg/day) | p value | 0.3293 | 0.0359 | 0.2955 | 0.0436 | 0.1127 |
| G6 | Mean | 1.59 | 2.49 | 0.62 | 0.47 | 3.59 |
| Rosemary | SD | 0.409 | 0.744 | 0.137 | 0.317 | 1.120 |
| (1000 mg/Kg/day) | p value | 0.0682 | 0.6075 | 0.5254 | 0.1826 | 0.9570 |

*Total fat is sum of the three fat pads (epididymal, retroperitoneal and perirenal fat)
p value: compare to HFD by t-test Table 97 shows that relative organ weights show similar results to those seen for absolute organ weights (shown in Table 96).

TABLE 97

Results of Relative Organ Weight Change in DIO Mice

| Group | | Liver | Epididymal Fat | Retroperitoneal Fat | PeriRenal Fat | Total Fat* |
|---|---|---|---|---|---|---|
| ND (Normal Diet) | Mean | 0.04 | 0.02 | 0.00 | 0.00 | 0.02 |
| | SD | 0.002 | 0.004 | 0.001 | 0.001 | 0.006 |
| | p value | 0.0691 | 0.0004 | 0.0000 | 0.0001 | 0.0000 |
| HFD (High Fat Diet) | Mean | 0.04 | 0.05 | 0.01 | 0.01 | 0.08 |
| | SD | 0.006 | 0.011 | 0.003 | 0.003 | 0.013 |
| ORI (40 mg/Kg/day) | Mean | 0.03 | 0.05 | 0.01 | 0.01 | 0.07 |
| | SD | 0.003 | 0.018 | 0.004 | 0.003 | 0.024 |
| | p value | 0.0007 | 0.7407 | 0.7513 | 0.0011 | 0.7628 |
| G1 Composition 1A (800 mg/Kg/day) | Mean | 0.04 | 0.06 | 0.01 | 0.01 | 0.08 |
| | SD | 0.002 | 0.009 | 0.003 | 0.001 | 0.013 |
| | p value | 0.0449 | 0.2021 | 0.1606 | 0.0002 | 0.6631 |
| G2 Magnolia (100 mg/Kg/day) | Mean | 0.03 | 0.06 | 0.02 | 0.01 | 0.09 |
| | SD | 0.004 | 0.006 | 0.002 | 0.002 | 0.007 |
| | p value | 0.0014 | 0.0108 | 0.0132 | 0.0069 | 0.0279 |
| G3 Mate (500 mg/Kg/day) | Mean | 0.04 | 0.05 | 0.01 | 0.01 | 0.08 |
| | SD | 0.008 | 0.009 | 0.003 | 0.003 | 0.011 |
| | p value | 0.2066 | 0.4308 | 0.4915 | 0.3310 | 0.5468 |
| G4 Morus (200 mg/Kg/day) | Mean | 0.04 | 0.06 | 0.02 | 0.01 | 0.09 |
| | SD | 0.006 | 0.009 | 0.002 | 0.001 | 0.010 |
| | p value | 0.1561 | 0.0470 | 0.0818 | 0.0098 | 0.0973 |
| G5 Rosemary (500 mg/Kg/day) | Mean | 0.04 | 0.06 | 0.01 | 0.01 | 0.09 |
| | SD | 0.009 | 0.011 | 0.004 | 0.002 | 0.013 |
| | p value | 0.3783 | 0.0422 | 0.2069 | 0.0364 | 0.0834 |
| G6 Rosemary (1000 mg/Kg/day) | Mean | 0.04 | 0.06 | 0.02 | 0.01 | 0.09 |
| | SD | 0.005 | 0.014 | 0.003 | 0.006 | 0.019 |
| | p value | 0.1763 | 0.1587 | 0.1027 | 0.2684 | 0.2608 |

*Total fat is sum of the three fat pads (epididymal, retroperitoneal and perirenal fat)
p value: compare to HFD by t-test Example 64

Effect of *Morus alba* Ethyl Acetate Extract 18 Combined with *Magnolia* Extract 29A and Yerba Mate Extract 27 on DIO Mice

*Morus alba* precipitate from ethanol extract 18, produced as described in Example 18, *Magnolia* extract 29A, produced as described in Example 29, and Yerba Mate extract 27 produced according to Example 27, were combined and blended to a ratio of 2:1:10 by weight to make combination Composition 1 as described in Example 38. Composition 1 was orally administrated twice per day to DIO mice as described in Example 48 at two different dosages. Treatment group G1 was administered 650 mg/kg of animal weight (100 mg/Kg Morus, 50 mg/Kg *Magnolia*, and 500 mg/Kg Mate) and treatment group G2 was administered 1300 mg/kg of animal weight (200 mg/Kg Morus, 100 mg/Kg *Magnolia*, and 1000 mg/Kg Mate). The study time period was seven weeks. Table 98 shows the effects of the Composition 1 on weight gain.

TABLE 98

Effect of Composition 1 (*Morus, Magnolia*, and Mate) on Weight Gain in DIO Mice

| Group | | Weeks | | | | | | |
|---|---|---|---|---|---|---|---|---|
| | | 1 | 2 | 3 | 4 | 5 | 6 | 7 |
| ND (Normal Diet) | Mean | -0.25 | -0.39 | -0.31 | -0.60 | -0.28 | 0.01 | 0.74 |
| | SD | 0.698 | 0.670 | 0.418 | 0.543 | 0.448 | 0.702 | 0.768 |
| | p value | 0.0585 | 0.0268 | 0.9565 | 0.0270 | 0.0063 | 0.0008 | 0.0009 |
| HFD (High Fat Diet) | Mean | -1.01 | -1.59 | -0.35 | 1.25 | 2.88 | 4.11 | 4.68 |
| | SD | 0.531 | 0.246 | 0.775 | 1.344 | 1.564 | 1.569 | 1.556 |
| ORI (40 mg/kg) | Mean | -5.43 | -6.69 | -5.27 | -3.47 | -2.34 | -1.08 | 0.02 |
| | SD | 1.106 | 1.822 | 1.249 | 1.010 | 1.450 | 1.721 | 1.806 |
| | p value | 0.0000 | 0.0000 | 0.0000 | 0.0001 | 0.0005 | 0.0004 | 0.0010 |

TABLE 98-continued

Effect of Composition 1 (*Morus*, *Magnolia*, and Mate) on Weight Gain in DIO Mice

| Group | | 1 | 2 | 3 | 4 | 5 | 6 | 7 |
|---|---|---|---|---|---|---|---|---|
| | | | | | Weeks | | | |
| G1 | Mean | −2.31 | −3.72 | −2.95 | −1.44 | −0.46 | 0.25 | 1.05 |
| (650 mg/kg) | SD | 0.740 | 0.826 | 1.680 | 1.571 | 2.452 | 2.853 | 3.303 |
| | p value | 0.0068 | 0.0021 | 0.0087 | 0.0143 | 0.0233 | 0.0122 | 0.0234 |
| G2 | Mean | −1.85 | −3.32 | −2.63 | −2.17 | −0.67 | 1.03 | 1.39 |
| (1300 mg/kg) | SD | 0.831 | 1.646 | 1.664 | 1.752 | 2.050 | 2.700 | 3.089 |
| | p value | 0.0709 | 0.0314 | 0.0179 | 0.0038 | 0.0126 | 0.0345 | 0.0320 | p value: compare to HFD by t-test

The data in Table 98 show that the animals in the Composition 1 (Morus, *Magnolia*, and Mate) treatment group (G1) and the positive control ORI group both exhibited statistically significant decreases in body weight gain from week 1 through to week 7 as compared to the HFD group. Treatment group (G2) exhibited statistically significant decreases in body weight gain from week 2 through to week 7 as compared to the HFD group.

Table 99 shows the effects of the Composition 1 (*Morus, Magnolia*, and Mate) on DIO mice for the following end points: average body weight gain per day of the study, average food intake per day of the study, and the food efficiency ratio (FER).

TABLE 99

Effect of Composition 1 (*Morus, Magnolia*, and Mate) on DIO Mice

| Group | | Weight Gain (g/day) | Food Intake (g/day) | Food Efficiency Ratio (FER) |
|---|---|---|---|---|
| ND | Mean | 0.016 | 3.401 | 0.005 |
| (Normal | SD | 0.016 | 0.556 | 0.005 |
| Diet) | p value | 0.0009 | 0.0000 | 0.0007 |
| HFD | Mean | 0.100 | 2.592 | 0.038 |
| (High Fat | SD | 0.033 | 0.521 | 0.013 |
| Diet) | | | | |
| ORI | Mean | 0.000 | 3.195 | 0.000 |
| (40 mg/kg) | SD | 0.038 | 0.752 | 0.012 |
| | p value | 0.0010 | 0.0000 | 0.0007 |
| G1 | Mean | 0.022 | 2.617 | 0.009 |
| (650 mg/kg) | SD | 0.070 | 0.754 | 0.027 |
| | p value | 0.0234 | 0.9052 | 0.0225 |
| G2 | Mean | 0.030 | 2.315 | 0.013 |
| (1300 mg/kg) | SD | 0.066 | 0.618 | 0.028 |
| | p value | 0.0320 | 0.0004 | 0.0512 |

Feed Efficacy Ratio (FER) = Body weight Gain (g/day)/Food Intake (g/day)
p value: compare to HFD by t-test The data in Table 99 show that the Composition 1 (*Morus, Magnolia*, and Mate) treatment group G1 showed a statistically significant effect on lowering average weight gain per day and a lower Food Efficiency Ratio as compared to the HFD group. Treatment group G2 showed a statistically significant effect on lowering of the average weight gain per day and Food Intake as compared to the HFD group. But, the effect on Food Efficiency Ratio was not statistically significant. The ORI positive control treatment group showed statically lower values than the HFD group for average weight gain per day, average Food Intake per day, and Food Efficiency Ratio.

Table 100 shows the effects of the Composition 1 (*Morus, Magnolia*, and Mate) on measurements in DIO mice of Alanine Transaminase (ALT), Aspartate transaminase (AST), triglyceride (TG), total cholesterol (T-chol), and LDL-cholesterol (LDL-C) as measured in blood samples obtained at the end of the study.

TABLE 100

Effect of Composition 1 (*Morus, Magnolia*, and Mate) on Biochemistry Parameters in DIO Mice

| Group | | ALT (U/L) | AST (U/L) | T-chol (mg/dL) | TG (mg/dL) | LDL-C (mg/dL) |
|---|---|---|---|---|---|---|
| ND | Mean | 19.51 | 48.56 | 116.78 | 10.00 | 4.00 |
| (Normal | SD | 1.561 | 6.396 | 6.418 | 2.872 | 0.682 |
| Diet) | p value | 0.0277 | 0.0088 | 0.0016 | 0.0001 | 0.0126 |
| HFD | Mean | 51.32 | 87.77 | 181.70 | 33.10 | 8.23 |
| (High Fat | SD | 38.335 | 37.269 | 46.466 | 10.816 | 4.300 |
| Diet) | | | | | | |
| ORI | Mean | 21.83 | 65.65 | 137.33 | 27.83 | 4.03 |
| (40 mg/kg) | SD | 5.707 | 17.307 | 28.261 | 6.555 | 0.301 |
| | p value | 0.0389 | 0.1970 | 0.0543 | 0.3020 | 0.0130 |
| G1 | Mean | 20.69 | 59.44 | 150.14 | 12.67 | 5.00 |
| (650 mg/kg) | SD | 6.722 | 12.564 | 39.418 | 5.007 | 1.243 |
| | p value | 0.0334 | 0.0462 | 0.1642 | 0.0007 | 0.0473 |
| G2 | Mean | 23.61 | 52.74 | 170.00 | 8.43 | 6.13 |
| (1300 | SD | 6.923 | 4.977 | 39.383 | 1.988 | 1.652 |
| mg/kg) | p value | 0.0500 | 0.0158 | 0.5955 | 0.0000 | 0.1848 | p value: compare to HFD by t-test

The data in Table 100 shows that the Composition 1 (*Morus, Magnolia*, and Mate) treatment group G1 exhibited a statistically significant decreases in ALT, AST, triglyceride, and LDL-cholesterol as compared to the HFD group. Treatment group G2 showed statistically significant decreases in ALT, AST, triglyceride as compared to the HFD group. Whereas the ORI treatment group showed a statistically significant decreases in ALT and LDL-cholesterol as compared to the HFD group.

Table 101 shows the effects of the Composition 1 (*Morus, Magnolia*, and Mate) on measurements in DIO mice on several histopathological measures of fatty liver and the resulting calculated Non-Alcoholic Staetohepatitis (NASH) score of the liver.

TABLE 101

Effects of Composition 1 (*Morus, Magnolia*, and Mate) on Liver Pathology

| | | Pathology Indications | | | |
|---|---|---|---|---|---|
| Group | | Steatosis (0-3) | Lobular Inflammation (0-3) | Hepatocellular ballooning (0-2) | NSAH (sum) |
| ND | Mean | 0.00 | 1.33 | 0.00 | 1.33 |
| (Normal | SD | 0.000 | 0.500 | 0.000 | 0.500 |
| Diet) | p value | 0.0000 | 0.1226 | 0.0000 | 0.0000 |

TABLE 101-continued

Effects of Composition 1 (*Morus*, *Magnolia*, and Mate) on Liver Pathology

| Group | | Steatosis (0-3) | Lobular Inflammation (0-3) | Hepatocellular ballooning (0-2) | NSAH (sum) |
|---|---|---|---|---|---|
| HFD (High Fat Diet) | Mean | 2.20 | 1.70 | 1.50 | 5.40 |
| | SD | 0.919 | 0.483 | 0.527 | 1.647 |
| ORI (40 mg/kg) | Mean | 0.67 | 1.33 | 0.67 | 2.67 |
| | SD | 0.516 | 0.516 | 0.516 | 1.366 |
| | p value | 0.0023 | 0.1736 | 0.0081 | 0.0042 |
| G1 (650 mg/kg) | Mean | 1.14 | 1.71 | 0.86 | 3.71 |
| | SD | 0.690 | 0.488 | 0.690 | 1.113 |
| | p value | 0.0214 | 0.9531 | 0.0454 | 0.0330 |
| G2 (1300 mg/kg) | Mean | 1.57 | 1.43 | 0.86 | 3.86 |
| | SD | 0.976 | 0.535 | 0.690 | 1.864 |
| | p value | 0.1958 | 0.2920 | 0.0454 | 0.0916 | p value: compare to HFD by t-test

The data in Table 101 show that there is a statistically significant difference in the amount of Steatosis, Hepatocellular ballooning and NASH score between the ND control group, fed a normal diet having a moderate caloric intact of fat, and the HFD group. Treatment group G1 and the ORI treatment group both showed statistically significant decreases in Steatosis, Hepatocellular ballooning and NASH score as compared with the HFD group. Treatment group G2 showed statistically significant decrease in Hepatocellular ballooning as compared with the HFD group. These data, demonstrate that Composition 1 (*Morus*, *Magnolia*, and Mate) was effective in reducing the amount of liver damage present in mice fed a high fat diet.

Overall, the data presented in this Example 48 show that the *Morus-Magnolia*-Mate combination composition was effective in lowering body weight and the rate of body weight gain in mice fed a high fat diet.

Example 65

Effect of *Morus alba* Ethyl Acetate Extract 18 Combined with *Magnolia* Extract 29A and Yerba Mate Extract 27 on DIO Rats

*Morus alba* precipitate from ethanol extract 18, produced as described in Example 18, *Magnolia* extract 29A, produced as described in Example 29, and Yerba Mate extract 27 produced according to Example 27, were combined and blended to a ratio of 2:1:10 by weight to make combination Composition 1 as described in Example 38. Composition 1 was orally administrated twice per day to DIO rats as described in Example 49 at two different dosages. Treatment group G1 was administered at 650 mg/kg of animal weight (100 mg/Kg Morus, 50 mg/Kg *Magnolia*, and 500 mg/Kg Mate) and treatment group G2 was administered 1300 mg/kg of animal weight (200 mg/Kg Morus, 100 mg/Kg *Magnolia*, and 1000 mg/Kg Mate). The study time period was 55 days. Table 102 shows the effects of the *Morus-Magnolia*-Mate Composition 1 on weight gain.

TABLE 102

Effect of Composition 1 (*Morus*, *Magnolia*, and Mate) on Weight Gain in DIO Rats

| Group | | Days | | | | | | | |
|---|---|---|---|---|---|---|---|---|---|
| | | 3 | 7 | 10 | 14 | 17 | 21 | 24 | 28 |
| ND | Mean | 4.83 | 11.86 | 18.42 | 23.43 | 23.61 | 32.45 | 39.57 | 44.19 |
| | SD | 5.54 | 7.84 | 7.31 | 8.03 | 13.36 | 13.98 | 13.08 | 13.85 |
| | p value | 0.018 | 0.064 | 0.028 | 0.008 | 0.010 | 0.009 | 0.013 | 0.004 |
| HFD | Mean | 13.22 | 22.38 | 32.85 | 49.08 | 52.91 | 63.73 | 72.81 | 81.45 |
| | SD | 6.81 | 12.32 | 14.21 | 19.87 | 23.30 | 24.20 | 28.42 | 25.48 |
| ORI 80 mg/kg | Mean | 2.80 | 1.04 | 0.82 | 3.40 | 3.34 | 15.89 | 19.89 | 28.19 |
| | SD | 13.85 | 15.80 | 17.11 | 18.18 | 20.72 | 21.08 | 20.72 | 22.69 |
| | p value | 0.085 | 0.010 | 0.001 | 0.000 | 0.001 | 0.001 | 0.001 | 0.001 |
| G1 650 mg/kg | Mean | 5.41 | 10.66 | 16.37 | 23.46 | 27.10 | 35.47 | 39.45 | 50.43 |
| | SD | 7.91 | 15.65 | 17.89 | 21.15 | 23.91 | 26.95 | 26.12 | 23.36 |
| | p value | 0.053 | 0.119 | 0.062 | 0.026 | 0.046 | 0.045 | 0.028 | 0.024 |
| G2 1300 mg/kg | Mean | 3.34 | 11.73 | 13.71 | 23.51 | 27.28 | 30.82 | 32.74 | 39.96 |
| | SD | 7.13 | 12.66 | 16.49 | 22.14 | 28.51 | 31.25 | 30.99 | 30.99 |
| | p value | 0.013 | 0.110 | 0.026 | 0.029 | 0.070 | 0.035 | 0.018 | 0.011 |

| Group | | Days | | | | | | | |
|---|---|---|---|---|---|---|---|---|---|
| | | 31 | 35 | 37 | 42 | 45 | 49 | 52 | 55 |
| ND | Mean | 51.02 | 52.69 | 55.89 | 62.78 | 66.06 | 75.05 | 80.44 | 78.60 |
| | SD | 16.00 | 14.55 | 12.98 | 14.33 | 19.09 | 18.66 | 20.38 | 19.52 |
| | p value | 0.006 | 0.001 | 0.002 | 0.001 | 0.001 | 0.002 | 0.001 | 0.001 |
| HFD | Mean | 89.85 | 98.23 | 103.01 | 113.20 | 124.09 | 130.99 | 141.23 | 143.39 |
| | SD | 28.13 | 26.72 | 29.41 | 29.26 | 31.14 | 33.04 | 32.99 | 34.29 |
| ORI 80 mg/kg | Mean | 33.33 | 38.43 | 43.95 | 49.06 | 59.88 | 63.68 | 71.12 | 68.11 |
| | SD | 24.86 | 25.56 | 28.85 | 30.54 | 29.53 | 30.43 | 29.27 | 29.33 |
| | p value | 0.001 | 0.000 | 0.001 | 0.001 | 0.001 | 0.001 | 0.001 | 0.000 |
| G1 650 mg/kg | Mean | 55.77 | 59.14 | 66.27 | 76.79 | 84.95 | 91.78 | 102.42 | 101.21 |
| | SD | 24.86 | 24.97 | 23.92 | 23.19 | 24.56 | 22.05 | 21.64 | 18.93 |
| | p value | 0.023 | 0.009 | 0.016 | 0.015 | 0.016 | 0.016 | 0.016 | 0.011 |
| G2 1300 mg/kg | Mean | 44.32 | 50.17 | 56.75 | 60.92 | 70.72 | 76.03 | 83.73 | 83.84 |
| | SD | 36.09 | 34.43 | 32.51 | 32.25 | 33.38 | 32.29 | 30.68 | 30.62 |
| | p value | 0.014 | 0.008 | 0.010 | 0.004 | 0.005 | 0.005 | 0.003 | 0.003 | p value: Compared to HFD group

The data in Table 102 show that the animals in the Composition 1 (Morus, Magnolia, and Mate) treatment group (G1) exhibited statistically significant decreases in body weight gain from day 14 through to day 55 of the study as compared to the HFD group. Treatment group (G2) exhibited statistically significant decreases in body weight gain on day 3, day 10, day 14 and day 21 through to day 55 of the study as compared to the HFD group. Treatment group (ORI) exhibited statistically significant decreases in body weight gain on day 7 through to day 55 of the study as compared to the HFD group.

Table 103 shows the effect of Composition 1 (Morns, Magnolia, and Mate) on DOI rats for the following end points: average body weight gain per day of the study, average food intake per day of the study, and the food efficiency ratio (FER).

TABLE 103

Effect of Composition 1 (Morus, Magnolia, and Mate) on DIO Rats

| Group | | Body Weight Gain (g/day) | Food Intake (g/day) | Food Efficiency Ratio (FER) |
|---|---|---|---|---|
| ND | Mean | 1.40 | 24.26 | 0.06 |
| (Normal Diet) | SD | 0.35 | 0.72 | 0.01 |
| | p value | 0.001 | 0.073 | 0.000 |
| HFD | Mean | 2.56 | 21.14 | 0.12 |
| (High Fat Diet) | SD | 0.61 | 2.37 | 0.02 |
| ORI | Mean | 1.22 | 25.71 | 0.05 |
| (80 mg/kg) | SD | 0.52 | 1.09 | 0.02 |
| | p value | 0.000 | 0.023 | 0.000 |
| G1 | Mean | 1.81 | 19.62 | 0.09 |
| (650 mg/kg) | SD | 0.34 | 1.00 | 0.02 |
| | p value | 0.011 | 0.303 | 0.009 |
| G2 | Mean | 1.50 | 19.57 | 0.08 |
| (1300 mg/kg) | SD | 0.55 | 1.31 | 0.03 |
| | p value | 0.003 | 0.302 | 0.002 |

Feed Efficacy Ratio (FER) = Body weight Gain (g/day)/Food Intake (g/day)
p value: Compared to HFD group The data in Table 103 show that Composition 1 (Mores, Magnolia, and Mate) treatment groups G1 and G2 both showed a statistically significant effect on lowering average Body Weight Gain per day and a lower Food Efficiency Ratio as compared to the HFD rat group. The ORI positive control treatment group showed statistically lower values than the HFD group for average Body Weight Gain per day, average Food Intake per day and Food Efficiency Ratio.

Table 104 shows the effects of Composition 1 (Mores, Magnolia, and Mate) on several specific fatty tissues that are known to increase in fat content in rats subjected to a high fat diet.

TABLE 104

Effect of Composition 1 (Morus, Magnolia, and Mate) on Fatty Tissue Weights in DIO Rats

| Group | | Epididymal | Retroperitoneal | Perirenal | Total Fat |
|---|---|---|---|---|---|
| ND | Mean | 11.14 | 12.41 | 3.70 | 27.25 |
| (Normal Diet) | SD | 2.32 | 3.04 | 0.65 | 5.47 |
| | p value | 0.000 | 0.000 | 0.000 | 0.000 |
| HFD | Mean | 22.84 | 28.27 | 8.90 | 60.01 |
| (High Fat Diet) | SD | 2.82 | 6.58 | 1.93 | 7.98 |
| ORI | Mean | 17.87 | 19.21 | 6.11 | 43.19 |
| (80 mg/kg) | SD | 5.44 | 3.00 | 1.69 | 9.56 |
| | p value | 0.044 | 0.005 | 0.008 | 0.002 |

TABLE 104-continued

Effect of Composition 1 (Morus, Magnolia, and Mate) on Fatty Tissue Weights in DIO Rats

| Group | | Epididymal | Retroperitoneal | Perirenal | Total Fat |
|---|---|---|---|---|---|
| G1 | Mean | 18.40 | 21.73 | 6.71 | 46.83 |
| (650 mg/kg) | SD | 3.05 | 4.37 | 1.66 | 7.93 |
| | p value | 0.009 | 0.037 | 0.029 | 0.005 |
| G2 | Mean | 15.01 | 18.44 | 5.15 | 38.60 |
| (1300 mg/kg) | SD | 3.11 | 5.58 | 1.07 | 8.78 |
| | p value | 0.000 | 0.006 | 0.001 | 0.000 | p value: Compared to HFD group

The data in Table 104 show that there is a statistically significant difference between Epididymal Fat, Retroperitoneal Fat, Perirenal Fat and Total Fat between the ND control group, fed a normal nutritional diet having a moderate caloric intact of fat, and the HFD group. Treatment groups ORI, G1 and G2, all showed statistically significant decreases in all categories of fat measurement as compared with the HFD group, showing that Composition 1 (Morus, Magnolia, and Mate) had a statistically significant effect on lowering the accumulation of fat deposits in rats fed a high fat diet.

Table 105 shows the effect of Composition 1 (Morus, Magnolia, and Mate) on DOI rats on several histopathological measures of fatty liver and the resulting calculated Non-Alcoholic Staetohepatitis (NASH) score of the liver.

TABLE 105

Effects of Composition 1 (Morus, Magnolia, and Mate) on Liver Pathology

| | | Pathological Indications | | | |
|---|---|---|---|---|---|
| Group | | Steatosis (0-3) | Lobular Inflammation (0-3) | Hepatocellular ballooning (0-2) | NASH (sum) |
| ND | Mean | 0.000 | 1.857 | 0.000 | 1.857 |
| (Normal Diet) | SD | 0.000 | 0.378 | 0.000 | 0.378 |
| | p value | 0.000 | 0.180 | 0.000 | 0.000 |
| HFD | Mean | 1.875 | 2.125 | 1.625 | 5.625 |
| (High Fat Diet) | SD | 1.126 | 0.354 | 0.744 | 1.923 |
| ORI | Mean | 0.750 | 1.500 | 0.625 | 2.875 |
| (80 mg/kg) | SD | 0.707 | 0.535 | 0.744 | 1.727 |
| | p value | 0.031 | 0.015 | 0.018 | 0.009 |
| G1 | Mean | 0.625 | 1.625 | 0.250 | 2.500 |
| (650 mg/kg) | SD | 0.518 | 0.518 | 0.463 | 1.069 |
| | p value | 0.013 | 0.041 | 0.001 | 0.001 |
| G2 | Mean | 0.500 | 1.500 | 0.500 | 2.500 |
| (1300 mg/kg) | SD | 0.535 | 0.535 | 0.535 | 0.926 |
| | p value | 0.008 | 0.015 | 0.004 | 0.001 | p value: Compared to HFD group

The data in Table 105 show Composition 1 (Morus, Magnolia, and Mate) treatment groups G1 and G2, as well as the positive control treatment group (ORI), all showed statistically significant decreases in Steatosis, Lobular Inflammation, Hepatocellular ballooning and NASH score as compared with the HFD group. These data, demonstrate the Composition 1 (Morus, Magnolia, and Mate) was effective in reducing the amount of liver damage present in rats fed a high fat diet.

Table 106 shows the effects of Composition 1 (Morus, Magnolia, and Mate) on measurements in DIO mice of Alanine Transaminase (ALT), Aspartate transaminase (AST), and triglyceride (TG), as measured in blood samples obtained at the end of the study.

TABLE 106

Effect of Composition 1 (*Morus, Magnolia*, and Mate) on Biochemistry Parameters in DIO Rats

| Group | | ALT (U/L) | AST (U/L) | TG (mg/dL) |
|---|---|---|---|---|
| ND | Mean | 41.13 | 152.69 | 105.25 |
| (Normal Diet) | SD | 9.27 | 27.97 | 64.38 |
| | p value | 0.204 | 0.416 | 0.259 |
| HFD | Mean | 54.75 | 168.00 | 137.13 |
| (High Fat Diet) | SD | 26.46 | 43.12 | 40.50 |
| ORI | Mean | 35.65 | 146.39 | 216.38 |
| (80 mg/kg) | SD | 7.54 | 24.18 | 100.04 |
| | p value | 0.085 | 0.242 | 0.067 |
| G1 | Mean | 34.00 | 127.29 | 83.63 |
| (650 mg/kg) | SD | 9.10 | 25.14 | 28.79 |
| | p value | 0.067 | 0.041 | 0.010 |

TABLE 106-continued

Effect of Composition 1 (*Morus, Magnolia*, and Mate) on Biochemistry Parameters in DIO Rats

| Group | | ALT (U/L) | AST (U/L) | TG (mg/dL) |
|---|---|---|---|---|
| G2 | Mean | 39.35 | 114.89 | 97.00 |
| (1300 mg/kg) | SD | 6.19 | 17.66 | 30.45 |
| | p value | 0.149 | 0.010 | 0.043 | p value: compare to HFD by t-test

The data in Table 106 shows that Composition 1 (*Morus, Magnolia,* and Mate) treatment groups G1 and G2, exhibited a statistically significant decreases in AST and total glucose as compared to the HFD group. Whereas the ORI treatment group showed no statistically significant decreases in any of the measured blood components compared to the HFD group.

Overall, the data presented in this example show that Composition 1 (*Morus, Magnolia*, and Mate) was effective in lowering body weight and the rate of body weight gain in rats fed a high fat diet, and in lowered a number of measures of the effects of a high fat diet on rat physiology.

Example 66

Effect of *Morus alba* Ethyl Acetate Extract Precipitate 18 Combined with Rosemary Extract 24 and Yerba Mate Extract 27 on DIO Mice

*Morus alba* precipitate from ethanol extract 18, produced as described in Example 18, Rosemary extract 24, produced as described in Example 24, and Yerba Mate extract 27 produced according to Example 27, were combined and blended to a ratio of 2:5:10 by weight to make combination Composition 3 as described in Example 39. The Morus-Rosemary-Mate combination Composition 3 was orally administered twice per day to DIO mice as described in Example 48. Treatment group G1 was administered 1700 mg/kg of animal weight (200 mg/Kg Morus, 500 mg/Kg Rosemary, and 1000 mg/Kg Mate) of the combination composition each day, divided between the two doses. The study time period was seven weeks. Table 107 shows the effects of Composition 3 on body weight gain.

TABLE 107

Effect of Composition 3 on Weight Gain in DIO Mice

| Group | | Weeks | | | | | | |
|---|---|---|---|---|---|---|---|---|
| | | 1 | 2 | 3 | 4 | 5 | 6 | 7 |
| ND | Mean | −0.25 | −0.39 | −0.31 | −0.60 | −0.28 | 0.01 | 0.74 |
| | SD | 0.698 | 0.670 | 0.418 | 0.543 | 0.448 | 0.702 | 0.768 |
| | p value | 0.0585 | 0.0268 | 0.9565 | 0.0270 | 0.0063 | 0.0008 | 0.0009 |
| HFD | Mean | −1.01 | −1.59 | −0.35 | 1.25 | 2.88 | 4.11 | 4.68 |
| | SD | 0.531 | 0.246 | 0.775 | 1.344 | 1.564 | 1.569 | 1.556 |
| ORI | Mean | −5.43 | −6.69 | −5.27 | −3.47 | −2.34 | −1.08 | 0.02 |
| 40 mg/kg | SD | 1.106 | 1.822 | 1.249 | 1.010 | 1.450 | 1.721 | 1.806 |
| | p value | 0.0000 | 0.0000 | 0.0000 | 0.0001 | 0.0005 | 0.0004 | 0.0010 |
| G1 | Mean | −2.34 | −3.69 | −3.34 | −2.45 | −0.72 | 0.17 | 0.32 |
| 1700 mg/kg | SD | 0.628 | 0.551 | 0.709 | 1.148 | 1.639 | 1.969 | 1.959 |
| | p value | 0.0043 | 0.0007 | 0.0004 | 0.0010 | 0.0086 | 0.0048 | 0.0021 | p value: compare to HFD by t-test

The data in Table 107 show that the animals in the Composition 3 treatment group (G1) and the positive control treatment group (ORI) all exhibited statistically significant decreases in body weight gain from week 1 through to week 7 as compared to the HFD group.

Table 108 shows the effects of Composition 3 on DIO mice for the following end points: average body weight gain per day of the study, average food intake per day of the study, and the food efficiency ratio (FER) which is calculated as the average body weight gain per day over the study period, divided by the average food intake per day over the study period.

TABLE 108

Effect of Composition 3 on DIO Mice

| Group | | Weight Gain (g/day) | Food Intake (g/day) | Food Efficiency Ratio (FER) |
|---|---|---|---|---|
| ND | Mean | 0.016 | 3.401 | 0.005 |
| (Normal Diet) | SD | 0.016 | 0.556 | 0.005 |
| | p value | 0.0009 | 0.0000 | 0.0007 |
| HFD | Mean | 0.100 | 2.592 | 0.038 |
| (High Fat | SD | 0.033 | 0.521 | 0.013 |

TABLE 108-continued

Effect of Composition 3 on DIO Mice

| Group | | Weight Gain (g/day) | Food Intake (g/day) | Food Efficiency Ratio (FER) |
|---|---|---|---|---|
| Diet) | | | | |
| ORI | Mean | 0.000 | 3.195 | 0.000 |
| (40 mg/kg) | SD | 0.038 | 0.752 | 0.012 |
| | p value | 0.0010 | 0.0000 | 0.0007 |
| G1 | Mean | 0.007 | 2.384 | 0.003 |
| (1700 mg/kg) | SD | 0.042 | 0.603 | 0.017 |
| | p value | 0.0021 | 0.0051 | 0.0026 |

Feed Efficacy Ratio (FER) = Body weight gain(g/day)/Food intake(g/day)
p value: compare to HFD by t-test The data in Table 108 show that both the Composition 3 on treatment group G1 and ORI treatment group showed a statistically significant effect on lowering average Weight Gain per day, Food Intake per day, and a lower Food Efficiency Ratio as compared to the HFD group.

Table 109 shows the effects of Composition 3 treatment on measurements in DIO mice of Alanine Transaminase (ALT), Aspartate transaminase (AST), and triglyceride (TG) as measure in blood samples obtained at the end of the study.

TABLE 109

Effect of Composition 3 on Biochemistry Parameters in DIO Mice

| Group | | ALT (U/L) | AST (U/L) | TG (mg/dL) |
|---|---|---|---|---|
| ND | Mean | 19.51 | 48.56 | 10.00 |
| (Normal Diet) | SD | 1.561 | 6.396 | 2.872 |
| | p value | 0.0277 | 0.0088 | 0.0001 |
| HFD | Mean | 51.32 | 87.77 | 33.10 |
| (High Fat Diet) | SD | 38.335 | 37.269 | 10.816 |
| ORI | Mean | 21.83 | 65.65 | 27.83 |
| (40 mg/kg) | SD | 5.707 | 17.307 | 6.555 |
| | p value | 0.0389 | 0.1970 | 0.3020 |
| G1 | Mean | 20.41 | 56.14 | 6.86 |
| (1700 mg/kg) | SD | 3.291 | 15.588 | 2.545 |
| | p value | 0.0314 | 0.0323 | 0.0000 | p value: compare to HFD by t-test

The data in Table 109 shows that the combination composition treatment group G1, exhibited a statistically significant decreases in ALT, AST, and total glucose as compared to the HFD group. In contrast, the ORI treatment group showed a statistically significant decrease in ALT as compared to the HFD group Table 110 shows the effects of Composition 3 treatment on measurements in DIO mice on several histopathological measures of fatty liver and the resulting calculated Non-Alcoholic Staetohepatitis (NASH) score of the liver.

TABLE 110

Effects of Composition 3 on Liver Pathology

| | | Pathology Indications | | | |
|---|---|---|---|---|---|
| Group | | Steatosis (0-3) | Lobular Inflammation (0-3) | Hepatocellular ballooning (0-2) | NASH (sum) |
| ND | Mean | 0.00 | 1.33 | 0.00 | 1.33 |
| (Normal | SD | 0.000 | 0.500 | 0.000 | 0.500 |
| Diet) | p value | 0.0000 | 0.1226 | 0.0000 | 0.0000 |
| HFD | Mean | 2.20 | 1.70 | 1.50 | 5.40 |
| (High | SD | 0.919 | 0.483 | 0.527 | 1.647 |
| Fat | | | | | |
| Diet) | | | | | |
| ORI | Mean | 0.67 | 1.33 | 0.67 | 2.67 |
| (40 | SD | 0.516 | 0.516 | 0.516 | 1.366 |
| mg/kg) | p value | 0.0023 | 0.1736 | 0.0081 | 0.0042 |
| G1 | Mean | 0.57 | 1.43 | 0.57 | 2.57 |
| (1700 | SD | 0.535 | 0.535 | 0.535 | 1.512 |
| mg/kg) | p value | 0.0008 | 0.2920 | 0.0029 | 0.0026 | p value: compare to HFD by t-test

The data in Table 110 show that there is a statistically significant difference in the weight of Steatosis, Hepatocellular ballooning and NASH score between the ND control group, fed a normal diet having a moderate caloric intact of fat, and the HFD group. Treatment group G1 and the ORI treatment group both showed statistically significant decreases in Steatosis, Hepatocellular ballooning and NASH score as compared with the HFD group. These data, demonstrate that Composition 3 was effective in reducing the amount of liver damage present in mice fed a high fat diet.

Overall, the data presented in this example show that the Morus-Rosemary-Mate combination Composition 3 was effective in lowering body weight and the rate of body weight gain, and in lowered a number of measures of the effects of a high fat diet on mice physiology.

Example 67

Effect of *Morus alba* Ethyl Acetate Extract 18 Combined with Rosemary Extract 24 and Yerba Mate Extract 27 on DIO Rats

*Morus alba* precipitate from ethanol extract 18, produced as described in Example 18, Rosemary extract 24, produced as described in Example 24, and Yerba Mate extract 27 produced according to Example 27, were combined and blended to a ratio of 2:5:10 by weight to make combination Composition 3, as further described in Example 39. Composition 3 was orally administered twice per day to DIO mice as described in Example 40. Treatment group G1 was administered at 850 mg/kg of animal weight (100 mg/Kg Morus, 250 mg/Kg Rosemary, and 500 mg/Kg Mate) of the combination composition each day, divided between the two doses. Treatment group G2 was administered 1700 mg/kg of animal weight (200 mg/Kg Morus, 500 mg/Kg Rosemary, and 1000 mg/Kg Mate) of Composition 3 each day, divided between the two doses. The study time period was 55 days. Table 111 shows the effects of Composition 3 on weight gain in DIO rats.

TABLE 111

Effect of Composition 3 on Weight Gain in DIO Rats

| Group | | Days | | | | | | | |
|---|---|---|---|---|---|---|---|---|---|
| | | 3 | 7 | 10 | 14 | 17 | 21 | 24 | 28 |
| ND (Normal Diet) | Mean | 4.83 | 11.86 | 18.42 | 23.43 | 23.61 | 32.45 | 39.57 | 44.19 |
| | SD | 5.54 | 7.84 | 7.31 | 8.03 | 13.36 | 13.98 | 13.08 | 13.85 |
| | p value | 0.018 | 0.064 | 0.028 | 0.008 | 0.010 | 0.009 | 0.013 | 0.004 |
| HFD (High Fat Diet) | Mean | 13.22 | 22.38 | 32.85 | 49.08 | 52.91 | 63.73 | 72.81 | 81.45 |
| | SD | 6.81 | 12.32 | 14.21 | 19.87 | 23.30 | 24.20 | 28.42 | 25.48 |
| ORI 80 mg/kg | Mean | 2.80 | 1.04 | 0.82 | 3.40 | 3.34 | 15.89 | 19.89 | 28.19 |
| | SD | 13.85 | 15.80 | 17.11 | 18.18 | 20.72 | 21.08 | 20.72 | 22.69 |
| | p value | 0.085 | 0.010 | 0.001 | 0 | 0.001 | 0.001 | 0.001 | 0.001 |
| G1 850 mg/kg | Mean | 2.43 | 0.96 | −2.63 | 9.60 | 9.73 | 19.30 | 24.89 | 34.45 |
| | SD | 10.48 | 14.63 | 17.94 | 22.04 | 24.09 | 20.97 | 23.58 | 24.14 |
| | p value | 0.031 | 0.007 | 0.001 | 0.002 | 0.003 | 0.002 | 0.003 | 0.002 |
| G2 1700 mg/kg | Mean | 1.15 | 10.32 | 9.91 | 18.64 | 19.17 | 23.79 | 26.36 | 33.51 |
| | SD | 4.15 | 8.83 | 11.76 | 15.28 | 17.88 | 17.51 | 19.39 | 19.17 |
| | p value | 0.001 | 0.043 | 0.004 | 0.004 | 0.006 | 0.002 | 0.002 | 0.001 |

| Group | | Days | | | | | | | |
|---|---|---|---|---|---|---|---|---|---|
| | | 31 | 35 | 37 | 42 | 45 | 49 | 52 | 55 |
| ND (Normal Diet) | Mean | 51.02 | 52.69 | 55.89 | 62.78 | 66.06 | 75.05 | 80.44 | 78.60 |
| | SD | 16.00 | 14.55 | 12.98 | 14.33 | 19.09 | 18.66 | 20.38 | 19.52 |
| | p value | 0.006 | 0.001 | 0.002 | 0.001 | 0.001 | 0.002 | 0.001 | 0.001 |
| HFD (High Fat Diet) | Mean | 89.85 | 98.23 | 103.01 | 113.20 | 124.09 | 130.99 | 141.23 | 143.39 |
| | SD | 28.13 | 26.72 | 29.41 | 29.26 | 31.14 | 33.04 | 32.99 | 34.29 |
| ORI 80 mg/kg | Mean | 33.33 | 38.43 | 43.95 | 49.06 | 59.88 | 63.68 | 71.12 | 68.11 |
| | SD | 24.86 | 25.56 | 28.85 | 30.54 | 29.53 | 30.43 | 29.27 | 29.33 |
| | p value | 0.001 | 0 | 0.001 | 0.001 | 0.001 | 0.001 | 0.001 | 0 |
| G1 850 mg/kg | Mean | 38.94 | 49.14 | 59.49 | 66.72 | 72.17 | 77.28 | 89.07 | 90.26 |
| | SD | 27.15 | 29.57 | 29.43 | 30.02 | 32.84 | 31.98 | 32.63 | 31.29 |
| | p value | 0.002 | 0.004 | 0.010 | 0.007 | 0.006 | 0.005 | 0.007 | 0.006 |
| G2 1700 mg/kg | Mean | 36.98 | 40.18 | 48.93 | 56.27 | 60.77 | 67.82 | 77.31 | 76.09 |
| | SD | 16.28 | 18.19 | 20.30 | 23.41 | 23.04 | 23.37 | 22.97 | 18.93 |
| | p value | 0.001 | 0 | 0.001 | 0.001 | 0 | 0.001 | 0.001 | 0.001 | p value: Compared to HFD group

The data in Table 111 show that the animals in Composition 3 treatment groups (G1) and (G2) both exhibited statistically significant decreases in body weight gain from day 3 through to day 55 of the study as compared to the HFD group. The control treatment group (ORI) exhibited statistically significant decreases in body weight gain on day 7 through to day 55 of the study as compared to the HFD group.

Table 112 shows the effects of Composition 3 on DOI rats for the following end points: average body weight gain per day of the study, average food intake per day of the study, and the food efficiency ratio (FER) which is calculated as the average body weight gain per day over the study period, divided by the average food intake per day over the study period.

TABLE 112

Effect of Composition 3 on DIO Rats

| Group | | Body Weight Gain (g/day) | Food Intake (g/day) | Food Efficiency Ratio (FER) |
|---|---|---|---|---|
| ND (Normal Diet) | Mean | 1.40 | 24.26 | 0.06 |
| | SD | 0.35 | 0.72 | 0.01 |
| | p value | 0.001 | 0.073 | 0.000 |
| HFD (High Fat Diet) | Mean | 2.56 | 21.14 | 0.12 |
| | SD | 0.61 | 2.37 | 0.02 |
| ORI (80 mg/kg) | Mean | 1.22 | 25.71 | 0.05 |
| | SD | 0.52 | 1.09 | 0.02 |
| | p value | 0.000 | 0.023 | 0.000 |
| G1 (850 mg/kg) | Mean | 1.61 | 19.65 | 0.08 |
| | SD | 0.56 | 1.34 | 0.03 |
| | p value | 0.006 | 0.327 | 0.006 |
| G2 (1700 mg/kg) | Mean | 1.36 | 18.74 | 0.07 |
| | SD | 0.34 | 0.62 | 0.02 |
| | p value | 0.001 | 0.134 | 0.000 | p value: Compared to HFD group

The data in Table 112 show that Composition 3 treatment groups G1 and G2 both showed a statistically significant effect on lowering average weight gain per day and a lower Food Efficiency Ratio as compared to the HFD rat group. The ORI positive control treatment group showed statistically lower values than the HFD group for average weight gain per day, average Food Intake per day and Food Efficiency Ratio.

Table 113 shows the effects of the Morus-Rosemary-Mate combination composition (Lot# IRM-1101) on several specific fatty tissues that are known to increase in fat content in rats subjected to a high fat diet.

TABLE 113

Effects of the *Morus*-Rosemary-Mate combination composition (Lot# IRM-1101) on fatty tissue weights in rats fed high fat diet

| Group | | Epididymal | Retroperitoneal | Perirenal | Total Fat* |
|---|---|---|---|---|---|
| ND | Mean | 11.14 | 12.41 | 3.70 | 27.25 |
| (Normal | SD | 2.32 | 3.04 | 0.65 | 5.47 |
| Diet) | p value | 0.000 | 0.000 | 0.000 | 0.000 |
| HFD | Mean | 22.84 | 28.27 | 8.90 | 60.01 |
| (High Fat | SD | 2.82 | 6.58 | 1.93 | 7.98 |
| Diet) | | | | | |
| ORI | Mean | 17.87 | 19.21 | 6.11 | 43.19 |
| (80 | SD | 5.44 | 3.00 | 1.69 | 9.56 |
| mg/kg) | p value | 0.044 | 0.005 | 0.008 | 0.002 |
| G1 | Mean | 17.31 | 19.15 | 6.14 | 42.60 |
| (850 | SD | 2.82 | 5.11 | 1.22 | 5.93 |
| mg/kg) | p value | 0.002 | 0.008 | 0.005 | 0.000 |
| G2 | Mean | 14.57 | 17.20 | 5.59 | 37.36 |
| (1700 | SD | 3.67 | 4.11 | 1.60 | 9.03 |
| mg/kg) | p value | 0.000 | 0.002 | 0.002 | 0.000 |

*Total fat is sum of the three fat deposits (epididymal, retroperitoneal and perirenal fat)
p value: compare to HFD by t-test The data in Table 113 show that there is a statistically significant difference in the weight of Epididymal Fat, Retroperitoneal Fat, Perirenal Fat and Total Fat between the ND control group, fed a normal diet having a moderate caloric intact of fat, and the HFD group. In addition, Composition 3 treatment groups G1 and G2, as well as the positive control treatment group (ORI), all showed statistically significant decreases in Epididymal Fat, Retroperitoneal Fat, Perirenal Fat and Total Fat as compared with the HFD group. These data, demonstrate Composition 3 was effective in reducing the amount of fat present in DIO rats.

Table 114 shows the effects of Composition 3 on DIO rats on several histopathological measures of fatty liver and the resulting calculated Non-Alcoholic Staetohepatitis (NASH) score of the liver.

TABLE 114

Effects of Composition 3 on Liver Pathology in DIO Rats

| Group | | Pathology Indications | | | |
|---|---|---|---|---|---|
| | | Steatosis (0-3) | Lobular Inflammation (0-3) | Hepatocellular ballooning (0-2) | NASH (sum) |
| ND | Mean | 0.000 | 1.857 | 0.000 | 1.857 |
| (Normal | SD | 0.000 | 0.378 | 0.000 | 0.378 |
| Diet) | p value | 0.000 | 0.180 | 0.000 | 0.000 |
| HFD | Mean | 1.875 | 2.125 | 1.625 | 5.625 |
| (High | SD | 1.126 | 0.354 | 0.744 | 1.923 |
| Fat Diet) | | | | | |
| ORI | Mean | 0.750 | 1.500 | 0.625 | 2.875 |
| (80 | SD | 0.707 | 0.535 | 0.744 | 1.727 |
| mg/kg) | p value | 0.031 | 0.015 | 0.018 | 0.009 |
| G1 | Mean | 1.500 | 1.625 | 1.125 | 4.250 |
| (850 | SD | 0.535 | 0.518 | 0.641 | 1.389 |
| mg/kg) | p value | 0.409 | 0.041 | 0.172 | 0.123 |
| G2 | Mean | 0.875 | 1.625 | 0.500 | 3.000 |
| (1700 | SD | 0.354 | 0.518 | 0.535 | 0.756 |
| mg/kg) | p value | 0.031 | 0.041 | 0.004 | 0.003 | p value: Compared to HFD group

The data in Table 114 show that there is a statistically significant difference in the amount of Steatosis, Hepatocellular ballooning and NASH score between the ND control group, fed a normal diet having a moderate caloric intact of fat, and the HFD group. Composition 3 treatment group G1 showed a statistically significant decrease in Lobular Inflammation as compared with the HFD group. Composition 3 treatment group G2 and the ORI positive control treatment group both showed statistically significant decreases in Steatosis, Hepatocellular ballooning and NASH score as compared with the HFD group. These data, demonstrate Composition 3 was effective in reducing the amount of liver damage present in rats fed a high fat diet.

Table 115 shows the effects of Composition 3 treatment on measurements in DIO rats of Alanine Transaminase (ALT), Aspartate transaminase (AST), Alkaline Phospatase (ALP), total cholesterol (T-chol), triglyceride (T-Glu), and LDL-cholesterol (LDL-C) as measured in blood samples obtained at the end of the study.

TABLE 115

Effect of Composition 3 on Biochemistry Parameters in DIO Rats

| Group | | ALT (U/L) | AST (U/L) | ALP (U/L) | T-chol (mg/dL) | TG (mg/dL) | LDL-C (mg/dL) |
|---|---|---|---|---|---|---|---|
| ND | Mean | 41.13 | 152.69 | 361.23 | 100.00 | 105.25 | 10.05 |
| (Normal | SD | 9.27 | 27.97 | 89.16 | 12.34 | 64.38 | 2.30 |
| Diet) | p value | 0.204 | 0.416 | 0.821 | 0.006 | 0.259 | 0.249 |
| HFD | Mean | 54.75 | 168.00 | 348.58 | 124.63 | 137.13 | 11.15 |
| (High Fat Diet) | SD | 26.46 | 43.12 | 126.40 | 17.44 | 40.50 | 1.10 |
| ORI | Mean | 35.65 | 146.39 | 480.16 | 110.13 | 216.38 | 10.63 |
| (80 mg/kg) | SD | 7.54 | 24.18 | 288.95 | 21.16 | 100.04 | 1.36 |
| | p value | 0.085 | 0.242 | 0.266 | 0.158 | 0.067 | 0.411 |
| G1 | Mean | 34.36 | 106.55 | 218.34 | 83.00 | 77.25 | 6.46 |
| (850 mg/kg) | SD | 16.47 | 38.38 | 48.70 | 28.42 | 69.24 | 2.49 |
| | p value | 0.090 | 0.009 | 0.024 | 0.004 | 0.058 | 0.001 |

TABLE 115-continued

Effect of Composition 3 on Biochemistry Parameters in DIO Rats

| Group | | ALT (U/L) | AST (U/L) | ALP (U/L) | T-chol (mg/dL) | TG (mg/dL) | LDL-C (mg/dL) |
|---|---|---|---|---|---|---|---|
| G2 (1700 mg/kg) | Mean | 30.35 | 78.53 | 197.31 | 71.88 | 48.75 | 5.80 |
| | SD | 5.36 | 21.66 | 77.04 | 16.16 | 15.29 | 1.39 |
| | p value | 0.035 | 0.000 | 0.014 | 0.000 | 0.000 | 0.000 | p value: compare to HFD by t-test

The data in Table 115 shows that the combination composition treatment group G1, exhibited a statistically significant decreases in AST, ALP, total cholesterol, and LDL-cholesterol as compared to the HFD group. Treatment group G2 showed statistically significant decreases in AST, ALT, AST, ASP, total—cholesterol, triglyceride, and LDL-cholesterol as compared to the HFD group. Whereas the ORI treatment group did not show any statistically significant decreases in any of the measured blood chemistry components as compared to the HFD group.

Overall, the data presented in this example show that the Morus-Rosemary-Mate combination Composition 3 was effective in lowering body weight and the rate of body weight gain, and in lowered a number of different measures of the effects of a high fat diet on rat physiology.

Example 68

Efficacy Study of Mutamba Ethanol Extract 35 Combined with *Magnolia* Extract 29 and Yerba Mate Extract 26 in DIO Mice Mutamba ethanol extract 35 produced according to Example 35 and *Magnolia* extract 29 produced according to Example 29 and Yerba Mate extract 26 produced according to Example 26 was combined by blending three components in a ratio of 5:1:5 to create Composition 10. The combined three ingredient composition was orally administered to DIO mice as described in the example 48 at a dosage of 1,100 mg/kg (G1) twice a day.

The total body weight of mice was significantly decreased after the third week in the group treated with Mutamba: Magnolia:Yerba Mate Composition 10 (treatment group G1) (Table 116).

TABLE 116

Effect of Mutamba:*Magnolia*:Yerba Mate Composition 10 on Total Weight in DIO Mice

| Group | | Weeks | | | | | | | | |
|---|---|---|---|---|---|---|---|---|---|---|
| | | 0 | 1 | 2 | 3 | 4 | 5 | 6 | 7 | 8 |
| ND | Mean | 29.24 | 29.11 | 29.03 | 29.47 | 29.36 | 29.51 | 29.75 | 29.76 | 30.14 |
| | SD | 1.020 | 0.967 | 1.201 | 1.166 | 1.428 | 1.309 | 1.509 | 1.270 | 1.321 |
| | p value | 0.0001 | 0.0001 | 0.0001 | 0.0000 | 0.0000 | 0.0000 | 0.0000 | 0.0000 | 0.0000 |
| HFD | Mean | 41.31 | 41.73 | 1100.00 | 43.64 | 44.94 | 46.25 | 47.78 | 48.43 | 49.29 |
| | SD | 2.932 | 2.771 | 2.856 | 2.884 | 2.870 | 3.172 | 3.247 | 3.224 | 2.783 |
| ORI | Mean | 40.22 | 37.98 | 34.08 | 35.32 | 36.38 | 37.65 | 38.75 | 39.96 | 39.99 |
| | SD | 2.816 | 2.547 | 1.277 | 1.186 | 1.867 | 2.284 | 2.931 | 3.235 | 3.633 |
| | p value | 0.9795 | 0.5280 | 0.0351 | 0.0001 | 0.0001 | 0.0001 | 0.0003 | 0.0005 | 0.0011 |
| G1 | Mean | 40.33 | 39.53 | 38.38 | 38.24 | 38.66 | 39.30 | 40.04 | 40.86 | 42.05 |
| | SD | 2.619 | 2.629 | 2.333 | 3.240 | 3.631 | 3.511 | 3.866 | 3.839 | 4.445 |
| | p value | 0.9605 | 0.5544 | 0.1886 | 0.0324 | 0.0122 | 0.0077 | 0.0049 | 0.0038 | 0.0041 | p value: compare to HFD by t-test

The weight gain in the Mutamba:Magnolia:Yerba Mate Composition 10 treatment group (G1) was significantly decreased after the first week of treatment (Table 117).

TABLE 117

Effect of Mutamba:*Magnolia*:Yerba Mate Composition 10 on Weight Gain in DIO Mice

| Group | | Weeks | | | | | | | |
|---|---|---|---|---|---|---|---|---|---|
| | | 1 | 2 | 3 | 4 | 5 | 6 | 7 | 8 |
| ND | Mean | −0.13 | −0.22 | 0.22 | 0.11 | 0.27 | 0.50 | 0.52 | 0.89 |
| | SD | 0.367 | 0.377 | 0.238 | 0.463 | 0.390 | 0.635 | 0.447 | 0.562 |
| | p value | 0.0057 | 0.0011 | 0.0080 | 0.0010 | 0.0005 | 0.0004 | 0.0002 | 0.0002 |
| HFD | Mean | 0.42 | 0.81 | 2.34 | 3.64 | 4.94 | 6.47 | 7.13 | 7.98 |
| | SD | 0.2382 | 0.63623 | 1.229 | 1.3426 | 1.5261 | 1.8734 | 1.8149 | 1.9044 |

TABLE 117-continued

Effect of Mutamba:*Magnolia*:Yerba Mate Composition 10 on Weight Gain in DIO Mice

| Group | | 1 | 2 | 3 | 4 | 5 | 6 | 7 | 8 |
|---|---|---|---|---|---|---|---|---|---|
| ORI | Mean | −2.24 | −6.14 | −4.91 | −3.84 | −2.57 | −1.47 | −0.26 | −0.23 |
| | SD | 1.123 | 2.286 | 1.286 | 1.228 | 1.355 | 1.507 | 1.728 | 2.055 |
| | p value | 0.0018 | 0.0005 | 0.0000 | 0.0000 | 0.0000 | 0.0000 | 0.0001 | 0.0000 |
| G1 | Mean | −0.80 | −1.94 | −2.09 | −1.67 | −1.02 | −0.29 | 0.53 | 1.73 |
| | SD | 0.359 | 0.861 | 1.102 | 1.507 | 1.420 | 1.733 | 1.700 | 2.169 |
| | p value | 0.0000 | 0.0001 | 0.0001 | 0.0001 | 0.0000 | 0.0001 | 0.0001 | 0.0003 | p value: compare to HFD by t-test

Food efficiency ratio (FER) was significantly lowered in the treatment group (G1) as compared to the high fat diet group (Table 118).

TABLE 118

Effect of Mutamba:*Magnolia*:Yerba Mate Composition 10 on DIO Mice

| Group | | Body weight gain (g/day) | Food intake (g/day) | FER (Food efficiency ratio) |
|---|---|---|---|---|
| ND | Mean | 0.017 | 3.181 | 0.005 |
| | SD | 0.011 | 0.906 | 0.003 |
| | p value | 0.0002 | 0.0202 | 0.0002 |
| HFD | Mean | 0.153 | 2.752 | 0.056 |
| | SD | 0.037 | 0.178 | 0.013 |
| ORI | Mean | −0.004 | 3.147 | −0.001 |
| | SD | 0.040 | 0.371 | 0.013 |
| | p value | 0.0000 | 0.0000 | 0.0000 |
| G1 | Mean | 0.033 | 2.397 | 0.014 |
| | SD | 0.042 | 0.383 | 0.017 |
| | p value | 0.0003 | 0.0001 | 0.0009 |

FER(Feed efficacy ratio) = Body weight gain(g/day)/Food intake(g/day)
p value: compare to HFD by t-test Plasma glucose and TG was significantly decreased in the Mutamba:Magnolia:Yerba Mate Composition 10 treatment group (G1) as compared to the high fat diet group (Table 119).

TABLE 119

Effect of Mutamba:*Magnolia*:Yerba Mate Composition 10 on Biochemistry Parameters in DIO Mice

| Group | | ALT (U/L) | AST (U/L) | T-chol (mg/dL) | TG (mg/dL) | TP (g/dL) | LDL-C (mg/dL) |
|---|---|---|---|---|---|---|---|
| ND | Mean | 16.84 | 39.90 | 107.40 | 23.40 | 5.22 | 3.72 |
| | SD | 0.899 | 0.781 | 6.107 | 3.715 | 0.164 | 0.683 |
| | p value | 0.0718 | 0.3426 | 0.0100 | 0.0504 | 0.0924 | 0.0539 |
| HFD | Mean | 88.83 | 72.99 | 229.75 | 38.50 | 5.65 | 10.13 |
| | SD | 52.704 | 58.845 | 42.883 | 9.983 | 0.465 | 4.200 |
| ORI | Mean | 23.03 | 51.40 | 155.83 | 88.33 | 5.08 | 4.28 |
| | SD | 6.720 | 8.052 | 23.558 | 32.222 | 0.172 | 0.770 |
| | p value | 0.0872 | 0.5174 | 0.0074 | 0.0185 | 0.0240 | 0.0673 |
| G1 | Mean | 26.82 | 57.90 | 198.40 | 20.20 | 4.98 | 8.74 |
| | SD | 5.287 | 12.930 | 15.307 | 9.680 | 0.130 | 1.016 |
| | p value | 0.0995 | 0.5890 | 0.1677 | 0.0273 | 0.0596 | 0.5615 |

TABLE 120

Effect of Mutamba:*Magnolia*:Yerba Mate Composition 10 on Absolute Organ Weights in DIO Mice

| Group | | Liver | Epididymal Fat | Retroperitoneal Fat | PeriRenal Fat | Total Fat* |
|---|---|---|---|---|---|---|
| ND | Mean | 1.07 | 0.46 | 0.11 | 0.06 | 0.63 |
| | SD | 0.062 | 0.126 | 0.042 | 0.017 | 0.181 |
| | p value | 0.0000 | 0.0009 | 0.0001 | 0.0000 | 0.0001 |
| HFD | Mean | 2.11 | 2.30 | 0.57 | 0.68 | 3.56 |
| | SD | 0.368 | 0.400 | 0.090 | 0.141 | 0.454 |
| ORI | Mean | 1.19 | 2.03 | 0.50 | 0.29 | 2.82 |
| | SD | 0.093 | 0.831 | 0.191 | 0.129 | 1.137 |
| | p value | 0.0005 | 0.0013 | 0.4854 | 0.4229 | 0.0005 |
| G1 | Mean | 1.48 | 2.92 | 0.68 | 0.40 | 4.00 |
| | SD | 0.306 | 0.218 | 0.037 | 0.107 | 0.289 |
| | p value | 0.0036 | 0.4972 | 0.1737 | 0.0004 | 0.9531 |

*Total fat is sum of the three fat pads(epididymal, retroperitoneal and perirenal fat)
p value: compare to HFD by t-test Absolute weight of liver and perirenal fat pads were significantly decreased in the treatment group (G1) as compared with the high fat diet group (Table 120).

The NASH score was significantly decreased in the treatment group (G1) as compared with the high fat diet group (Table 121).

TABLE 121

Effect of Mutamba:*Magnolia*:Yerba Mate Composition 10 on Liver Pathology in DIO mice

| Group | | Indications | | | |
|---|---|---|---|---|---|
| | | Steatosis (0-3) | Lobular Inflammation (0-3) | Hepatocellular ballooning (0-2) | NSAH (sum) |
| ND | Mean | 0.00 | 1.00 | 0.00 | 1.00 |
| | SD | 0.000 | 0.000 | 0.000 | 0.000 |
| | p value | 0.0000 | 0.0104 | — | 0.0000 |
| HFD | Mean | 2.83 | 1.50 | 2.00 | 6.33 |
| | SD | 0.408 | 0.548 | 0.000 | 0.816 |
| ORI | Mean | 0.33 | 1.50 | 0.33 | 2.17 |
| | SD | 0.516 | 0.548 | 0.516 | 1.472 |
| | p value | 0.0000 | 1.0000 | 0.0000 | 0.0001 |
| G1 | Mean | 1.67 | 1.50 | 1.17 | 4.33 |
| | SD | 0.816 | 0.548 | 0.408 | 1.506 |
| | p value | 0.0107 | 1.0000 | 0.0005 | 0.0169 | p value: compare to HFD by t-test

These data show that body weight, body weight gain, FER (food efficiency ratio), visceral fat weights and NASH score in liver were significantly decreased by Mutamba:Magnolia:Yerba Mate Composition 10. Also, TG was decreased by treatment with this triple combination. Therefore, this example shows that the combination of Mutamba:Magnolia:Yerba Mate as provided in Composition 10 is useful as a body weight reducer, as well as a dyslipidemia and fatty liver reducer.

Example 69

Efficacy Study of Mutamba EtOH Extract 35 in Combination with *Magnolia* Extract 29 and *Morus alba* Ethyl Acetate Fraction 15 in DIO Mice Mutamba ethanol extract 35 produced according to Example 35, *Magnolia* extract 29 produced according to Example 29, and *Morus alba* ethyl acetate fraction 15 produced according to Example 15 were combined by blending three components in a ratio of 5:1:2 to generate Composition 2. The combined three ingredient Composition 2 was orally administrated to DIO mice as described in the example 48 at a dosage of 800 mg/kg (G1) twice a day.

The body weight was significantly decreased in the Mutamba:Magnolia:Morus Composition 2 treatment group (G1) after the second week treatment (Table 122).

TABLE 122

Effect of Mutamba:*Magnolia*:*Morus* Composition 2 on Total Weight in DIO Mice

| Group | | Weeks | | | | | | | | |
|---|---|---|---|---|---|---|---|---|---|---|
| | | 0 | 1 | 2 | 3 | 4 | 5 | 6 | 7 | 8 |
| ND | Mean | 29.24 | 29.11 | 29.03 | 29.47 | 29.36 | 29.51 | 29.75 | 29.76 | 30.14 |
| | SD | 1.020 | 0.967 | 1.201 | 1.166 | 1.428 | 1.309 | 1.509 | 1.270 | 1.321 |
| | p value | 0.0001 | 0.0001 | 0.0001 | 0.0000 | 0.0000 | 0.0000 | 0.0000 | 0.0000 | 0.0000 |
| HFD | Mean | 41.31 | 41.73 | 42.12 | 43.64 | 44.94 | 46.25 | 47.78 | 48.43 | 49.29 |
| | SD | 2.932 | 2.771 | 2.856 | 2.884 | 2.870 | 3.172 | 3.247 | 3.224 | 2.783 |
| ORI | Mean | 40.22 | 37.98 | 34.08 | 35.32 | 36.38 | 37.65 | 38.75 | 39.96 | 39.99 |
| | SD | 2.816 | 2.547 | 1.277 | 1.186 | 1.867 | 2.284 | 2.931 | 3.235 | 3.633 |
| | p value | 0.9795 | 0.5280 | 0.0351 | 0.0001 | 0.0001 | 0.0001 | 0.0003 | 0.0005 | 0.0011 |
| G1 | Mean | 39.43 | 35.89 | 32.37 | 34.48 | 35.19 | 34.97 | 34.87 | 35.43 | 35.84 |
| | SD | 1.286 | 1.100 | 2.028 | 1.569 | 2.115 | 2.445 | 2.082 | 2.548 | 3.005 |
| | p value | 0.4966 | 0.2684 | 0.0043 | 0.0004 | 0.0004 | 0.0004 | 0.0003 | 0.0001 | 0.0001 | p value: compare to HFD by t-test

The body weight gain was significantly decreased in the Mutamba:Magnolia:Morus Composition 2 treatment group G1 after the first week of treatment as compared to the high fat diet group (Table 123).

TABLE 123

Effect of Mutamba:*Magnolia*:*Morus* Composition 2 on Weight Gain in DIO Mice

| Group | | Weeks | | | | | | | |
|---|---|---|---|---|---|---|---|---|---|
| | | 1 | 2 | 3 | 4 | 5 | 6 | 7 | 8 |
| ND | Mean | -0.13 | -0.22 | 0.22 | 0.11 | 0.27 | 0.50 | 0.52 | 0.89 |
| | SD | 0.367 | 0.377 | 0.238 | 0.463 | 0.390 | 0.635 | 0.447 | 0.562 |
| | p value | 0.0057 | 0.0011 | 0.0080 | 0.0010 | 0.0005 | 0.0004 | 0.0002 | 0.0002 |
| HFD | Mean | 0.42 | 0.81 | 2.34 | 3.64 | 4.94 | 6.47 | 7.13 | 7.98 |
| | SD | 0.238 | 0.636 | 1.229 | 1.343 | 1.526 | 1.873 | 1.815 | 1.904 |
| ORI | Mean | -2.24 | -6.14 | -4.91 | -3.84 | -2.57 | -1.47 | -0.26 | -0.23 |
| | SD | 1.123 | 2.286 | 1.286 | 1.228 | 1.355 | 1.507 | 1.728 | 2.055 |
| | p value | 0.0018 | 0.0005 | 0.0000 | 0.0000 | 0.0000 | 0.0000 | 0.0001 | 0.0000 |

TABLE 123-continued

Effect of Mutamba:*Magnolia*:Morus Composition 2 on Weight Gain in DIO Mice

| | | Weeks | | | | | | | |
|---|---|---|---|---|---|---|---|---|---|
| Group | | 1 | 2 | 3 | 4 | 5 | 6 | 7 | 8 |
| G1 | Mean | −3.54 | −7.06 | −4.95 | −4.24 | −4.46 | −4.56 | −4.00 | −3.59 |
| | SD | 2.241 | 3.041 | 1.944 | 1.735 | 1.894 | 1.115 | 1.365 | 1.982 |
| | p value | 0.0001 | 0.0001 | 0.0001 | 0.0001 | 0.0000 | 0.0001 | 0.0001 | 0.0003 | p value: compare to HFD by t-test

Food efficiency ratio (FER) was significantly lowered in the Mutamba:Magnolia:Morus Composition 2 treatment group (G1) as compared to the high fat diet group (Table 124).

TABLE 124

Effect of Mutamba:*Magnolia*:Morus Composition 2 on DIO Mice

| Group | | Body weight gain (g/day) | Food intake (g/day) | FER (Food efficiency ratio) |
|---|---|---|---|---|
| ND | Mean | 0.017 | 3.181 | 0.005 |
| | SD | 0.011 | 0.906 | 0.003 |
| | p value | 0.0002 | 0.0202 | 0.0002 |
| HFD | Mean | 0.153 | 2.752 | 0.056 |
| | SD | 0.037 | 0.178 | 0.013 |

TABLE 124-continued

Effect of Mutamba:*Magnolia*:Morus Composition 2 on DIO Mice

| Group | | Body weight gain (g/day) | Food intake (g/day) | FER (Food efficiency ratio) |
|---|---|---|---|---|
| ORI | Mean | −0.004 | 3.147 | −0.001 |
| | SD | 0.040 | 0.371 | 0.013 |
| | p value | 0.0000 | 0.0000 | 0.0000 |
| G1 | Mean | −0.069 | 2.391 | −0.029 |
| | SD | 0.038 | 0.795 | 0.016 |
| | p value | 0.0003 | 0.0107 | 0.0009 |

FER(Feed efficacy ratio) = Body weight gain(g/day)/Food intake(g/day)
p value: compare to HFD by t-test ALP and total cholesterol were significantly decreased in the Mutamba:Magnolia:Morus Composition 2 treatment group (G1) as compared to the high fat diet group (Table 125).

TABLE 125

Effect of Mutamba:*Magnolia*:Morus Composition 2 on Biochemical Parameters in DIO Mice

| Group | | ALT (U/L) | AST (U/L) | ALP (U/L) | T-chol (mg/dL) | TG (mg/dL) | TP (g/dL) | LDL-C (mg/dL) |
|---|---|---|---|---|---|---|---|---|
| ND | Mean | 16.84 | 39.90 | 195.74 | 107.40 | 23.40 | 5.22 | 3.72 |
| | SD | 0.899 | 0.781 | 42.213 | 6.107 | 3.715 | 0.164 | 0.683 |
| | p value | 0.0718 | 0.0464 | 0.1655 | 0.0100 | 0.0504 | 0.0924 | 0.0539 |
| HFD | Mean | 88.83 | 97.80 | 235.03 | 229.75 | 38.50 | 5.65 | 10.13 |
| | SD | 52.704 | 35.293 | 31.025 | 42.883 | 9.983 | 0.465 | 4.200 |
| ORI | Mean | 23.03 | 51.40 | 177.35 | 155.83 | 88.33 | 5.08 | 4.28 |
| | SD | 6.720 | 8.052 | 13.486 | 23.558 | 32.222 | 0.172 | 0.770 |
| | p value | 0.0872 | 0.0760 | 0.0034 | 0.0074 | 0.0185 | 0.0240 | 0.0673 |
| G1 | Mean | 20.53 | 50.43 | 174.75 | 172.50 | 20.50 | 4.80 | 5.63 |
| | SD | 5.437 | 6.001 | 24.604 | 10.661 | 11.733 | 0.000 | 0.903 |
| | p value | 0.0802 | 0.0728 | 0.0227 | 0.0411 | 0.0581 | 0.0107 | 0.1195 |

Absolute weights of liver and perirenal fat pads were significantly decreased in the treatment group (G1) as compared to the high fat diet group (Table 126).

TABLE 126

Effect of Mutamba:*Magnolia*:Morus Composition 2 on Absolute Organ Weights in DIO Mice

| Group | | Liver | Epididymal fat | Retroperitoneal fat | Peri-Renal fat | Total Fat* |
|---|---|---|---|---|---|---|
| ND | Mean | 1.07 | 0.46 | 0.11 | 0.06 | 0.63 |
| | SD | 0.062 | 0.126 | 0.042 | 0.017 | 0.181 |
| | p value | 0.0000 | 0.0009 | 0.0001 | 0.0000 | 0.0001 |
| HFD | Mean | 2.11 | 2.30 | 0.57 | 0.68 | 3.56 |
| | SD | 0.368 | 0.400 | 0.090 | 0.141 | 0.454 |
| ORI | Mean | 1.19 | 2.03 | 0.50 | 0.29 | 2.82 |
| | SD | 0.093 | 0.831 | 0.191 | 0.129 | 1.137 |
| | p value | 0.0005 | 0.0013 | 0.4854 | 0.4229 | 0.0005 |

TABLE 126-continued

Effect of Mutamba:*Magnolia*:*Morus* Composition 2 on Absolute Organ Weights in DIO Mice

| Group | | Liver | Epididymal fat | Retroperitoneal fat | Perirenal fat | Total Fat* |
|---|---|---|---|---|---|---|
| G1 | Mean | 1.27 | 1.71 | 0.46 | 0.21 | 2.38 |
| | SD | 0.091 | 0.464 | 0.152 | 0.048 | 0.657 |
| | p value | 0.0036 | 0.4972 | 0.1737 | 0.0004 | 0.9531 |

*Total fat is sum of the three fat pads (epididymal, retroperitoneal and perirenal fat)
p value: compare to HFD by t-test The NASH score was significantly decreased in the Mutamba:Magnolia:Morus Composition 2 treatment group (G1) as compared to the high fat diet (Table 127).

TABLE 127

Effect of Mutamba:*Magnolia*:Morus Composition 2 on Liver Pathology in DIO Mice

| Group | | Steatosis (0-3) | Lobular Inflammation (0-3) | Hepatocellular ballooning (0-2) | NASH (sum) |
|---|---|---|---|---|---|
| ND | Mean | 0.00 | 1.00 | 0.00 | 1.00 |
| | SD | 0.000 | 0.000 | 0.000 | 0.000 |
| | p value | 0.0000 | 0.0104 | — | 0.0000 |
| HFD | Mean | 2.83 | 1.50 | 2.00 | 6.33 |
| | SD | 0.408 | 0.548 | 0.000 | 0.816 |
| ORI | Mean | 0.33 | 1.50 | 0.33 | 2.17 |
| | SD | 0.516 | 0.548 | 0.516 | 1.472 |
| | p value | 0.0000 | 1.0000 | 0.0000 | 0.0001 |
| G1 | Mean | 0.25 | 1.25 | 0.25 | 1.75 |
| | SD | 0.500 | 0.500 | 0.500 | 0.957 |
| | p value | 0.0000 | 0.4860 | 0.0000 | 0.0000 | p value: compare to HFD by t-test

Overall these results show that total body weight, weight gain, FER (food efficiency ratio), visceral fat weights and NASH score in liver were significantly decreased by treatment with Mutamba:Magnolia:Morus Composition 2. In addition, ALP and total cholesterol were decreased by treatment of this combination. Therefore, Mutamba:Magnolia:Morus Composition 2 can be used as a body weight reducer, dyslipidemia and fatty liver reducer.

Example 70

Efficacy Study of Mutamba EtOH Extract 35 Combined with Yerba Mate Extract 26 and *Morus alba* Ethyl Acetate Fraction 15 in DIO Mice Mutamba ethanol extract 35 produced according to Example 35 and Yerba Mate extract 26 produced according to Example 26, and *Morus alba* ethyl acetate fraction 15 produced according to Example 15 were combined by blending the three components in a ratio of 5:5:2, respectively. The three ingredient Mutamba:Yerba Mate:Morus Composition 2 was orally administered to DIO mice as described in Example 48 at a dosage of 1,200 mg/kg (G1) twice a day.

The body weight was significantly decreased in the Mutamba:Yerba Mate:Morus Composition 2 treatment group (G1) after the second week treatment of the experiment (Table 128).

TABLE 128

Effect of Mutamba:Yerba Mate:*Morus* Composition 2 on Total Body Weight in DIO Mice

| Group | | Weeks | | | | | | | | |
|---|---|---|---|---|---|---|---|---|---|---|
| | | 0 | 1 | 2 | 3 | 4 | 5 | 6 | 7 | 8 |
| ND | Mean | 29.24 | 29.11 | 29.03 | 29.47 | 29.36 | 29.51 | 29.75 | 29.76 | 30.14 |
| | SD | 1.020 | 0.967 | 1.201 | 1.166 | 1.428 | 1.309 | 1.509 | 1.270 | 1.321 |
| | p value | 0.0001 | 0.0001 | 0.0001 | 0.0000 | 0.000 | 0.000 | 0.000 | 0.000 | 0.000 |
| HFD | Mean | 41.31 | 41.73 | 42.12 | 43.64 | 44.94 | 46.25 | 47.78 | 48.43 | 49.29 |
| | SD | 2.932 | 2.771 | 2.856 | 2.884 | 2.870 | 3.172 | 3.247 | 3.224 | 2.783 |
| ORI | Mean | 40.22 | 37.98 | 34.08 | 35.32 | 36.38 | 37.65 | 38.75 | 39.96 | 39.99 |
| | SD | 2.816 | 2.547 | 1.277 | 1.186 | 1.867 | 2.284 | 2.931 | 3.235 | 3.633 |
| | p value | 0.980 | 0.528 | 0.035 | 0.0001 | 0.0001 | 0.0001 | 0.0003 | 0.0005 | 0.0011 |
| G1 | Mean | 40.34 | 38.20 | 34.45 | 36.47 | 38.27 | 39.49 | 40.66 | 41.34 | 42.12 |
| | SD | 2.315 | 2.636 | 5.926 | 4.533 | 3.764 | 3.702 | 3.471 | 4.117 | 4.080 |
| | p value | 0.933 | 0.540 | 0.048 | 0.017 | 0.008 | 0.006 | 0.007 | 0.004 | 0.008 | p value: compare to HFD by t-test

Weight gain was significantly decreased after the first week of treatment in mice of the Mutamba:Yerba Mate:Morus Composition 2 treatment group (G1) (Table 129).

Absolute weights of liver and perirenal fat pads were significantly decreased in the Mutamba:Yerba Mate:Morus Composition 2 treatment group (G1) as compared to the high fat diet group (Table 132).

TABLE 129

Effect of Mutamba:Yerba Mate:*Morus* Composition 2 on Weight Gain in DIO Mice

| Group | | Weeks | | | | | | | |
|---|---|---|---|---|---|---|---|---|---|
| | | 1 | 2 | 3 | 4 | 5 | 6 | 7 | 8 |
| ND | Mean | −0.13 | −0.22 | 0.22 | 0.11 | 0.27 | 0.50 | 0.52 | 0.89 |
| | SD | 0.367 | 0.377 | 0.238 | 0.463 | 0.390 | 0.635 | 0.447 | 0.562 |
| | p value | 0.0057 | 0.0011 | 0.0080 | 0.0010 | 0.0005 | 0.0004 | 0.0002 | 0.0002 |
| HFD | Mean | 0.42 | 0.81 | 2.34 | 3.64 | 4.94 | 6.47 | 7.13 | 7.98 |
| | SD | 0.238 | 0.636 | 1.229 | 1.343 | 1.526 | 1.873 | 1.815 | 1.904 |
| ORI | Mean | −2.24 | −6.14 | −4.91 | −3.84 | −2.57 | −1.47 | −0.26 | −0.23 |
| | SD | 1.123 | 2.286 | 1.286 | 1.228 | 1.355 | 1.507 | 1.728 | 2.055 |
| | p value | 0.0018 | 0.0005 | 0.0000 | 0.0000 | 0.0000 | 0.0000 | 0.0001 | 0.0000 |
| G1 | Mean | −2.14 | −5.89 | −3.87 | −2.07 | −0.85 | 0.32 | 1.00 | 1.78 |
| | SD | 1.727 | 5.455 | 4.013 | 3.209 | 3.197 | 3.079 | 3.717 | 3.966 |
| | p value | 0.0380 | 0.0126 | 0.0016 | 0.0000 | 0.0000 | 0.0000 | 0.0000 | 0.0000 | p value: compare to HFD by t-test

The food efficiency ratio (FER) was significantly lowered in the Mutamba:Yerba Mate:Morus Composition 2 treatment group (G1) as compared to the high fat diet group (Table 130).

TABLE 130

Effect of Mutamba:Yerba Mate:*Morus* Composition 2 on DIO Mice

| Group | | Weight Gain (g/day) | Food Intake (g/day) | FER (Food Efficiency Ratio) |
|---|---|---|---|---|
| ND | Mean | 0.017 | 3.181 | 0.005 |
| | SD | 0.011 | 0.906 | 0.003 |
| | p value | 0.0002 | 0.0202 | 0.0002 |
| HFD | Mean | 0.033 | 2.752 | 0.014 |
| | SD | 0.037 | 0.178 | 0.013 |
| ORI | Mean | −0.004 | 3.147 | −0.001 |
| | SD | 0.040 | 0.371 | 0.013 |
| | p value | 0.0000 | 0.0000 | 0.0000 |
| G1 | Mean | 0.034 | 2.586 | 0.013 |
| | SD | 0.076 | 0.509 | 0.029 |
| | p value | 0.0000 | 0.1122 | 0.0000 |

FER(Feed efficacy ratio) = Body weight gain(g/day)/Food intake(g/day)
p value: compare to HFD by t-test TG was significantly decreased in the Mutamba:Yerba Mate:Morus Composition 2 treatment group (G1) as compared to the high fat diet group (Table 131).

TABLE 131

Effect of Mutamba:Yerba Mate:*Morus* Composition 2 on Biochemistry Parameters

| Group | | ALT (U/L) | AST (U/L) | T-chol (mg/dL) | TG (mg/dL) | TP (g/dL) | LDL-C (mg/dL) |
|---|---|---|---|---|---|---|---|
| ND | Mean | 16.84 | 39.90 | 107.40 | 23.40 | 5.22 | 3.72 |
| | SD | 0.899 | 0.781 | 6.107 | 3.715 | 0.164 | 0.683 |
| | p value | 0.0718 | 0.0464 | 0.0100 | 0.0504 | 0.0924 | 0.0539 |
| HFD | Mean | 88.83 | 97.80 | 229.75 | 38.50 | 5.65 | 10.13 |
| | SD | 52.704 | 35.293 | 42.883 | 9.983 | 0.465 | 4.200 |
| ORI | Mean | 23.03 | 51.40 | 155.83 | 88.33 | 5.08 | 4.28 |
| | SD | 6.720 | 8.052 | 23.558 | 32.22 | 0.172 | 0.770 |
| | p value | 0.0872 | 0.0760 | 0.0074 | 0.0185 | 0.0240 | 0.0673 |
| G1 | Mean | 27.87 | 55.83 | 194.00 | 8.50 | 5.15 | 8.47 |
| | SD | 7.631 | 9.902 | 15.887 | 2.429 | 0.105 | 1.731 |
| | p value | 0.1029 | 0.0949 | 0.0936 | 0.0078 | 0.1192 | 0.4036 |

TABLE 132

Effect of Mutamba:Yerba Mate:*Morus* Composition 2 on Absolute Organ Weights in DIO Mice

| Group | | Liver | Epididymal Fat | Retroperitoneal Fat | PeriRenal Fat | Total Fat* |
|---|---|---|---|---|---|---|
| ND | Mean | 1.07 | 0.46 | 0.11 | 0.06 | 0.63 |
| | SD | 0.062 | 0.126 | 0.042 | 0.017 | 0.181 |
| | p value | 0.0000 | 0.0009 | 0.0001 | 0.0000 | 0.0001 |
| HFD | Mean | 2.11 | 2.30 | 0.57 | 0.68 | 3.56 |
| | SD | 0.368 | 0.400 | 0.090 | 0.141 | 0.454 |
| ORI | Mean | 1.19 | 2.03 | 0.50 | 0.29 | 2.82 |
| | SD | 0.093 | 0.831 | 0.191 | 0.129 | 1.137 |
| | p value | 0.0005 | 0.0013 | 0.4854 | 0.4229 | 0.0005 |
| G1 | Mean | 1.47 | 2.54 | 0.64 | 0.35 | 3.54 |
| | SD | 0.184 | 0.723 | 0.071 | 0.066 | 0.786 |
| | p value | 0.0036 | 0.4972 | 0.1737 | 0.0004 | 0.9531 |

*Total fat is sum of the three fat pads(epididymal, retroperitoneal and perirenal fat)
p value: compare to HFD by t-test The treatment group (G1), NASH score was significantly decreased, when compared with the high fat diet (Table 133).

TABLE 133

Effect of Mutamba:Yerba Mate:*Morus* Composition 2 on Liver Pathology in DIO Mice

| Group | | Steatosis (0-3) | Lobular Inflammation (0-3) | Hepatocellular ballooning (0-2) | NSAH (sum) |
|---|---|---|---|---|---|
| ND | Mean | 0.00 | 1.00 | 0.00 | 1.00 |
| | SD | 0.000 | 0.000 | 0.000 | 0.000 |
| | p value | 0.0000 | 0.0104 | — | 0.0000 |
| HFD | Mean | 2.83 | 1.50 | 2.00 | 6.33 |
| | SD | 0.408 | 0.548 | 0.000 | 0.816 |
| ORI | Mean | 0.33 | 1.50 | 0.33 | 2.17 |
| | SD | 0.516 | 0.548 | 0.516 | 1.472 |
| | p value | 0.0000 | 1.0000 | 0.0000 | 0.0001 |
| G1 | Mean | 1.50 | 1.50 | 1.33 | 4.33 |
| | SD | 0.548 | 0.548 | 0.516 | 1.033 |
| | p value | 0.0007 | 1.0000 | 0.0101 | 0.0040 | p value: compare to HFD by t-test

Overall the data show that total body weight, weight gain, FER (food efficiency ratio), visceral fat weights, and NASH score in liver were significantly decreased in mice treated with Mutamba:Yerba Mate:Morus Composition 2. Also, TG was decreased by treatment with this triple combination. Therefore, the present results indicate that a Mutamba:Yerba Mate:Morus combination, such as Composition 2, can be used as a body weight reducer, as well as a dyslipidemia and fatty liver reducer.

Example 71

Efficacy Study of Mutamba, *Morus alba* and *Magnolia* Combination Composition 2 in DIO Mice The combination of Mutamba ethanol extract 36 produced according to Example 36, *Morus alba* precipitate from ethanol extract 18 produced according to the Example 18, and *Magnolia* extract 29A produced according to Example 29, was made by blending the three components in a ratio of 10:1:2, respectively. The combined three ingredient Composition 2 was orally administered to DIO mice as described in the example 48 at two different dosages of 650 mg/kg (G1 treatment group) and 1300 mg/kg (G2 treatment group), twice a day.

Low dose treatment group (G1) didn't show any change in total body weight, but the total body weight was significantly decreased in the high dose treatment group (G2) after the third week of treatment (Table 134).

TABLE 134

Effect of Mutamba:*Morus*:*Magnolia* Composition 2 on Total Weight in DIO Mice

| Group | | Weeks | | | | | | | |
|---|---|---|---|---|---|---|---|---|---|
| | | 0 | 1 | 2 | 3 | 4 | 5 | 6 | 7 |
| ND | Mean | 27.51 | 27.26 | 27.12 | 27.20 | 26.91 | 27.23 | 27.52 | 28.25 |
| | SD | 1.489 | 1.753 | 1.689 | 1.525 | 1.683 | 1.648 | 1.735 | 1.700 |
| | p value | 0.0000 | 0.0000 | 0.0000 | 0.0000 | 0.0000 | 0.0000 | 0.0000 | 0.0000 |
| HFD | Mean | 39.23 | 38.22 | 37.64 | 38.89 | 40.48 | 42.11 | 43.34 | 43.91 |
| | SD | 2.805 | 3.052 | 3.574 | 3.957 | 4.400 | 4.784 | 4.590 | 4.382 |
| ORI | Mean | 38.61 | 33.17 | 31.91 | 33.34 | 35.14 | 36.27 | 37.52 | 38.62 |
| | SD | 2.587 | 2.687 | 2.795 | 2.752 | 2.835 | 3.260 | 3.074 | 3.275 |
| | p value | 0.6475 | 0.0031 | 0.0030 | 0.0060 | 0.0130 | 0.0136 | 0.0108 | 0.0166 |
| G1 | Mean | 39.10 | 36.66 | 35.75 | 36.22 | 37.73 | 39.35 | 40.43 | 41.88 |
| | SD | 2.043 | 1.985 | 2.341 | 2.506 | 3.367 | 3.060 | 2.846 | 3.162 |
| | p value | 0.9167 | 0.2556 | 0.2424 | 0.1378 | 0.1847 | 0.2016 | 0.1591 | 0.3121 |
| G2 | Mean | 39.68 | 35.98 | 34.70 | 34.14 | 34.61 | 35.40 | 36.45 | 36.66 |
| | SD | 2.809 | 1.532 | 1.872 | 2.124 | 1.763 | 2.598 | 2.913 | 3.279 |
| | p value | 0.7507 | 0.0954 | 0.0668 | 0.0115 | 0.0023 | 0.0043 | 0.0033 | 0.0021 | p value: compare to HFD by t-test

The body weight gain of low (G1) and high (G2) dose treatment groups showed a significant decrease during the administration periods (Table 135).

TABLE 135

Effect of Mutamba:*Morus*:*Magnolia* Composition 2 on Weight Gain in DIO Mice

| Group | | Weeks | | | | | | |
|---|---|---|---|---|---|---|---|---|
| | | 1 | 2 | 3 | 4 | 5 | 6 | 7 |
| ND | Mean | -0.25 | -0.39 | -0.31 | -0.60 | -0.28 | 0.01 | 0.74 |
| | SD | 0.698 | 0.670 | 0.418 | 0.543 | 0.448 | 0.702 | 0.768 |
| | p value | 0.0585 | 0.0268 | 0.9565 | 0.0270 | 0.0063 | 0.0008 | 0.0009 |
| HFD | Mean | -1.01 | -1.59 | -0.35 | 1.25 | 2.88 | 4.11 | 4.68 |
| | SD | 0.531 | 0.246 | 0.775 | 1.344 | 1.564 | 1.569 | 1.556 |
| ORI | Mean | -5.43 | -6.69 | -5.27 | -3.47 | -2.34 | -1.08 | 0.02 |
| | SD | 1.106 | 1.822 | 1.249 | 1.010 | 1.450 | 1.721 | 1.806 |
| | p value | 0.0000 | 0.0000 | 0.0000 | 0.0001 | 0.0005 | 0.0004 | 0.0010 |
| G1 | Mean | -2.44 | -3.34 | -2.88 | -1.37 | 0.26 | 1.33 | 2.78 |
| | SD | 0.864 | 1.314 | 1.625 | 2.138 | 2.097 | 1.473 | 1.987 |
| | p value | 0.0053 | 0.0178 | 0.0096 | 0.0272 | 0.0550 | 0.0256 | 0.1278 |

TABLE 135-continued

Effect of Mutamba:*Morus*:*Magnolia* Composition 2 on Weight Gain in DIO Mice

| Group | | Weeks | | | | | | |
|---|---|---|---|---|---|---|---|---|
| | | 1 | 2 | 3 | 4 | 5 | 6 | 7 |
| G2 | Mean | −3.70 | −4.97 | −5.54 | −5.06 | −4.28 | −3.23 | −3.02 |
| | SD | 1.717 | 1.300 | 1.387 | 1.749 | 2.042 | 2.627 | 2.357 |
| | p value | 0.0007 | 0.0001 | 0.0000 | 0.0000 | 0.0000 | 0.0001 | 0.0000 | p value: compare to HFD by t-test

FER was significantly lower only in the high dose treatment group (G2) as compared to the HFD group (Table 136). The low dose treatment group (G1) showed only a significant change in food intake (g/day).

TABLE 136

Effect of Mutamba:*Morus*:*Magnolia* Composition 2 on DIO Mice

| Group | | Weight Gain (g/day) | Food Intake (g/day) | FER (Food efficiency ratio) |
|---|---|---|---|---|
| ND | Mean | 0.016 | 3.401 | 0.005 |
| | SD | 0.016 | 0.556 | 0.005 |
| | p value | 0.0009 | 0.0000 | 0.0007 |
| HFD | Mean | 0.100 | 2.592 | 0.038 |
| | SD | 0.033 | 0.521 | 0.013 |
| ORI | Mean | 0.000 | 3.195 | 0.000 |
| | SD | 0.038 | 0.752 | 0.012 |
| | p value | 0.0010 | 0.0000 | 0.0007 |

TABLE 136-continued

Effect of Mutamba:*Morus*:*Magnolia* Composition 2 on DIO Mice

| Group | | Weight Gain (g/day) | Food Intake (g/day) | FER (Food efficiency ratio) |
|---|---|---|---|---|
| G1 | Mean | 0.059 | 2.288 | 0.026 |
| | SD | 0.042 | 0.615 | 0.018 |
| | p value | 0.1278 | 0.0000 | 0.2300 |
| G2 | Mean | −0.064 | 2.112 | −0.030 |
| | SD | 0.050 | 0.587 | 0.024 |
| | p value | 0.0000 | 0.0000 | 0.0000 | p value: compare to HFD by t-test

AST and TG were significantly decreased in the low dose treatment group (G1) as compared to the high fat diet group. For the high dose treatment group (G2), ALT, AST, glucose, TG and LDL-cholesterol were significantly decreased as compared to the high fat diet group (Table 137).

TABLE 137

Effect of Mutamba:*Morus*:*Magnolia* Composition 2 on Biochemistry Parameters

| Group | | ALT (U/L) | AST (U/L) | Glu (mg/dL) | T-chol (mg/dL) | TG (mg/dL) | LDL-C (mg/dL) | HDL-C (mg/dL) |
|---|---|---|---|---|---|---|---|---|
| ND | Mean | 19.51 | 48.56 | 196.78 | 116.78 | 10.00 | 4.00 | 62.74 |
| | SD | 1.561 | 6.396 | 31.104 | 6.418 | 2.872 | 0.682 | 3.076 |
| | p value | 0.0277 | 0.0088 | 0.0153 | 0.0016 | 0.0001 | 0.0126 | 0.1600 |
| HFD | Mean | 51.32 | 87.77 | 234.70 | 181.70 | 33.10 | 8.23 | 67.86 |
| | SD | 38.335 | 37.269 | 30.159 | 46.466 | 10.816 | 4.300 | 10.217 |
| ORI | Mean | 21.83 | 65.65 | 194.00 | 137.33 | 27.83 | 4.03 | 62.42 |
| | SD | 5.707 | 17.307 | 47.147 | 28.261 | 6.555 | 0.301 | 9.746 |
| | p value | 0.0389 | 0.1970 | 0.0521 | 0.0543 | 0.3020 | 0.0130 | 0.3121 |
| G1 | Mean | 26.01 | 58.71 | 278.00 | 171.43 | 15.43 | 5.94 | 69.36 |
| | SD | 5.616 | 4.985 | 39.699 | 14.351 | 7.091 | 1.350 | 3.455 |
| | p value | 0.0681 | 0.0365 | 0.0217 | 0.5251 | 0.0018 | 0.1427 | 0.6753 |
| G2 | Mean | 22.94 | 50.77 | 206.71 | 156.86 | 12.71 | 4.87 | 71.83 |
| | SD | 4.301 | 5.880 | 19.129 | 8.726 | 3.450 | 0.948 | 2.622 |
| | p value | 0.0445 | 0.0120 | 0.0475 | 0.1304 | 0.0001 | 0.0376 | 0.2659 |

The visceral fat pads weights of high dose treatment group (G2) were significantly decreased as compared to the HFD group (Table 138).

TABLE 138

Effect of Mutamba:*Morus*:*Magnolia* Composition 2 on Absolute Organ Weights in DIO Mice

| Group | | Liver | Epididymal Fat | Retroperitoneal Fat | PeriRenal Fat | Total Fat* |
|---|---|---|---|---|---|---|
| ND | Mean | 0.99 | 0.50 | 0.13 | 0.07 | 0.71 |
| | SD | 0.062 | 0.099 | 0.041 | 0.020 | 0.145 |
| | p value | 0.0884 | 0.0000 | 0.0000 | 0.0001 | 0.0000 |
| HFD | Mean | 1.27 | 2.41 | 0.61 | 0.43 | 3.45 |
| | SD | 0.455 | 0.381 | 0.140 | 0.160 | 0.387 |

TABLE 138-continued

Effect of Mutamba:*Morus*:*Magnolia* Composition 2 on Absolute Organ Weights in DIO Mice

| Group | | Liver | Epididymal Fat | Retroperitoneal Fat | PeriRenal Fat | Total Fat* |
|---|---|---|---|---|---|---|
| ORI | Mean | 0.99 | 2.08 | 0.57 | 0.28 | 2.94 |
| | SD | 0.153 | 0.278 | 0.065 | 0.082 | 0.390 |
| | p value | 0.0988 | 0.0718 | 0.4852 | 0.0436 | 0.0169 |
| G1 | Mean | 1.34 | 2.54 | 0.66 | 0.40 | 3.60 |
| | SD | 0.212 | 0.315 | 0.063 | 0.080 | 0.402 |
| | p value | 0.7295 | 0.4823 | 0.4307 | 0.6849 | 0.4660 |
| G2 | Mean | 1.18 | 1.71 | 0.45 | 0.21 | 2.38 |
| | SD | 0.116 | 0.425 | 0.102 | 0.074 | 0.584 |
| | p value | 0.5600 | 0.0030 | 0.0180 | 0.0049 | 0.0004 |

*Total fat is sum of the three fat pads (epididymal, retroperitoneal and perirenal fat)
p value: compare to HFD by t-test Low dose treatment group (G1), NASH score didn't show any change but high dose treatment group (G2) showed significantly decreased (Table 139)

TABLE 139

Effect of Mutamba:*Morus*:*Magnolia* Composition 2 on Liver Pathology in DIO Mice

| | | Indications | | | |
|---|---|---|---|---|---|
| Group | | Steatosis (0-3) | Lobular Inflammation (0-3) | Hepatocellular ballooning (0-2) | NSAH (sum) |
| ND | Mean | 0.00 | 1.33 | 0.00 | 1.33 |
| | SD | 0.000 | 0.500 | 0.000 | 0.500 |
| | p value | 0.0000 | 0.1226 | 0.0000 | 0.0000 |
| HFD | Mean | 2.20 | 1.70 | 1.50 | 5.40 |
| | SD | 0.919 | 0.483 | 0.527 | 1.647 |
| ORI | Mean | 0.67 | 1.33 | 0.67 | 2.67 |
| | SD | 0.516 | 0.516 | 0.516 | 1.366 |
| | p value | 0.0023 | 0.1736 | 0.0081 | 0.0042 |
| G1 | Mean | 1.43 | 1.57 | 1.57 | 4.57 |
| | SD | 0.535 | 0.535 | 0.535 | 1.397 |
| | p value | 0.0656 | 0.6124 | 0.7882 | 0.2957 |
| G2 | Mean | 0.86 | 1.86 | 1.00 | 3.71 |
| | SD | 0.378 | 0.378 | 0.577 | 0.756 |
| | p value | 0.0025 | 0.4837 | 0.0837 | 0.0240 | p value: compare to HFD by t-test

Overall, these data show that body weight, body weight gain, FER (food efficiency ratio), visceral fat weights and NASH score in liver were significantly decreased in mice treated with a Mutamba:Morus alba:Magnolia extract combination, such as Composition 2. Also, ALT, AST, glucose, TG and LDL-cholesterol were decreased by treatment with Mutamba:Morus alba:Magnolia Composition 2. Therefore, this example indicates that a Mutamba:Morus alba:Magnolia combination can be used as a body weight, dyslipidemia and fatty liver reducer.

Example 72

Efficacy Study of Mutamba, *Morus alba* and *Magnolia* Combined Composition 2 in DIO Rats The combination of Mutamba ethanol extract 36 produced according to Example 36, *Morus alba* precipitate from ethanol extract 18 produced according to the Example 18, and *Magnolia* extract 29A produced according to Example 29, was made by blending the three components in a ratio of 10:1:2, respectively. The combined three ingredient Composition 2 was orally administrated to DIO rats as described in the Example 49 at two different dosages of 650 mg/kg (S3) and 1,300 mg/kg (S4), twice a day.

Both treatment groups showed significantly decreased weight gain as compared to the high fat diet group during the treatment period (Table 140).

TABLE 140

Effect of Mutamba:*Morus*:*Magnolia* Composition 2 on Weight Gain in DIO Rats

| Group | | Days | | | | | | | | | | | | | | | |
|---|---|---|---|---|---|---|---|---|---|---|---|---|---|---|---|---|---|
| | | 3 | 7 | 10 | 14 | 17 | 21 | 24 | 28 | 31 | 35 | 37 | 42 | 45 | 49 | 52 | 55 |
| ND | Mean | 4.83 | 11.86 | 18.42 | 23.43 | 23.61 | 32.45 | 39.57 | 44.19 | 51.02 | 52.69 | 55.89 | 62.78 | 66.06 | 75.05 | 80.44 | 78.60 |
| | SD | 5.54 | 7.84 | 7.31 | 8.03 | 13.36 | 13.98 | 13.08 | 13.85 | 16.00 | 14.55 | 12.98 | 14.33 | 19.09 | 18.66 | 20.38 | 19.52 |
| | p value | 0.018 | 0.064 | 0.028 | 0.008 | 0.010 | 0.009 | 0.013 | 0.004 | 0.006 | 0.001 | 0.002 | 0.001 | 0.001 | 0.002 | 0.001 | 0.001 |
| HFD | Mean | 13.22 | 22.38 | 32.85 | 49.08 | 52.91 | 63.73 | 72.81 | 81.45 | 89.85 | 98.23 | 103.01 | 113.20 | 124.09 | 130.99 | 141.23 | 143.39 |
| | SD | 6.81 | 12.32 | 14.21 | 19.87 | 23.30 | 24.20 | 28.42 | 25.48 | 28.13 | 26.72 | 29.41 | 29.26 | 31.14 | 33.04 | 32.99 | 34.29 |
| ORI | Mean | 2.80 | 1.04 | 0.82 | 3.40 | 3.34 | 15.89 | 19.89 | 28.19 | 33.33 | 38.43 | 43.95 | 49.06 | 59.88 | 63.68 | 71.12 | 68.11 |
| | SD | 13.85 | 15.80 | 17.11 | 18.18 | 20.72 | 21.08 | 20.72 | 22.69 | 24.86 | 25.56 | 28.85 | 30.54 | 29.53 | 30.43 | 29.27 | 29.33 |
| | p value | 0.085 | 0.010 | 0.001 | 0.000 | 0.001 | 0.001 | 0.001 | 0.001 | 0.001 | 0.000 | 0.001 | 0.001 | 0.001 | 0.001 | 0.001 | 0.000 |
| S3 | Mean | 3.13 | 8.39 | 7.24 | 15.28 | 18.67 | 28.05 | 33.78 | 46.44 | 49.33 | 57.29 | 64.63 | 75.22 | 81.57 | 89.39 | 93.54 | 94.40 |
| | SD | 6.37 | 11.46 | 18.77 | 25.03 | 25.18 | 24.62 | 27.20 | 29.85 | 32.53 | 33.53 | 36.23 | 36.50 | 40.84 | 41.18 | 41.99 | 42.09 |
| | p value | 0.008 | 0.034 | 0.009 | 0.010 | 0.014 | 0.011 | 0.014 | 0.025 | 0.019 | 0.018 | 0.036 | 0.038 | 0.036 | 0.044 | 0.025 | 0.024 |

TABLE 140-continued

Effect of Mutamba:*Morus*:*Magnolia* Composition 2 on Weight Gain in DIO Rats

| Group | | Days | | | | | | | | | | | | | | |
|---|---|---|---|---|---|---|---|---|---|---|---|---|---|---|---|---|
| | | 3 | 7 | 10 | 14 | 17 | 21 | 24 | 28 | 31 | 35 | 37 | 42 | 45 | 49 | 52 | 55 |
| S4 | Mean | 0.91 | 3.77 | 4.26 | 11.73 | 10.38 | 19.06 | 21.24 | 32.23 | 36.71 | 48.98 | 56.15 | 66.03 | 74.80 | 82.92 | 87.16 | 87.63 |
| | SD | 6.65 | 19.19 | 21.33 | 23.76 | 25.97 | 28.02 | 29.34 | 29.81 | 31.67 | 34.96 | 36.72 | 41.21 | 42.08 | 41.84 | 44.58 | 44.29 |
| | p value | 0.003 | 0.040 | 0.008 | 0.004 | 0.004 | 0.004 | 0.003 | 0.003 | 0.003 | 0.007 | 0.014 | 0.021 | 0.020 | 0.024 | 0.016 | 0.014 | p value: Compared to HFD group

Weight gain (g/day) and Food efficiency ratio (FER) were significantly decreased in both the low dose S3 and high dose S4 treatment groups as compared to the high fat diet group (Table 141).

TABLE 141

Effect of Mutamba:*Morus*:*Magnolia* Composition 2 on DIO Rats

| Group | | Weight gain (g/day) | Food intake (g/day) | FER (Food efficiency ratio) |
|---|---|---|---|---|
| ND | Mean | 1.40 | 24.26 | 0.06 |
| | SD | 0.35 | 0.72 | 0.01 |
| | p value | 0.001 | 0.073 | 0.000 |
| HFD | Mean | 2.56 | 21.14 | 0.12 |
| | SD | 0.61 | 2.37 | 0.02 |
| ORI | Mean | 1.22 | 25.71 | 0.05 |
| | SD | 0.52 | 1.09 | 0.02 |
| | p value | 0.000 | 0.023 | 0.000 |
| S3 | Mean | 1.69 | 19.55 | 0.08 |
| | SD | 0.75 | 1.78 | 0.03 |
| | p value | 0.024 | 0.327 | 0.024 |
| S4 | Mean | 1.56 | 19.47 | 0.08 |
| | SD | 0.79 | 1.96 | 0.04 |
| | p value | 0.014 | 0.320 | 0.017 | p value: Compared to HFD group

Absolute organ weight, as well as epididymal, retroperitoneal, perirenal and total fat pads, were significantly decreased in rats treated with low dose Composition 2 (S3) group of as compared to the high fat diet group. Absolute organ weight, as well as epididymal, perirenal and total fat pads, were significantly decreased in mice treated with high dose Composition 2 (S4) as compared to the high fat diet group (Table 142).

TABLE 142

Effect of Mutamba:*Morus*:*Magnolia* Composition 2 on Absolute Organ Weights in DIO Rats

| Group | | Epididymal Fat | Retroperitoneal Fat | Perirenal Fat | Total Fat |
|---|---|---|---|---|---|
| ND | Mean | 11.14 | 12.41 | 3.70 | 27.25 |
| | SD | 2.32 | 3.04 | 0.65 | 5.47 |
| | p value | 0.000 | 0.000 | 0.000 | 0.000 |
| HFD | Mean | 22.84 | 28.27 | 8.90 | 60.01 |
| | SD | 2.82 | 6.58 | 1.93 | 7.98 |
| ORI | Mean | 17.87 | 19.21 | 6.11 | 43.19 |
| | SD | 5.44 | 3.00 | 1.69 | 9.56 |
| | p value | 0.044 | 0.005 | 0.008 | 0.002 |
| S3 | Mean | 15.42 | 20.67 | 6.26 | 42.35 |
| | SD | 3.69 | 6.26 | 1.36 | 9.70 |
| | p value | 0.001 | 0.033 | 0.008 | 0.001 |
| S4 | Mean | 16.79 | 22.64 | 6.75 | 46.18 |
| | SD | 3.45 | 5.47 | 1.70 | 9.35 |
| | p value | 0.003 | 0.093 | 0.039 | 0.010 | p value: Compared to HFD group

Steatosis, Lobular inflammation, Hepatocellular ballooning and NASH scores were decreased in both the low dose S3 and high dose S4 treatment groups as compared to the high fat diet group (Table 143).

TABLE 143

Effect of Mutamba:*Morus*:*Magnolia* Composition 2 on Liver Pathology in DIO Rats

| Group | | Indications | | | |
|---|---|---|---|---|---|
| | | Steatosis (0-3) | Lobular Inflammation (0-3) | Hepatocellular ballooning (0-2) | NSAH (sum) |
| ND | Mean | 0.000 | 1.857 | 0.000 | 1.857 |
| | SD | 0.000 | 0.378 | 0.000 | 0.378 |
| | p value | #DIV/0! | 0.180 | #DIV/0! | 0.000 |
| HFD | Mean | 1.875 | 2.125 | 1.625 | 5.625 |
| | SD | 1.126 | 0.354 | 0.744 | 1.923 |
| ORI | Mean | 0.750 | 1.500 | 0.625 | 2.875 |
| | SD | 0.707 | 0.535 | 0.744 | 1.727 |
| | p value | 0.031 | 0.015 | 0.018 | 0.009 |
| S3 | Mean | 0.750 | 1.125 | 0.500 | 2.375 |
| | SD | 0.463 | 0.354 | 0.535 | 0.744 |
| | p value | 0.020 | 0.000 | 0.004 | 0.001 |
| S4 | Mean | 0.571 | 1.571 | 0.286 | 2.429 |
| | SD | 0.787 | 0.535 | 0.488 | 1.272 |
| | p value | 0.024 | 0.032 | 0.001 | 0.003 | p value: Compared to HFD group

T-Cholesterol, triglycerides (TG) and LDL-Cholesteol were decreased in both the low dose S3 and high dose S4 treatment groups as compared to the high fat diet group (Table 144).

TABLE 144

Effect of Mutamba:*Morus*:*Magnolia* Composition 2 on Biochemistry Parameters in DIO Rats

| Group | | T-chol (mg/dL) | TG (mg/dL) | LDL-C (mg/dL) |
|---|---|---|---|---|
| ND | Mean | 100.00 | 105.25 | 10.05 |
| | SD | 12.34 | 64.38 | 2.30 |
| | p value | 0.006 | 0.259 | 0.249 |
| HFD | Mean | 124.63 | 137.13 | 11.15 |
| | SD | 17.44 | 40.50 | 1.10 |
| ORI | Mean | 110.13 | 216.38 | 10.63 |
| | SD | 21.16 | 100.04 | 1.36 |
| | p value | 0.158 | 0.067 | 0.411 |
| S3 | Mean | 92.38 | 89.00 | 7.68 |
| | SD | 14.93 | 40.29 | 1.79 |
| | p value | 0.001 | 0.032 | 0.001 |
| S4 | Mean | 78.86 | 74.57 | 6.50 |
| | SD | 10.99 | 24.24 | 1.87 |
| | p value | 0.000 | 0.003 | 0.000 | p value: Compared to HFD group

Overall, these data show that total body weight, weight gain, FER (food efficiency ratio), visceral fat weight, and NASH score in liver were significantly decreased in mice treated with a mixture of Mutamba, *Morus alba* and *Mag-*

*nolia* extracts. Also, total-cholesterol, triglyceride (TG) and LDL-cholesterol were decreased by treatment with the triple combination of Mutamba, *Morus alba* and *Magnolia*. Therefore, this example indicates that combinations such as Composition 2 can be used as a body weight reducer, as well as dyslipidemia and fatty liver reducers.

Example 73

Efficacy of Mutamba Ethanol Extract 35, *Magnolia* Extract 29, Yerba Mate Extract 26 and *Morus* EtOAc Fraction 15 Mixed Composition 11 in DIO Mice Mutamba ethanol extract 35 produced according to Example 35, *Magnolia* extract 29 produced according to Example 29, Yerba Mate extract 26 produced according to example 26 and *Morus alba* ethyl acetate fraction 15 produced according to example 15, were combined by blending the four components in a ratio of 5:1:5:2, respectively. The combined four ingredient Composition 11 was orally administrated to DIO mice as described in the example 48 at a total dosage of 1,300 mg/kg (G1) twice a day.

Total body weight was significantly decreased in mice of treatment group (G1), which were given Mutamba:Magnolia:Yerba Mate:Morus Composition 11, after the second week treatment during the experiment (Table 145).

TABLE 145

Effect of Quadruple Composition 11 on Total Body Weight in DIO Mice

| Group | | 0 | 1 | 2 | 3 | 4 | 5 | 6 | 7 | 8 |
|---|---|---|---|---|---|---|---|---|---|---|
| ND | Mean | 29.24 | 29.11 | 29.03 | 29.47 | 29.36 | 29.51 | 29.75 | 29.76 | 30.14 |
|  | SD | 1.020 | 0.967 | 1.201 | 1.166 | 1.428 | 1.309 | 1.509 | 1.270 | 1.321 |
|  | p value | 0.0001 | 0.0001 | 0.0001 | 0.0000 | 0.0000 | 0.0000 | 0.0000 | 0.0000 | 0.0000 |
| HFD | Mean | 41.31 | 41.73 | 42.12 | 43.64 | 44.94 | 46.25 | 47.78 | 48.43 | 49.29 |
|  | SD | 2.932 | 2.771 | 2.856 | 2.884 | 2.870 | 3.172 | 3.247 | 3.224 | 2.783 |
| ORI | Mean | 40.22 | 37.98 | 34.08 | 35.32 | 36.38 | 37.65 | 38.75 | 39.96 | 39.99 |
|  | SD | 2.816 | 2.547 | 1.277 | 1.186 | 1.867 | 2.284 | 2.931 | 3.235 | 3.633 |
|  | p value | 0.9795 | 0.5280 | 0.0351 | 0.0001 | 0.0001 | 0.0001 | 0.0003 | 0.0005 | 0.0011 |
| G1 | Mean | 40.05 | 37.69 | 35.67 | 36.88 | 37.21 | 37.56 | 38.03 | 38.22 | 39.32 |
|  | SD | 2.838 | 2.191 | 2.473 | 2.830 | 2.280 | 2.356 | 2.496 | 3.072 | 3.470 |
|  | p value | 0.7625 | 0.4910 | 0.0270 | 0.0033 | 0.0036 | 0.0009 | 0.0007 | 0.0004 | 0.0005 | p value: compare to HFD by t-test

Weight gain was significantly decreased in the Mutamba:Magnolia:Yerba Mate:Morus Composition 11 treatment group (G1) after the first week treatment during the experiment (Table 146).

TABLE 146

Effect of Quadruple Composition 11 on Weight Gain in DIO Mice

| Group | | 1 | 2 | 3 | 4 | 5 | 6 | 7 | 8 |
|---|---|---|---|---|---|---|---|---|---|
| ND | Mean | −0.13 | −0.22 | 0.22 | 0.11 | 0.27 | 0.50 | 0.52 | 0.89 |
|  | SD | 0.367 | 0.377 | 0.238 | 0.463 | 0.390 | 0.635 | 0.447 | 0.562 |
|  | p value | 0.0057 | 0.0011 | 0.0080 | 0.0010 | 0.0005 | 0.0004 | 0.0002 | 0.0002 |
| HFD | Mean | 0.42 | 0.81 | 2.34 | 3.64 | 4.94 | 6.47 | 7.13 | 7.98 |
|  | SD | 0.238 | 0.636 | 1.229 | 1.343 | 1.526 | 1.873 | 1.815 | 1.904 |
| ORI | Mean | −2.24 | −6.14 | −4.91 | −3.84 | −2.57 | −1.47 | −0.26 | −0.23 |
|  | SD | 1.123 | 2.286 | 1.286 | 1.228 | 1.355 | 1.507 | 1.728 | 2.055 |
|  | p value | 0.0018 | 0.0005 | 0.0000 | 0.0000 | 0.0000 | 0.0000 | 0.0001 | 0.0000 |
| G1 | Mean | −2.36 | −4.38 | −3.17 | −2.84 | −2.49 | −2.02 | −1.83 | −0.73 |
|  | SD | 2.030 | 2.834 | 2.907 | 2.555 | 1.915 | 1.985 | 2.015 | 1.864 |
|  | p value | 0.0370 | 0.0136 | 0.0022 | 0.0004 | 0.0001 | 0.0000 | 0.0000 | 0.0000 | p value: compare to HFD by t-test

Food efficiency ratio (FER) was significantly lowered in the treatment group (G1) as compared to the high fat diet group (Table 147).

TABLE 147

Effect of Mutamba:*Magnolia*:Yerba Mate:*Morus* Composition on DIO Mice

| Group | | Body weight gain (g/day) | Food intake (g/day) | FER (Food efficiency ratio) |
|---|---|---|---|---|
| ND | Mean | 0.017 | 3.181 | 0.005 |
|  | SD | 0.011 | 0.906 | 0.003 |
|  | p value | 0.0002 | 0.0202 | 0.0002 |
| HFD | Mean | 0.153 | 2.752 | 0.056 |
|  | SD | 0.037 | 0.178 | 0.013 |
| ORI | Mean | −0.004 | 3.147 | −0.001 |
|  | SD | 0.040 | 0.371 | 0.013 |
|  | p value | 0.0000 | 0.0000 | 0.0000 |
| G1 | Mean | −0.014 | 2.470 | −0.006 |
|  | SD | 0.036 | 0.609 | 0.015 |
|  | p value | 0.0000 | 0.0253 | 0.0000 |

FER (Feed efficacy ratio) = Body weight gain(g/day)/Food intake(g/day)
p value: compared to HFD by t-test Plasma glucose, total cholesterol and TG were significantly decreased in treatment group G1 as compared to the high fat diet group (Table 148).

TABLE 148

Effect of Mutamba:*Magnolia*:Yerba Mate:*Morus* Composition 11 on Biochemistry Parameters in DIO Mice

| Group | | ALT (U/L) | AST (U/L) | ALP (U/L) | Glu (mg/dL) | T-chol (mg/dL) | TG (mg/dL) | TP (g/dL) | LDL-C (mg/dL) | HDL-C (mg/dL) |
|---|---|---|---|---|---|---|---|---|---|---|
| ND | Mean | 16.84 | 39.90 | 195.74 | 157.60 | 107.40 | 23.40 | 5.22 | 3.72 | 61.66 |
|  | SD | 0.899 | 0.781 | 42.213 | 25.265 | 6.107 | 3.715 | 0.164 | 0.683 | 2.970 |
|  | p value | 0.0718 | 0.0464 | 0.1655 | 0.0001 | 0.0100 | 0.0504 | 0.0924 | 0.0539 | 0.0037 |
| HFD | Mean | 88.83 | 97.80 | 235.03 | 347.00 | 229.75 | 38.50 | 5.65 | 10.13 | 75.05 |
|  | SD | 52.704 | 35.293 | 31.025 | 42.237 | 42.883 | 9.983 | 0.465 | 4.200 | 6.251 |
| ORI | Mean | 23.03 | 51.40 | 177.35 | 269.17 | 155.83 | 88.33 | 5.08 | 4.28 | 75.57 |
|  | SD | 6.720 | 8.052 | 13.486 | 46.232 | 23.558 | 32.222 | 0.172 | 0.770 | 5.837 |
|  | p value | 0.0872 | 0.0760 | 0.0034 | 0.0274 | 0.0074 | 0.0185 | 0.0240 | 0.0673 | 0.8971 |
| G1 | Mean | 19.00 | 52.28 | 207.40 | 278.60 | 173.40 | 10.00 | 5.10 | 6.14 | 70.80 |
|  | SD | 6.552 | 9.987 | 24.104 | 32.238 | 27.355 | 3.674 | 0.200 | 1.383 | 10.836 |
|  | p value | 0.0761 | 0.0781 | 0.1750 | 0.0278 | 0.0468 | 0.0006 | 0.0468 | 0.0832 | 0.5113 | p value: compare to HFD by t-test

Absolute weights of liver and total fat pads were significantly decreased in the Mutamba:Magnolia:Yerba Mate:Morus Composition 11 treatment group G1 as compared to the high fat diet group (Table 149).

TABLE 149

Effect of Mutamba:*Magnolia*:Yerba Mate:*Morus* Composition 11 on Absolute Organ Weights in DIO Mice

| Group | | Liver | Epididymal Fat | Retro-peritoneal Fat | PeriRenal Fat | Total Fat* |
|---|---|---|---|---|---|---|
| ND | Mean | 1.07 | 0.46 | 0.11 | 0.06 | 0.63 |
|  | SD | 0.062 | 0.126 | 0.042 | 0.017 | 0.181 |
|  | p value | 0.0000 | 0.0009 | 0.0001 | 0.0000 | 0.0001 |
| HFD | Mean | 2.11 | 2.30 | 0.57 | 0.68 | 3.56 |
|  | SD | 0.368 | 0.400 | 0.090 | 0.141 | 0.454 |
| ORI | Mean | 1.19 | 2.03 | 0.50 | 0.29 | 2.82 |
|  | SD | 0.093 | 0.831 | 0.191 | 0.129 | 1.137 |
|  | p value | 0.0005 | 0.0013 | 0.4854 | 0.4229 | 0.0005 |
| G1 | Mean | 1.38 | 2.12 | 0.56 | 0.25 | 2.92 |
|  | SD | 0.026 | 0.411 | 0.147 | 0.063 | 0.603 |
|  | p value | 0.0000 | 0.0046 | 0.4730 | 0.7973 | 0.0001 |

*Total fat is sum of the three fat pads(epididymal, retroperitoneal and perirenal fat)
p value: compare to HFD by t-test The NASH score was significantly decreased in the Mutamba:Magnolia:Yerba Mate:Morus Composition 11 treatment group (G1) as compared to the high fat diet mice (Table 150).

TABLE 150

Effect of Mutamba:*Magnolia*:Yerba Mate:*Morus* Composition 11 on Liver Pathology in DIO Mice

| Group | | Steatosis (0-3) | Lobular Inflammation (0-3) | Hepatocellular ballooning (0-2) | NSAH (sum) |
|---|---|---|---|---|---|
| ND | Mean | 0.00 | 1.00 | 0.00 | 1.00 |
|  | SD | 0.000 | 0.000 | 0.000 | 0.000 |
|  | p value | 0.0000 | 0.0104 | — | 0.0000 |
| HFD | Mean | 2.83 | 1.50 | 2.00 | 6.33 |
|  | SD | 0.408 | 0.548 | 0.000 | 0.816 |
| ORI | Mean | 0.33 | 1.50 | 0.33 | 2.17 |
|  | SD | 0.516 | 0.548 | 0.516 | 1.472 |
|  | p value | 0.0000 | 1.0000 | 0.0000 | 0.0001 |
| G1 | Mean | 1.00 | 1.40 | 0.80 | 3.20 |
|  | SD | 1.225 | 0.548 | 0.837 | 2.490 |
|  | p value | 0.0258 | 0.7699 | 0.0062 | 0.0457 | p value: compare to HFD by t-test

Overall, these data show that total body weight, weight gain, FER (food efficiency ratio), visceral fat weights and NASH score in liver were significantly decreased in mice treated with a mixture of Mutamba, *Magnolia*, Yerba Mate and *Morus alba* extracts. Also, plasma glucose, total cholesterol and TG were decreased in mice treated with this combination. Therefore, this example indicates that a combination such as Composition 11 can be used as a body weight reducer, as well as dyslipidemia and fatty liver controllers.

Example 74

Triple Extract Combinations Show a Synergistic Effect on Reducing Weight Gain

In this study, four different triple combination compositions and one quadruple combination composition were tested in diet induced obesity (DIO) mice, as described in Example 48, to examine their effect on total body weight and weight gain. The five compositions tested were as follows:
(1) Composition 1A of Example 63 (3 components)—*Magnolia* (100 mg/kg):*Morus alba* (200 mg/kg):Yerba Mate (500 mg/kg);
(2) Composition 2A (3 components)—*Magnolia* (100 mg/kg):*Morus alba* (200 mg/kg):Mutamba (500 mg/kg);
(3) Composition 10 of Example 68 (3 components)—*Magnolia* (100 mg/kg):Yerba Mate (500 mg/kg):Mutamba (500 mg/kg);
(4) Composition 12 (3 components)—*Morus alba* (200 mg/kg):Yerba Mate (500 mg/kg):Mutamba (500 mg/kg); and
(5) Composition 11 of Example 73 (4 components)—*Magnolia* (100 mg/kg):*Morus alba* (200 mg/kg):Yerba Mate (500 mg/kg):Mutamba (500 mg/kg).

Effect of Each Extract Tested Individually on Weight Loss

As shown in FIG. 1, a statistically significant difference in total weight is seen in weeks 2-8 for *Magnolia* extract and in weeks 3-5 for *Morus alba* extract as compared to the high fat diet (HFD) group. The total weight difference for the other treatment groups was not statistically significant as compared to the HFD group. When examining reductions in weight gain, however, the *Magnolia*, *Morus alba* and Rosemary treatment groups showed statistically significant reductions at more time points as compared to the HFD group. Yerba Mate and Mutamba treatment groups showed no obvious reduction in weight gain when compared to the HFD group, but a gradual trend of less weight gain was observed for both groups (though not statistically significant) over the course of the 8 week treatment.

Effect of Multicomponent Compositions on Mean Body Weight

Figure 2:
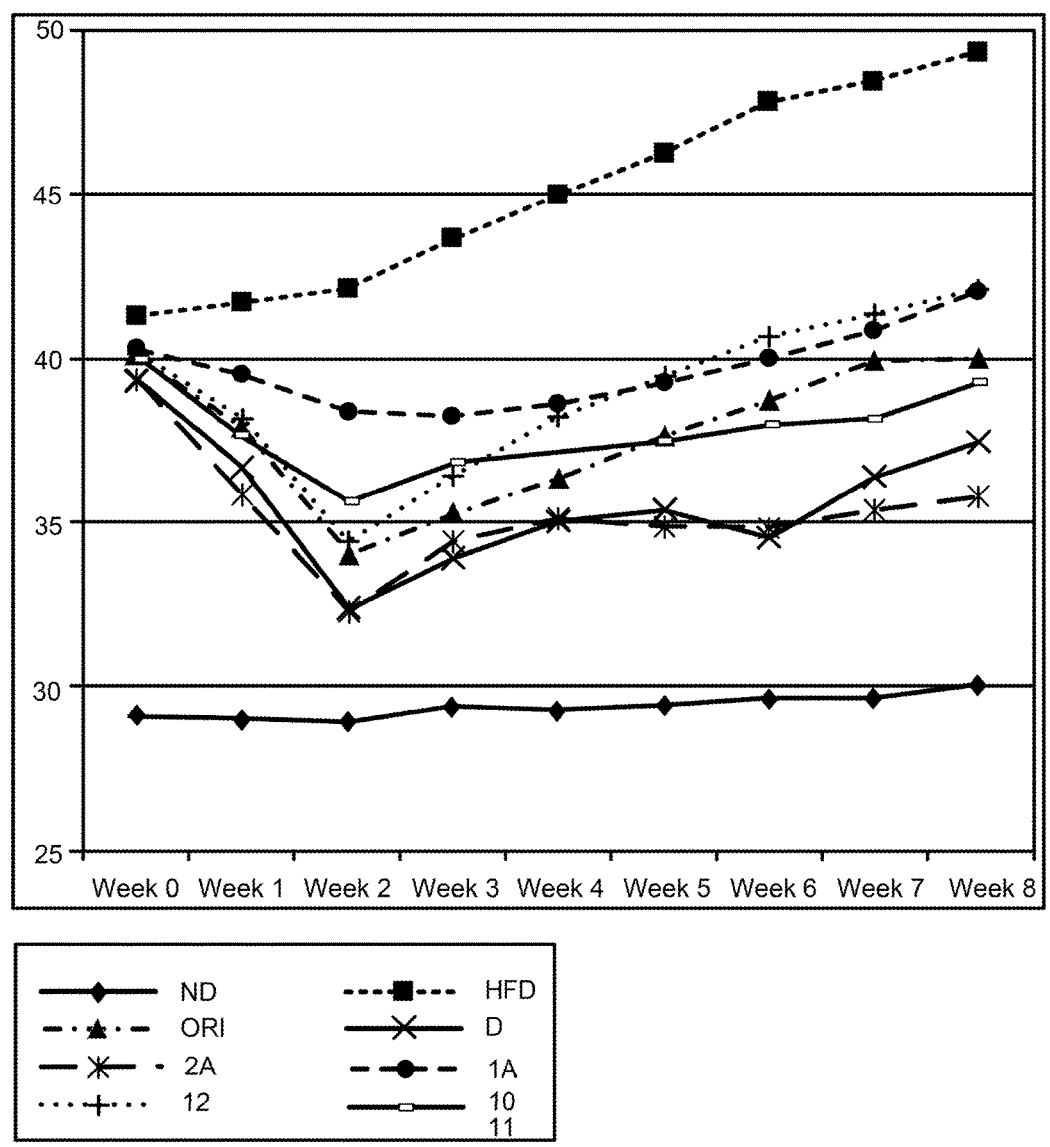
FIG. 2 shows a graph of mean body weights for mice on a high fat diet that had been treated for 8 weeks with one of the following combination of extracts: (1) Composition 1A of Example 63 (3 components)—*Magnolia* (100 mg/kg):*Morus alba* (200 mg/kg):Yerba Mate (500 mg/kg); (2) Composition 2A (3 components)—*Magnolia* (100 mg/kg):*Morus alba* (200 mg/kg):Mutamba (500 mg/kg); (3) Composition 10 of Example 68 (3 components)—*Magnolia* (100 mg/kg):Yerba Mate (500 mg/kg):Mutamba (500 mg/kg); (4) Composition 12 (3 components)—*Morus alba* (200 mg/kg):Yerba Mate (500 mg/kg):Mutamba (500 mg/kg); and (5) Composition 11 of Example 73 (4 components)—*Magnolia* (100 mg/kg):*Morus alba* (200 mg/kg):Yerba Mate (500 mg/kg):Mutamba (500 mg/kg). The negative controls included mice on the high fat diet that received no treatment (HFD) and mice kept on a normal diet (ND), while the positive control was mice on a high fat diet treated with orlistat (ORI).

As shown in FIG. 2, four of the five combinations showed statistically significant weight differences as compared to the HFD group within one week of oral treatment. The only group that did not have a statistically significant weight loss at week one was the group treated with Composition 10 (note this group does not include the *Morus alba* extract), but statistically significant less body weight when compared to the HFD group was observed for this group and the rest of the treatment groups from week 2 through the end of the experiment (FIG. 2). In addition, weight gain was reduced in all combination groups beginning in week one after treatment and this effect lasted through the end of the experiment (see FIG. 2 and Table 151). Such a quick onset, together with the long lasting, weight loss and reduced weight gain caused by each of the combination compositions was unexpected.

Based on the data from DIO mice treated with the individual components, a theoretical calculation of the additive weight gain was made and these calculated values are provided in Table 151. All five compositions showed an unexpected synergy because each composition caused a greater weight loss than was predicted from the additive effect of each individual component.

TABLE 151

Weight Gain in DIO Mice 2 Weeks after Treatment with a Multicomponent Composition

| Group | Dosage (mg/kg) | Weight Gain/Loss (g) | Composition 1A | 10 | 2A | 12 | 11 |
|---|---|---|---|---|---|---|---|
| *Morus* | 200 | −2.16 g | x |  | x | x | x |
| *Magnolia* | 100 | −2.01 g | x | x | x |  | x |
| Yerba Mate | 500 | 1.55 g | x | x |  | x | x |
| Mutamba | 500 | 0.79 g |  | x | x | x | x |
| HFD | — | 0.81 g |  |  |  |  |  |
| Weight Gain/Loss |  | Expected | −2.62 g | +0.33 g | −3.38 g | +0.18 g | −1.83 g |
|  |  | Observed | −7.56 g | −1.95 g | −6.34 g | −5.89 g | −4.74 g |

Furthermore, by the end of treatment (8 weeks), mice treated with Composition 1A, 2A, and 11 showed less mean body weights than positive control Orlistat, while mice treated with Compositions 10 and 12 were essentially the same weight and slightly above the Orlistat treated group (FIG. 2). At the end of the 8 week treatment, mice treated with Composition 1A, 2A, and 11 showed a weight reduction ranging from about 0.73 g to about 3.6 g, which was better than the slight weight decrease (0.23 gram) seen in the Orlistat group. Mice treated with Compositions 10 and 12 had marginal body weight gains of 1.73 g and 1.78 g, respectively, which is much less than the 3.5 g to 7.3 g weight gains observed in mice treated with the components individually at the end of the 8 week treatment (see FIGS. 1 and 2).

Overall, these data show that the combinations of three or four components containing Diels-Alder Adducts of chalcone and prenylphenol showed unexpected quicker and long lasting reductions in both body weight and weight gain as compared to mice fed a high fat diet. Other unexpected benefits include a reduced food efficiency ratio, reduced triglyceride and total cholesterol levels, improved NASH scores, and reduced fat deposits in liver (data not shown).

Example 75

Effect of Isolated *Morus* Extract Active Ingredients on Acute Food Intake in Sprague-Dawley Rats This Example presents a 24-hour food intake test carried according to the Example 45 to determine the effect of food intake by rats administered active ingredients (Kuwanon G and Albanin G) isolated from EtOAc *Morus alba* root bark extract. S-D rats were administered *Morus alba* Isolate Composition A containing 48.3% Kuwanon G and 46.6% Albanin G with a combined Diels-Alder adduct of chalcone and prenylphenol having about 94.9% purity, which was produced using a method similar to that described in Example 5, in a solution of 0.5% CMC (carboxymethyl cellulose) 30 minutes prior to the start of dark-phase feeding cycle. The *Morus alba* Isolate Composition A was administered at a dose of 92.5 and 185 mg/kg (this dose is essentially the same active content as found in the 500 and 1000 mg/kg of *Morus alba* EtOAc extract 15 described in Example 15) with 10 animals per group.

Table 152 shows the weight gain results for rats treated with a single dose of *Morus alba* Isolate Composition A at two different amounts compared to control animals.

TABLE 152

Weight Gain in Non-Obese Fasting Rats Fed a High Fat Diet

| Group | Dose (mg/kg) | | Weight Gain after Treatment (hours) | | |
|---|---|---|---|---|---|
| | | | 2 | 8 | 24 |
| Control | — | Mean | 6.71 | 18.30 | 12.31 |
| | | S.D. | 2.33 | 4.88 | 3.61 |
| Isolate Composition A | 92.5 | Mean | 3.11 | 11.26 | 12.16 |
| | | S.D. | 3.42 | 5.86 | 3.92 |
| | | p value | 0.0126 | 0.0062 | 0.9247 |
| | 185 | Mean | 3.81 | 8.26 | 10.22 |
| | | S.D. | 3.26 | 8.21 | 8.64 |
| | | p value | 0.0321 | 0.0040 | 0.4871 |

The data of Table 152 show that *Morus alba* Isolate Composition A (which includes 94.9% total Kuwanon G and Albanin G) is capable of inducing a statistically significant reduction in weight gain for at least 8 hours after treatment.

Table 153 shows the food intake test results for rats treated with a single dose of *Morus alba* Isolate Composition A at two different amounts compared to control animals.

TABLE 153

Cumulative Food Intake in Non-Obese Fasting Rats Fed a High Fat Diet

| Group | Dose (mg/kg) | | Cumulative Food Intake (hour) | | | | | | |
|---|---|---|---|---|---|---|---|---|---|
| | | | 1 | 2 | 4 | 6 | 8 | 10 | 24 |
| Control | — | Mean | 2.12 | 5.97 | 10.75 | 13.78 | 20.36 | 22.66 | 27.35 |
| | | SD | 1.65 | 1.70 | 1.92 | 2.16 | 2.94 | 2.43 | 2.26 |
| Isolate Composition | 92.5 | Mean | 0.89 | 3.47 | 7.18 | 9.81 | 14.33 | 17.12 | 25.71 |
| | | SD | 0.90 | 2.75 | 4.29 | 3.82 | 4.42 | 3.54 | 3.87 |
| | | p value | 0.0590 | 0.0273 | 0.0326 | 0.0123 | 0.0025 | 0.0009 | 0.2672 |
| | 185 | Mean | 1.13 | 2.74 | 4.51 | 6.16 | 8.14 | 9.43 | 17.94 |
| | | SD | 0.84 | 1.36 | 2.74 | 4.48 | 6.44 | 7.54 | 9.07 |
| | | p value | 0.1137 | 0.0002 | 0.0000 | 0.0003 | 0.0001 | 0.0003 | 0.0096 |

These data together show that both *Morus alba* treatment groups exhibited a statistically significant reduction in cumulative food intake. Further, a dose dependent reduction in food intake was observed in the second hour of food intake measurement through to completion of study. These results demonstrate that active ingredients Kuwanon G and Albanin G isolated from a *Morus alba* extract has a statistically significant effect on food intake in rats indicating that Kuwanon G and Albanin G from *Morus alba* extracts can be used in body weight control compositions that inhibit food intake. Also, the reduced food intake from a single oral dose of the isolated *Morus alba* active ingredients lasted more than 10 hours. Thus, it is feasible to achieve a reduced appetite, enhanced satiety, or reduced food or caloric intake by once or twice per day oral administration of a composition comprising Diels-Alder Adducts of chalcone and prenylphenol Kuwanon G and Albanin G isolated from *Morus alba* root bark extract.

Example 76

Effect of Various Compositions Having *Morus* Extract on Weight Gain, Feed Intake, and Levels of Leptin, Ghrelin and Cck Peptide in DIO Mice Obese mice were treated with various three component compositions to test the anti-obesity and appetite effects of such compositions. Three component Composition 1 (Magnolia:Morus:Yerba Mate) produced according to the Example 38, three component Composition 2 (Magnolia:Morus:Mutamba) produced according to the Example 42, three component Composition 3 (Morus:Rosemary:Yerba Mate) produced according to the Example 39, and three component Composition 9 (Morus:Rosemary:Areca) produced according to the Example 41, were each separately administrated orally to DIO mice as described in the Example 48. The high fat diet (HFD) mice were divided into multiple treatment groups with a total of 10 animals per group. The mice were treated with one of the following: Composition 1 (1300 mg/kg/day), Composition 2 (1300 mg/kg/day), Composition 3 (1700 mg/kg/day), or Composition 9 (1700 mg/kg/day). Control groups included a normal diet group given vehicle only (ND, negative control), a high fat diet group given vehicle only (HFD, negative control), an orlistat group (ORI, 40 mg/kg, 2 times/day, positive control), and a sibutramine group (10 mg/kg, 1 time/day, positive control). Body weight and feed intake were measured daily for 2 weeks after treatment and then twice a week until the end of the 7 week study. At week 2 and week 7 after treatment, mice were fasted for 16 hours and then five animals were examined to measure plasma concentrations of leptin and ghrelin. Leptin and ghrelin levels were measured by using commercial ELISA kits specific for leptin or ghrelin (Millipore Co., Billerica, Mass.) according to the manufacturer's instructions. Measurements were taken using a microplate reader (Victor™ X3, PerkinElmer Inc., USA) and analyzed with PerkinElmer 2030 workstation computer software.

After 2 weeks of treatment, all treatment groups showed a tendency toward having decreased body weight gain. Mice treated with Compositions 1, 2 and 9 showed significantly decreased body weight gain by the end of the study (Table 154). Similarly, the orlistat positive control showed significant reduction in body weight gain at 7 weeks, but those treated with Sibutramine did not.

TABLE 154

Effect of Different *Morus* Compositions on Weight Gain

| Group | Weight Gain 2-week | T-test vs HFD | Weight Gain 7-week | T-test vs HFD |
|---|---|---|---|---|
| ND | −0.91 | 0.303 | 0.79 | 0.004 |
| HFD | −1.68 | — | 5.73 | — |
| Orlistat | −5.07 | 0.031 | 0.56 | 0.013 |
| Sibutramine | −1.40 | 0.675 | 6.12 | 0.761 |
| Composition 1 | −2.61 | 0.457 | 1.89 | 0.047 |
| Composition 2 | −2.54 | 0.245 | −0.77 | 0.001 |
| Composition 3 | −0.80 | 0.458 | 3.88 | 0.302 |
| Composition 9 | −2.45 | 0.428 | −0.04 | 0.002 |

After 7 weeks of treatment, the feed intake of all treatment groups except orlistat showed a tendency toward decreased feed intake when compared to the HFD group. In particular, groups treated with Sibutramine, Composition 1, and Composition 9 showed a statistically significant reduction of average food intake after 7 weeks of treatment (Table 155).

TABLE 155

Effect of Different *Morus* Compositions on Feed Intake

| Group | Average Feed Intake 2-week | T-test vs HFD | Average Feed Intake 7-week | T-test vs HFD |
|---|---|---|---|---|
| ND | 3.63 | 0.002 | 3.85 | 0.014 |
| HFD | 2.62 | — | 3.05 | — |
| Orlistat | 2.79 | 0.233 | 3.09 | 0.894 |
| Sibutramine | 2.87 | 0.292 | 2.67 | 0.037 |
| Composition 1 | 2.64 | 0.930 | 2.65 | 0.096 |
| Composition 2 | 2.19 | 0.455 | 1.99 | 0.001 |
| Composition 3 | 2.43 | 0.483 | 2.73 | 0.281 |
| Composition 9 | 2.13 | 0.132 | 1.95 | 0.010 |

Moreover, the food efficiency ratio (FER) was decreased in all Composition treatment groups during the entire period of dosing. The group treated with Composition 2 showed a significant decrease both after 2 weeks and 7 weeks of treatment, while Composition 1 showed significant changes after 2 weeks of treatment and Composition 9 was significant only after 7 weeks of treatment. Positive control orlistat significantly reduced FER, while the changes observed in the sibutramine and Composition 3 treatment group were not statistically significant (Table 156).

TABLE 156

Effect of Different *Morus* Compositions on FER

| Group | | Food Efficiency Ratio (FER)* 2 weeks | 7 weeks |
|---|---|---|---|
| ND | Mean | −0.023 | 0.004 |
| | SD | 0.014 | 0.005 |
| | p value[†] | 0.0349 | 0.0098 |

TABLE 156-continued

Effect of Different *Morus* Compositions on FER

| Group | | Food Efficiency Ratio (FER)* 2 weeks | 7 weeks |
|---|---|---|---|
| HFD | Mean | −0.059 | 0.050 |
| | SD | 0.045 | 0.023 |
| Orlistat | Mean | −0.223 | 0.005 |
| | SD | 0.095 | 0.020 |
| | p value | 0.0003 | 0.0106 |
| Sibutramine | Mean | −0.099 | 0.054 |
| | SD | 0.048 | 0.008 |
| | p value | 0.0698 | 0.7289 |
| Composition 1 | Mean | −0.127 | 0.019 |
| | SD | 0.078 | 0.025 |
| | p value | 0.0276 | 0.0713 |
| Composition 2 | Mean | −0.164 | −0.009 |
| | SD | 0.062 | 0.014 |
| | p value | 0.0495 | 0.0011 |
| Composition 3 | Mean | −0.049 | 0.036 |
| | SD | 0.066 | 0.025 |
| | p value | 0.6976 | 0.3792 |
| Composition 9 | Mean | −0.089 | 0.000 |
| | SD | 0.053 | 0.012 |
| | p value | 0.1877 | 0.0024 |

*Feed Efficiency Ratio (FER) = Weight Gain (g/day)/Feed Intake (g/day)
[†]p value: Compared to HFD by t-test Plasma leptin and active ghrelin levels in DIO mice after 2 weeks and 7 weeks of treatment with Compositions 1, 2, 3 and 9 are listed in Table 157. HFD animals had a dramatically increased leptin level compared to normal diet control (ND) animals at week 2 and at week 7. The active ghrelin level in the HFD animals was dramatically reduced in comparison to ND mice, with an even more dramatic reduction detectable after 7 weeks of treatment as compared to the reduction after 2 weeks of treatment. The orlistat positive control significantly reduced leptin level after 2 weeks of treatment as compared to the HFD negative control group, but showed similar levels at 7 weeks. Orlistat had no effect on active ghrelin levels at either week 2 or week 7 as compared to the HFD negative control group. The same time frame (2 weeks after treatment) in which a noticeable change in leptin level was observed after treatment with orlistat was also the same time frame that the greatest reduction in weight gain was observed, while no average feed intake reduction was observed throughout the treatment period. The sibutramine positive control showed somewhat reduced leptin level after 2 weeks of treatment as compared to the HFD group, and showed no leptin level change at week 7. Similar to orlistat, sibutramine had no effect on active ghrelin levels at either week 2 or week 7 as compared to the HFD negative control group.

TABLE 157

Effect of Different *Morus* Compositions on Leptin and Ghrelin Levels

| Group | Leptin (ng/ml) 2-week | 7-week | Active Ghrelin (pg/ml) 2-week | 7-week |
|---|---|---|---|---|
| ND | 1.7 ± 0.04 | 5.0 ± 0.08 | 1258.2 | 1203.2 |
| HFD | 20.1 ± 0.20 | 20.1 ± 0.16 | 975.3 | 578.8 |
| Orlistat | 11.6 ± 0.06 | 19.0 ± 0.24 | 1316.4 | 1353.7 |
| Sibutramine | 17.0 ± 0.43 | 20.4 ± 0.00 | 1001.3 | 600.1 |
| Composition 1 | 15.7 ± 0.26 | 19.6 ± 0.05 | 1254.6 | 1141.0 |
| Composition 2 | 11.4 ± 0.70 | 17.9 ± 0.05 | 1084.1 | 1354.5 |
| Composition 3 | 17.6 ± 0.36 | 19.9 ± 0.39 | 682.6 | 831.0 |
| Composition 9 | 16.0 ± 0.16 | 18.7 ± 0.04 | 1618.7 | 1234.2 |

Composition 2 showed a similar level of leptin reduction as observed for orlistat, and had the most reduced leptin level at week 7 as compared to the Composition 1, 3, and 9 treatment groups. Furthermore, at the end of 7 weeks, the Composition 2 treated group showed greatest reduction in (or least amount of) weight gain as compared to the Composition 1, 3, and 9 treatment groups. The reduction in leptin level from all four Composition treatment groups paralleled the observed reduction in weight gain, feed intake, and FERs, with Composition 2 showing the best efficacy followed by Compositions 9, 1, and 3.

Cholecystokinin (CCK) is a peptide hormone that is a physiological ligand for the gastrin/CCK-B receptor, while the CCK-A receptor binds only sulfated CCK peptides. CCK peptides, mainly produced in small intestinal endocrine I-cells, regulate pancreatic enzyme secretion and growth, gallbladder contraction, intestinal motility, satiety, and inhibit gastric acid secretion. CCK peptides also stimulate digestion of fat and protein. Secretion of CCK by the duodenal and intestinal mucosa is stimulated by fat- or protein-rich chyme entering the duodenum. CCK then inhibits gastric emptying, gastric acid secretion, and mediates digestion in the duodenum. CCK stimulates the acinar cells of the pancreas to release water and ions and stimulates the secretion of pancreatic digestive enzymes that catalyze the digestion of fat, protein, and carbohydrates.

Therefore, the effect on CCK peptide levels in mice from treatment with Composition 2 (Magnolia:Morus:Mutamba), produced according to the Example 42, or Composition 3 (Morus:Rosemary:Yerba Mate), produced according to the Example 39, was examined to determine the extent to which weight gain and/or appetite were affected through this peptide hormone pathway. Briefly, CCK peptide levels were measured after 7 weeks of administering Compositions 1 and 3 to mice on a high fat diet as described in Example 48. Negative controls include mice on a normal diet (NC) and mice on a high fat diet (HFD), each group administered vehicle only. The positive controls were orlistat and sibutrimine. CCK levels were detected using a CCK ELISA assay kit according to the manufacturer's instructions (Abnova, Taipei City, Tiawan). Measurements were performed using microplate reader Victor™ X3 (PerkinElmer Inc., Waltham, Mass.) and computer software on the PerkinElmer 2030 workstation.

TABLE 158

Effect of Morus-Containing Compositions on CCK Peptide Levels

| Group | % CCK binding % ± SD | P-value* |
|---|---|---|
| NC | 30.5 ± 3.8 | 0.033 |
| HFD | 7.7 ± 1.9 | — |
| Orlistat | 72.5 ± 3.4 | 0.017 |
| Sibutramine | 12.3 ± 1.6 | 0.121 |
| Composition 2 | 12.8 ± 1.3 | 0.047 |
| Composition 3 | 18.2 ± 2.9 | 0.036 |

*$P < 0.05$ versus the HFD control group

As shown in Table 158, the CCK levels of the treated groups were increased compared to those of the negative control (HFD) group indicating that at least one of the components of Composition 2 and Composition 3 affect CCK modulation in mice.

Example 77

Effect of Morus-Containing Compositions and Rosemary Extract on Lipid Accumulation The ability to regulate the cell cycle and differentiation of adipocytes are important in the development and physiology of obesity. Adipocytes arise from multipotent mesenchymal precursor cells that commit to become preadipocytes, which can either remain dormant or differentiate into adipocytes. During terminal differentiation, the fibroblast-like preadipocytes undergo a series of morphological and biochemical changes to eventually accumulate lipid droplets. These in vitro differentiated adipocytes share similar morphology with adipocytes in vivo. Mouse embryo fibroblast cell line, 3T3-L1, is a well-characterized cell line used to examine insulin-induced glucose uptake and mechanisms of obesity development (e.g., lipid accumulation).

Three component Composition 3 (Morus:Rosemary:Yerba Mate) produced according to the Example 39, three component Composition 2 (Magnolia:Morus:Mutamba) produced according to the Example 42, and Rosemary EtOH extract 22 produced according to the Example 22, were examined for their effect on lipid accumulation in 3T3-L1 adipocytes. Briefly, 3T3 L1 cells (American Type Culture Collection) were cultured in Dulbecco's modified Eagle's medium (DMEM) (GIBCO) containing 10% bovine calf serum until confluent. Two days post-confluence (D0), cells were stimulated to differentiate with DMEM containing 10% fetal bovine serum (FBS), 5 µg/ml insulin, 0.5 mM 3-isobutyl-1-methylxanthine (IBMX) and 1 µM dexamethasone for two days (D2). Differentiated cells were then maintained in 10% FBS/DMEM medium with 5 µg/ml insulin for another two days (D4), followed by culturing with 10% FBS/DMEM medium for four days (D8).

TABLE 159

Effect of Composition 3 (Morus:Rosemary:Yerba Mate) on Lipid Accumulation

| Samples | Concentration | Inhibition (%) |
|---|---|---|
| TNF-α | 10 ng/ml | 61.0 |
| Composition 3 | 40 µg/ml | 0.5 |
|  | 80 µg/ml | 31.6 |
|  | 120 µg/ml | 62.4 |
|  | 160 µg/ml | 85.2 |

To examine lipid accumulation, four different concentrations of Composition 3 (40, 80, 120 and 160 ug/ml) were tested with medium from Days 0 to 8 of adipogenesis. The culture medium was replaced every two days, and the cells were stained with Oil-Red 0 on Day 8. The lipid staining showed that an 8 day incubation with Composition 3 during the differentiation period significantly inhibited 3T3-L1 adipogenesis in a dose-dependent manner (Table 159).

TABLE 160

Effect of Composition 2 (Magnolia:Morus:Mutamba) on Lipid Accumulation

| Samples | Concentration | Inhibition (%) |
|---|---|---|
| TNF-α | 10 ng/ml | 68.9 |
| Composition 2 | 80 µg/ml | 15.3 |
|  | 120 µg/ml | 74.7 |
|  | 160 µg/ml | 88.4 |

Composition 2, used at 10, 80, 120 and 160 µg/ml, also showed high level efficacy of inhibiting lipid accumulation, particularly at a concentration of about 120 µg/ml or more (Table 160).

TABLE 161

Effect of Rosemary EtOH extract 22 on Lipid Accumulation

| Samples | Concentration | Inhibition (%) |
|---|---|---|
| TNF-α | 10 ng/ml | 74.1 ± 6.06 |
| Rosemary | 20 µg/ml | 22.4 ± 5.76 |
|  | 40 µg/ml | 56.5 ± 0.86 |
|  | 80 µg/ml | 61.3 ± 5.93 |
|  | 160 µg/ml | 75.3 ± 1.02 |

Similarly, lipid accumulation in cells treated with Rosemary EtOH extract 22 at 20, 40, 80 and 160 µg/ml, which also showed high level, dose-dependent efficacy on inhibiting lipid accumulation (Table 161).

Example 78

Effect of Morus:Rosemary:Yerba Mate Composition on Triglyceride Accumulation

Using the same adipocyte differentiation model as described in Example 77, triglyceride levels were analyzed using an enzymatic ELISA assay according to the manufacturer's instructions (Cayman Chemical Co., Ann Arbor, Mich.). Briefly, 3T3-L1 cells were treated with three component Composition 3 (Morus:Rosemary:Yerba Mate), produced according to the Example 39, at concentrations of 80, 120 and 160 µg/ml in 6 well plates during adipocyte differentiation for 8 days. The cells were washed with PBS, scraped with homogenizing solution, residual cell lysate was centrifuged at 3,000 g for 5 minutes to remove fat layers, and the supernatants were assayed for triglyceride levels.

TABLE 162

Effect of Composition 3 (Morus:Rosemary:Yerba Mate) on Intracellular Triglyceride Accumulation

| Samples | Concentration | Inhibition (%) |
|---|---|---|
| TNF-α | 10 ng/ml | 19.4 |
| Composition 3 | 80 µg/ml | 11.6 |
|  | 120 µg/ml | 35.7 |
|  | 160 µg/ml | 49.9 |

As adipocytes differentiate, their intracellular levels of triglyceride increase continuously. This study shows that Composition 3 effectively inhibited triglyceride accumulation in differentiating 3T3-L1 preadipocytes, with concentrations of about 120 µg/ml or more significantly decreasing triglyceride accumulation (Table 162).

Example 79

Effect of Morus-Containing Compositions on Lipolysis

To determine the extent of lipolysis induced by Morus-containing compositions, fully differentiated 3T3-L1 adipocytes (mature adipocytes) were treated with three component Composition 1 (Magnolia:Morus:Yerba Mate) produced according to the Example 38 or with three component Composition 3 (Morus:Rosemary:Yerba Mate) produced according to the Example 39, for 24 hr and 48 hr with serum free DMEM. Isoproterenol (10 µM) was used as a positive control. The conditioned medium was recovered and free glycerol released was assayed by using a lipolysis assay kit (Sigma-Aldrich Inc., USA) following the manufacturer's instructions.

TABLE 163

Effect of Morus-Containing Compositions on Lipolysis

| | | % of Control | |
|---|---|---|---|
| Samples | Concentration | 24 hrs | 48 hrs |
| Control | — | 100 | 100 |
| Isoproterenol | 10 µM | 464.2 | 525.0 |
| Composition 1 | 62.5 µg/ml | 74.6 | 104.5 |
|  | 125 µg/ml | 87.6 | 120.6 |
|  | 250 µg/ml | 178.0 | 128.8 |
| Composition 3 | 62.5 µg/ml | 61.6 | 183.0 |
|  | 125 µg/ml | 88.3 | 211.6 |
|  | 250 µg/ml | 138.5 | 212.5 |

Composition 1 induced lipolysis in a dose dependent manner and also may induce early phase lipolysis, while Composition 3 induced lipolysis in a dose and time dependent manner (Table 163).

Example 80

Anti-Oxidant Effect of Various Different Extracts and Various Morus-Containing Compositions Oxygen radicals, expected to be increased in obese subjects, have an important role in the pathogenesis of many diseases. Oxidative stress results when free radical formation is greatly increased or protective antioxidant mechanisms are compromised. Cells have developed an enzymatic anti-oxidant pathway against reactive oxygen species (ROS) that are generated during oxidative metabolism: first, the dismutation of superoxide anion ($O_2^-$) to hydrogen peroxide ($H_2O_2$) catalyzed by superoxide dismutase (SOD); and then, the conversion of $H_2O_2$ to $H_2O$ by glutathione peroxidase (GPx) or catalase (CAT) (Dalle-Donne et al., Clin. Chem. 52:601, 2006). The activity of first- and second-step anti-oxidant enzymes must be balanced to prevent oxidative damage in cells, which may contribute to various pathological processes.

The DPPH (2,2-diphenyl-1-picrylhydrazyl) test is quick and simple test for measuring anti-oxidation activity. The DPPH radical has a violet color in solution, but changes to light yellow or colorless when reduced to DPPH-H (2,2-diphenyl-1-picrylhydrazin) after reaction with free radicals. The color change can be followed spectrophotometrically at 517 nm to determine the anti-oxidative potential of a composition. Briefly, a 0.2 mM solution of DPPH in DMSO was mixed with each test sample at concentrations of 20, 40, 80 and 160 µg/ml. Ascorbic acid was used as a positive control. After a 30 minute incubation in the dark, the color change (i.e., decrease in absorbance) was measured at 517 nm in a spectrophotometer. DPPH inhibitory activity is expressed as a percent inhibition (Table 164).

The following samples were tested: (1) Rosemary EtOH extract 22 produced according to the Example 22, (2) Magnolia extract 29 produced according to the Example 29, (3) Mutamba extract 35 produced according to the Example 35, (4) Yerba Mate EtOH extract was produced according to the Example 26, (5) Morus EtOH precipitate extract 18 produced according to the Example 35, (6) three component Composition 1 (Magnolia:Morus:Yerba Mate) produced according to the Example 38, (7) three component Composition 2 (Magnolia:Morus:Mutamba) produced according to the Example 42, and (8) three component Composition 3 (Morus:Rosemary:Yerba Mate) produced according to the Example 39.

TABLE 164

Anti-Oxidative Activity of Various Extracts and Compositions

| Samples | Inhibition (%) | | | |
|---|---|---|---|---|
| | 20 μg/ml | 40 μg/ml | 80 μg/ml | 160 μg/ml |
| Ascorbic acid | 50.8 ± 0.83 | 53.6 ± 1.72 | 64.2 ± 0.86 | 76.6 ± 0.30 |
| Rosemary extract | 32.8 ± 1.57 | 49.5 ± 1.28 | 51.6 ± 0.85 | 62.8 ± 1.00 |
| Magnolia extract | 33.0 ± 0.67 | 39.6 ± 0.64 | 41.3 ± 0.32 | 50.0 ± 0.42 |
| Mutamba extract | 42.2 ± 0.52 | 41.8 ± 0.57 | 43.8 ± 0.89 | 46.3 ± 0.72 |
| Mate extract | 41.0 ± 0.26 | 42.7 ± 0.43 | 43.3 ± 0.25 | 45.7 ± 0.41 |
| Morus extract | 28.3 ± 1.68 | 42.0 ± 1.75 | 61.8 ± 2.00 | 87.1 ± 1.21 |
| Composition 1 | 38.3 ± 0.77 | 43.4 ± 0.48 | 45.4 ± 0.88 | 46.4 ± 0.73 |
| Composition 2 | 44.5 ± 1.16 | 44.4 ± 1.10 | 46.8 ± 0.87 | 50.8 ± 1.02 |
| Composition 3 | 35.8 ± 1.24 | 45.1 ± 0.88 | 45.5 ± 0.15 | 50.9 ± 0.10 |

All test samples showed DPPH inhibitory effects (Table 164). The DPPH scavenging activity of the test samples (in decreasing order) was as follows: Morusextract>Rosemary extract>Compositions 2, 3 and 1, and all other extracts of Mate, Mutamba and Magnolia.

Example 81

Clinical Safety and Efficacy Dose-Escalation Evaluation of Combination Compositions for Weight Loss in Humans A safety and efficacy dose escalation study of Composition 1A (see Example 63), Composition 2A (see Example 74), and Composition 3 (see Example 39) were each tested at three dose levels in six subjects per study arm. Each composition was formulated in capsule form, wherein each capsule contains 250 mg of Composition 1A, 2A, or 3. Composition 1A is a combination of Magnolia extract, Morus alba extract, and Yerba Mate extract at a ratio of 1:2:5, respectively. Composition 2A is a combination of Magnolia extract, Morus alba extract, and Mutamba extract at a ratio of 1:2:5, respectively. Composition 3 is a combination of Morus alba extract, Rosemary extract, and Yerba Mate extract at a ratio of 2:5:10, respectively. Placebo capsules formulated for the studies contain CMC (carboxymethyl cellulose) and are identical in appearance to the capsules of Compositions 1A, 2A, and 3.

The test compositions (Composition 1A, Composition 2A, or Composition 3) were taken with meals three times per day. Study participants received instructions for dosing and storage conditions of the test product. The study population included a total of 54 subjects (male and female) between 18 and 50 years of age, having a body mass index (BMI) ranging from about 30 to about 40, and in generally good health as determined by a medical history. The test compositions were evaluated at 750 mg/day, 1,500 mg/day and 2,250 mgs/day. The study did not include a placebo control except for stabilization, as explained further below. The study was a double blind study for a period of six weeks, first two weeks on placebo for stabilization and then crossing over to a low dose active arm. After three individuals completed a study arm, all safety parameters were evaluated and a decision was made whether to continue enrolling for that dose level. If that lower dose level was safe, then subjects for the next higher dose were enrolled. The duration of the treatment with Composition 1A, Composition 2A, and Composition 3 was for six weeks (including the two week placebo stabilization period) for each participant. The total duration of the study for each patient was about 8-10 weeks, which included screening, randomization, and active treatment.

The primary objective of the study was to establish a maximum tolerated dose (MTD), dose limiting toxicities, and/or maximum feasible dose of the study product. The following parameters were evaluated: CBC with Manual Differential, EKG, Blood Pressure, Vitals, CMP (including Kidney and Liver function tests) and Adverse Event Analysis.

A secondary objective was to evaluate the effect of various doses on lipid profiles (TG, Chol, HDL, LDL), as well as fasting glucose and insulin levels.

A tertiary objective was to evaluate the effect of multiple doses on satiety and dietary intake.

A quaternary objective was to evaluate the efficacy of the study product on anthropometric measurements, such as change in weight, change in BMI, change in waist/hip ratio, arm circumference, and thigh circumference, each as compared to baseline.

The protocol was approved by the IRB prior to the initiation of any study related procedures and all subjects signed the IRB reviewed Informed Consent.

Statistical Analysis

The study included three dose levels (Dose 1, Dose 2 and Dose 3), and differences within time periods for each arm (within groups tested), differences between two of three dose levels for each time point (between groups tested), and differences among three dose levels for each time point (among groups tested) were analyzed for each endpoint.

For all endpoints in all types of variable, non-parametric statistical methods were tested. The differences among dose levels were tested for nominal significance using Kruskal-Wallis. The differences between dose levels (i.e., Dose 1 versus Dose 2, Dose 1 versus Dose 3, and Dose 2 versus Dose 3) were tested for nominal significance using the Wilcoxon Mann-Whitney test. The differences within time periods for each dose levels were tested for nominal significance using Wilcoxon Signed Ranks test or Sign test. For categorical endpoints, the difference in the distribution between dose levels was tested using non-parametric Chi-square Test.

A Modified per Protocol (Mod PP) analysis was performed and used to assess the efficacy variables of the study. The Mod PP population involves analyzing together all subjects randomly assigned to one of the treatments, excluding the subjects who didn't take the study product. Subjects with at least one post-dose visit completed were included in the analysis.

All safety endpoints were analyzed using non-parametric statistical methods. CBC with manual differential, EKG, Blood Pressure, Vitals, CMP (including Kidney and Liver function tests) were analyzed using Kruskal-Wallis for comparison among Dose Levels, and Wilcoxon Mann Whitney for comparison between Dose Levels. Comparison within time periods for each Dose Level was assessed using Wilcoxon Signed Ranks test or Sign Test.

In obtaining comparable documentation on adverse events (AEs), the investigator asked the subject the following open, standardized, questions at each visit. Frequency and intensity of AE's and serious AE's were recorded in detail, based on the subject's interviews during each visit. Recorded AE's were grouped by general type of event (body system). Differences in AE patterns between product groups were assessed by Cochran-Q test. Moreover, McNemar Change test were used to assess the differences in AE patterns between product groups.

All efficacy endpoints were analyzed using non-parametric methods. Lipid Panels, Change in fasting glucose and insulin, Change in weight, BMI, waist/hip Ratio, Arm and Thigh circumference, Satiety and Dietary Intake were analyzed using Kruskal-Wallis for comparison among Dose Levels, Wilcoxon Mann Whitney for comparison between Dose Levels. Comparisons within time periods for each Dose Level were assessed using Wilcoxon Signed Ranks Test or Sign Test.

Clinical Results

After completing the treatment of all subjects, there were no significant changes from baseline until the end of treatment at all three doses for all three compositions on all CBC, comprehensive metabolic Penal (CMP), EKG, systolic and diastolic blood pressure, body temperature, pulse rate, and respiratory rate measurements. There were no reported serious adverse events (SAEs) during the study.

Other clinical studies have shown that modest weight losses are sufficient to produce clinically significant improvements in cardiovascular risk factors in overweight and obese subjects. The improvements in blood pressure, glycemic control, and lipids, with the notable exception of LDL cholesterol, have been observed in multiple weight loss studies. These same positive trends were observed in the instant clinical pilot test of Compositions 1A, 2A and 3 at all three dose levels, particularly in the improvement of lipid profile with increased high density lipoprotein and reduced triglycerides, LDL and cholesterol. The reduction of fasting glucose and insulin level from the three different compositions demonstrated improved glucose metabolism. The positive changes in lipid and glucose metabolism observed with all three compositions are consistent with the observations in the animal efficacy studies described herein.

The compositions with the major changes in the evaluation parameters were observed for Composition 2A—high dose (Table C), Composition 1A—low dose (Table B), and Composition 3—high dose (Table D).

TABLE B

Effect of Composition 1A on Weight and Cardiovascular Risk Factors

| Endpoint | Low Dose (750 mg/day) Effect |
| --- | --- |
| Total Cholesterol | Decreased |
| High Density Lipoprotein | Increased |
| Triglycerides | Decreased |
| Glucose | Decreased |
| Weight | Decreased |

| Endpoint | Mid Dose (1,500 mg/day) Effect |
| --- | --- |
| High Density Lipoprotein | Increased |
| Low Density Lipoprotein | Decreased |
| Triglycerides | Decreased |
| Glucose | Decreased |

| Endpoint | High Dose (2,250 mg/day) Effect |
| --- | --- |
| High Density Lipoprotein | Increased |
| Low Density Lipoprotein | Decreased |
| Triglycerides | Decreased |
| Glucose | Decreased |

After 4 weeks of treatment with Composition 1A (6 weeks total including two week stabilization with placebo), subjects in all three dose groups showed increased high lipoprotein; decreased triglycerides and glucose. Subjects treated with 1,500 mg/day and 2,250 mg/day also experienced reduced low density lipoprotein. Low dose group subjects had a tendency to present with decreased body weight and reduced total cholesterol.

TABLE C

Effect of Composition 2A on Weight and Cardiovascular Risk Factors

| Endpoint | Low Dose (750 mg/day) Effect |
| --- | --- |
| High Density Lipoprotein | Increased |
| Glucose | Decreased |
| Weight | Decreased |

| Endpoint | Mid Dose (1,500 mg/day) Effect |
| --- | --- |
| High Density Lipoprotein | Increased |
| Triglycerides | Decreased |
| Glucose | Decreased |
| Weight | Decreased |

| Endpoint | High Dose (2,250 mg/day) Effect |
| --- | --- |
| Total Cholesterol | Decreased |
| High Density Lipoprotein | Increased |
| Low Density Lipoprotein | Decreased |
| Triglycerides | Decreased |
| Insulin | Decreased |
| Weight | Decreased |

After 4 weeks of treatment with Composition 2A (6 weeks total including two week stabilization with placebo), subjects treated with 2,250 mg/day showed the most positive changes with increased high density lipoprotein; and decreased total cholesterol, low density lipoprotein, triglycerides, insulin; and a tendency to present with decreased body weight. Subjects treated with 1,500 mg/day of Composition 2A showed increased high density lipoprotein; and decreased triglycerides, glucose; and tendency to present with decreased body weight. Subjects treated with 750 mg/day of Composition 2A showed increased high density lipoprotein; decreased glucose; and tendency to present with decreased body weight.

TABLE D

Effect of Composition 3 on Weight and Cardiovascular Risk Factors

| Endpoint | Low Dose (750 mg/day) Effect |
| --- | --- |
| High Density Lipoprotein | Increased |
| Glucose | Decreased |
| Insulin | Decreased |
| Weight | Decreased |

| Endpoint | Mid Dose (1,500 mg/day) Effect |
| --- | --- |
| Total Cholesterol | Decreased |
| High Density Lipoprotein | Increased |
| Glucose | Decreased |
| Weight | Decreased |

| Endpoint | High Dose (2,250 mg/day) Effect |
| --- | --- |
| High Density Lipoprotein | Increased |
| Low Density Lipoprotein | Decreased |
| Triglycerides | Decreased |
| Glucose | Decreased |
| Insulin | Decreased |

After 4 weeks of oral treatment with Composition 3, subjects treated with 2,250 mg/day showed increased high density lipoprotein; and decreased low density lipoprotein, triglycerides, glucose and insulin. Subjects treated with 1,500 mg/day of Composition 3 showed increased high density lipoprotein; and decreased total cholesterol, glucose; and tendency to present with decreased body weight. Subjects treated with 750 mg/day of Composition 3 showed increased high density lipoprotein; decreased glucose and insulin; and tendency to present with decreased body weight.

Example 82

Mutamba EtOH Extracts from Various Plant Parts and Various Sources

Plant material from Mutamba (*Guazuma ulmifolia*) was ground to a particle size of no larger than two millimeters (mm), and transferred (150 g) to a one liter round bottom flask. An approximate 5-fold volume of either 95% ethyl alcohol or 70% ethyl alcohol in water (v/v) was added to the flask. The extraction was carried out with reflux for one hour, filtered to remove biomass, and then subjected to reflux two more times. The filtrates were combined and concentrated with a rotary evaporator at 50° C. under vacuum to remove the ethanol, and then vacuum freeze-dried to obtain the extract. Table 165 lists the extraction results of Mutamba from various plant parts and various different countries.

TABLE 165

Extraction Yield from Different Mutamba Plant Parts and Source

| Extract | % EtOH | Plant Part | Plant Origin | Yield |
| --- | --- | --- | --- | --- |
| 82P1 | 95 | Stem Bark | Panama | 16% |
| 82P2 | 95 | Bark | Brazil | 14% |
| 82D1 | 70 | Stem | Belize | 9% |
| 82D2 | 70 | Bark | Belize | 17% |
| 82D3 | 70 | Stem | Belize | 7% |
| 82D4 | 70 | Bark | Belize | 12% |
| 82D5 | 70 | Bark | Belize | 17% |
| 82D6 | 70 | Stem | Belize | 7% |
| 82D7 | 70 | Bark | Belize | 15% |
| 82D8 | 70 | Stem | Belize | 7% |
| 82D9 | 70 | Bark | Belize | 12% |
| 82D10 | 70 | Stem | Belize | 5% |
| 82D11 | 70 | Stem Bark | Peru Highland | 10% |
| 82D12 | 70 | Stem Bark | Peru Highland | 10% |
| 82D13 | 70 | Stem Bark | Peru Highland | 15% |
| 82D14 | 70 | Bark | Peru Highland | 9% |
| 82D15 | 70 | Bark | Peru Lowland | 16% |
| 82D16 | 70 | Bark | Peru Lowland | 20% |
| 82D17 | 70 | Bark | Peru Lowland | 6% |
| 82D18 | 70 | Stem | Peru Lowland | 16% |
| 82D19 | 70 | Stem | Peru Lowland | 15% |

Plants from Peru tended to provide the best yield of active ingredients from Mutamba, regardless of which plant part was used (e.g., the highest yield being 20% from bark from the Peru lowland). For Mutamaba from Belize, a greater yield was obtained from bark as compared to stems. Use of 70% ethanol was as effective as 95% ethanol to extract active ingredients from Mutamba.

Example 83

HPLC Analysis of Mutamba EtOH Extract Active Ingredients

High performance liquid chromatography coupled to a photodiode-array (HPLC/PDA) was used with a C18 reversed-phase column (Agilent, USA, Eclipse 3.5 um, 150 mm×4.6 mm) to detect and quantify components of Mutamba EtOH extracts, such as Procyanidin B2, Epicatechin, Procyanidin C1, and other minor components (including tetramer Arecatannin A2). A binary gradient of 0.05% trifluoroacetic acid in purified water (mobile phase A) and acetonitrile (mobile phase B) was used to elute Mutamba extract components as described in Table 166. The flow rate was set to 0.8 ml/min passing through the Eclipse C18 column at a column temperature of 35° C. The UV detector was set to read absorbance at 275 nm.

TABLE 166

Mutamba HPLC Gradient Elution Scheme

| Time (min) | Mobile phase A % | Mobile phase B % |
| --- | --- | --- |
| 0 | 3 | 97 |
| 3 | 3 | 97 |
| 8 | 9 | 91 |
| 25 | 16 | 84 |
| 35 | 60 | 40 |
| 45 | 100 | 0 |
| 50 | 100 | 0 |
| 52 | 3 | 97 |
| 60 | 97 | 3 |

The quantification standards included pure reference samples epicatechin, procyanidin B2, and procyanidin C1 (Sigma-Aldrich Co., USA; Chendu Biopurify Phytochemicals, Ltd., China; and ChromaDex Inc., USA, respectively). The highest concentration level of epicatechin was 0.05 mg/ml and diluted to L5 from L1 (0.003 mg/ml) using 50% methanol in water. The highest concentration ranges of procyanidin B2 and procyanidin C1 were 0.05 mg/ml and diluted to L5 from L1 (0.003 mg/ml) using 50% methanol in water. The concentration of Mutamba extract samples were adjusted to about 2 mg/ml in 50% methanol in water and sonicated until dissolved (approximately 20 minutes), cooled to room temperature, mixed well, and then filtered through a 0.45 um nylon syringe filter. A 10 μl volume of each sample was examined by HPLC. HPLC quantification results for procyanidin B2, epicatechin and procyanidin C1 content for Mutamba extracts are provided in Tables 167 and 168.

TABLE 167

HPLC of Mutamba Extracts from Different Plant Parts, Age and Gender

| Extract No. | Plant Part | Gender (Age) | Contents (%) | | | |
| --- | --- | --- | --- | --- | --- | --- |
| | | | Procyanidin B2 | Epicatechin | Procyanidin C1 | Total |
| 82D1 | Stem | Female (1 yr) | 0.7 | 0.5 | 0.26 | 1.46 |
| 82D2 | Bark | Female (1 yr.) | 1.24 | 0.69 | 0.66 | 2.59 |
| 82D2 | Bark | Female | 4.67 | 2.47 | 1.80 | 8.94 |
| 82D2 | Stem | Female | 1.07 | 0.63 | 0.42 | 2.12 |

TABLE 167-continued

HPLC of Mutamba Extracts from Different Plant Parts, Age and Gender

| Extract No. | Plant Part | Gender (Age) | Procyanidin B2 | Epicatechin | Procyanidin C1 | Total |
|---|---|---|---|---|---|---|
| 82D2 | Bark | Male (mature) | 4.12 | 2.15 | 1.56 | 7.83 |
| 82D2 | Stem | Male (mature) | 0.33 | 0.13 | 0.11 | 0.57 |
| 82D2 | Stem bark | Female (young) | 0.61 | 0.18 | 0.34 | 1.13 |
| 82D2 | Stem bark | Female (mature) | 1.73 | 0.72 | 0.98 | 3.43 |
| 82D2 | Stem bark | Male (young) | 1.26 | 0.42 | 0.82 | 2.50 |

As shown in Table 167, a total of 9 samples were analyzed to compare extract content from Mutamba plants at different ages, gender, and plant part.

TABLE 168

HPLC of Mutamba Extracts from Different Plant Parts and Countries

| Extract No. | Plant Part | Origin | Procyanidin B2 | Epicatechin | Procyanidin C1 | Total |
|---|---|---|---|---|---|---|
| 36 | Bark | Belize | 1.12 | 0.89 | 0.49 | 2.50 |
| 82D20 | Bark | Peru | 1.14 | 0.62 | 0.38 | 2.14 |
| 82D21 | Bark | Mexico | 0.98 | 0.36 | 0.20 | 1.54 |
| 82D22 | Bark | Belize | 1.31 | 0.62 | 0.38 | 2.31 |
| 82P3 | Bark | Belize | 0.71 | 0.43 | 0.19 | 1.33 |
| 82P3 | Bark | Belize | 2.21 | 1.51 | 0.67 | 4.39 |
| 82P1 | Stem bark | Panama | 1.31 | 0.86 | 0.34 | 2.51 |
| 82D23 | Bark | Belize | 1.7 | 0.36 | 0.66 | 2.72 |
| 82D24 | Bark | England | 0.31 | 0.05 | 0.27 | 0.63 |
| 82D25 | Bark | Peru | 1.36 | 0.61 | 0.68 | 2.65 |

Further quantification analyses of Mutamba extracts collected from plants originating in different countries/regions and extracted from different plant parts are provided in Table 168 to identify the best raw material source.

Example 84

Preparation of Mutamba Stem Bark EtOH Extract and Extract Fractions

Mutamba (*Guazuma ulmifolia*) EtOH extract 84 was produced as follows: 97.4 kg of dried Mutamba stem bark was cut, crushed and extracted with approximately 8-fold volume (800 L) of 70% ethyl alcohol in water (v/v); the extraction was performed at 100° C. for 4 hours. The residue was filtered to obtain the extraction solution. The above-described procedure was repeated 2 times. The extraction solutions were combined and concentrated with a rotary evaporator at 40° C. under vacuum until the volume was 1/25 volume, and then the concentrated solution was dried by vacuum freeze-drying process to obtain 70% EtOH extract powder from Mutamba stem bark. A total of 13.1 kg of Mutamba EtOH extract 84 was obtained from 97.4 kg of raw material, and the extraction yield was approximately 13.47% (w/w).

This crude Mutamba stem bark EtOH extract 84 (200 g) was suspended in 0.6 liter of 20% aqueous ethyl alcohol, and then loaded onto pre-conditioned HP-20 gel column (10× 150 cm column with 7 L of HP-20 resin, Diaion™, Mitsubishi Chemical, Japan) with 20% aqueous ethyl alcohol solution. The column was eluted with a stepwise gradient solvent mixture and a total of 20 fractions was collected as follows: 10 L of 20% EtOH elution to collect 2 fractions (F1-2), 10 L of 40% EtOH elution to collect 5 fractions (F3-7), 10 L of 60% EtOH elution to collect 5 fractions (F8-12), 10 L of 80% EtOH elution to collect 3 fractions (F13-15), 10 L of 100% EtOH elution to collect 2 fractions (F16-17), 10 L of acetone-MeOH (1:1) washing to collect 3 fractions (F18-20).

TABLE 169

HP-20 Column fractions of Mutamba EtOH Extract

| Fraction | Solvent gradient | Dry yield (g) | Fraction ratio |
|---|---|---|---|
| Fractions 1-5 | 20%, 40% | 89 g | 47.0% |
| Fraction 6 | 40% | 47.6 g | 25.1% |
| Fraction 7 | 40% | 13.87 g | 7.3% |
| Fraction 8 | 60% | 13.12 g | 6.9% |
| Fractions 9-12 | 60% | 14.5 g | 7.7% |
| Fractions 13-17 | 80%, 100% | 5.15 g | 2.7% |
| Fractions 18-20 | Acetone/MeOH(1:1) | 6.24 g | 3.3% |
| Total yield | | 189.5 g (~95%) | 100% |

As shown in Table 169, the fractions were combined based on HPLC chemical profiling, and the most of weight is distributed at early elution portion with an excellent recovery yield of about 95% in the mass balance. Fractions 7, 8 and 9-12 were further combined for in vivo assays. Three Mutamba stem bark EtOH extract 84 fractions of 84/F1-5, 84/F6 and 84/F7-12 were examined for in vivo efficacy in a diet induced obesity (DIO) mice model.

Example 85

HPLC Analysis of Additional Mutamba EtOH Extract Fractions

Mutamba (*Guazuma ulmifolia*) 70% EtOH extracts (2 g) were dissolved in 4 ml 20% EtOH/water, mixed with 13.5 g of HP-20 resin (Sigma), and loaded onto the top space of a pre-packed SNAP HP-20 column (Biotage, 38×157 mm). Before sample loading, the HP-20 column was conditioned with 20% EtOH/water for 30 min at 20 ml/min flow rate delivered by a Hitachi High Throughput Purification (HTP) system. The columns were eluted with a linear gradient ranging from 20% EtOH/water to 100% EtOH in 50 min, and kept with 100% EtOH for additional 16 minutes to wash all components off the column. A total of 97 fractions were collected. Similar fractions in chemical profile and color were combined to give equivalent pre-F6, F6 and post-F6 best pools. The column recovery yields ranged from 88 to 100%.

TABLE 170

HPLC Analysis of Fraction 6 from Various Mutamba EtOH Extracts

| Extract No. | Fraction Weight Distribution | | | Pro-cyanidin B2 | Epicatechin | Pro-cyanidin C1 |
| --- | --- | --- | --- | --- | --- | --- |
| | Pre-F6 | F6 | Post-F6 | | Content (%) in F6 | |
| 82D1 | 46% | 35% | 18% | 0.38 | 0.37 | 0.23 |
| 82D2 | 56% | 35% | 9% | 1.53 | 0.93 | 1.07 |
| 82D3 | 51% | 28% | 21% | 1.06 | 0.91 | 0.63 |
| 82D4 | 44% | 42% | 14% | 1.96 | 1.25 | 1.00 |
| 82D5 | 42% | 45% | 12% | 4.88 | 2.80 | 2.27 |
| 82D6 | 61% | 27% | 11% | 1.71 | 1.16 | 0.94 |
| 82D26 | 47% | 44% | 9% | 4.01 | 2.08 | 2.32 |
| 82D27 | 33% | 50% | 17% | 1.49 | 0.96 | 0.87 |
| 82D7 | 40% | 48% | 12% | 4.52 | 2.96 | 2.41 |
| 82D8 | 59% | 26% | 16% | 0.63 | 0.35 | 0.33 |
| 82D9 | 44% | 45% | 11% | 4.57 | 2.70 | 2.20 |
| 82D10 | 58% | 28% | 14% | 0.43 | 0.44 | N.D |
| 82D28 | 50% | 40% | 10% | 2.74 | 0.63 | 1.83 |
| 82D29 | 47% | 43% | 11% | 2.96 | 1.36 | 1.78 |
| 82D15 | 45% | 45% | 10% | 2.26 | 0.81 | 1.26 |
| 82D14 | 37% | 50% | 13% | 1.86 | 0.46 | 1.07 |
| 82D30 | 77% | 16% | 7% | 0.97 | 0.49 | 0.78 |

Example 86

NMR Analysis of Mutamba EtOH Extract Fractions

NMR data were collected for HP-20 fractions F1-F20 on a Varian VNMRS-500 MHz spectrometer to further understand what active components are present in each fraction. The $^1$H-NMR spectra were acquired by VNMR-J 2.2 c with 1H-19F/15N-31P 5 mm PFG AutoX DB probe and processed by ACD/Labs 10.0 software. Based on NMR data analysis, fractions 1-5 contained mainly oligosaccharides and polysaccharides with huge overlapping peaks around 3-5 ppm region. The proton NMR spectra of fractions 6, 7, and 8 showed very similar patterns and these match with procyanidin-type compounds (e.g., condensed tannins) Proton data analysis of fractions 9, 10 and 11 indicated the presence of a mixture of condensed tannins and hydrolyzable tannins with the increasing proton signals in the 3.5-4.5 ppm region and decreasing signals around 6.0 ppm. The proton NMR spectra of fractions 12, 13, and 14 showed that the main components of these fractions are the hydrolyzable tannins Fractions 17 and 18 contained mainly fat molecules.

Based on the NMR data, fractions 6, 7, and 8 are the three main fractions that contain condensed tannins with a total ratio of 39.3%, wherein these components are the major active ingredients of the Mutamba extracts.

Example 87

MALDI-TOF Mass Spectrometry Analysis of Mutamba Fraction 84/F6

Figure 3:
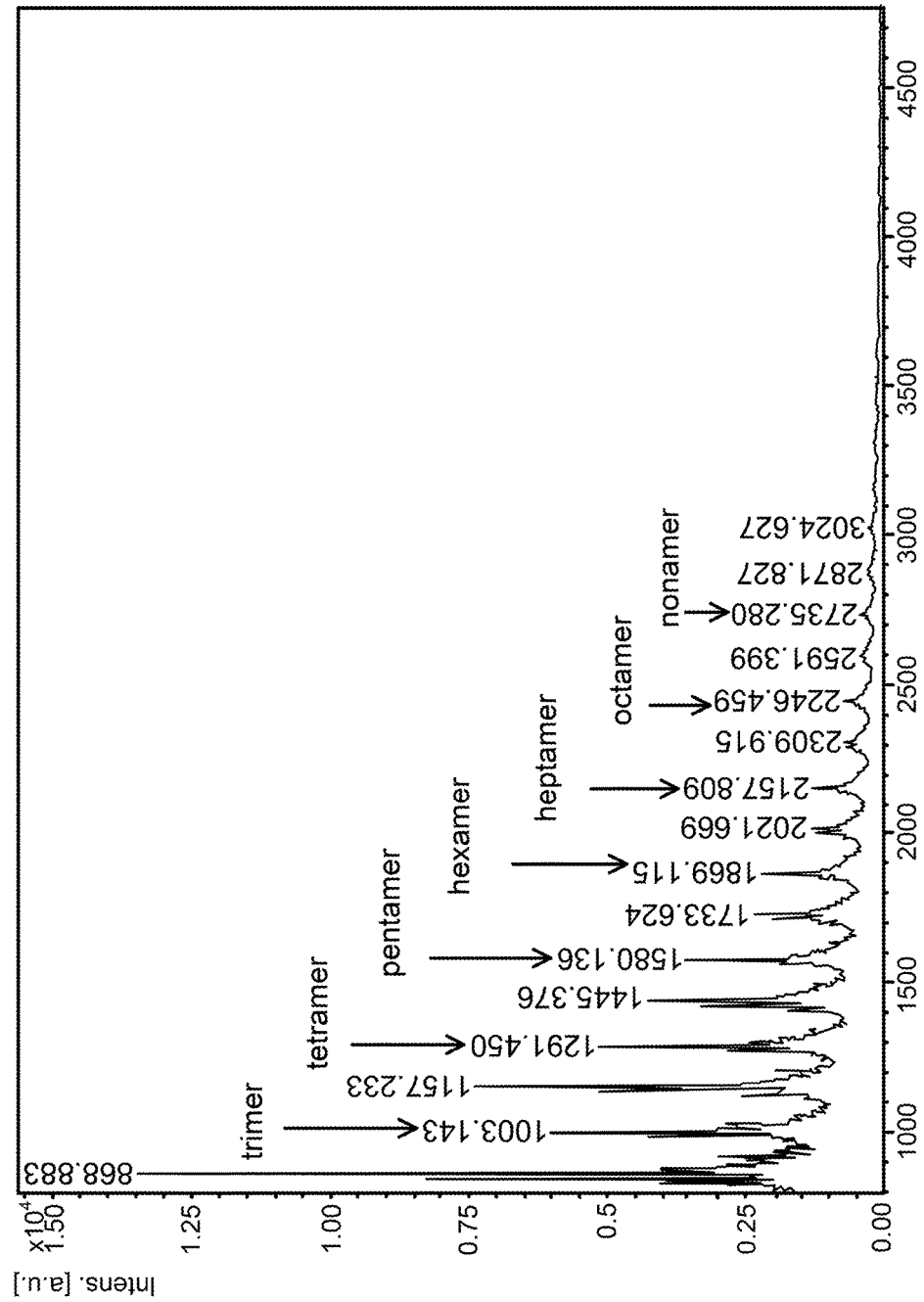
FIG. 3 shows MALDI-TOF positive ion mode mass spectrum of Mutamba fraction 84/F6 generated from Mutamba stem bark EtOH extract 84.

The MALDI-TOF mass spectrometry (MS) spectra were recorded on Bruker Autoflex II MALDI. The sample was dissolved in MeOH, while CsCl was dissolved in H$_2$O (about 1.5 mg/mL). Sample solution (20 µL) was mixed with the CsCl solution (5 uL), and then a 0.5 µl of solution mixture was spotted on the MALDI plate followed by 2 µL of a saturated solution of DHB in acetonitrile. After drying, the plate was put into the MALDI. Acquisition was done in linear positive mode. The MALDI-TOF mass spectra of Mutamba fraction 84/F6 produced in Example 84, which was recorded as both [M+Cs]$^+$ and [M+H]$^+$ in the positive mode, showed a series of peaks grouped at intervals of 288 Da, corresponding to addition of one catechin/epicatechin unit (FIG. 3).

TABLE 171

MALDI-TOF Data of Mutamba Extract Fraction 84/F6

| Polymer | [M + H]$^+$ | [M + Cs]$^+$ |
| --- | --- | --- |
| Trimer | 867 | 999 |
| Tetramer | 1155 | 1287 |
| Pentamer | 1465 | 1575 |
| Hexamer | 1753 | 1863 |
| Heptamer | 2041 | 2151 |

The results indicate that the active components in Mutamba bark contains primarily procyanidins made up of dimers, trimers, tetramers, pentamers, hexamers, heptamers, octamers, and nonamers (up to decamers or even higher molecular weight polymers).

Example 88

Thiolysis and Chromatography of Mutamba Extract Active Fractions

Thiolysis was carried out according to the methods of Torres and Selga (*Chromatographia* 57:441, 2003) with modification. Cysteamine hydrochloride was chosen as alternative thiol reagent for the depolymerization reaction. Mutamba fraction 84/F6 produced in Example 84 or Mutamba fraction 82D4/F6 produced in Example 85 were each individually dissolved in methanol to yield a 10 mg/mL solution. An aliquot (50 µL) was placed in a vial with 50 µL hydrochloride in methanol (3.3%, v/v), and then cysteamine hydrochloride in methanol (50 mg/mL, 100 µL) was added. The mixture was heated at 65° C. for 20 minutes, the reaction was quenched with 0.1% (v/v) aqueous TFA 0.3 mL, and then cooled to room temperature. After filtration through a 0.45 µm membrane filter, the solutions were analyzed by HPLC chromatography.

Analytical HPLC chromatography was performed on an LC-MS (Hitachi M-8000) and PDA (Hitachi L-4500A) system with a ODS column (Phenomex, Luna C18, 4.6×250 mm, 10 µm) with mobile phase A (0.1% FA in water) and B (acetonitrile). The gradient elution was 3% B for 5 minutes, 3 to 9% over 10 minutes, 9 to 16% over 30 minutes, 16-100% in 1 minute, and washed with 100% B for 7 minutes at a flow rate of 1 mL/min with UV wavelength 280 nm. Catechin, epicatechin, catechin-cysteamine and epicatechin-cysteamine derivative peaks were identified. The mDP of the procyanidin fractions was calculated based on the peak areas. The calculated mDP (average degree of polymerization) value was 4.12 for Mutamba fraction 84/F6 and 6.27 for Mutamba fraction 82D4/F6.

This result indicates that catechin and epicatechin served as both terminal and extension units of the Mutamba procyanidins and epicatechin was the major component in the polymeric procyanidins from Mutamba bark. The active components in Mutamba bark primarily include procyanidins with average number of four epicatechin/catechin units, but also including dimers, trimers, tetramers, pentamers, hexamers, heptamers, octamers, nonamers and up to decamers, or even higher molecular weight polymers.

Example 89

Fractionation of Mutamba Extract Fraction 84/F6 and Thiolysis

Active fraction 6 obtained from Mutamba extract 84, referred to as 84/F6, was further fractionated by size exclusion chromatography. Fraction 84/F6 (100.5 mg) was loaded onto a LH-20 gel column with 5 g LH-20 Sephadex gel beads pre-conditioned with water. The column was eluted with 125 mL water, 125 mL 20% MeOH in water, 200 mL 50% MeOH, and finally washed off with 200 mL 70% acetone in water. Five subfractions (84/F6-01-84/F6-05) were collected. Each fraction was depolymerized with cysteamine-HCl as described in Example 88 to determine the average degree of polymerization.

TABLE 172

Subfractions of Mutamba Extract Fraction 84/F6

| Subfraction | Weight (mg) | Ratio | mDP |
|---|---|---|---|
| 84/F6-01 | 6.2 | 6.17% | 8.33 |
| 84/F6-02 | 12.1 | 12.04% | 6.87 |
| 84/F6-03 | 16.7 | 16.62% | 1.71 |
| 84/F6-04 | 64.8 | 64.48% | 6.23 |
| 84/F6-05 | 5.0 | 4.98% | 8.44 |

Subfraction 84/F6-01 (6.17%) and 84/F6-02 (12.04%) contained polymeric procyanidins with an mDP value of 8.33 and 6.87, respectively. Subfraction 84/F6-03 (16.6%) eluted with 50% MeOH and contained mainly epicatechin, procyanidin B2, procyanidn C1, and a small portion of oligomeric procyanidins with a mDP value at 1.71. The major fraction 84/F6-06 (64.48%) was eluted by 70% Me$_2$CO—H$_2$O and contained procyanidins with an mDP value at 6.23.

Example 90

Fractionation of Mutamba Extract Fraction 82D4/F6 and Thiolysis

Active fraction 6 equivalent obtained from Mutamba extract 82D4 (see Example 82), referred to as 82D4/F6, was further fractionated by size exclusion chromatography. Fraction 82D4/F6 (620.8 mg) was loaded onto an LH-20 gel column with 5 g LH-20 Sephadex gel beads pre-conditioned with water. The column was eluted with 150 mL water, 250 mL 20% MeOH in water, 100 mL 40% MeOH, and finally 300 mL 100% MeOH (recovery yield was 77.6%). Five subfractions (82D4/F6-01-82D4/F6-05) were collected. About 22% of substances from the fraction remained on the LH-20 column. Each fraction was depolymerized with cysteamine-HCl as described in Example 88 to determine the average degree of polymerization.

TABLE 173

Subfractions of Mutamba Extract Fraction 82D4/F6

| Subfraction | Weight (mg) | Ratio | mDP |
|---|---|---|---|
| 82D4/F6-01 | 67.9 | 10.94% | 13.43 |
| 82D4/F6-02 | 112.3 | 18.09% | — |
| 82D4/F6-03 | 66.4 | 10.70% | 5.87 |
| 82D4/F6-04 | 163.2 | 26.29% | 4.24 |
| 82D4/F6-05 | 71.9 | 11.58% | 7.38 |

Subfraction 82D4/F6-01 contained 10.9% polymeric procyanidins with an mDP value at 13.43.

Example 91

Analysis of Condensed Tannin Content in Mutamba Extracts

The Butanol-HCl assay is one colorimetric method commonly used to determine the amount of condensed tannins, particularly procyanidins, in a sample. The method described by Porter et al. (*Phytochemistry* 25:223, 1986) was followed as a standard method for determination of the condensed tannin content in Mutamba extracts. Butanol-HCl reagent was prepared by mixing 950 mL of n-Butanol with 50 mL concentrated HCl. Ferric reagent was prepared by dissolving 0.5 g FeNH$_4$(SO$_4$) in 25 mL of 2N HCl. In a tube and in duplicate, 1 ml Mutamba extract at a 0.2 mg/mL concentration in 70% acetone was added to 6 mL acid butanol reagent, then 0.2 mL iron reagent was added and absorbance at 550 nm measured. The tubes were capped, shaken, and then put in boiling water bath for 50 minutes. After cooling the tubes, the absorbance at 550 nm was measured. The absorbance of each sample before heating was subtracted from the absorbance of the heated mixtures as a blank. Subfraction 84/F6-04 (tannin fraction) was used as the standard for quantification. Condensed tannins (% in dry matter) as compared to the tannin standard equivalent were calculated based on the absorbance at 550 nm.

TABLE 174

Condensed Tannin Content in Mutamba EtOH Extracts

| Extract No. | Extract Content (%)* | Bark Content (%)* |
|---|---|---|
| 36 | 48.68% | 7.9% |
| 84 | 38.09% | 5.0% |
| 82P2 | 68.93% | 10.3% |
| 82P1 | 72.77% | 11.8% |
| 82D5 | 66.90% | 11.4% |
| 82D27 | 38.90% | 3.5% |
| 82D7 | 60.45% | 9.1% |
| 82D9 | 57.95% | 7.0% |
| 82D11 | 22.46% | 2.2% |
| 82D31 | 48.67% | 5.8% |
| 82D32 | 55.58% | 10.6% |
| 82D33 | 62.98% | 10.1% |
| 82D34 | 33.92% | 4.4% |
| 82D35 | 71.62% | 13.6% |
| 82D36 | 38.21% | 7.3% |
| 82D37 | 57.08% | 5.7% |
| 82D38 | 50.08% | 6.0% |
| 82D38 | 50.58% | 5.6% |

*Expressed as tannin standard compound equivalents

The condensed tannin content of the Mutamba EtOH extracts varied greatly, ranging from 20% up to as much as 73% (see Table 174), depending on the plant part, age of the plant, plant collection location, and season. Mature bark and stem bark tend to have the highest levels of condensed tannins Based on the measured condensed tannin content in Mutamba extracts and corrected for extraction yield, the content in the raw plant material was calculated to range from about 2% to about 14%.

Using this method on two batches of Composition 2 (Magnolia:Morus:Mutamba) produced according to the Example 42, the condensed tannin content in each of the two batches was 35.26% and 31.63%, respectively.

Example 92

Analysis of Condensed Tannin Content in Mutamba Extract Fractions

Mutamba fractions from Mutamba 70% EtOH extract 84 were prepared at a concentration of 0.1 mg/mL in 70% acetone for use in the butanol-HCl assay described in Example 91. The condensed tannin content was quantified by the same method as described in Example 91, with data shown in the Table 175.

TABLE 175

Condensed Tannin Content in Mutamba EtOH Extract Fractions

| Fraction No. | Content* |
|---|---|
| 84/F1-5 | 11.22% |
| 84/F6 | 91.61% |
| 84/F7 | 77.67% |
| 84/F8 | 71.74% |
| 84/F9 | 67.21% |

*Expressed as tannin standard compound equivalents

The most active fraction, 84/F6, has a higher content of condensed tannins as compared with other the other fractions.

Example 93

Short Term In Vivo Efficacy of Mutamba EtOH Extract Fraction

A 14-day study was used to evaluate the effect of Mutamba EtOH extract fraction 84/F6 on body weight gain in high-fat-diet (HFD) fed C57B1/6J mice. Male C57BL/6J mice at the age of 6 weeks were purchased from Charles River Laboratories (Wilmington, Mass.) and acclimated for one week. On the day 0 (treatment start), body weights were taken for all the mice and randomly assigned to a group of four treatment groups as follows: (1) 8 mice/group received positive control=Alli; (2) 15 mice/group received Mutamba fraction 84/F6; (3) 8 mice/group received vehicle only (0.5% carboxymethyl cellulose) given to HFD control; and (4) 8 mice/group received vehicle only given to untreated normal diet control. Mice received a daily oral dose of Alli at 30 mg/kg and Mutamba 84/F6 at 1 g/kg for 14 days. Once mice received their first respective dose, they were provided ad libitum a 60% kcal high fat-diet, except for the normal diet group. Body weights were taken daily for the duration of study except on weekends. At the end of the study (on the $15^{th}$ day), mice were fasted for 5 hours and blood glucose, triglyceride and total cholesterol levels were taken. Blood glucose levels were measured using the Contour blood glucose monitoring kit (Bayer Health Care). Total triglyceride and cholesterol levels were measured using the CardioChek Analyzer with PTS panel test strips (Polymer Technology System, Inc, Indianapolis, Ind.).

TABLE 176

Effect of Mutamba EtOH Extract Fraction on Body Weight Gain

| Group | Body weight (g)† | | | | | | | | | | |
|---|---|---|---|---|---|---|---|---|---|---|---|
| | Day 1 | Day 2 | Day 3 | Day 4 | Day 7 | Day 8 | Day 9 | Day 10 | Day 11 | Day 14 |
| HFD | 21.1 ± 0.72 | 21.5 ± 1.0 | 21.3 ± 1.14 | 21.8 ± 0.88 | 22.9 ± 1.07 | 23.1 ± 1.06 | 23.1 ± 0.98 | 23.3 ± 1.06 | 23.6 ± 1.09 | 24.5 ± 1.06 |
| 84/F6 1 g/kg | 21.2 ± 0.74 | 21.3 ± 1.03 | 21.7 ± 0.94 | 21.7 ± 1.18 | 22.4 ± 1.26 | 22.1 ± 1.09 | 21.7 ± 1.07* | 22.2 ± 1.25* | 22.6 ± 1.08** | 23.0 ± 1.62* |
| Alli 30 mg/kg | 21.3 ± 0.72 | 21.5 ± 1.00 | 21.8 ± 1.14 | 22.2 ± 0.88 | 22.6 ± 1.07 | 22.7 ± 1.06 | 22.4 ± 0.98 | 22.3 ± 1.06 | 22.3 ± 1.09 | 22.8 ± 1.06* |

†Data are expressed as Mean ± SD.
*P ≤ 0.05;
**P ≤ 0.07

As seen in Table 176, mice receiving Mutamba 84/F6 showed statistically significant less weight gain beginning day 9 after treatment as compared to the vehicle treated HFD group. On the other hand, the positive control, Alli, treated mice showed the decrease in weight gain only on day 14 of treatment as compared to the vehicle treated HFD group.

TABLE 177

Effect of Mutamba EtOH Extract Fraction on Metabolism†

| Group | Dose (mg/kg) | Cholesterol (mg/dl) | Triglyceride (mg/dl) | Glucose (mg/dl) |
|---|---|---|---|---|
| HFD | 0 | 117.3 ± 14.7 | 79.4 ± 9.5 | 212.3 ± 37.2 |
| Alli | 30 | 104.5 ± 10.2 (P = 0.06) | 109.5 ± 18.2 (P = 0.001) | 164.3 ± 46.8 (P = 0.04) |
| Mutamba 84/F6 | 1000 | 102.4 ± 76.7 (P = 0.02) | 81.3 ± 7.8 (P = 0.67) | 156.9 ± 42.1(P = 0.01) |
| Normal diet | 0 | 100.3 ± 0.7 (P = 0.01) | 107.6 ± 21.6 (P = 0.001) | 175.0 ± 25.1 (P = 0.03) |

†Data are expressed as Mean ± SD.
P-values for each group are indicated in parenthesis Similarly, after day 14 of oral treatments, a statistically significant decrease in fasting blood total cholesterol and glucose levels were observed for mice treated with Mutamba 84/F6 as compared to the vehicle treated HFD group (Table 177). These low levels of fasting blood glucose and total cholesterol were comparable to the levels observed for mice fed a normal diet. No difference in triglyceride levels were observed between Mutamba and vehicle treated HFD groups. In contrast, the Alli and vehicle treated regular diet fed mice showed statistically significant higher levels of fasting triglyceride as compared to the HFD group.

Example 94

In Vivo Efficacy of Mutamba Stem Bark EtOH Extract and Fractions

Mutamba 70% EtOH extract 84 and three column fractions of Mutamba 84/F1-5, 84/F6, and 84/F7-12 produced according to the Example 84 were tested in the DIO mouse model as described in Example 48. The Mutamba 70% EtOH extract treatment group (G1), Mutamba fraction 84/F1-5 (G2), Mutamba fraction 84/F6 (G3) and Mutamba fraction 84/F7-12 (G4) were orally administered a dose of 1000 mg/kg by gavage two times per day.

TABLE 178

Effect of Mutamba EtOH Extract and Fractions on Body Weight
Animal Body Weight (gram)

| Group | | 0 | 1 | 2 | 3 | 4 | 5 | 6 | 7 |
|---|---|---|---|---|---|---|---|---|---|
| NC | Mean | 28.99 | 28.56 | 28.48 | 28.35 | 28.51 | 29.10 | 29.42 | 29.66 |
| | SD | 1.641 | 1.341 | 1.350 | 1.403 | 1.420 | 1.542 | 1.695 | 1.886 |
| | p value* | 0.0000 | 0.0000 | 0.0000 | 0.0000 | 0.0000 | 0.0000 | 0.0000 | 0.0000 |
| HFD | Mean | 41.47 | 40.78 | 40.16 | 41.51 | 42.48 | 44.00 | 45.91 | 47.39 |
| | SD | 3.417 | 3.595 | 3.838 | 3.778 | 4.175 | 3.887 | 3.609 | 3.080 |
| ORI | Mean | 41.44 | 40.17 | 36.20 | 34.80 | 36.09 | 37.06 | 38.91 | 40.22 |
| | SD | 3.405 | 3.079 | 3.338 | 3.399 | 3.886 | 3.448 | 4.111 | 4.372 |
| | p value | 0.9881 | 0.7047 | 0.0326 | 0.0011 | 0.0040 | 0.0010 | 0.0015 | 0.0010 |
| G1 | Mean | 41.41 | 41.51 | 41.39 | 42.05 | 43.61 | 45.30 | 46.92 | 47.81 |
| | SD | 3.308 | 3.313 | 3.802 | 4.001 | 4.219 | 4.637 | 4.552 | 4.131 |
| | p value | 0.9708 | 0.6602 | 0.5070 | 0.7730 | 0.5744 | 0.5301 | 0.6075 | 0.8070 |
| G2 | Mean | 41.63 | 40.90 | 40.92 | 41.71 | 43.00 | 44.64 | 45.90 | 46.59 |
| | SD | 3.361 | 3.339 | 3.523 | 3.581 | 3.829 | 3.523 | 3.493 | 2.917 |
| | p value | 0.9215 | 0.9435 | 0.6707 | 0.9115 | 0.7843 | 0.7196 | 0.9958 | 0.5794 |
| G3 | Mean | 41.61 | 40.72 | 38.72 | 39.09 | 39.46 | 39.41 | 39.31 | 39.72 |
| | SD | 3.339 | 3.946 | 3.668 | 3.739 | 4.301 | 4.550 | 4.731 | 4.485 |
| | p value | 0.9283 | 0.9725 | 0.4277 | 0.2051 | 0.1630 | 0.0402 | 0.0053 | 0.0008 |
| G4 | Mean | 41.73 | 40.96 | 40.54 | 41.38 | 42.81 | 44.14 | 45.18 | 45.46 |
| | SD | 3.318 | 3.556 | 3.954 | 4.278 | 4.739 | 4.878 | 4.837 | 5.108 |
| | p value | 0.8709 | 0.9178 | 0.8424 | 0.9438 | 0.8762 | 0.9497 | 0.7218 | 0.3472 |

*p value: compare to HFD by t-test

Table 178 shows that the 1000 mg/kg treatment group G3 showed significantly decreased body weight after weeks 5, 6 and 7 of treatment.

TABLE 179

Effect of Mutamba EtOH Extract and Fractions on Weight Gain
Animal Weight Gain (gram)

| Group | | 1 | 2 | 3 | 4 | 5 | 6 | 7 |
|---|---|---|---|---|---|---|---|---|
| NC | Mean | −0.08 | −0.21 | −0.06 | 0.53 | 0.86 | 1.10 | 1.51 |
| | SD | 0.640 | 0.812 | 1.002 | 0.864 | 1.235 | 1.208 | 1.308 |
| | p value | 0.0843 | 0.0126 | 0.0113 | 0.0002 | 0.0000 | 0.0000 | 0.0000 |
| HFD | Mean | −0.61 | 0.73 | 1.70 | 3.22 | 5.13 | 6.61 | 7.25 |
| | SD | 0.631 | 0.645 | 1.646 | 1.516 | 1.453 | 1.310 | 1.651 |
| ORI | Mean | −3.97 | −5.37 | −4.08 | −3.11 | −1.26 | 0.05 | 0.72 |
| | SD | 0.538 | 1.150 | 1.333 | 1.519 | 1.544 | 1.798 | 1.954 |
| | p value | 0.0000 | 0.0000 | 0.0000 | 0.0000 | 0.0000 | 0.0000 | 0.0000 |
| G1 | Mean | −0.12 | 0.54 | 2.10 | 3.79 | 5.41 | 6.31 | 6.85 |
| | SD | 0.827 | 0.944 | 1.099 | 1.343 | 1.342 | 1.280 | 1.443 |
| | p value | 0.1748 | 0.6216 | 0.5485 | 0.4154 | 0.6720 | 0.6260 | 0.5949 |
| G2 | Mean | 0.02 | 0.81 | 2.10 | 3.75 | 5.00 | 5.69 | 6.76 |
| | SD | 0.815 | 0.828 | 1.160 | 1.070 | 1.242 | 1.539 | 2.189 |
| | p value | 0.0835 | 0.8259 | 0.5520 | 0.4118 | 0.8449 | 0.1919 | 0.6017 |

TABLE 179-continued

Effect of Mutamba EtOH Extract and Fractions on Weight Gain
Animal Weight Gain (gram)

| Group | | 1 | 2 | 3 | 4 | 5 | 6 | 7 |
|---|---|---|---|---|---|---|---|---|
| G3 | Mean | −1.99 | −1.46 | −1.09 | −1.14 | −1.24 | −0.83 | −0.21 |
| | SD | 2.773 | 1.634 | 1.220 | 1.253 | 2.048 | 1.967 | 1.903 |
| | p value | 0.1807 | 0.0063 | 0.0014 | 0.0000 | 0.0000 | 0.0000 | 0.0000 |
| G4 | Mean | −0.42 | 0.42 | 1.85 | 3.18 | 4.22 | 4.51 | 5.30 |
| | SD | 0.777 | 1.315 | 1.753 | 1.986 | 2.110 | 2.298 | 2.381 |
| | p value | 0.5681 | 0.5307 | 0.8475 | 0.9591 | 0.3047 | 0.0298 | 0.0603 |

* p value: compare to HFD by t-test

The body weight gains from 1000 mg/kg Mutamba fraction 84/F6 group (G3) was significantly decreased after the second week of treatment and such effect lasted until the end of the treatment period.

TABLE 180

Effect of Mutamba EtOH Extract and Fractions on Food Intake and FER

| Group | | Weight Gain (g/day) | Food intake (g/day) | FER* (Food efficiency ratio) |
|---|---|---|---|---|
| NC | Mean | 0.031 | 3.309 | 0.009 |
| | SD | 0.027 | 0.450 | 0.008 |
| | p value† | 0.0000 | 0.0000 | 0.0000 |
| HFD | Mean | 0.151 | 2.548 | 0.059 |
| | SD | 0.034 | 0.442 | 0.014 |
| ORI | Mean | 0.015 | 2.675 | 0.006 |
| | SD | 0.041 | 0.690 | 0.015 |
| | p value | 0.0000 | 0.0737 | 0.0000 |
| G1 | Mean | 0.143 | 2.532 | 0.056 |
| | SD | 0.030 | 0.546 | 0.012 |
| | p value | 0.5949 | 0.7917 | 0.6363 |
| G2 | Mean | 0.141 | 2.365 | 0.060 |
| | SD | 0.046 | 0.489 | 0.019 |
| | p value | 0.6017 | 0.0014 | 0.9684 |
| G3 | Mean | −0.004 | 1.994 | −0.002 |
| | SD | 0.040 | 0.692 | 0.020 |
| | p value | 0.0000 | 0.0000 | 0.0000 |
| G4 | Mean | 0.110 | 2.349 | 0.047 |
| | SD | 0.050 | 0.560 | 0.021 |
| | p value | 0.0603 | 0.0013 | 0.1611 |

*FER (Feed efficacy ratio) = Weight Gain (g/day)/Food intake (g/day)
†p value as compared to HFD by Student's t-test Food intake and Food Efficiency Ratio (FER) were significantly reduced by oral treatment of DIO mice with Mutamba fraction 84/F6 (G3) at 1000 mg/kg when compared to the high fat diet group treated with vehicle only.

TABLE 181

Effect of Mutamba EtOH Extract and Fractions on Absolute Organ Weight

| Group | | Liver | Epididymal Fat | Retro-peritoneal Fat | Peri-Renal Fat | Total Fat* |
|---|---|---|---|---|---|---|
| NC | Mean | 1.091 | 0.740 | 0.216 | 0.113 | 1.069 |
| | SD | 0.078 | 0.202 | 0.072 | 0.034 | 0.275 |
| | p value† | 0.0038 | 0.0000 | 0.0000 | 0.0000 | 0.0000 |
| HFD | Mean | 1.785 | 2.335 | 0.505 | 0.634 | 3.474 |
| | SD | 0.519 | 0.510 | 0.025 | 0.145 | 0.507 |
| ORI | Mean | 1.184 | 1.998 | 0.567 | 0.388 | 2.952 |
| | SD | 0.215 | 0.330 | 0.086 | 0.091 | 0.405 |
| | p value | 0.0086 | 0.1182 | 0.0571 | 0.0008 | 0.0288 |
| G1 | Mean | 1.973 | 2.259 | 0.542 | 0.616 | 3.417 |
| | SD | 0.462 | 0.455 | 0.082 | 0.137 | 0.428 |
| | p value | 0.4292 | 0.7418 | 0.2140 | 0.7891 | 0.7989 |
| G2 | Mean | 1.696 | 2.230 | 0.512 | 0.582 | 3.323 |
| | SD | 0.472 | 0.674 | 0.108 | 0.098 | 0.710 |
| | p value | 0.7080 | 0.7134 | 0.8611 | 0.3869 | 0.6113 |
| G3 | Mean | 1.196 | 1.949 | 0.495 | 0.396 | 2.841 |
| | SD | 0.228 | 0.346 | 0.058 | 0.193 | 0.306 |
| | p value | 0.0101 | 0.0919 | 0.6424 | 0.0111 | 0.0073 |
| G4 | Mean | 1.850 | 1.938 | 0.484 | 0.544 | 2.966 |
| | SD | 0.688 | 0.375 | 0.084 | 0.150 | 0.333 |
| | p value | 0.8254 | 0.0779 | 0.4886 | 0.2153 | 0.0251 |

*Total fat is the sum of the three fat pads (epididymal, retroperitoneal, perirenal)
†p value as compared to HFD by Student's t-test In Mutamba fraction 84/F6 treated group (G3), absolute weights of liver, peri-renal fat and total fat pads were significantly decreased when compared with the high fat diet control group.

TABLE 182

Effect of Mutamba EtOH Extract and Fractions on Biochemistry Parameters

| Group | | ALT U/L | AST U/L | ALP U/L | Glu mg/dL | T-chol mg/dL | TG mg/dL | TP g/dL | LDL-C mg/dL | HDL-C mg/dL |
|---|---|---|---|---|---|---|---|---|---|---|
| NC | Mean | 17.45 | 35.74 | 214.53 | 226.00 | 125.60 | 17.50 | 5.04 | 4.61 | 64.91 |
| | SD | 2.37 | 7.29 | 20.26 | 35.79 | 9.67 | 5.17 | 0.26 | 0.81 | 5.01 |
| | p value* | 0.0001 | 0.0008 | 0.7258 | 0.1744 | 0.0004 | 0.0091 | 0.2168 | 0.0003 | 0.3780 |
| HFD | Mean | 96.63 | 112.57 | 224.07 | 253.60 | 210.67 | 27.00 | 4.91 | 12.52 | 68.11 |
| | SD | 31.09 | 44.95 | 76.68 | 48.92 | 45.05 | 8.66 | 0.16 | 4.08 | 9.88 |
| ORI | Mean | 35.12 | 62.03 | 186.51 | 267.22 | 175.44 | 43.78 | 4.89 | 7.56 | 74.22 |
| | SD | 15.54 | 16.20 | 24.08 | 38.57 | 17.85 | 18.56 | 0.25 | 2.52 | 5.31 |
| | p value | 0.0001 | 0.0099 | 0.1926 | 0.5232 | 0.0530 | 0.0312 | 0.8243 | 0.0068 | 0.1217 |
| G3 | Mean | 62.15 | 74.50 | 149.83 | 206.50 | 168.13 | 30.13 | 4.79 | 6.64 | 71.26 |
| | SD | 40.16 | 27.86 | 18.12 | 40.01 | 17.96 | 17.20 | 0.24 | 1.21 | 3.33 |
| | p value | 0.0259 | 0.0303 | 0.0094 | 0.0190 | 0.0211 | 0.4542 | 0.2175 | 0.0012 | 0.3565 |

TABLE 182-continued

Effect of Mutamba EtOH Extract and Fractions on Biochemistry Parameters

| Group | | ALT U/L | AST U/L | ALP U/L | Glu mg/dL | T-chol mg/dL | TG mg/dL | TP g/dL | LDL-C mg/dL | HDL-C mg/dL |
|---|---|---|---|---|---|---|---|---|---|---|
| G4 | Mean | 145.60 | 125.01 | 208.07 | 255.00 | 200.67 | 25.11 | 5.11 | 9.92 | 67.76 |
|  | SD | 96.63 | 63.40 | 45.39 | 25.92 | 32.52 | 8.15 | 0.33 | 3.11 | 3.97 |
|  | p value | 0.2222 | 0.7534 | 0.4193 | 0.7637 | 0.5493 | 1.0000 | 0.1344 | 0.0977 | 0.9704 |

*p-value as compared to HFD by Student's t-test

Mutamba fraction 84/F6 treatment (G3) reduced total cholesterol and LDL-cholesterol significantly when compared with the high fat diet group.

In summary, the 1000 mg/kg Mutamba fraction 84/F6 treatment group (G3) showed significantly decreased body weight, body weight gain, food efficiency ratio (FER), total cholesterol, LDL-cholesterol and absolute organ weight of peri-renal fat and total fat pads. These data, taken together, indicate that Mutamba fraction 84/F6 contains the major active anti-obesity components from Mutamba stem bark, which can be used as is or standardized in a Mutamba extract for managing body weight, blood cholesterol, body fat, or any combination thereof.

The various embodiments described above can be combined to provide further embodiments. All of the U.S. patents, U.S. patent application publications, U.S. patent applications, foreign patents, foreign patent applications and non-patent publications referred to in this specification or listed in the Application Data Sheet are incorporated herein by reference, in their entirety. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A tablet or capsule pharmaceutical or nutraceutical formulation, comprising a mixture of:
   a *Morus alba* extract with an increased amount of Albanin G, Kuwanon G, Morusin, or any combination thereof, as compared to the amount of Albanin G, Kuwanon G, Morusin, or any combination thereof in unextracted *Morus alba*;
   a *Magnolia* officinalis extract with an increased amount of magnolol, honokiol, or both, as compared to the amount of magnolol, honokiol, or both in unextracted *Magnolia* officinalis;
   a Yerba Mate extract with an increased amount of caffeine, dicaffeoylquinic acid, or both as compared to the amount of caffeine, dicaffeoylquinic acid, or both in unextracted Yerba Mate; and
   a pharmaceutically or nutraceutically acceptable carrier, diluent, or excipient;
   wherein the tablet or capsule comprises about 0.5 weight percent (wt %) to about 90 wt % of active ingredients of the extract mixture.

* * * * *